US 9,340,556 B2

(12) United States Patent
Liao et al.

(10) Patent No.: US 9,340,556 B2
(45) Date of Patent: May 17, 2016

(54) ANTIBACTERIAL COMPOUNDS

(71) Applicants: GLAXO GROUP LIMITED, Greenford, Middlesex (GB); SHIONOGI & CO., LTD, Osaka (JP)

(72) Inventors: Xiangmin Liao, Collegeville, PA (US); Neil David Pearson, Collegeville, PA (US); Israil Pendrak, Collegeville, PA (US); Masayuki Sano, Osaka (JP)

(73) Assignees: GLAXO GROUP LIMITED, Greenford, Middlesex (GB); SHIONOGI & CO., LTD, Osaka (JP)

( * ) Notice: Subject to any disclaimer, the term of this patent is extended or adjusted under 35 U.S.C. 154(b) by 0 days.

(21) Appl. No.: 14/349,754

(22) PCT Filed: Oct. 4, 2012

(86) PCT No.: PCT/US2012/058595
§ 371 (c)(1),
(2) Date: Apr. 4, 2014

(87) PCT Pub. No.: WO2013/052568
PCT Pub. Date: Apr. 11, 2013

(65) Prior Publication Data
US 2014/0249126 A1 Sep. 4, 2014

Related U.S. Application Data

(60) Provisional application No. 61/543,075, filed on Oct. 4, 2011.

(51) Int. Cl.
*A61K 31/546* (2006.01)
*C07D 501/60* (2006.01)
*C07D 501/56* (2006.01)

(52) U.S. Cl.
CPC ............ *C07D 501/60* (2013.01); *A61K 31/546* (2013.01); *C07D 501/56* (2013.01)

(58) Field of Classification Search
USPC .......................... 514/203, 202; 540/225, 222
See application file for complete search history.

(56) References Cited

U.S. PATENT DOCUMENTS

| | | | |
|---|---|---|---|
| 4,632,918 A | 12/1986 | Angerbauer et al. | |
| 5,019,570 A | 5/1991 | Arnould et al. | |
| 5,401,734 A * | 3/1995 | Yamanaka et al. | ............ 514/206 |
| 7,384,928 B2 | 6/2008 | Nishitani et al. | |
| 8,883,773 B2 | 11/2014 | Yamawaki et al. | |
| 2011/0190254 A1 | 8/2011 | Nishitani et al. | |

FOREIGN PATENT DOCUMENTS

| | | |
|---|---|---|
| EP | 0 345 671 A2 | 12/1989 |
| EP | 2 341 053 A1 | 7/2011 |
| WO | WO 92/21683 A1 | 12/1992 |

OTHER PUBLICATIONS

Tsuji, et al., "In Vitro Activity of BMY-28142 in Comparison with Those of Other 1-Lactam Antimicrobial Agents", *Antimicrobial Agents and Chemotherapy*, vol. 27, No. 4, pp. 515-519 (1985).
White, et al., "Targeting metalloenzymes: a strategy that works", *Current Opinion in Pharmacology*, vol. 3, pp. 502-507 (2003).
Page, Malcolm G. P., "Anti-MRSA β-lactams in development", *Current Opinion in Pharmacology*, vol. 6, pp. 480-485 (2006).
PU65023 EP Extended European Search Report dated Mar. 13, 2015, 6 pages.

* cited by examiner

*Primary Examiner* — Kristin Vajda
(74) *Attorney, Agent, or Firm* — Grace C. Hsu; Kathryn A. Lutomski; Edward R. Gimmi

(57) ABSTRACT

The present invention relates to cephalosporin antibacterial compounds of Formula (I):

(I)

or corresponding pharmaceutically acceptable salts thereof, corresponding pharmaceutical compositions, compound preparation and treatment methods for bacterial infections, especially those caused by gram-negative bacteria.

37 Claims, No Drawings

ANTIBACTERIAL COMPOUNDS

This application is a 371 of Internationl Application No. PCT/US2012/058595, filed 4 Oct. 2012, which is incorporated herein by reference. This application claims priority to and The benefit of U.S. Provisional Application No. 61/543,075, filed 4 Oct. 2011.

FIELD OF THE INVENTION

The present invention relates to cephalosporin antibacterial compounds, corresponding pharmaceutical compositions, compound preparation and treatment methods for bacterial infections.

BACKGROUND OF THE INVENTION

Over the past several decades, the frequency of antimicrobial resistance and its association with serious infectious diseases has increased at alarming rates.

For example, in the United States, the Centers for Disease Control and Prevention estimate that roughly 1.7 million hospital-associated infections, from all types of microorganisms, including bacteria, combined, cause or contribute to 99,000 deaths each year. In Europe, where hospital surveys have been conducted, the category of Gram-negative infections are estimated to account for two-thirds of the 25,000 deaths each year. Nosocomial infections can cause severe pneumonia and infections of the urinary tract, bloodstream and other parts of the body. Many types are difficult to attack with antibiotics, and antibiotic resistance is spreading to Gram-negative bacteria that can infect people outside the hospital (see, Pollack, Andrew. "Rising Threat of Infections Unfazed by Antibiotics" *New York Times*, Feb. 27, 2010). This high rate of resistance increases the morbidity, mortality, and costs associated with nosocomial infections.

The problem of antibacterial resistance is compounded by the existence of bacterial strains resistant to multiple antibacterials. It is conventionally taught in the art that among:

Gram-positive organisms, resistant pathogens include methicillin-(oxacillin) resistant *Staphylococcus aureus*, beta-lactam-resistant and multidrug-resistant pneumococci, and vancomycin-resistant enterococci; and that Gram-negative resistance includes extended-spectrum beta-lactamases (ESBLs) in *Klebsiella pneumoniae*, *Escherichia coli*, and *Proteus mirabilis*, high-level third-generation cephalosporin (Amp C) beta-lactamase resistance among *Enterobacter species* and *Citrobacter freundii*, and multidrug-resistance genes observed in *Pseudomonas aeruginosa*, *Acinetobacter*, and *Stenotrophomonas maltophilia*.

To date, a variety of beta-lactam drugs have been developed and beta-lactam drugs have become clinically extremely important antimicrobial drugs.

However, there are increasing number of bacterial types which have obtained resistance against β-lactam drugs by producing β-lactamase, which degrade β-lactam drugs.

According to the Ambler molecular classification, β-lactamases are largely classified into four classes. Specifically, these are Class A (TEM type, SHV type, CTX-M type and the like), Class B (IMP type, VIM type, L-1 type and the like), Class C (AmpC type) and Class D (OXA type and the like). Amongst these, Classes A, C and D types are largely classified into serine-β-lactamase, and on the other hand, Class B type is classified into metallo-β-lactamase. It has been known that both have respectively different mechanisms to each other in terms of hydrolysis of β-lactam drugs.

Recently, clinical problems have been occurring due to the existence of Gram negative bacteria which have become highly resistant to β-lactam drugs including Cephems and Carbapenems, by production of Class A (ESBL) or D type serine-β-lactamases and Class B type metallo-β-lactamases which have extended their substrate spectrum. Particularly, metallo-β-lactamases are known to be one of the causes of obtaining multi-resistant Gram negative bacteria. Cephem compounds which exhibit intermediate activity against metallo-β-lactamase producing Gram negative bacteria are known (i.e., e.g., see, International Patent Publication No. WO 2007/119511 to Astellas Pharma. Inc. and Wakunaga Pharmaceuticals Inc., Intern.'l Pub. Date: Oct. 25, 2007 and Takeda et al., "In Vitro Antibacterial Activity of a New Cephalosporin, FR 295389, against IMP-type Metallo-β-Lactamase-Producters", The Journal of Antibiotics, vol. 61, pp. 36-39 (January 2008)).

However, there is a demand for development of Cephem compounds which exhibit more potent antimicrobial activity, in particular effectiveness against a variety of β-lactamase producing Gram negative bacteria.

One of the known antimicrobials to have poetnt anti-Gram negative bactericidal activity are Cephem compounds having a catechol group intramolecularly (i.e., e.g., see Sanada et al., "Comparison of Transport Pathways of Catechol-Substituted Cephalosporins. BO-1236 AND BO-1341, Through the Outer Membrane of *ESCHERICHIA COLI*", The Journal of Antibiotics, vol. 43, No. 12, pp. 1617-1620 (1990); Weissberger et al, "L-658, 310, A New Injectable Cephalosporin I. *In Vitro Antibacterial Properties*", The Journal of Antibiotics, vol. 42, No. 5, pp. 795-806 (1989); Okita et al., "Synthesis and Antibacterial Activity of Cephalosporins Having a Catechol in the C3 Side Chain", The Journal of Antibiotics, vol. 46, No. 5, pp. 833-839 (1993)). The action thereof is that the catechol group forms a chelate with $Fe^{3+}$, thereby the compound is efficiently incorporated into the bacterial body by means of the $Fe^{3+}$ transportation system across the cellular membrane (tonB-dependent iron transport system).

Thus there is a need for new antibacterials, particularly antibacterials with novel mechanisms of action.

In light of the above, a need exists to develop compounds of the present invention, which provides Cephem compounds that exhibit potent antimicrobial spectrum against a variety of bacteria including Gram negative bacteria and/or Gram positive bacteria, corresponding pharmaceutical compositions and treatment methods for bacterial infections. More importantly, there is a need to develop Cephem compounds of the present invention, which exhibit:

potent antimicrobial activity against beta-lactamase producing Gram negative bacteria;

potent antimicrobial activity against multi-drug resistant microbes, in particular, Class B type metallo-beta-lactamase producing Gram negative bacteria;

effective antimicrobial activity against extended-spectrum beta-lactamase (ESBL) producing bacteria; and a lack of cross-resistance against known Cephem drug or Carbapenem drugs.

The present invention is directed to overcoming these and other problems encountered in the art.

SUMMARY OF THE INVENTION

In general, the present invention relates to cephalosporin antibacterial compounds, corresponding pharmaceutical compositions, compound preparation and treatment methods for bacterial infections, especially those caused by gram-negative bacteria and gram-positive bacteria.

In particular, the present invention relates to novel compounds of Formulas (I) to (IX), respectively, or pharmaceutically acceptable salts thereof and corresponding pharmaceutical compositions, respectively.

The present invention also relates to processes for making compounds of Formulas (I) to (IX), respectively, or pharmaceutically acceptable salt thereof.

The present invention also relates to methods for treating bacterial infections, which comprises administering to a subject in need thereof an effective amount of a compound of Formulas (I) to (IX), respectively, or a pharmaceutically acceptable salt thereof or a corresponding pharmaceutical composition, respectively.

DETAILED DESCRIPTION OF THE INVENTION

In general, the present invention relates to cephalosporin antibacterial compounds, corresponding pharmaceutical compositions, compound preparation and treatment methods for bacterial infections, especially those caused by gram-negative bacteria and gram-positive bacteria.
Compounds In particular, the present invention relates to novel compounds of Formulas (I) to (IX), respectively, or pharmaceutically acceptable salts thereof.

In one aspect, the present invention relates to a compound of Formula (I):

(I)

wherein:
W is —$CH_2$—, —S—, or —O—;
U is —$CH_2$—, —S—, or —O—;
  provided that:
    when W is —$CH_2$—, U is —$CH_2$—, —S—, or —O—;
    when W is —S— or —O—, U is —$CH_2$—;
X is N, or C—$R^a$;
$R^1$ and $R^2$ each are hydrogen, ($C_{1-6}$)alkyl, or ($CH_2$)p—C(O)O$R^b$;
$R^3$ and $R^4$ each are hydrogen, OH or O$R^c$;
  wherein:
    $R^a$ is hydrogen or halogen;
    $R^b$ or $R^c$ each is H, ($C_{1-6}$)-alkyl or an alkali metal;
$R^{19}$ is hydrogen, —$OCH_3$, or —NH—NH(=O);
A is $R^5$ or —N$R^d$C(O)$R^5$
  wherein:
    $R^d$ is H or ($C_{1-6}$)-alkyl
$R^5$ is an optionally saturated or unsaturated monocyclic heterocyclic ring or an optionally saturated or unsaturated bi-cyclic or fused heterocyclic ring;
  wherein:
    each monocyclic heterocyclic ring has from 3 to 7 ring atoms and contains up to four heteroatoms;
    each fused heterocyclic ring optionally includes carbocyclic rings or heterocyclic rings of up to four heteroatoms;
$R^5$ optionally is substituted by one or more of the following substituents selected from —H, —OH, Oxo (=O), —CN, —$NO_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)$R^e$, —C(O)O$R^f$, —O($CH_2$)$_y$O$R^g$, —N$R^h$$R^i$, —$SO_2$$R^j$, —S($CH_2$)$_q$ $R^k$, —N$R^l$C(O)$R^m$, aryl or heteroaryl;
wherein:
  hetero atoms are selected from oxygen, nitrogen or sulphur;
  carbocyclic rings or heterocyclic rings for each fused heterocyclic ring systems include non-aromatic rings or aromatic rings;
  monocyclic heterocyclic rings or fused heterocyclic rings include substituted aromatic and non-aromatics;
  each $R^e$, $R^f$, $R^g$, $R^h$, $R^i$, $R^j$, $R^k$, $R^l$, or $R^m$ each is selected from H, $C_{1-6}$ alkyl, $C_{1-6}$ haloalkyl, $C_{1-6}$ alkoxy;
  each aryl or heteroaryl as defined above optionally is substituted H, —OH, —CN, —$NO_2$, -halogen, $C_{1-16}$-alkyl, $C_{1-6}$-haloalkyl, $C_{1-6}$-alkoxy, —OC(O)OH, —OC(O)$R^n$, —C(O)O$R^o$, —O($CH_2$)$_y$—O$R^p$, —N$R^q$$R^r$, —$SO_2$$R^s$, —S($CH_2$)$_y$—$R^t$, —N$R^u$C(O)$R^v$;
  wherein:
    $R^n$, $R^o$, $R^p$, $R^q$, $R^r$, $R^s$, $R^t$, $R^u$, or $R^v$ each are selected from $C_{1-6}$ alkyl, $C_{1-6}$-haloalkyl, or $C_{1-6}$-alkoxy;
n, m, o, p, q or y each are 0 or an integer from 1 to 5; or
a pharmaceutically acceptable salt thereof.

In one aspect, the present invention relates to a compound of Formula (I), where W is —$CH_2$—, and U is —S—; or a pharmaceutically acceptable salt thereof.

In another aspect, the present invention relates to a compound of Formula (I), where W is —$CH_2$—, U is —S—, and $R^{19}$ is hydrogen; or a pharmaceutically acceptable salt thereof.

In one aspect, the present invention relates to a compound of Formula (I), which definition referred to herein may include, but is not limited to the following related sub-generic Formulas (II) to (IX).

In one aspect, the present invention relates to a compound of Formula (II):

(II)

where:
X is N, or C—$R^a$;
$R^1$ and $R^2$ each are hydrogen, ($C_{1-6}$)alkyl, or ($CH_2$)p-C(O)O$R^b$;
$R^3$ and $R^4$ each are hydrogen, OH or O$R^c$;

where:
  $R^a$ is hydrogen or halogen;
  $R^b$ or $R^c$ each is H, ($C_{1-6}$)-alkyl, an alkali metal or negative charge;
A is $R^5$ or —$NR^dC(O)R^5$
  where $R^d$ is H or ($C_{1-6}$)-alkyl
$R^5$ is an optionally saturated or unsaturated monocyclic heterocyclic ring or an optionally saturated or unsaturated bi-cyclic or fused heterocyclic ring;
  where:
    each monocyclic heterocyclic ring has from 3 to 7 ring atoms and contains up to four heteroatoms;
    each fused heterocyclic ring optionally includes carbocyclic rings or heterocyclic rings of up to four heteroatoms; and
    $R^5$ optionally is substituted by one or more of the following substituents selected from —H, —OH, Oxo (=O), —CN, —NO$_2$, -halogen, -straight or branched $C_{1-6}$ alkyl, $C_{3-6}$cycloalkyl, -straight or branched $C_{1-6}$ haloalkyl, -straight or branched $C_{1-6}$ straight or branched alkoxy, —OC(O)OH, —OC(O)$R^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;
    where:
      heteroatoms are selected from oxygen, nitrogen or sulphur;

carbocyclic rings or heterocyclic rings for each fused heterocyclic ring systems include non-aromatic rings or aromatic rings;

monocyclic heterocyclic rings or fused heterocyclic rings include substituted aromatic and non-aromatics;

each $R^e$, $R^f$, $R^g$, $R^h$, $R^i$, $R^j$, $R^k$, $R^l$, or $R^m$ each is selected from H, $C_{1-6}$ alkyl, $C_{1-6}$haloalkyl, $C_{1-6}$ alkoxy;

each aryl or heteroaryl as defined above is optionally substituted with one or more of the following substituents selected from H, —OH, —CN, —NO$_2$, -halogen, $C_{1-6}$-alkyl, $C_{1-6}$haloalkyl, $C_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;
      where:
        $R^n$, $R^o$, $R^p$, $R^q$, $R^r$, $R^s$, $R^t$, $R^u$, or $R^v$ each are selected from $C_{1-6}$ alkyl, $C_{1-6}$-haloalkyl, or $C_{1-6}$-alkoxy;
n, m, o, p, q or y each are 0 or an integer from 1 to 5; or
a pharmaceutically acceptable salt thereof.

In another aspect, the present invention relates to a compound of Formula (II), where X is C—$R^a$, where $R^a$ is hydrogen or halogen.

In another aspect, the present invention relates to a compound of Formula (II), where X is C—$R^a$ and $R^a$ is hydrogen.

In one aspect, the present invention relates to a compound of Formula (III):

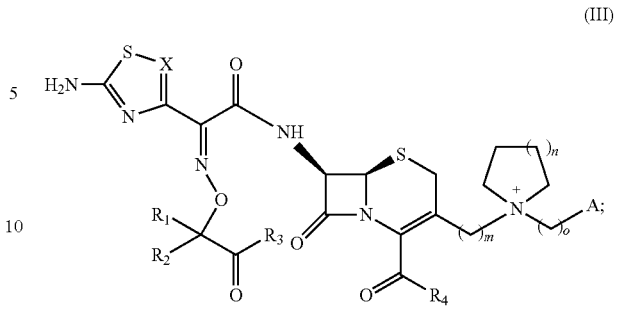

(III)

where:
X is N, or C—$R^a$;
$R^1$ and $R^2$ each are hydrogen, ($C_{1-6}$)alkyl, or (CH$_2$)p-C(O)OR$^b$;
$R^3$ and $R^4$ each are hydrogen, OH or OR$^c$;
  where:
    $R^a$ is hydrogen or halogen;
    $R^b$ or $R^c$ each is H, ($C_{1-6}$)-alkyl, an alkali metal or negative charge;
A is $R^5$ or —$NR^dC(O)R^5$
  where $R^d$ is H or ($C_{1-6}$)-alkyl
$R^5$ is a monocyclic 3 to 7 membered heterocyclic ring or a bicyclic 10 membered heterocyclic ring;
  where:
    each 3 to 7 membered heterocyclic ring contains up to four heteroatoms;
    each bicyclic 10 membered heterocyclic ring contains up to four heteroatoms;
  where:
    each heteroatom is selected from oxygen, nitrogen or sulphur;
    each 10 membered heterocyclic ring optionally contains carbocyclic rings or heterocyclic rings;
    where:
      carbocylic rings or heterocyclic rings for each 10 membered heterocyclic ring systems contain non-aromatic rings or aromatic rings;
    $R^5$ optionally is substituted by one or more of the following substituents selected from —H, —OH, Oxo (=O), —CN, —NO$_2$, -halogen, -straight or branched $C_{1-6}$ alkyl, -straight or branched $C_{1-6}$ haloalkyl, $C_{1-6}$-cycloalkyl, -straight or branched $C_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$ R$^k$, —NR$^l$C(O)R$^m$, aryl or heteroaryl;
  where:
    each $R^e$, $R^f$, $R^g$, $R^h$, $R^i$, $R^j$, $R^k$, $R^l$, or $R^m$ as defined above is selected from H, $C_{1-6}$ alkyl, $C_{1-6}$ haloalkyl, $C_{1-6}$ alkoxy;
    each aryl or heteroaryl as defined above is optionally substituted with one or more of the following substituents selected from H, —OH, —CN, —NO$_2$, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH$_2$)$_y$OR$^p$, —NR$^q$R$^r$, —SO$_2$R$^s$, —S(CH$_2$)$_y$—R$^t$, —NR$^u$C(O)R$^v$;
    where:
      $R^n$, $R^o$, $R^p$, $R^q$, $R^r$, $R^s$, $R^t$, $R^u$, or $R^v$ each as defined above are selected from $C_{1-6}$ alkyl, $C_{1-6}$-haloalkyl, or $C_{1-6}$-alkoxy;
n, m, o, p, q or y each are 0 or an integer from 1 to 5; or
a pharmaceutically acceptable salt thereof.

In another aspect, the present invention relates to a compound of Formula (III), where X is C—$R^a$, where $R^a$ is hydrogen or halogen.

In another aspect, the present invention relates to a compound of Formula (III), where X is C—$R^a$ and $R^a$ is hydrogen.

In another aspect, the present invention relates to a compound of Formulas (I) to (IX) as defined herein, where A, may include, but is not limited to:

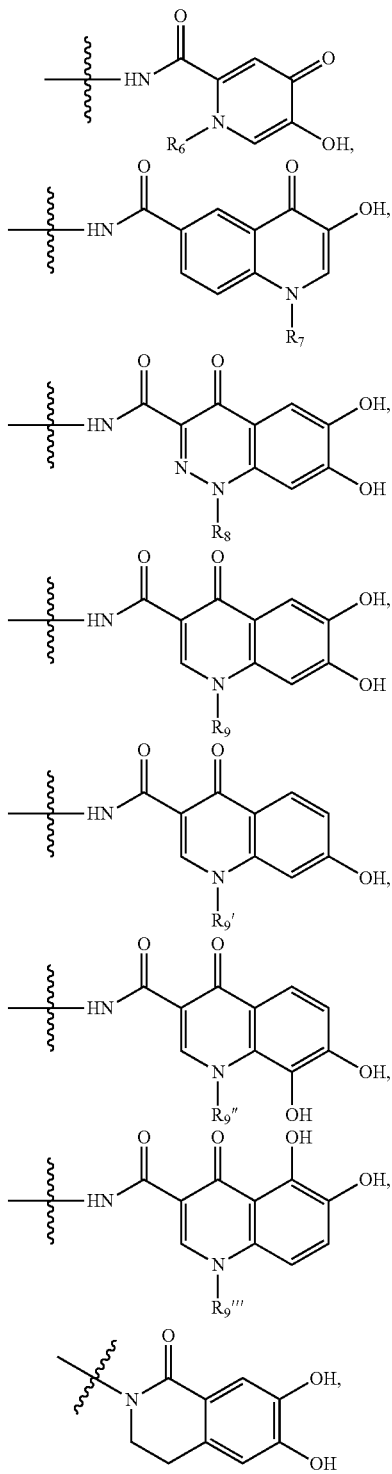

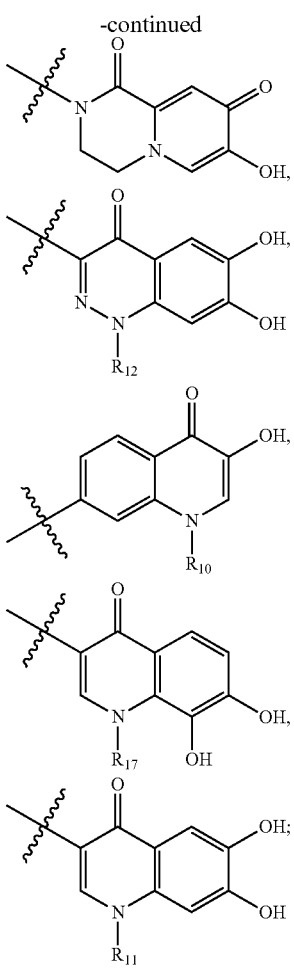

where:
$R_6$, $R_7$, $R_8$, $R_9$, $R_9'$, $R_9''$, $R_9'''$, $R_{10}$, $R_{11}$, $R_{12}$ or $R_{17}$ is H, straight or branched($C_{1-6}$)-alkyl or $C_{3-6}$-cycloalkyl;

each A optionally further is substituted by one or more of the following substituents selected from —H, —OH, Oxo (=O), —CN, —$NO_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)$R^e$, —C(O)O$R^f$, —O($CH_2$)$_y$O$R^g$, —N$R^h$$R^i$, —$SO_2$$R^j$, —S($CH_2$)$_q$$R^k$, —N$R^l$C(O)$R^m$, aryl or heteroaryl;
where:
each $R^e$, $R^f$, $R^g$, $R^h$, $R^i$, $R^j$, $R^k$, $R^l$, or $R^m$ as defined above is selected from H, $C_{1-6}$ alkyl, $C_{1-6}$ haloalkyl, $C_{1-6}$ alkoxy;
each aryl or heteroaryl as defined above is optionally substituted with one or more of the following substituents selected from H, —OH, —CN, —$NO_2$, -halogen, $C_{1-6}$-alkyl, $C_{1-6}$-haloalkyl, $C_{1-6}$-alkoxy, —OC(O)OH, —OC(O)$R^n$, —C(O)O$R^o$, —O($CH_2$)$_y$—O$R^p$, —N$R^q$$R^r$, —$SO_2$$R^s$, —S($CH_2$)$_y$—$R^t$, —N$R^u$C(O)$R^v$;
where:
$R^n$, $R^o$, $R^p$, $R^q$, $R^r$, $R^s$, $R^t$, $R^u$, or $R^v$ each as defined above are selected from $C_{1-6}$ alkyl, $C_{1-6}$-haloalkyl, or $C_{1-6}$-alkoxy; and
n, m, o, p, q or y each are 0 or an integer from 1 to 5.

In another aspect, the present invention relates to a compound of Formulas (I) to (IX), respectively, as defined herein, where A, may include, but is not limited to:

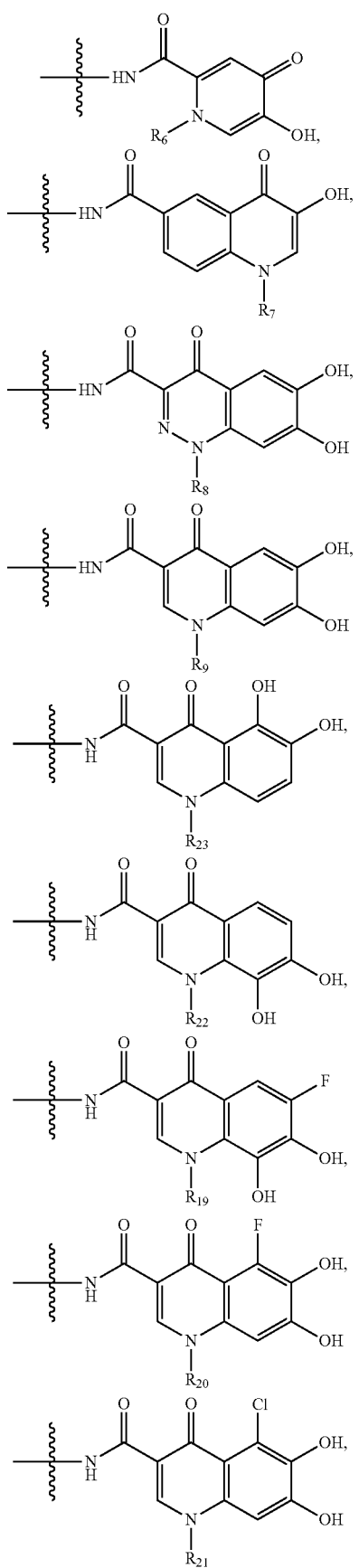
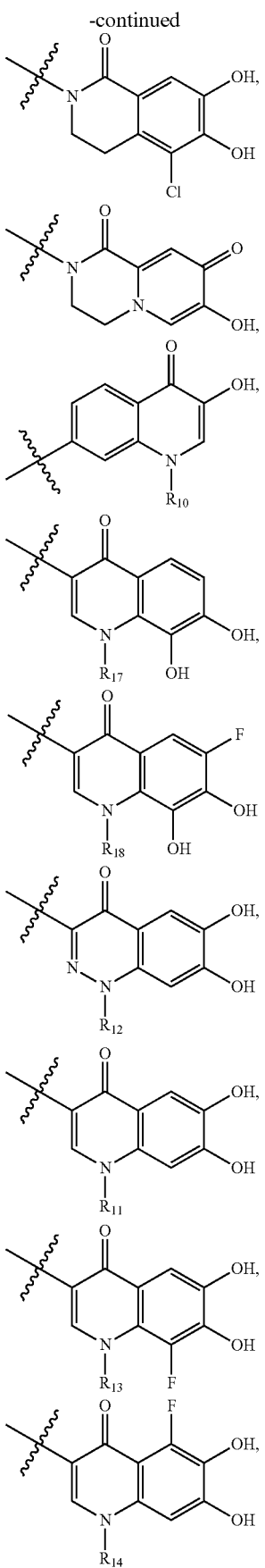

-continued

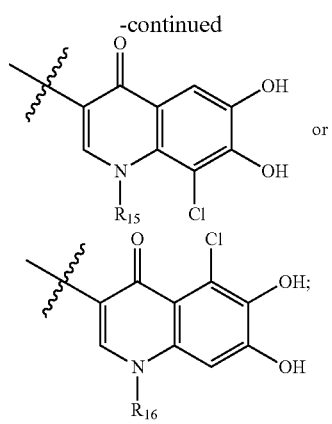
or

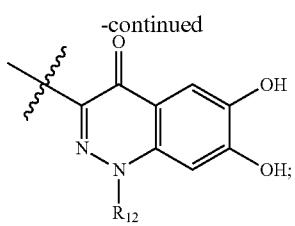

where:
R₆, R₇, R₈, R₉, R₁₀, R₁₁ or R₁₂, R₁₃, R₁₄, R₁₅, R₁₆, R₁₇, R₁₈, R₁₉, R₂₀, R₂₁, R₂₂, or R₂₃ is H, straight or branched($C_{1-6}$)-alkyl or $C_{3-6}$-cycloalkyl.

each A optionally further is substituted by one or more of the following substituents selected from —H, —OH, Oxo (=O), —CN, —NO₂, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH₂)$_y$OR$^g$, —NR$^h$R$^i$, —SO₂R$^j$, —S(CH₂)$_q$R$^k$, —NR$^l$C(O)R$^m$, aryl or heteroaryl;
  where:
    each R$^e$, R$^f$, R$^g$, R$^h$, R$^i$, R$^j$, R$^k$, R$^l$, or R$^m$ as defined above is selected from H, $C_{1-6}$ alkyl, $C_{1-6}$ haloalkyl, $C_{1-6}$ alkoxy;
    each aryl or heteroaryl as defined above is optionally substituted with one or more of the following substituents selected from H, —OH, —CN, —NO₂, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH₂)$_y$—OR$^p$, —NR$^q$R$^r$, —SO₂R$^s$, —S(CH₂)$_y$—R$^t$, —NR$^u$C(O)R$^v$;
      where:
        R$^n$, R$^o$, R$^p$, R$^q$, R$^r$, R$^s$, R$^t$, R$^u$, or R$^v$ each as defined above are selected from $C_{1-6}$ alkyl, $C_{1-6}$-haloalkyl, or $C_{1-6}$-alkoxy; and
n, m, o, p, q or y each are 0 or an integer from 1 to 5.

In another aspect, the present invention relates to a compound of Formula (III),
where:
Ra is hydrogen;
R¹ and R² each are ($C_{1-6}$)alkyl;
R³ and R⁴ each are OH or OR$^c$;
  where:
    R$^c$ is H, ($C_{1-6}$)-alkyl or an alkali metal;
A is

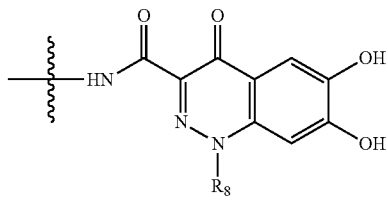
or

R⁸ or R¹² is H, -straight or branched($C_{1-6}$)-alkyl or —$C_{3-6}$-cycloalkyl;
n is 1; or
a pharmaceutically acceptable salt thereof.

In another aspect, the present invention relates to a compound of Formula (IV):

(IV)

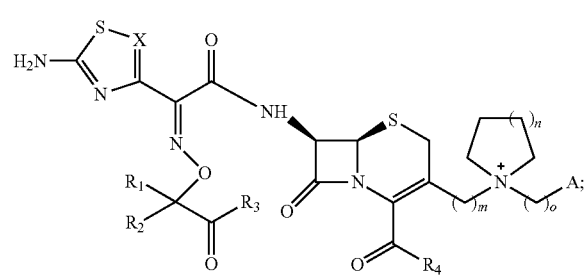

where:
X is C—R$^a$;
R¹ and R² each are hydrogen, ($C_{1-6}$)alkyl, or (CH₂)p—C(O)OR$^b$;
R³ and R⁴ each are hydrogen, OH or OR$^c$;
  where:
    R$^a$ is hydrogen or halogen;
    R$^b$ or R$^c$ each is H, ($C_{1-6}$)-alkyl, an alkali metal or negative charge;
A is R⁵ or —NR$^d$C(O)R⁵
  where R$^d$ is H or ($C_{1-6}$)-alkyl
R⁵ is an optionally saturated or unsaturated monocyclic heterocyclic ring or an optionally saturated or unsaturated bi-cyclic or fused heterocyclic ring;
  where:
    each monocyclic heterocyclic ring has from 3 to 7 ring atoms and contains up to four heteroatoms;
    each fused heterocyclic ring optionally includes carbocyclic rings or heterocyclic rings of up to four heteroatoms;
    R⁵ optionally is substituted by one or more of the following substituents selected from —H, —OH, Oxo (=O), —CN, —NO₂, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH₂)$_y$OR$^g$, —NR$^h$R$^i$, —SO₂R$^j$, —S(CH₂)$_q$R$^k$, —NR$^l$C(O)R$^m$, aryl or heteroaryl;
    where:
      hetero atoms are selected from oxygen, nitrogen or sulphur;
      carbocyclic rings or heterocyclic rings for each fused heterocyclic ring systems include non-aromatic rings or aromatic rings;
      monocyclic heterocyclic rings or fused heterocyclic rings include substituted aromatic and non-aromatics;

each $R^e$, $R^f$, $R^g$, $R^h$, $R^i$, $R^j$, $R^k$, $R^l$, or $R^m$ each is selected from H, $C_{1-6}$alkyl, $C_{1-6}$ haloalkyl, $C_{1-6}$ alkoxy;

each aryl or heteroaryl as defined above is optionally substituted with one or more of the following substituents selected from H, —OH, —CN, —NO$_2$, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;

where:
$R^n$, $R^o$, $R^p$, $R^q$, $R^r$, $R^s$, $R^t$, $R^u$, or $R^v$ each are selected from $C_{1-6}$ alkyl, $C_{1-6}$-haloalkyl, or $C_{1-6}$-alkoxy;

n, m, o, p, q or y each are 0 or an integer from 1 to 5; or a pharmaceutically acceptable salt thereof.

In another aspect, the present invention relates to a compound of Formula (IV), where X is C—R$^a$ and R$^a$ is hydrogen.

In another aspect, the present invention relates to a compound of Formula (V):

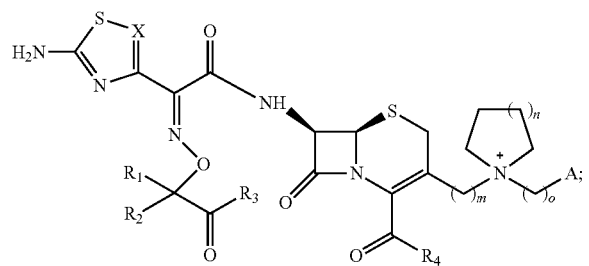

(V)

where:
X is C—R$^a$;
$R^1$ and $R^2$ each are hydrogen, (C$_{1-6}$)alkyl, or (CH$_2$)p-C(O)OR$^b$;
$R^3$ and $R^4$ each are hydrogen, OH or OR$^c$;
  where:
    $R^a$ is hydrogen or halogen;
    $R^b$ or $R^c$ each is H, (C$_{1-6}$)-alkyl, an alkali metal or negative charge;
A is R$^5$ or —NR$^d$C(O)R$^5$
  where R$^d$ is H or (C$_{1-6}$)-alkyl
$R^5$ is a monocyclic 3 to 7 membered heterocyclic ring or a bicyclic 10 membered heterocyclic ring;
  where:
    each 3 to 7 membered heterocyclic ring contains up to four heteroatoms;
    each bicyclic 10 membered heterocyclic ring contains up to four heteroatoms;
    where:
    heteroatoms are selected from oxygen, nitrogen or sulphur;
    each 10 membered heterocyclic ring optionally contains carbocyclic rings or heterocyclic rings;
      where:
        carbocyclic rings or heterocyclic rings for each 10 membered heterocyclic ring systems contain non-aromatic rings or aromatic rings;
    $R^5$ optionally is substituted by one or more of the following substituents selected from —H, —OH, Oxo (=O), —CN, —NO$_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;

where:
each $R^e$, $R^f$, $R^g$, $R^h$, $R^i$, $R^j$, $R^k$, $R^l$, or $R^m$ as defined above is selected from H, $C_{1-6}$ alkyl, $C_{1-6}$ haloalkyl, $C_{1-6}$ alkoxy;

each aryl or heteroaryl as defined above is optionally substituted with one or more of the following substituents selected from H, —OH, —CN, —NO$_2$, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH$_2$)$_y$OR$^p$, —NR$^q$R$^r$, —SO$_2$R$^s$, —S(CH$_2$)$_y$—R$^t$, —NR$^u$C(O)R$^v$;

where:
$R^n$, $R^o$, $R^p$, $R^q$, $R^r$, $R^s$, $R^t$, $R^u$, or $R^v$ each as defined above are selected from $C_{1-6}$ alkyl, $C_{1-6}$-haloalkyl, or $C_{1-6}$-alkoxy;

n, m, o, p, q or y each are 0 or an integer from 1 to 5; or a pharmaceutically acceptable salt thereof.

In another aspect, the present invention relates to a compound of Formula (V), where X is C—R$^a$ and R$^a$ is hydrogen.

In another aspect, the present invention relates to a compound of Formula (VI):

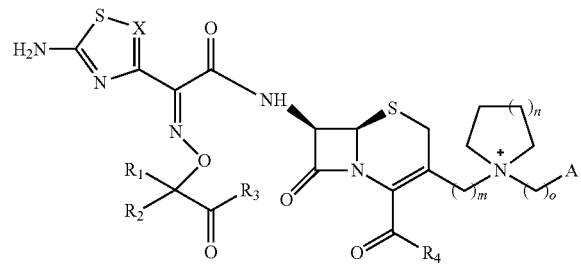

(VI)

where:
X is C—R$^a$;
$R^1$ and $R^2$ each are hydrogen, (C$_{1-6}$)alkyl, or (CH$_2$)p-C(O)OR$^b$;
$R^3$ and $R^4$ each are hydrogen, OH or OR$^c$;
  where:
    $R^a$ is hydrogen or halogen;
    $R^b$ or $R^c$ each is H, (C$_{1-6}$)-alkyl, an alkali metal or negative charge;
A is

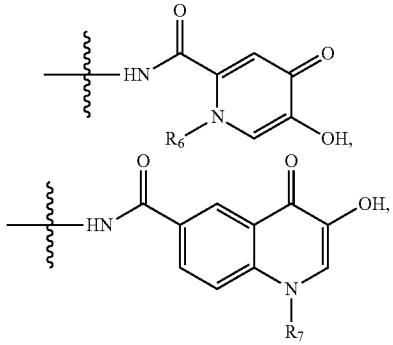

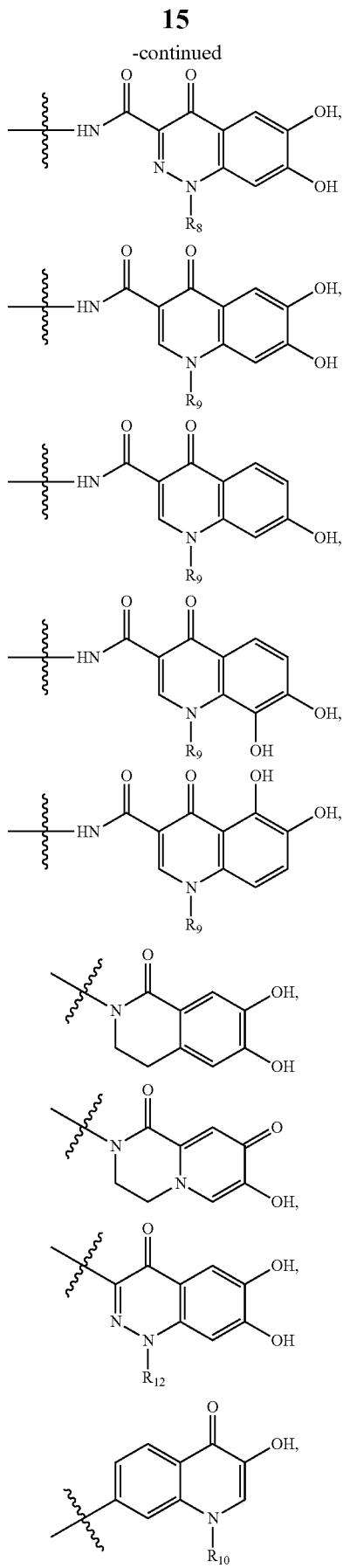

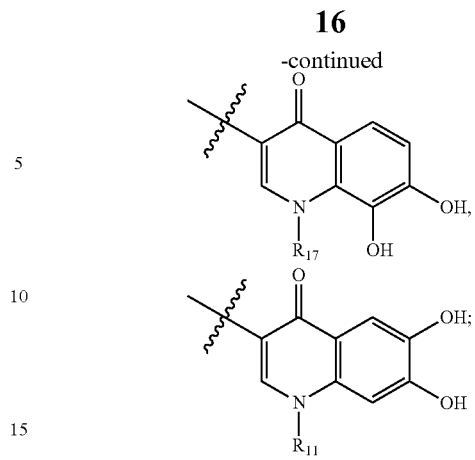

where:
R₆, R₇, R₈, R₉, R₁₀, R₁₁, R₁₂ or R₁₇ is H, straight or branched($C_{1-6}$)-alkyl or $C_{3-6}$-cycloalkyl;

each A optionally further is substituted by one or more of the following substituents selected from —H, —OH, Oxo (=O), —CN, —NO₂, -halogen, -straight or branched $C_{1-6}$ alkyl, -straight or branched $C_{1-6}$haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH₂)$_y$OR$^g$, —NR$^h$R$^i$, —SO₂R$^j$, —S(CH₂)$_q$R$^k$, —NR$^l$C(O)R$^m$, aryl or heteroaryl;

where:
each R$^e$, R$^f$, R$^g$, R$^h$, R$^i$, R$^j$, R$^k$, R$^l$, or R$^m$ as defined above is selected from H, $C_{1-6}$ alkyl, $C_{1-6}$ haloalkyl, $C_{1-6}$ alkoxy;

each aryl or heteroaryl as defined above is optionally substituted with one or more of the following substituents selected from H, —OH, —CN, —NO₂, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH₂)$_y$—OR$^p$, —NR$^q$R$^r$, —SO₂R$^s$, —S(CH₂)$_y$—R$^t$, —NR$^u$C(O)R$^v$;

where:
R$^n$, R$^o$, R$^p$, R$^q$, R$^r$, R$^s$, R$^t$, R$^u$, or R$^v$ each as defined above are selected from $C_{1-6}$ alkyl, $C_{1-6}$-haloalkyl, or $C_{1-6}$-alkoxy; and n, m, o, p, q or y each are 0 or an integer from 1 to 5; or a pharmaceutically acceptable salt thereof.

In another aspect, the present invention relates to a compound of Formula (VII):

(VII)

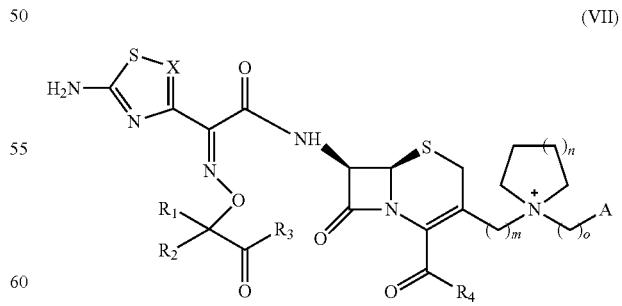

where:
X is C—R$^a$;
R¹ and R² each are hydrogen, ($C_{1-6}$)alkyl, or (CH₂)$_p$—C(O)OR$^b$;
R³ and R⁴ each are hydrogen, OH or OR$^c$;

where:
R$^a$ is hydrogen or halogen;
R$^b$ or R$^c$ each is H, (C$_{1-6}$)-alkyl, an alkali metal or negative charge;
A is
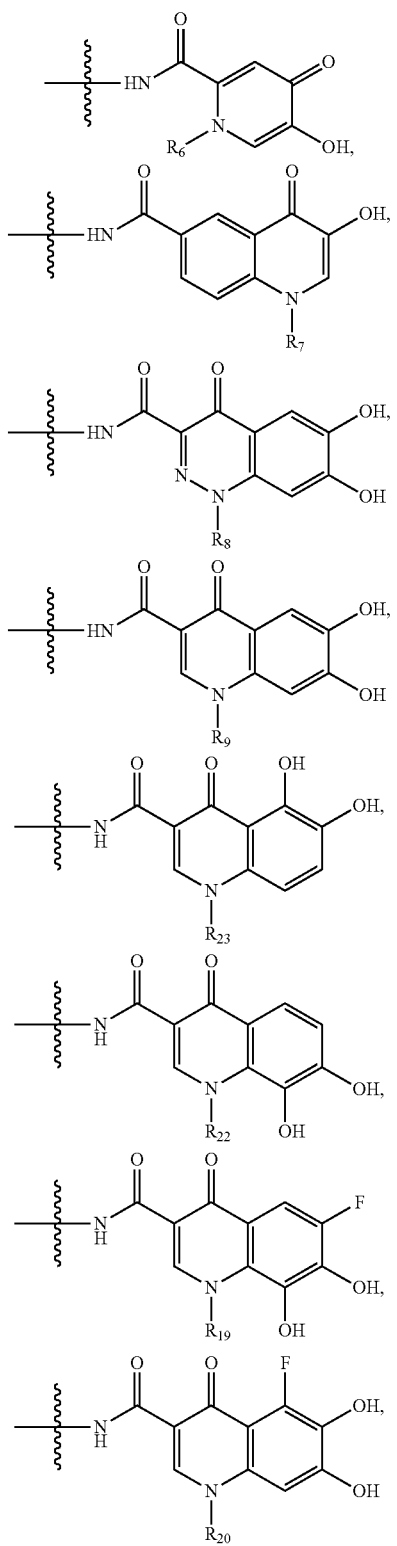
-continued
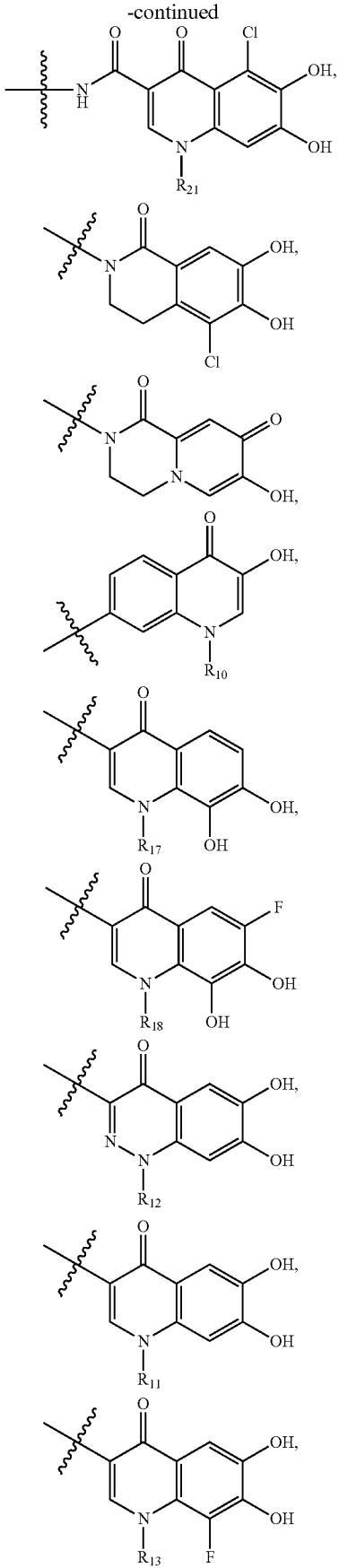

19
-continued

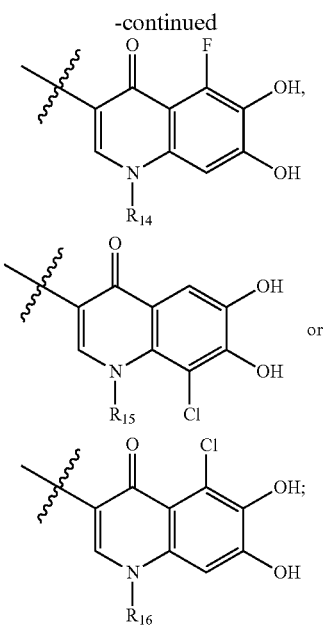

where:

R$_6$, R$_7$, R$_8$, R$_9$, R$_{10}$, R$_{11}$ or R$_{12}$, R$_{13}$, R$_{14}$, R$_{15}$, R$_{16}$, R$_{17}$, R$_{18}$, R$_{19}$, R$_{20}$, R$_{21}$, R$_{22}$, or R$_{23}$ is H, straight or branched(C$_{1-6}$)-alkyl or C$_{3-6}$-cycloalkyl.

each A optionally further is substituted by one or more of the following substituents selected from —H, —OH, Oxo (=O), —CN, —NO$_2$, -halogen, -straight or branched C$_{1-6}$ alkyl, -straight or branched C$_{1-6}$ haloalkyl, C$_{3-6}$-cycloalkyl, -straight or branched C$_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;

where:
each R$^e$, R$^f$, R$^g$, R$^h$, R$^i$, R$^j$, R$^k$, R$^l$, or R$^m$ as defined above is selected from H, C$_{1-6}$ alkyl, C$_{1-6}$ haloalkyl, C$_{1-6}$ alkoxy;

each aryl or heteroaryl as defined above is optionally substituted with one or more of the following substituents selected from H, —OH, —CN, —NO$_2$, -halogen, C$_{1-6}$-alkyl, C$_{1-6}$-haloalkyl, C$_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;

where:
R$^n$, R$^o$, R$^p$, R$^q$, R$^r$, R$^s$, R$^t$, R$^u$, or R$^v$ each as defined above are selected from C$_{1-6}$ alkyl, C$_{1-6}$-haloalkyl, or C$_{1-6}$-alkoxy; and n, m, o, p, q or y each are 0 or an integer from 1 to 5.

In another aspect, the present invention relates to a compound of Formula (VII)
where:
Ra is hydrogen;
R$^1$ and R$^2$ each are (C$_{1-6}$)alkyl;
R$^3$ and R$^4$ each are OH or OR$^c$;

20 where:
R$^c$ is H, (C$_{1-6}$)-alkyl, an alkali metal or negative charge;
A is

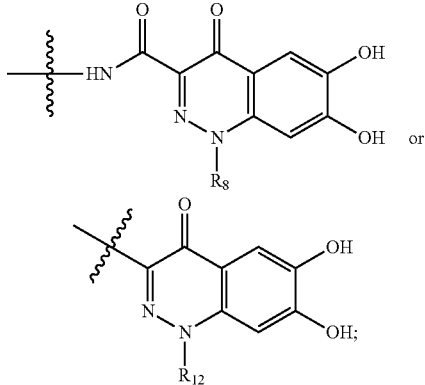

R$^8$ or R$^{12}$ is H, (C$_{1-6}$)-alkyl, or C$_{3-6}$-cycloalkyl;
n is 1; or
a pharmaceutically acceptable salt thereof.

In another aspect, the present invention relates to a compound of Formula (VIII):

(VIII)

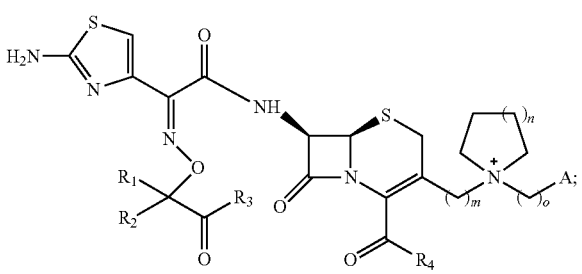

where:
R$^1$ and R$^2$ each are hydrogen, (C$_{1-6}$)alkyl, or (CH$_2$)p-C(O)OR$^b$;
R$^3$ and R$^4$ each are hydrogen, OH or OR$^c$;
where:
R$^b$ or R$^c$ each is H, (C$_{1-6}$)-alkyl, an alkali metal or negative charge;
A is R$^5$ or —NR$^d$C(O)R$^5$
where R$^d$ is H or (C$_{1-6}$)-alkyl
R$^5$ is an optionally saturated or unsaturated monocyclic heterocyclic ring or an optionally saturated or unsaturated bicyclic or fused heterocyclic ring;
where:
each monocyclic heterocyclic ring has from 3 to 7 ring atoms and contains up to four heteroatoms;
each fused heterocyclic ring optionally includes carbocyclic rings or heterocyclic rings of up to four heteroatoms;
R5 optionally is substituted by one or more of the following substituents selected from —H, —OH, Oxo (=O), —CN, —NO$_2$, -halogen, -straight or branched C$_{1-6}$ alkyl, -straight or branched C$_{1-6}$ haloalkyl, C$_{3-6}$-cycloalkyl, -straight or branched C$_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$ R$^k$, —NR$^l$C(O)R$^m$, aryl or heteroaryl;

where:
hetero atoms are selected from oxygen, nitrogen or sulphur;
carbocyclic rings or heterocyclic rings for each fused heterocyclic ring systems include non-aromatic rings or aromatic rings;
monocyclic heterocyclic rings or fused heterocyclic rings include substituted aromatic and non-aromatics;
each $R^e$, $R^f$, $R^g$, $R^h$, $R^i$, $R^j$, $R^k$, $R^l$, or $R^m$ each is selected from H, $C_{1-6}$ alkyl, $C_{1-6}$ haloalkyl, $C_{1-6}$ alkoxy;
each aryl or heteroaryl as defined above optionally is optionally substituted with one or more of the following substituents selected from H, —OH, —CN, —NO$_2$, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;
where:
$R^n$, $R^o$, $R^p$, $R^q$, $R^r$, $R^s$, $R^t$, $R^u$, or $R^v$ each are selected from $C_{1-6}$ alkyl, $C_{1-6}$-haloalkyl, or $C_{1-6}$-alkoxy;
n, m, o, p, q or y each are 0 or an integer from 1 to 5; or
a pharmaceutically acceptable salt thereof.

In another aspect, the present invention relates to a compound of Formula (VIII), where X is C—R$^a$ and R$^a$ is hydrogen.

In another aspect, the present invention relates to a compound of Formula (VIII), where A is:

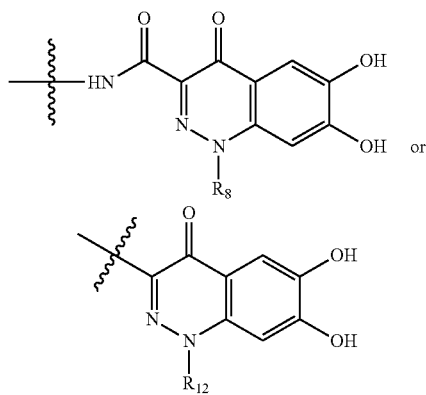

where $R^8$ or $R^{12}$ is H, (C$_{1-6}$)-alkyl or C$_{3-6}$-cycloalkyl.

In another aspect, the present invention relates to a compound of Formula (IX):

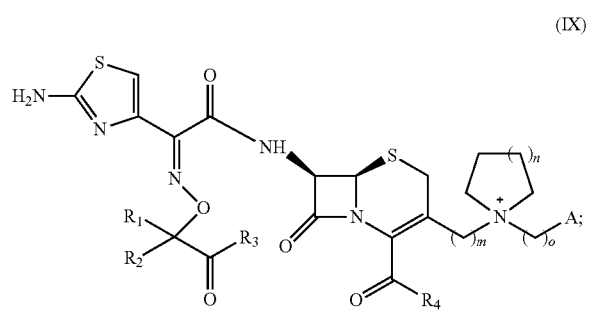

where:
$R^1$ and $R^2$ each are hydrogen, (C$_{1-6}$)alkyl, or (CH$_2$)p-C(O)OR$^b$;
$R^3$ and $R^4$ each are hydrogen, OH or OR$^c$;
where:
R$^b$ or R$^c$ each is H, (C$_{1-6}$)-alkyl, an alkali metal or negative charge;
A is R$^5$ or —NR$^d$C(O)R$^5$
where R$^d$ is H or (C$_{1-6}$)-alkyl
R$^5$ is a monocyclic 3 to 7 membered heterocyclic ring or a bicyclic 10 membered heterocyclic ring;
where:
each 3 to 7 membered heterocyclic ring contains up to four heteroatoms;
each bicyclic 10 membered heterocyclic ring contains up to four heteroatoms;
where:
heteroatoms are selected from oxygen, nitrogen or sulphur;
each 10 membered heterocyclic ring optionally contains carbocyclic rings or heterocyclic rings;
where:
carbocyclic rings or heterocyclic rings for each 10 membered heterocyclic ring systems contain non-aromatic rings or aromatic rings;
R$^5$ optionally is substituted by one or more of the following substituents selected from —H, —OH, Oxo (═O), —CN, —NO$_2$, -halogen, -straight or branched C$_{1-6}$ alkyl, -straight or branched C$_{1-6}$ haloalkyl, C$_{3-6}$-cycloalkyl, -straight or branched C$_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$ R$^k$, —NR$^l$C(O)R$^m$, aryl or heteroaryl;
where:
each $R^e$, $R^f$, $R^g$, $R^h$, $R^i$, $R^j$, $R^k$, $R^l$, or $R^m$ as defined above is selected from H, C$_{1-6}$ alkyl, C$_{1-6}$ haloalkyl, C$_{1-6}$ alkoxy;
each aryl or heteroaryl as defined above is optionally substituted with one or more of the following substituents selected from H, —OH, —CN, —NO$_2$, -halogen, C$_{1-6}$-alkyl, C$_{1-6}$-haloalkyl, C$_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;
where:
R$^n$, R$^o$, R$^p$, R$^q$, R$^r$, R$^s$, R$^t$, R$^u$, or R$^v$ each as defined above are selected from C$_{1-6}$ alkyl, C$_{1-6}$-haloalkyl, or C$_{1-6}$-alkoxy;
n, m, o, p, q or y each are 0 or an integer from 1 to 5; or
a pharmaceutically acceptable salt thereof.

In another aspect, the present invention relates to a compound of Formula (IX), where X is C—R$^a$ and R$^a$ is hydrogen.

In another aspect, the present invention relates to a compound of Formula (IX), where A is:

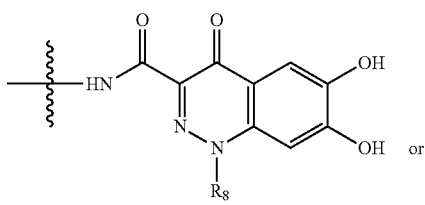

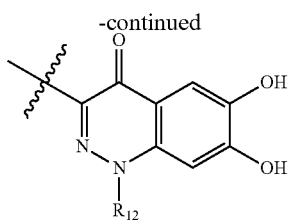

where $R^8$ or $R^{12}$ is H, $(C_{1-6})$-alkyl or $C_{3-6}$-cycloalkyl.

In another aspect, the present invention relates to a compound or compound species which is:

1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium;

(6R,7R)-7-((Z)-2-(2-aminothiazol-4-yl)-2-(((S)-1,2-dicarboxyethoxy)imino)acetamido)-3-((1-(2-(5-hydroxy-1-methyl-4-oxo-1,4-dihydropyridine-2-carboxamido) ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((3-hydroxy-1-methyl-4-oxo-1,4-dihydroquinolin-6-yl)methyl)pyrrolidin-1-ium-1-yl)methyl)-8-oxo-5-thia-1-azabicyclo[4.2.0]oct-2-ene-2-carboxylate;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium;

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium;

1-(((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo- 5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydroquinoline-3-carboxamido)ethyl)pyrrolidin-1-ium;

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)piperidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-8-carboxamido)ethyl)pyrrolidin-1-ium;

(6R,7R)-7-((Z)-2-(2-aminothiazol-4-yl)-2-(((2-carboxypropan-2-yl)oxy)imino)acetamido)-3-((1-((1-ethyl-8-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxylatopropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo [4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo [4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino) acetamido)-3-((1-(2-(5-chloro-1-ethyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo [4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0] oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-ethyl-6,7-dihydroxy-4-oxo-1,4-dihydrocinnoline-3-carboxamido)ethyl) pyrrolidin-1-ium-1-yl)methyl)-8-oxo-5-thia-1-azabicyclo [4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate;

1-(((6R,7R)-7-((Z)-2-(2-amino-5-chlorothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydrocinnoline-3-carboxamido)ethan-1-ylium-1-yl) pyrrolidin-1-ium;

(6R,7R)-7-((Z)-2-(2-amino-5-chlorothiazol-4-yl)-2-(((S)-1,2-dicarboxyethoxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo [4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy) imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-fluouro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo [4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-ethyl-5-fluoro-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo [4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-6-fluoro-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-ethyl-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido) ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido) ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl) pyrrolidin-1-ium-1-yl)methyl)-8-oxo-5-thia-1-azabicyclo [4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-(tert-butyl)-6,7-dihydroxy-4-oxo-1,4-dihydroquinolin-3-yl)methyl)pyrrolidin-1-ium-1-yl)methyl)-8-oxo-5-thia-1-azabicyclo[4.2.0] oct-2-ene-2-carboxylate.

(6R,7R)-7-((Z)-2-(2-aminothiazol-4-yl)-2-(((S)-1,2-dicarboxyethoxy)imino)acetamido)-3-((1-(2-(1-(tert-butyl)-6,7-dihydroxy-4-oxo-1,4-dihydroquinoline-3-carboxamido) ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0] oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(5-chloro-1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((6,7-dihydroxy-1-isopropyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydroquinoline-3-carboxamido)ethyl)pyrrolidin-1-ium;

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(1-ethyl-8-fluoro-6,7-dihydroxy-4-oxo-1,4-dihydroquinoline-3-carboxamido)ethyl)pyrrolidin-1-ium;

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-((1-ethyl-8-fluoro-6,7-dihydroxy-4-oxo-1,4-dihydroquinolin-3-yl)methyl)pyrrolidin-1-ium;

(6R,7R)-7-((Z)-2-(2-aminothiazol-4-yl)-2-(((S)-1,2-dicarboxyethoxy)imino)acetamido)-3-((1-((5-chloro-6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate; or
a pharmaceutically acceptable salt thereof.

In another aspect, the present invention relates to a compound or compound species or a pharmaceutically acceptable salt, where the pharmaceutically acceptable salt is a sodium salt, a di-sodium salt or a trifluoroacetic acid salt.

In another aspect, the present invention relates to a compound or compound species which is:

1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium, 2 sodium salt;

(6R,7R)-7-((Z)-2-(2-aminothiazol-4-yl)-2-(((S)-1,2-dicarboxyethoxy)imino)acetamido)-3-((1-(2-(5-hydroxy-1-methyl-4-oxo-1,4-dihydropyridine-2-carboxamido)ethyl)pyrrolidin-1-ium-1-yl)methyl)-8-oxo-5-thia-1-azabicyclo[4.2.0]oct-2-ene-2-carboxylate, 3 Sodium salt;

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate 3 Sodium salt;

(6R,7R)-7-((Z)-2-(2-aminothiazol-4-yl)-2-(((S)-1,2-dicarboxyethoxy)imino)acetamido)-3-((1-((3-hydroxy-1-methyl-4-oxo-1,4-dihydroquinolin-6-yl)methyl)pyrrolidin-1-ium-1-yl)methyl)-8-oxo-5-thia-1-azabicyclo[4.2.0]oct-2-ene-2-carboxylate, 3 Sodium salt;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium, sodium salt;

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium, disodium salt;

1-(((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium disodium salt;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydroquinoline-3-carboxamido)ethyl)pyrrolidin-1-ium;

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)piperidin-1-ium, disodium salt;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-8-carboxamido)ethyl)pyrrolidin-1-ium;

(6R,7R)-7-((Z)-2-(2-aminothiazol-4-yl)-2-(((2-carboxypropan-2-yl)oxy)imino)acetamido)-3-((1-((1-ethyl-8-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-aza bicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt;

(6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxylatopropan-2-yl)oxy)imino) acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((S)-1,2-dicarboxyethoxy)imino) acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-aza bicyclo[4.2.0]oct-2-ene-2-carboxylate, Sodium salt;

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-(2-(5-chloro-1-ethyl-6,7-dihydroxy-4-oxo-1,4-dihydroquinoline-8-carboxamido)ethyl)pyrrolidin-1-ium-1-yl)methyl)-8-oxo-5-thia-1-azabicyclo[4.2.0]oct-2-ene-2-carboxylate, sodium salt;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((S)-1,2-dicarboxyethoxy)imino) acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-(2-(1-ethyl-6,7-dihydroxy-4-oxo-1,4-dihydrocinnoline-3-carboxamido)ethyl)pyrrolidin-1-ium-1-yl)methyl)-8-oxo-5-thia-1-azabicyclo[4.2.0]oct-2-ene-2-carboxylate, sodium salt;

(6R,7R)-7-((Z)-2-(2-aminothiazol-4-yl)-2-(((2-carboxypropan-2-yl)oxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate. Sodium salt;

1-(((6R,7R)-7-((Z)-2-(2-amino-5-chlorothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydrocinnoline-3-carboxamido)ethan-1-ylium-1-yl)pyrrolidin-1-ium, Sodium salt;

(6R,7R)-7-((Z)-2-(2-amino-5-chlorothiazol-4-yl)-2-(((S)-1,2-dicarboxyethoxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-aza bicyclo[4.2.0]oct-2-ene-2-carboxylate, Sodium salt;

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((S)-1,2-dicarboxyethoxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((2-carboxypropan-2-yl)oxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino) acetamido)-3-((1-((5-fluoro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-(2-(1-ethyl-5-fluoro-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, sodium salt;

(6R,7R)-7-((Z)-2-(2-amino-5-chlorothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((2-carboxypropan-2-yl)oxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino) acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, sodium salt;

(6R,7R)-7-((Z)-2-(2-aminothiazol-4-yl)-2-(((2-carboxypropan-2-yl)oxy)imino)acetamido)-3-((1-(2-(1-ethyl-6-fluoro-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-ethyl-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, sodium salt;

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, 2 Sodium salt;

(6R,7R)-7-((Z)-2-(2-aminothiazol-4-yl)-2-(((S)-1,2-dicarboxyethoxy)imino)acetamido)-3-((1-((1-(tert-butyl)-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-(2-(1-(tert-butyl)-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate. Sodium salt;

(6R,7R)-7-((Z)-2-(2-aminothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-amino-5-chlorothiazol-4-yl)-2-(((2-carboxypropan-2-yl)oxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-(2-(1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, 2 Sodium salt;

(6R,7R)-7-((Z)-2-(2-aminothiazol-4-yl)-2-(((S)-1,2-dicarboxyethoxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt;

(6R,7R)-7-((Z)-2-(2-aminothiazol-4-yl)-2-(((2-carboxypropan-2-yl)oxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((2-carboxypropan-2-yl)oxy)imino) acetamido)-3-((1-(2-(5-chloro-1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt;

(6R,7R)-7-((Z)-2-(2-aminothiazol-4-yl)-2-(((S)-1,2-dicarboxyethoxy)imino)acetamido)-3-((1-((6,7-dihydroxy-1-methyl-4-oxo-1,4-dihydroquinolin-3-yl)methyl) pyrrolidin-1-ium-1-yl)methyl)-8-oxo-5-thia-1-azabicyclo[4.2.0]oct-2-ene-2-carboxylate, 2 Sodium salt;

(6R,7R)-7-((Z)-2-(2-aminothiazol-4-yl)-2-(((S)-1,2-dicarboxyethoxy)imino)acetamido)-3-((1-((6,7-dihydroxy-1-isopropyl-4-oxo-1,4-dihydroquinolin-3-yl)methyl) pyrrolidin-1-ium-1-yl)methyl)-8-oxo-5-thia-1-azabicyclo[4.2.0] oct-2-ene-2-carboxylate, 2 Sodium salt;

1-((((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydroquinoline-3-carboxamido)ethyl)pyrrolidin-1-ium, Trifluoroacetic acid salt;

1-((((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(1-ethyl-8-fluoro-6,7-dihydroxy-4-oxo-1,4-dihydroquinoline-3-carboxamido)ethyl)pyrrolidin-1-ium, Trifluoroacetic acid salt;

1-((((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-((1-ethyl-8-fluoro-6,7-dihydroxy-4-oxo-1,4-dihydroquinolin-3-yl)methyl)pyrrolidin-1-ium, Trifluoroacetic acid salt; or (6R,7R)-7-((Z)-2-(2-aminothiazol-4-yl)-2-(((S)-1,2-dicarboxyethoxy)imino)acetamido)-3-((1-((5-chloro-6,7-dihydroxy-1-methyl-4-oxo-1,4-dihydroquinolin-3-yl)methyl) pyrrolidin-1-ium-1-yl)methyl)-8-oxo-5-thia-1-azabicyclo[4.2.0]oct-2-ene-2-carboxylate, 2 Sodium salt;

In another aspect the present invention relates to a compound which is 1-((((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium disodium salt:

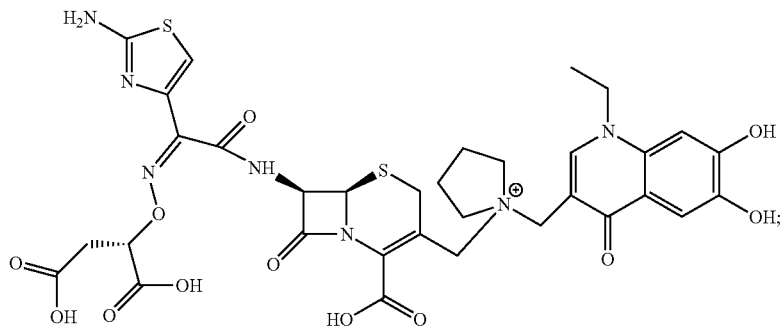 [SMILES: CCn1cc(C[N+]2(CC3=C(C(=O)O)N4C(=O)[C@@H](NC(=O)/C(=N\O[C@@H](CC(=O)O)C(=O)O)c5csc(N)n5)[C@H]4SC3)CCCC2)c(=O)c2cc(O)c(O)cc21]

or
a pharmaceutically acceptable salt thereof.

In another aspect, the present invention relates to a compound which is 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium:

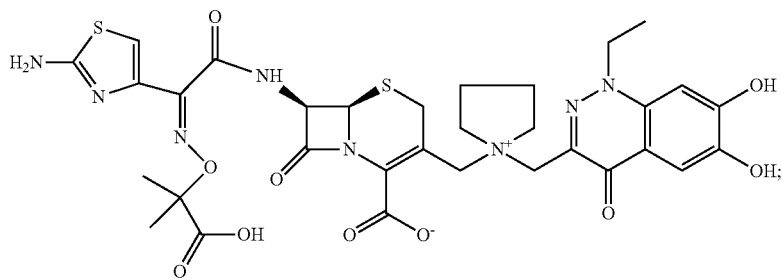 [SMILES: CCn1nc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)cc21]

or
a pharmaceutically acceptable salt thereof.

In another aspect, the present invention relates to a compound which is 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium:

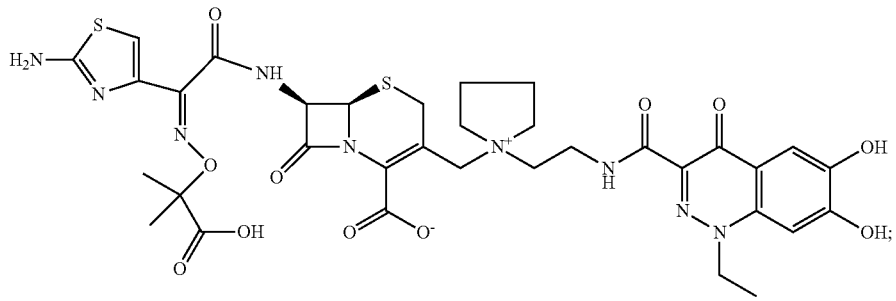 [SMILES: CCn1nc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)cc21]

or
a pharmaceutically acceptable salt thereof.

It is recognized that the compounds of Formulas (I) to (IX), respectively, or pharmaceutically acceptable salts thereof of the present invention as defined above may exist in forms as stereoisomers, regioisomers, or diastereiomers. These compounds may contain one or more asymmetric carbon atoms and may exist in racemic and optically active forms. For example, compounds of the present invention may exist as a racemic mixture of R(+) and S(−) enantiomers, or in separate respectively optical forms, i.e., existing separately as either the R(+) enantiomer form or in the S(+) enantiomer form. All of these individual compounds, isomers, and mixtures thereof are included within the scope of the present invention.

Substituent Definitions

As used herein, the term alkali metal is intended to mean the Group I elements, which include, but are not limited to lithium (Li), sodium (Na), or potassium (K) and the like. The term alkali earth metal include, but are not limited to calcium (Ca) or magnesium (Mg) and the like.

As used herein, the term "alkyl" represents a saturated, straight or branched hydrocarbon moiety, which may be unsubstituted or substituted by one, or more of the substituents defined herein. Exemplary alkyls include, but are not limited to methyl (Me), ethyl (Et), propyl, isopropyl, butyl, isobutyl, t-butyl, pentyl and the like. The term "C1-C6" refers to an alkyl containing from 1 to 6 carbon atoms.

When the term "alkyl" is used in combination with other substituent groups, such as "haloalkyl" or "hydroxyalkyl", "arylalkyl", the term "alkyl" is intended to encompass a divalent straight or branched-chain hydrocarbon radical.

The terms "halogen" and "halo" represent chloro, fluoro, bromo or iodo substituents.

"Hydroxy" or "hydroxyl" is intended to mean the radical —OH.

For example, haloalkyl is intended to mean a saturated, straight or branched hydrocarbon moiety substituted with one or more halogen groups, where halogen is fluoro, chloro, bromo or iodo. Representative haloalkyls include, but are not limited to trifluoromethyl (—$CF_3$), tetrafluoroethyl (—$CF_2CHF_2$), pentafluoroethyl (—$CF_2CF_3$) and the like. For example, hydroxyalkyl is intended to mean a saturated, straight or branched hydrocarbon moiety substituted with one or more hydroxy groups.

As used herein, the term "alkenyl" refers to a straight or branched hydrocarbon moiety containing at least 1 and up to 3 carbon-carbon double bonds. Examples include ethenyl and propenyl.

As used herein, the term "alkynyl" refers to a straight or branched hydrocarbon moiety containing at least 1 and up to 3 carbon-carbon triple bonds. Examples include ethynyl and propynyl.

As used herein, the term "cycloalkyl" refers to a non-aromatic, saturated, cyclic hydrocarbon ring. The term "($C_3$-$C_8$)cycloalkyl" refers to a non-aromatic cyclic hydrocarbon ring having from three to eight ring carbon atoms. Exemplary "(C3-C8)cycloalkyl" groups useful in the present invention include cyclopropyl, cyclobutyl, cyclopentyl, cyclohexyl, cycloheptyl, and cyclooctyl.

"Alkoxy" refers to a group containing an alkyl radical attached through an oxygen linking atom. The term "($C_1$-$C_6$)alkoxy" refers to a straight- or branched-chain hydrocarbon radical having at least 1 and up to 6 carbon atoms attached through an oxygen linking atom. Exemplary "($C_1$-$C_4$)-alkoxy" groups useful in the present invention include, but are not limited to, methoxy, ethoxy, n-propoxy, isopropoxy, n-butoxy, s-butoxy, and t-butoxy. Representative haloalkoxy include, but are not limited to difluoromethoxy (—$OCHCF_2$), trifluoromethoxy (—$OCF_3$), tetrafluoroethoxy (—$OCF_2CHF_2$) and the like.

"Alkylthio-" refers to a group containing an alkyl radical atoms attached through an sulfur linking atom. The term "(C1-C4)alkylthio-" refers to a straight- or branched-chain hydrocarbon radical having at least 1 and up to 4 carbon atoms attached through a sulfur linking atom. Exemplary "(C1-C4)alkylthio-" groups useful in the present invention include, but are not limited to, methylthio-, ethylthio-, n-propylthio-, isopropylthio-, n-butylthio-, s-butylthio-, t-butylthio- and the like.

Carbocyclic ring refers to a ring in which all ring atoms are carbon atoms, which may be aromatic or non-aromatic, fused or non-fused and the like. Examples of carbocyclic rings, may include, but are not limited to cycloalkyls, such as cyclopropane, cyclobutane, cyclopentane, cyclohexane and the like, aromatic or aryl rings, which include, but are not limited to rings such as benzene, naphthalene and the like, which include, but are not limited to fused ring compounds, such as 1,2,3,4-tetrahydronaphthalene and the like.

"Cycloalkyloxy", "cycloalkylthio", "cycloalkylamino" refers to a group containing a saturated carbocyclic ring atoms attached through an oxygen, nitrogen or sulfur linking atom, respectively.

"Aryl" represents a group or moiety comprising an aromatic, monovalent monocyclic or bicyclic hydrocarbon radical containing from 6 to 10 carbon ring atoms, which may be unsubstituted or substituted by one or more of the substituents defined herein, and to which may be fused one or more cycloalkyl rings, which may be unsubstituted or substituted by one or more substituents defined herein. Representative aryl groups suitable for use in the present invention, may include, but are not limited to phenyl, naphthalenyl, fluorenyl, and the like.

Heteroatoms are defined as oxygen, nitrogen, sulfur and the like.

Heterocyclic groups may be heteroaryl or heterocycloalkyl groups.

Each monocyclic heterocyclic ring of the present invention has from 3 to 7 ring atoms and contains up to four heteroatoms. Monocyclic heterocyclic rings or fused heterocyclic rings include substituted aromatic and non-aromatics;

Each fused heterocyclic ring of the present invention optionally includes carbocyclic rings or heterocyclic rings;

"Heterocycloalkyl" represents a group or moiety comprising a monovalent monocyclic or bicyclic radical, which is saturated or partially unsaturated (non-aromatic), containing 3 to 10 ring atoms, which includes 1 to 4 heteroatoms independently selected from nitrogen, oxygen and sulfur, and which may be unsubstituted or substituted by one or more of the substituents defined herein. Illustrative examples of heterocycloalkyls include, but are not limited to, azetidinyl, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl and the like.

Generally, in the compounds of this invention, heterocycloalkyl groups are 5-membered and/or 6-membered heterocycloalkyl groups, such as pyrrolidyl (or pyrrolidinyl), tetrahydrofuryl (or tetrahydrofuranyl), tetrahydrothienyl, dihydrofuryl, oxazolinyl, thiazolinyl or pyrazolinyl, piperidyl (or piperidinyl), piperazinyl, morpholinyl, tetrahydropyranyl, dihydropyranyl, 1,3-dioxanyl, tetrahydro-2H-1,4-thiazinyl, 1,4-dioxanyl, 1,3-oxathianyl, and 1,3-dithianyl.

Additional examples of substituted heterocycloalkyl groups, which are partially saturated non-aromatic groups that are suitable in the present invention, may include, but are not limited to: pyridin-4(1H)-one, 3-hydroxy-1-methylpyridin-4(1H)-one, 3,4-dihydroisoquinolin-1(2H)-one, quinolin-4(1H)-one, 3-hydroxyquinolin-4(1H)-one, 3-hydroxy-1-methylquinolin-4(1H)-one, 5-chloro-1-ethyl-6,7-dihydroxyquinolin-4(1H)-one, 5-chloro-6,7-dihydroxy-1-methylquinolin-4(1H)-one, 1-ethyl-8-fluoro-6,7-dihydroxyquinolin-4(1H)-one, 5-chloro-1-ethyl-6,7-dihydroxyquinolin-4(1H)-one, 1-ethyl-5-fluoro-6,7-dihydroxyquinolin-4(1H)-one, 1-ethyl-6-fluoro-7,8-dihydroxyquinolin-4(1H)-one, 1-ethyl-7,8-dihydroxyquinolin-4(1H)-one, 6,7-dihydroxy-1-isopropylquinolin-4(1H)-one, 1-ethyl-5,6-dihydroxyquinolin-4(1H)-one, 5-chloro-1-cyclopropyl-6,7-dihydroxyquinolin-4(1H)-one, 1-cyclopropyl-6,7-dihydroxyquinolin-4(1H)-one, 1-(tert-butyl)-6,7-dihydroxyquinolin-4(1H)-one, 6,7-dihydroxy-1-methylquinolin-4(1H)-one, cinnolin-4(1H)-one, 1-ethyl-6,7-dihydroxycinnolin-4(1H)-one, 5-chloro-1-ethyl-6,7-dihydroxycinnolin-4(1H)-one, 1-ethyl-5-fluoro-6,7-dihydroxycinnolin-4(1H)-one, 1-ethyl-6,7-dihydroxycinnolin-4(1H)-one and the like.

Additional examples of substituted heterocycloalkyl groups, which are non-aromatic that are suitable in the present invention, may include, but are not limited to:

5-chloro-6,7-bis((4-methoxybenzyl)oxy)-1-oxo-3,4-dihydroisoquinolin-2(1H)-yl;

5-hydroxy-1-methyl-4-oxo-1,4-dihydropyridine-2-carboxamido;

7-hydroxy-1,8-dioxo-3,4-dihydro-1H-pyrido[1,2-a]pyrazin-2(8H)-yl);

3-hydroxy-1-methyl-4-oxo-1,4-dihydroquinolin-6-yl;

3-hydroxy-1-methyl-4-oxo-1,4-dihydroquinoline-6-carboxamido;

1-ethyl-6,7-dihydroxy-4-oxo-1,4-dihydrocinnolin-3-yl;

1-ethyl-6,7-dihydroxy-4-oxo-1,4-dihydrocinnoline-3-carboxamido;

1-ethyl-6,7-dihydroxy-4-oxo-1,4-dihydroquinoline-3-carboxamido;

3-hydroxy-1-methyl-4-oxo-1,4-dihydroquinoline-8-carboxamido;

1-ethyl-8-fluoro-6,7-dihydroxy-4-oxo-1,4-dihydroquinolin-3-yl;

5-chloro-1-ethyl-6,7-dihydroxy-4-oxo-1,4-dihydroquinolin-3-yl;

1-ethyl-6,7-dihydroxy-4-oxo-1,4-dihydroquinolin-3-yl;

5-chloro-1-ethyl-6,7-dihydroxy-4-oxo-1,4-dihydroquinoline-3-carboxamido;

1-ethyl-6,7-dihydroxy-4-oxo-1,4-dihydrocinnolin-3-yl;

1-ethyl-6,7-dihydroxy-4-oxo-1,4-dihydrocinnoline-3-carboxamido;

5-chloro-1-ethyl-6,7-dihydroxy-4-oxo-1,4-dihydrocinnoline-3-carboxamido;

5-chloro-1-ethyl-6,7-dihydroxy-4-oxo-1,4-dihydrocinnolin-3-yl;

1-ethyl-5-fluoro-6,7-dihydroxy-4-oxo-1,4-dihydroquinolin-3-yl;

5-fluoro-1-ethyl-6,7-dihydroxy-4-oxo-1,4-dihydroquinolin-3-yl;

1-ethyl-5-fluoro-6,7-dihydroxy-4-oxo-1,4-dihydroquinoline-3-carboxamido;

1-ethyl-6-fluoro-7,8-dihydroxy-4-oxo-1,4-dihydroquinolin-3-yl;

1-ethyl-6-fluoro-7,8-dihydroxy-4-oxo-1,4-dihydroquinoline-3-carboxamido;

1-ethyl-7,8-dihydroxy-4-oxo-1,4-dihydroquinolin-3-yl;

1-ethyl-7,8-dihydroxy-4-oxo-1,4-dihydroquinoline-3-carboxamido;

1-ethyl-5,6-dihydroxy-4-oxo-1,4-dihydroquinoline-3-carboxamido;

1-(tert-butyl)-6,7-dihydroxy-4-oxo-1,4-dihydroquinolin-3-yl;

1-(tert-butyl)-6,7-dihydroxy-4-oxo-1,4-dihydroquinoline-3-carboxamido;

1-cyclopropyl-6,7-dihydroxy-4-oxo-1,4-dihydroquinolin-3-yl;

1-cyclopropyl-6,7-dihydroxy-4-oxo-1,4-dihydroquinoline-3-carboxamido;

5-chloro-1-cyclopropyl-6,7-dihydroxy-4-oxo-1,4-dihydroquinolin-3-yl;

5-chloro-1-cyclopropyl-6,7-dihydroxy-4-oxo-1,4-dihydroquinoline-3-carboxamido;

6,7-dihydroxy-1-methyl-4-oxo-1,4-dihydroquinolin-3-yl;

6,7-dihydroxy-1-isopropyl-4-oxo-1,4-dihydroquinolin-3-yl 5-chloro-1-ethyl-6,7-dihydroxy-4-oxo-1,4-dihydroquinoline-3-carboxamido;

1-ethyl-8-fluoro-6,7-dihydroxy-4-oxo-1,4-dihydroquinoline-3-carboxamido;

1-ethyl-8-fluoro-6,7-dihydroxy-4-oxo-1,4-dihydroquinolin-3-yl;

5-chloro-6,7-dihydroxy-1-methyl-4-oxo-1,4-dihydroquinolin-3-yl and the like.

"Heteroaryl" represents a group or moiety comprising an aromatic monovalent monocyclic or bicyclic radical, containing 5 to 10 ring atoms, including 1 to 4 heteroatoms independently selected from nitrogen, oxygen and sulfur, which may be unsubstituted or substituted by one or more of the substituents defined herein. This term also encompasses bicyclic heterocyclic-aryl compounds containing an aryl ring moiety fused to a heterocycloalkyl ring moiety, containing 5 to 10 ring atoms, including 1 to 4 heteroatoms independently selected from nitrogen, oxygen and sulfur, which may be unsubstituted or substituted by one or more of the substituents defined herein. Illustrative examples of heteroaryls include, but are not limited to, thienyl, pyrrolyl, imidazolyl, pyrazolyl, furyl (or furanyl), isothiazolyl, furazanyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl, isothiazolyl, carbazolyl, 1,2,3,4 tetrahydro isoquinolinyl and the like.

Generally, the heteroaryl groups present in the compounds of this invention are 5-membered and/or 6-membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl, isothiazolyl, furazanyl, isoxazolyl, oxazolyl, oxadiazolyl, thiazolyl, triazolyl, and tetrazolyl or pyridyl, pyrazinyl, pyrimidinyl, pyridazinyl, and triazinyl.

"Oxo" represents a double-bonded oxygen moiety; for example, if attached directly to a carbon atom forms a carbonyl moiety (C=O), or attached to an N or S forms oxides, N-oxides, sulfones or sulfoxides.

As used herein, the term "compound(s) of the invention" means a compound of Formulas (I) to (IX), respectively (as defined above) in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

As used herein, the term "optionally substituted" means that a group, such as, which may include, but is not limited to alkyl, aryl, heteroaryl, etc., may be unsubstituted, or the group may be substituted with one or more substituent(s) as defined. In the case where groups may be selected from a number of alternative groups the selected groups may be the same or different.

The term "independently" means that where more than one substituent is selected from a number of possible substituents, those substituents may be the same or different.

The present invention relates to a compound of Formulas (I) to (IX), which definition referred herein includes, but are not limited to the following related sub-generic Formulas (II) and (IX).

The alternative definitions for the various groups and substitutent groups of Formulas (I) to (IX), respectively, or a pharmaceutically acceptable salt thereof, provided throughout the specification are intended to particularly describe each compound species disclosed herein, individually, as well as groups of one or more compound species. The scope of this invention includes any combination of these group and substituent group definitions.

The alternative definitions for the various groups and substitutent groups of Formulas (I) to (IX), respectively, or a pharmaceutically acceptable salt thereof, provided throughout the specification are intended to particularly describe each compound species disclosed herein, individually, as well as groups of one or more compound species. The scope of this invention includes any combination of these group and substituent group definitions.

Enantiomers, Diastereomers and Polymorphs

The compounds according to Formulas (I) to (IX), respectively, or a pharmaceutically acceptable salt thereof of the present invention may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formulas (I) to (IX), respectively, or a pharmaceutically acceptable salt thereof, or in any chemical structure illustrated herein, is not specified the structure is intended to encompass all individual stereoisomers and all mixtures thereof. Thus, compounds according to Formulas (I) to (IX), respectively, or a pharmaceutically acceptable salt thereof, containing one or more chiral center may be used as racemic mixtures, enantiomerically enriched mixtures, or as enantiomerically pure individual stereoisomers.

Individual stereoisomers of a compound according to Formulas (I) to (IX), respectively, or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation. When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Salts

Because of their potential use in medicine, the salts of the compounds of Formulas (I) to (IX), respectively, are preferably pharmaceutically acceptable salts. Suitable pharmaceutically acceptable salts include those described by Berge, Bighley and Monkhouse J. Pharm. Sci (1977) 66, pp 1-19.

When a compound of the invention is a base (contain a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention. e.g., a sodium salt or a disodium salt.

Carboxylate functional groups of compounds of the present invention have coordinated mono or di-valent cations, where such cations may include, but are not limited to alkali metals, which may include, but are not limited to lithium (Li), sodium (Na), potassium, or mixtures thereof and the like.

Quarternary amine functional groups of compounds of the present invention, which are positively charged species, also may have coordinated anions, where such anions may include, but are not limited to halogens, which may include, but are not limited to chlorides, fluorides, bromides, iodides and the like.

Compounds of Formulas (I) to (IX) of the present invention, also may form a zwitterion(s) (formerly called a dipolar ion), which is a neutral molecule with a positive and a negative electrical charge (i.e., not dipoles) at different locations within that molecule. Zwitterions are sometimes also called inner salts.

Solvates

For solvates of the compounds of the invention, or salts thereof, that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Deuterated Compounds

The invention also includes various deuterated forms of the compounds of Formulas (I) to (IX), respectively, or a pharmaceutically acceptable salt thereof. Each available hydrogen atom attached to a carbon atom may be independently replaced with a deuterium atom. A person of ordinary skill in the art will know how to synthesize deuterated forms of the compounds of Formulas (I) to (IX), respectively, or a pharmaceutically acceptable salt thereof of the present invention. For example, deuterated materials, such as alkyl groups may be prepared by conventional techniques (see for example: methyl-$d_3$-amine available from Aldrich Chemical Co., Milwaukee, Wis., Cat. No. 489, 689-2).

Isotoptes

The subject invention also includes isotopically-labeled compounds which are identical to those recited in Formulas (I) to (IX), respectively, or a pharmaceutically acceptable salt thereof but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3H$, and carbon-14, ie. $^{14}C$, isotopes are particularly preferred for their ease of preparation and detectability. $^{11}C$ and $^{18}F$ isotopes are particularly useful in PET (positron emission tomography).

Purity

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Synthetic Schemes and General Methods of Preparation

The compounds of Formulas (I) to (IX), respectively, or a pharmaceutically acceptable salt thereof, may be obtained by using synthetic procedures illustrated in the Schemes below or by drawing on the knowledge of a skilled organic chemist.

The synthesis provided in these Schemes are applicable for producing compounds of the invention having a variety of different $R^1$ and $R^2$ groups employing appropriate precursors, which are suitably protected if needed, to achieve compatibility with the reactions outlined herein. Subsequent deprotection, where needed, affords compounds of the nature generally disclosed. While the Schemes are shown with compounds only of Formulas (I) to (IX), respectively, or a pharmaceutically acceptable salt thereof, they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

The present invention also relates to processes for making compounds of Formulas (I) to (IX), respectively, or a pharmaceutically acceptable salt thereof.

The compounds of the present invention may be obtained by using synthetic procedures illustrated in Schemes below or by drawing on the knowledge of a skilled organic chemist.

The synthesis provided in these Schemes are applicable for producing compounds of the invention as defined by Formulas (I) to (IX), respectively, or a pharmaceutically acceptable salt thereof, respectively, having a variety of different functional groups as defined employing appropriate precursors, which are suitably protected if needed, to achieve compatibility with the reactions outlined herein. Subsequent deprotection, where needed, affords compounds of the nature generally disclosed. While the Schemes shown with compounds only as defined therein, they are illustrative of processes that may be used to make the compounds of the invention.

Intermediates (compounds used in the preparation of the compounds of the invention) also may be present as salts. Thus, in reference to intermediates, the phrase "compound(s) of formula (number)" means a compound having that structural formula or a pharmaceutically acceptable salt thereof.

The compounds according to Formulas (I) to (IX), respectively, or a pharmaceutically acceptable salt thereof, or pharmaceutically acceptable salts thereof, are prepared using conventional organic syntheses. Suitable synthetic routes are depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Synthetic Schemes
Scheme I

Scheme 1 represents a general scheme for the preparation of compounds of the present invention as shown below.

where:
X is N, or C—$R^a$.
$R^a$ is hydrogen, chlorine or halogen;
$R^1$ and $R^2$ each are hydrogen, (C1-6)-alkyl, or $(CH_2)p$-C(O)$OR^{18}$
where: p is an integer from 1 to 5
U is S or S—O
$P^-$ is a counter anion of a quaternary amine;
$R^{13}$, $R^{16}$, $R^{18}$ represent an ester residue such as a carboxyl-protecting group. $R^{15}$ is a hydrogen or a carboxy protecting group. Such esters include those esters that are readily metabolized in the body to form a carboxylic state. The aforementioned carboxyl-protecting group may be of any group as long as it can be protected and/or deprotected by a method described in Protective Groups in Organic Synthesis, Theodora W Green (John Wiley & Sons), or the like. Examples of suitable protecting groups may include, but are not limited to lower alkyl (e.g., methyl, ethyl, t-butyl), lower alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl(t-butyl)silyl), and the like.

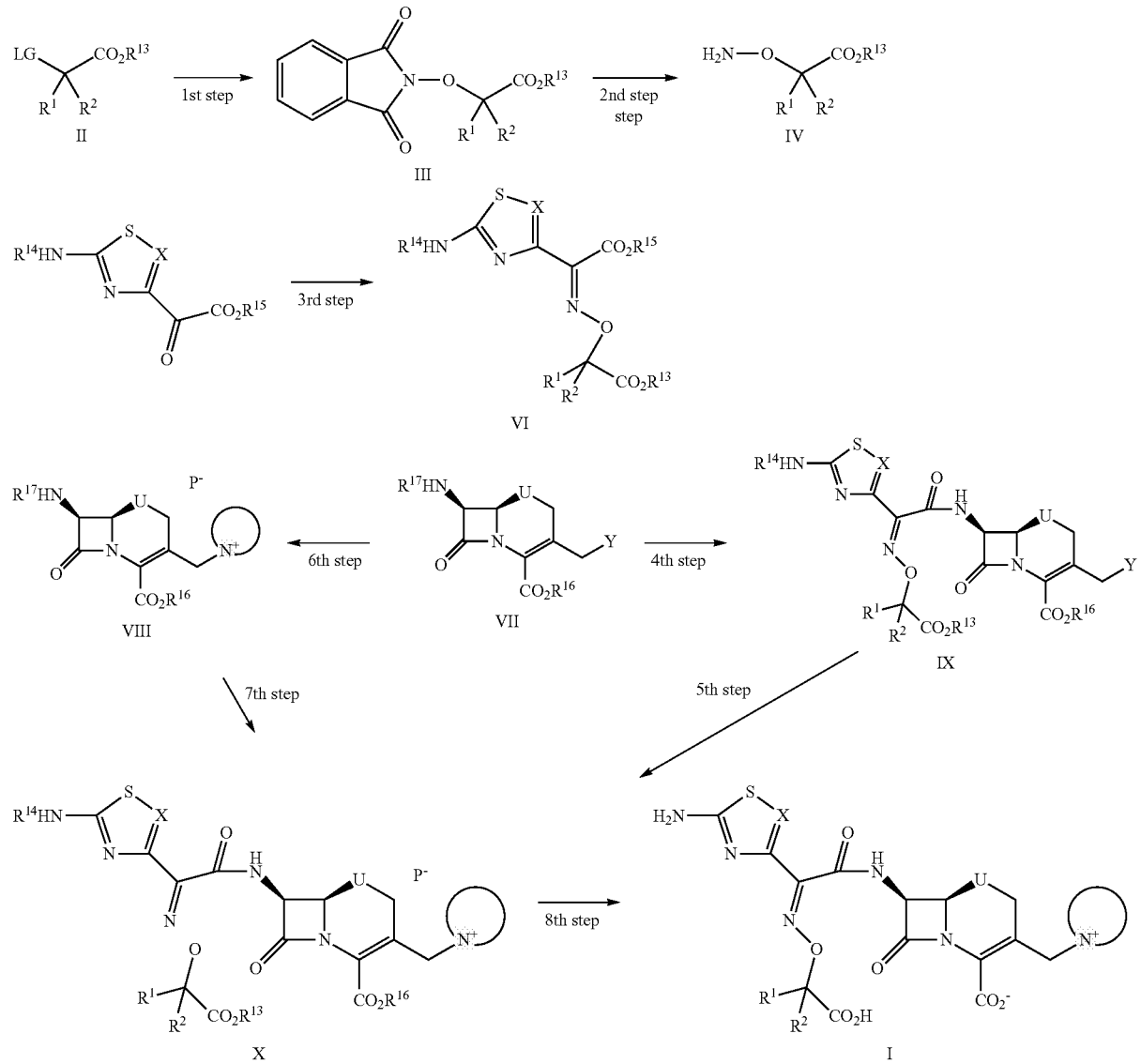

$R^{14}$ represent an amino-protecting group.

$R^{17}$ is a hydrogen or an amino protecting group. Such amino-protecting groups include those groups that are readily metabolized in the body to form amino. The aforementioned amino-protecting group may be of any group as long as it can be protected and/or deprotected by a method described in Protective Groups in Organic Synthesis, Theodora W Green (John Wiley & Sons), or the like. Examples of suitable protecting groups, may include, but are not limited to may include lower alkoxycarbonyl (e.g., t-butoxycarbonyl, benzyloxycarbonyl, p-nitrobenzyloxycarbonyl), optionally substituted aralkanoyl (e.g., benzoyl, p-nitrobenzoyl), acyl (e.g. formyl, chloroacetyl), and the like.

LG and Y as defined above represent leaving groups (for example, hydroxy, halogen (Cl, Br, I), optionally substituted by such groups, which may include, but are not limited to carbamoyloxy, acyloxy, methanesulfonyloxy, and toluenesulfonyloxy, etc.;. The following structure:

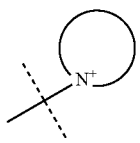

is a moiety of Formulas (I) and (II) including a quaternary ammonium group moiety of 3-side chain: where each symbol is defined as above;

(1) Raw Materials of the 7-Side Chain: Synthesis of Compound (VI) First Step:

Compound (III) is obtained by reacting N-hydroxyphthalimide in the presence of Compound (II) (LG is hydroxy) and a Mitsunobu reagent, or in the presence of Compound (II) (LG is another leaving group) and a base (such as sodium hydroxide, sodium methoxide).

The amount of N-hydroxyphthalimide used is generally in the range from 1 to 5 molar equivalents, more specifically in the range from 1 to 2 molar equivalents, relative to Compound (II).

Examples of reaction solvents, may include, but are not limited to ethers (e.g., dioxane, tetrahydrofuran, diethyl ether, tert-butyl methyl ether, diisopropyl ether), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), and the like, and mixed solvents and the like thereof.

A reaction temperature is in a range of, generally, about −50 to 100° C., preferably about −40 to 50° C., and more preferably about −30 to 0° C.

Second Step:

N-Methylhydrazine or hydrazine is added and reacted to Compound (III) to provide Compound (IV).

The amount of N-methylhydrazine or hydrazine used is in a range of about 1-10 molar equivalents, preferably 1-5 molar equivalents, more preferably 1-2 molar equivalents, relative to Compound (III).

Examples of reaction solvents, which may include, but are not limited to ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, about 0 to 100° C., preferably about 0 to 50° C., more preferably about 10 to 30° C.

Third Step:

Compound (IV) is added and reacted with Compound (V), which is commercially available or obtained by a known method, to provide Compound (VI). (For example, it is described in Bioorganic & Medicinal Chemistry, vol. 15, pp. 6716-6732 (2007)).

N-Methylhydrazine or hydrazine is added and reacted with Compound (III) to provide Compound (IV).

Examples of reaction solvents, which may include, but are not limited to ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g. n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and the like, and mixed solvents and the like thereof.

A reaction temperature is in a range of, generally, about 0 to 100° C., preferably about 0 to 50° C., more preferably about 10 to 30° C.

(2) 7-Amidation and Formation of the 3-Side Chain: Synthesis of Compound (X) Fourth Step (7-Amidation Reaction):

Compound (IX) is obtained by reacting Compound (VI) and Compound (VII), which are commercially available or synthesized according to methods described in a document (e.g., Japanese Laid-Open Publication No. 60-231684, Japanese Laid-Open Publication No. 62-149682, etc.). In this case, preferably, $R^{13}$ and $R^{16}$ are carboxy protecting groups, $R^{14}$ is an amino protecting group, and $R^{15}$ and $R^{17}$ are hydrogen.

The amount of Compound (VI) used is in a range of, generally, about 1-5 moles, preferably 1-2 moles, relative to 1 mole of Compound (VII).

Examples of reaction solvents may include, but are not limited to ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, about −40 to 80° C., preferably about −20 to 50° C., more preferably about −10 to 30° C.

The above-described amidation reaction may be carried out after the carboxy moiety is converted into a reactive derivative (e.g., which may include, but are not limited to inorganic base salt(s), organic base salt(s), acid halide(s), acid azide(s), acid anhydride(s), mixed acid anhydride(s), active amide(s), active ester(s), and active thioester(s) and the like). Examples of such inorganic bases may include, but are not limited to alkali metal (e.g., Na, K, and the like), alkali earth metal (e.g., Ca, Mg), and the like. Examples of organic bases suitable for use in the present invention, may include, but are not limited to trimethylamine, triethylamine, tert-butyldimethylamine, dibenzylmethylamine, benzyldimethylamine, N-methylmorpholine, diisopropylethylamine, and the like. Examples of acid halides, may include, but are not limited to acid chlorides, acid bromides, and the like. Examples of mixed acid anhydrides, may include, but are not limited to mixed acid anhydrides of mono-alkyl carbonates, mixed acid anhydrides of aliphatic carboxylic acid, mixed acid anhydrides of aromatic carboxylic acid, mixed acid anhydrides of organic sulfonic acid, and the like. Examples of active amides, may include, but are not limited to amides with nitrogen-containing heterocyclic compound, and the like. Examples of active esters, may include, but are not limited to organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like.

Furthermore, in the above-described reaction, a suitable condensing agent may be used as desired. For example, hydrochloric acid salt of each of the following, which may include, but are not limited to 1-dimethylaminopropyl-3-ethylcarbodiimide (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.

Fifth Step (3-Side Chain Forming Reaction):

Compound (X) is obtained by reacting Compound (IX) and a corresponding tertiary amine. In this case, preferably, $R^{13}$ and $R^{16}$ are carboxy protecting groups, and $R^{14}$ is an amino protecting group.

An amount of the corresponding tertiary amine used is in a range of, generally, 1-5 moles, preferably 1-2 moles, relative to 1 mole of Compound (IX).

Examples of reaction solvents, may include, but are not limited to ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature generally is suitably in a range of about −20 to 60° C., more suitably is in a range of about −10 to 40° C., or most suitably is in a range of about 0 to 20° C.

Furthermore, a compound of which U is S in Compound (X) can be obtained by reducing the compound of which U is SO in Compound (X). Examples of reducing agents, may include, but are not limited to potassium iodide, acetyl chloride or phosphorous tribromide and the like.

(3) 3-Side Chain Formation and 7-Amidation: Synthesis of Compound (X) Sixth Step (3-Side Chain Forming Reaction):

Compound (VIII) is obtained by reacting Compound (VII) with a corresponding tertiary amine. In this case, preferably, $R^{16}$ is a carboxy protecting group, and $R^{17}$ is an amino protecting group.

An amount of the corresponding tertiary amine used is in a range of, generally, 1-5 moles, preferably 1-2 moles, relative to 1 mole of Compound (VII).

Examples of reaction solvents, may include, but are not limited to (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g. acetone, methyl ethyl ketone), nitriles (e.g., MeCN, propionitrile), dimethylsulfoxide, water, and the like, and mixed solvents and the like thereof.

A reaction temperature generally is suitably in a range of about −20 to 60° C., more suitably is in a range of about −10 to 40° C., or most suitably is in a range of about 0 to 20° C.

Both tertiary amine moieties used in the 3-side chain forming reactions of the fifth and the sixth steps can be obtained as a commercially available reagent, by a known method, and/or by a method described herein.

Seventh Step (7-Amidation Reaction):

Compound (X) is obtained by reacting Compound (VIII) and Compound (VI). In this case, preferably. $R^{13}$ and $R^{16}$ are carboxy protecting groups, $R^{14}$ is an amino protecting group, $R^{15}$ and $R^{17}$ are hydrogen.

The amount of Compound (VI) generally used is suitably in a range of about 1-5 moles, more suitably in a range of about 1 to 2 moles, relative to 1 mole of Compound (VIII).

Examples of reaction solvents, which may include, but are not limited to ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature generally is suitably in a range of about −40 to 80° C., more suitably in a range of about −20 to 50° C. or most suitably is in a range of about −10 to 30° C.

The above-described amidation reaction may be carried out after a carboxyl moiety is converted to a reactive derivative (e.g., which may include, but are not limited to inorganic base salt, organic base salt, acid halide, acid azide, acid anhydride, mixed acid anhydride, active amide, active ester, and active thioester). Examples of suitable inorganic bases for use in the present invention include alkali metal (e.g., Na, K, and the like), alkali earth metal (e.g., Ca, Mg), and the like. Examples of suitable organic bases for use in the present invention, which may include, but are not limited to trimethylamine, triethylamine, tert-butyldimethylamine, dibenzylmethylamine, benzyldimethylamine, N-methylmorpholine, diisopropylethylamine, and the like. Examples of acid halides, which may include, but are not limited to acid chlorides, acid bromides, and the like. Examples of mixed acid anhydrides, which may include, but are not limited to mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides, which may include, but are not limited to amides with nitrogen-containing heterocyclic compound, and the like. Examples of active esters, which may include, but are limited to organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters, which may include, but are not limited to esters with aromatic heterocyclic thiol compound (e.g., 2-pyridylthiol esters), and the like. Examples of active thioesters, which may include, but are not limited to esters with aromatic heterocyclic thiol compound (e.g., 2-pyridylthiol esters), and the like. Furthermore, in the above-described reaction, a suitable condensing agent may be used as desired. For example, hydrochloric acid salt of each of the following, which may include, but are not limited to 1-dimethylaminopropyl-3-ethylcarbodiimide (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.

(4) Deprotection Reaction

Eighth Step:

Compound (I) is obtained by subjecting Compound (X) to a deprotection reaction with a method well-known to those skilled in the art.

Examples of reaction solvents, which may include, but are not limited to ethers (e.g., anisole, dioxane, tetrahydrofuran, diethyl ether, tert-butyl methyl ether, diisopropyl ether), esters (e.g., ethyl formate, ethyl acetate, n-butyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, water, and the like. These solvents may be used alone or in a combination using two or more of such solvents.

A reaction temperature generally is suitably in a range of about −30 to 100° C., more suitably in a range of about 0 to 50° C., most suitably in a range of about 0 to 10° C.

As a suitable catalyst for use in the present invention, may include, but is not limited to Lewis acid(s) (e.g., $AlCl_3$, $SnCl_4$, $TiCl_4$), protonic acid(s) (e.g., HCl, HBr, $H_2SO_4$, HCOOH, $CF_3CO_2H$), and the like.

The obtained Compound (I) is or may be further chemically modified, and thereby an ester, or a compound of which an amino on the thiazole ring at the 7-position thereof is protected, or a pharmaceutically acceptable salt, or a solvate thereof can be synthesized.

Pharmaceutical Compositions, Dosage Forms and Regimens

The present invention relates to pharmaceutical compositions comprised of novel compounds of Formulas (I) to (IX), respectively, or a pharmaceutically acceptable salt thereof and at least one pharmaceutically acceptable excipient(s).

The compounds of the invention will normally, but not necessarily, be formulated into a pharmaceutical composition prior to administration to a patient.

Accordingly, the present invention is directed to pharmaceutical compositions or formulations, which comprise a compound or compound species of the present invention and pharmaceutically-acceptable excipient(s). In particular, the present invention also may relate to a pharmaceutical composition or formulation, which comprises a compound as defined by Formulas (I) to (IX), respectively, or a pharmaceutically acceptable salt thereof, and at least one pharmaceutically acceptable excipient(s), and optionally one or more other therapeutic ingredients.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formulas (I) to (IX), respectively, or a pharmaceutically acceptable salt thereof, particularly a pharmaceutically acceptable salt, thereof). When prepared in unit dosage form, the pharmaceutical compositions or formulations may contain from 1 mg to 1000 mg of a compound of this invention.

The pharmaceutical compositions or formulations as defined herein typically contain one compound of the present invention. However, in certain embodiments, the pharmaceutical compositions may contain more than one compound of the present invention. In addition, the pharmaceutical compositions of the present invention may optionally further comprise one or more additional pharmaceutically active compounds.

As used herein, "pharmaceutically-acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically-acceptable are avoided. In addition, each excipient must of course be of sufficiently high purity to render it pharmaceutically-acceptable.

Suitable pharmaceutically-acceptable excipients will vary depending upon the particular dosage form chosen. In addition, suitable pharmaceutically-acceptable excipients may be chosen for a particular function that they may serve in the composition.

For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance. Moreover, pharmaceutical compositions, formulations, dosage forms, and the like, etc. may conveniently be presented in unit dosage form and may be prepared by any of the methods well known in the art of pharmacy.

All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The compounds of the invention and the pharmaceutically-acceptable excipient or excipients will typically be formulated into a dosage form adapted for administration to the patient by the desired route of administration.

With regard to the present invention, conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

The pharmaceutical compositions or formulations of the invention are prepared using techniques and methods known to those skilled in the art. Some of the methods commonly used in the art are described in *Remington's Pharmaceutical Sciences* (Mack Publishing Company).

In general, pharmaceutical compositions of the present invention are prepared using conventional materials and techniques, such as mixing, blending and the like.

The term "active agent" is defined for purposes of the present invention as any chemical substance or composition of the present invention, which can be delivered from the device into an environment of use to obtain a desired result.

The percentage of the compound in compositions can, of course, be varied as the amount of active in such therapeutically useful compositions is such that a suitable dosage will be obtained.

In one aspect, the present invention is directed to a pharmaceutical composition comprising a compound of Formulas (I) to (IX), respectively, or a pharmaceutically acceptable salt thereof and one or more pharmaceutically acceptable excipients.

In another aspect, the present invention is directed to a pharmaceutical composition comprising a compound of Formulas (I) to (IX), respectively, or a pharmaceutically acceptable salt thereof and one or more pharmaceutically acceptable excipients.

In another aspect, the present invention is directed to a pharmaceutical composition comprising a compound or compound species or a pharmaceutically acceptable salt thereof of the present invention as defined herein and one or more pharmaceutically acceptable excipients.

It will be appreciated that the actual preferred dosages of the compounds being used in the compositions of this invention will vary according to the particular composition formulated, the mode of administration, the particular site of administration and the host being treated.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet, etc.

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethyl aspartamide phenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Methods of Treatment

The present invention also relates to methods for treating bacterial infections, which comprises administering to a subject in need thereof an effective amount of a compound of Formulas (I) to (IX), respectively, or a pharmaceutically acceptable salt thereof or a corresponding pharmaceutical composition.

As used herein, "patient" refers to a human or other mammal.

Methods of Use and Treatment of Diseases

In one aspect, a compound of Formulas (I) to (IX), respectively, or a pharmaceutically acceptable salt or corresponding pharmaceutical compositions of the present invention have a wide antimicrobial activity spectrum, and may be used for prevention or therapy against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

Compounds of Formulas (I) to (IX), respectively, or a pharmaceutically acceptable salt thereof and/or corresponding pharmaceutical compositions of the present invention exhibit high antimicrobial activity in particular against Gram negative bacteria, preferably, Gram negative bacteria of enterobacteria (*E. coli, Klebsiella, Serratia, Enterobacter, Citrobacter, Morganella, Providencia, Proteus* and the like), Gram negative bacteria colonized in respiratory system (*Haemophilus, Moraxella* and the like), and Gram negative bacteria of glucose non fermentation (*Pseudomonas aeruginosa, Pseudomonas* other than *P. aeruginosa, Stenotrophomonas, Burkholderia, Acinetobacter* and the like).

Compounds of Formulas (I) to (IX), respectively, or a pharmaceutically acceptable salt thereof of the present invention are stable against beta-lactamase belonging to classes A, B, C and D which beta-lactamase is produced by these Gram negative bacteria, and have high antimicrobial activity against a variety of beta-lactam drug resistant Gram negative bacteria, such as extended spectrum β-lactamase (ESBL) producing bacteria and the like. These are extremely stable against metallo-beta-lactamase belonging to Class B including in particular IMP type, VIM type, L-1 type and the like. Thus, these are effective against a variety of beta-lactam drug resistant Gram negative bacteria including Cephem and Carbapenem. Moreover, the compounds of the subject invention has antimicrobial activity against Gram positive bacteria including methicillin-resistant *Staphylococcus aureus* (MRSA), penicillin-resistant *Streptococcus pneumoniae* (PRSP), and the like. Still more preferable compounds have features regarding kinetics in the body, such as blood concentration in which such is highly bioavailable, long duration of effects, and/or significant tissue migration. More preferable compounds are safe in terms of side effects. More preferable compounds have high water solubility, and thus preferable as an injecting drug, in particular.

Compounds of Formulas (I) to (IX), respectively, or a pharmaceutically acceptable salt thereof and/or corresponding pharmaceutical compositions may be administered parenterally or orally as an injecting agent, capsules, tablets, and granules, and preferably, administered as an injecting agent. Amounts to be administered may usually be, per 1 kg of body weight of a patient or animal, about 0.1 to 100 mg/day, preferably, about 0.5 to 50 mg/day, if desired, divided into 2-4 times per day. Carriers when used as an injecting agent is for example, distilled water, saline and the like, and base and the like may be used for pH adjustment.

When used as capsules, granules or tablets, carriers may be known excipients (e.g., starch, lactose, sucrose, calcium carbonate, calcium phosphate and the like), binders (e.g., starch, acacia gum, carboxymethyl cellulose, hydroxypropyl cellulose, crystalline cellulose, and the like), lubricants (e.g. magnesium stearate, talc and the like), and the like.

Still compounds of the present invention have features regarding kinetics in the body, such as blood concentration in which such is highly bioavailable, long duration of effects, and/or significant tissue migration. More preferable compounds are safe in terms of side effects. More preferable compounds have high water solubility, and thus preferable as an injecting drug, in particular.

Suitable compounds of Formulas (I) to (IX), respectively, or a pharmaceutically acceptable salt thereof and/or corresponding pharmaceutical compositions of the present invention are useful in treatment of infections caused by causative bacteria in a variety of mammals including humans, which include, but are not limited to infectious diseases, urinary system infectious diseases, resipiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like Suitably the compounds of Formulas (I) to (IX), respectively, or a pharmaceutically acceptable salt thereof and/or corresponding pharmaceutical compositions of the present invention are useful in the treatment of bacterial infections, more particularly gram negative bacterial infections caused by:

Gram negative bacteria of enterobacteria, which include, but are not limited to *E. coli, Klebsiella, Serratia, Enterobacter, Citrobacter, Morganella, Providencia, Proteus* and the like;

Gram negative bacteria colonized in respiratory system, which include, but are not limited to *Haemophilus, Moraxella* and the like; and Gram negative bacteria of glucose non fermentation, which include, but are not limited to *Pseudomonas aeruginosa, Pseudomonas* other than *P. aeruginosa, Stenotrophomonas, Burkholderia, Acinetobacter* and the like.

The compounds of Formulas (I) to (IX), respectively, or a pharmaceutically acceptable salt thereof and/or corresponding pharmaceutical compositions of the present invention also are stable against beta-lactamase belonging to classes A, B, C and D which beta-lactamase is produced by these Gram negative bacteria, and have high antimicrobial activity against a variety of beta-lactam drug resistant Gram negative bacteria, such as ESBL producing bacteria and the like. These are extremely stable against metallo-beta-lactamase belonging to Class B including in particular IMP type, VIM type. L-1 type and the like. Thus, these are effective against a variety of beta-lactam drug resistant Gram negative bacteria including Cephem and Carbapenem.

Suitably the compounds of Formulas (I) to (IX), respectively, or a pharmaceutically acceptable salt thereof and/or corresponding pharmaceutical compositions of the present invention have antimicrobial activity against Gram positive bacteria including methicillin-resistant *Staphylococcus aureus* (MRSA), penicillin-resistant *Streptococcus pneumoniae* (PRSP), and the like.

Still compounds of Formulas (I) to (IX), respectively, or a pharmaceutically acceptable salt thereof and/or corresponding pharmaceutical compositions of the present invention have features regarding kinetics in the body, such as blood concentration in which such is highly bioavailable, long duration of effects, and/or significant tissue migration. More preferable compounds are safe in terms of side effects.

Compounds of Formulas (I) to (IX), respectively, or a pharmaceutically acceptable salt thereof and/or pharmaceutical compositions of the present invention have high water solubility, and thus preferable as an injecting drug, in particular.

The present invention specifically relate to methods for the treatment infectious diseases including bacterial infections, comprise administering an effective amount of a compound according to Formulas (I) to (IX), respectively, or a pharmaceutically acceptable salt thereof and/or corresponding pharmaceutical compositions to a patient in need thereof.

One embodiment of the present invention provides for a method for treating a bacterial infection, which comprises administering a compound of Formulas (I) to (IX), respectively, or a pharmaceutically acceptable salt thereof.

Another embodiment of the present invention provides for a method of treating a bacterial infection, which comprises administering a pharmaceutical composition comprising a compound of Formulas (I) to (IX), respectively, or a pharmaceutically acceptable salt thereof and at least one pharmaceutically acceptable adjuvant, carrier or excipient.

In another embodiment of the present invention provides for a method of treating a bacterial infection in humans comprising administration of a compound or compound species or a pharmaceutically acceptable salt thereof as defined herein.

In one aspect, the present invention relates to a method of treating a bacterial infection comprising administering a therapeutically effective amount of a compound of Formulas (I) to (IX), respectively, or a pharmaceutically acceptable salt thereof to a human in need thereof.

In another aspect, the present invention relates to a method of treating a bacterial infection, where the bacterial infection is caused by Gram negative bacteria.

In another aspect, the present invention relates to a method of treating a bacterial infection, where the Gram negative bacteria selected from Gram negative bacteria of enterobacteria, Gram negative bacteria colonized in respiratory, Gram negative bacteria of glucose non fermentation or β-lactam drug resistant Gram negative bacteria.

In another aspect, the present invention relates to a method of treating a bacterial infection, where:
the Gram negative bacteria of enterobacteria selected from *E. coli, Klebsiella, Serratia, Enterobacter, Citrobacter, Morganella, Providencia* or *Proteus;*
the Gram negative bacteria colonized in respiratory system selected from *Haemophilus* or *Moraxella;*
the Gram negative bacteria of glucose non fermentation selected from *Pseudomonas aeruginosa, Pseudomonas* other than *P. aeruginosa, Stenotrophomonas* or *Burkholderia, Acinetobacter*; and
the beta-lactam drug resistant Gram negative bacteria is selected from ESBL producing bacteria.

In another aspect, the present invention relates to a method, where the bacterial infection is an airway infection, urinary system infection, resipiratory system infection, sepsis infection, nephritis, cholecystitis, oral cavity infection, endocarditis, pneumonia, bone marrow membrane myelitis, otitis media, enteritis, empyema, wound infection or an opportunistic infection.

In another aspect, the present invention relates to a method of treating a bacterial infection comprising administering a therapeutically effective amount of a compound of Formulas (I) to (IX), respectively, or a pharmaceutically acceptable salt thereof to a human in need thereof.

In another aspect, the present invention relates to a method for treating a gram-negative infection comprising administering a therapeutically effective amount of a compound of Formulas (I) to (IX), respectively, or a pharmaceutically acceptable salt thereof to a human in need thereof.

In another aspect, the present invention relates to a method for treating a gram-negative infection comprising administering a therapeutically effective amount of a compound of Formulas (I) to (IX), respectively, or a pharmaceutically acceptable salt thereof to a human in need thereof.

In another aspect, the present invention relates to a method for inhibiting activity of UDP-3-O—(R-3-hydroxydecanoyl)-N-acetylglucosamine deacetylase (LpxC) comprising administering a therapeutically effective amount of a compound of Formulas (I) to (IX), respectively, or a pharmaceutically acceptable salt thereof to a human in need thereof.

In another aspect, the present invention relates to a method for treating antimicrobial activity against Gram positive bacteria comprising administering a therapeutically effective amount of a compound of Formulas (I) to (IX), respectively, or a pharmaceutically acceptable salt thereof to a human in need thereof.

In another aspect, the present invention relates to a method for treating antimicrobial activity against Gram positive bacteria, where the Gram positive bacteria is selected from methicillin-resistant *Staphylococcus aureus* (MRSA) or penicillin-resistant *Streptococcus pneumoniae* (PRSP).

In another aspect, the present invention relates to a method for treating methicillin-resistant *Staphylococcus aureus* (MRSA), comprising administering a therapeutically effective amount of a compound of Formulas (I) to (IX), respectively, or a pharmaceutically acceptable salt thereof to a human in need thereof.

In another aspect, the present invention relates to a method for treating penicillin-resistant *Streptococcus pneumoniae* (PRSP), comprising administering a therapeutically effective amount of a compound of Formulas (I) to (IX), respectively, or a pharmaceutically acceptable salt thereof to a human in need thereof.

The present invention specifically relate to methods for the treatment infectious diseases including bacterial infections, comprise administering an effective amount of a pharmaceutical composition comprising a compound according to Formulas (I) to (IX), respectively, or a pharmaceutically acceptable salt thereof, to a patient in need thereof.

One embodiment of the present invention provides for a method for treating a bacterial infection, which comprises administering a pharmaceutical composition comprising compound of Formulas (I) to (IX), respectively, or a pharmaceutically acceptable salt thereof.

Another embodiment of the present invention provides for a method of treating a bacterial infection, which comprises administering a pharmaceutical composition comprising a compound of Formulas (I) to (IX), respectively, or a pharmaceutically acceptable salt thereof and at least one pharmaceutically acceptable excipient.

In another embodiment of the present invention provides for a method of treating a bacterial infection in humans comprising administration of a pharmaceutical composition comprising a compound or compound species or a pharmaceutically acceptable salt thereof as defined herein.

In one aspect, the present invention relates to a method of treating a bacterial infection comprising administering a therapeutically effective amount of a pharmaceutical composition comprising a compound of Formulas (I) to (IX), respectively, or a pharmaceutically acceptable salt thereof to a human in need thereof.

In another aspect, the present invention relates to a method of treating a bacterial infection, where the bacterial infection is caused by Gram negative bacteria.

In another aspect, the present invention relates to a method of treating a bacterial infection, where the Gram negative bacteria selected from Gram negative bacteria of enterobacteria, Gram negative bacteria colonized in respiratory, Gram negative bacteria of glucose non fermentation or β-lactam drug resistant Gram negative bacteria.

In another aspect, the present invention relates to a method of treating a bacterial infection, where:
the Gram negative bacteria of enterobacteria selected from *E. coli, Klebsiella, Serratia, Enterobacter, Citrobacter, Morganella, Providencia* or *Proteus;*
the Gram negative bacteria colonized in respiratory system selected from *Haemophilus* or *Moraxella;* the Gram negative bacteria of glucose non fermentation selected from *Pseudomonas aeruginosa, Pseudomonas* other than *P. aeruginosa, Stenotrophomonas* or *Burkholderia, Acinetobacter*; and the beta-lactam drug resistant Gram negative bacteria is selected from ESBL producing bacteria.

In another aspect, the present invention relates to a method, where the bacterial infection is an airway infection, urinary system infection, resipiratory system infection, sepsis infection, nephritis, cholecystitis, oral cavity infection, endocarditis, pneumonia, bone marrow membrane myelitis, otitis media, enteritis, empyema, wound infection or an opportunistic infection.

In another aspect, the present invention relates to a method of treating a bacterial infection comprising administering a therapeutically effective amount of a pharmaceutical composition comprising a compound of Formulas (I) to (IX), respectively, or a pharmaceutically acceptable salt thereof to a human in need thereof.

In another aspect, the present invention relates to a method for treating a gram-negative infection comprising administering a therapeutically effective amount of a pharmaceutical composition comprising a compound of Formulas (I) to (IX), respectively, or a pharmaceutically acceptable salt thereof to a human in need thereof.

In another aspect, the present invention relates to a method for inhibiting activity of UDP-3-O—(R-3-hydrydecanoyl)-N-acetylglucosamine deacetylase (LpxC) comprising administering a therapeutically effective amount of a compound of Formulas (I) to (IX), respectively, or a pharmaceutically acceptable salt thereof to a human in need thereof.

In another aspect, the present invention relates to a method for treating antimicrobial activity against Gram positive bacteria comprising administering a therapeutically effective amount of a compound of Formulas (I) to (IX), respectively, or a pharmaceutically acceptable salt thereof to a human in need thereof.

In another aspect, the present invention relates to a method for treating antimicrobial activity against Gram positive bacteria, where the Gram positive bacteria is selected from methicillin-resistant *Staphylococcus aureus* (MRSA) or penicillin-resistant *Streptococcus pneumoniae* (PRSP).

In another aspect, the present invention relates to a method for treating methicillin-resistant *Staphylococcus aureus* (MRSA), comprising administering a therapeutically effective amount of a pharmaceutical composition comprising a compound of Formulas (I) to (IX), respectively, or a pharmaceutically acceptable salt thereof to a human in need thereof.

In another aspect, the present invention relates to a method for treating penicillin-resistant *Streptococcus pneumoniae* (PRSP), comprising administering a therapeutically effective amount of a pharmaceutical composition comprising a compound of Formulas (I) to (IX), respectively, or a pharmaceutically acceptable salt thereof to a human in need thereof.

As used herein, "infectious disease" refers to any disease characterized by the presence of a microbial infection, such as a bacterial infection.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "effective amount" in reference to a compound of the invention means an amount of the compound sufficient to treat the patient's condition, but low enough to avoid serious side effects (at a reasonable benefit/risk ratio) within the scope of sound medical judgment. An effective amount of a compound will vary with the particular compound chosen (e.g., consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, and can be routinely determined by the skilled artisan.

Administration

Treatment regimen for the administration of compounds of Formulas (I) to (IX), respectively, or pharmaceutically acceptable salts thereof or corresponding pharmaceutical compositions of the present invention also may be determined readily by those with ordinary skill in art.

The quantity of the compound, pharmaceutical composition, or dosage form of the present invention administered may vary over a wide range to provide in a unit dosage in an effective amount based upon the body weight of the patient per day to achieve the desired effect and as based upon the mode of administration.

The scope of the present invention includes all compounds, pharmaceutical compositions, or controlled-release formulations or dosage forms, which is contained in an amount effective to achieve its intended purpose. While individual needs vary, determination of optimal ranges of effective amounts of each component is within the skill of the art.

Compounds of Formulas (I) to (IX), respectively, or pharmaceutically acceptable salts thereof or corresponding pharmaceutical compositions of the present invention may be administered by any suitable route of administration, including both systemic administration and topical administration. Systemic administration includes oral administration, parenteral administration, transdermal administration, rectal administration, and administration by inhalation.

Parenteral administration refers to routes of administration other than enteral, transdermal, or by inhalation, and is typically by injection or infusion. Parenteral administration includes intravenous, intramuscular, and subcutaneous injection or infusion.

Inhalation refers to administration into the patient's lungs whether inhaled through the mouth or through the nasal passages. In one aspect, pharmaceutical compositions, formulations, dosages, dosage forms or dosing regimens of the present invention are adapted for administration by inhalation.

Topical administration includes application to the skin as well as intraocular, intravaginal, and intranasal administration.

Compounds of Formulas (I) to (IX), respectively, or pharmaceutically acceptable salts thereof or corresponding pharmaceutical compositions of the present invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect.

Suitable dosing regimens for compounds of Formulas (I) to (IX), respectively, or pharmaceutically acceptable salts thereof or corresponding pharmaceutical compositions of the present invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient being treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to parenteral administration. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Typical daily dosages may vary depending upon the particular route of administration chosen. Typical daily dosages for oral administration, to a human weighing approximately 70 kg, would range from 7 mg to 7 g, suitably 3.5 mg to 3.5 g of a compound of the invention a day.

Compounds of Formulas (I) to (IX), respectively, or pharmaceutically acceptable salts thereof or corresponding pharmaceutical compositions of the present invention may be administered parenterally or orally as an injecting agent, capsules, tablets, and granules, and preferably, administered as an injecting agent. Amounts to be administered may usually be, per 1 kg of body weight of a patient or animal, about 0.1 to 100 mg/day, preferably, about 0.5 to 50 mg/day, if desired, divided into 2-4 times per day. Carriers when used as an injecting agent is for example, distilled water, saline and the like, and base and the like may be used for pH adjustment. When used as capsules, granules or tablets, carriers may be known excipients (e.g., starch, lactose, sucrose, calcium carbonate, calcium phosphate and the like), binders (e.g., starch, acacia gum, carboxymethyl cellulose, hydroxypropyl cellulose, crystalline cellulose, and the like), lubricants (e.g., magnesium stearate, talc and the like), and the like.

For all methods of use disclosed herein for the compounds of Formulas (I) to (IX), the daily oral dosage regimen will preferably be from about 0.05 to about 80 mg/kg of total body weight, preferably from about 0.1 to 30 mg/kg, more preferably from about 0.5 mg to 15 mg/kg, administered in one or more daily doses. For example, the daily parenteral dosage regimen about 0.1 to about 80 mg/kg of total body weight, preferably from about 0.2 to about 30 mg/kg, and more preferably from about 0.5 mg to 15 mg/kg, administered in one or more daily doses. The daily topical dosage regimen will preferably be from 0.01 mg to 150 mg, administered one to four times daily. The daily inhalation dosage regimen will preferably be from about 0.05 microgram/kg to about 5 mg/kg per day, or from about 0.2 microgram/kg to about 20 microgram/kg, administered in one or more daily doses.

It will also be recognized by one of skill in the art that the optimal quantity and spacing of individual dosages of a compound of Formulas (I) to (IX), respectively, or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formulas (I) to (IX), respectively, or a pharmaceutically acceptable salt thereof given per day for a defined number of days, can be ascertained by those skilled in the art using conventional course of treatment determination tests.

The amount of a compounds of Formulas (I) to (IX), respectively, or pharmaceutically acceptable salts thereof or corresponding pharmaceutical compositions of the present invention which is required to achieve a therapeutic effect will, of course, vary with the particular compound, the route of administration, the subject under treatment, and the particular disorder or disease being treated.

Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compounds of the present invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, particularly in bacterial infections. Thus, in a further aspect, the invention is directed to the use of a compound according to Formulas (I) to (IX), respectively, or a pharmaceutically-acceptable salt thereof in the preparation of a medicament for the treatment of bacterial infections.

Combination Therapies

Active drug or therapeutic agents, when employed in combination with the compounds, or pharmaceutical compositions of the present invention, may be used or administered, for example, in dosage amounts indicated in the Physicians' Desk Reference (PDR) or as otherwise determined by one of ordinary skill in the art.

In the context of this specification, the term "simultaneously" when referring to simultaneous administration of the relevant drugs means at exactly the same time, as would be the case, for example in embodiments where the drugs are combined in a single preparation. In other embodiments, "simultaneously" can mean one drug taken a short duration after another, wherein "a short duration" means a duration which allows the drugs to have their intended synergistic effect.

In light of the foregoing, the present invention also relates to a combination therapy, which may be a comprised of a simultaneous or co-administration, or serial administration of a combination of compounds or pharmaceutical compositions of the present invention with other active drug or therapeutic agents, such as described above, and where such administration also is determined by one of ordinary skill in the art.

In addition, the present invention also relates to a combination therapy for the treatment or prevention of repiratory tract or respiratory diseases as described herein, which is comprised of a composition, dosage form or formulation formed from a synergistic combination or mixture of compounds, controlled release compositions, dosage forms or formulations of the present invention and another active drug or therapeutic agent or agents as those described above and optionally which comprises pharmaceutically acceptable carrier, diluent or adjuvent. In such an aforementioned combination composition, dosage form or formulation of the present invention, each of the active drug components are contained in therapeutically effective and synergistic dosage amounts.

The Examples set forth below are illustrative of the present invention and are not intended to limit, in any way, the scope of the present invention.

EXAMPLES

The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

Biology and Biological Assays

As stated above, compounds according to Formulas (I) to (IX), respectively, or pharmaceutically acceptable salts thereof are UDP-3-O—(R-3-hydroxydecanoyl)-N-acetyl-glucosamine deacetylase (LpxC) inhibitors, which are useful in the treatment of bacterial infections. The biological activity of the compounds according to Formulas (I) and (IX), respectively, can be determined using suitable assays such as those measuring such inhibition and those evaluating the ability of the compounds to inhibit bacterial growth in vitro or in animal models of infection.

Antimicrobial Activity Assay

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically". In some cases, broth microdilution MICs were determined using IsoSensitest broth (Oxoid) in place of CLSI recommended cation adjusted Mueller-Hinton broth. The compounds were tested in serial two-fold dilutions ranging from 0.064 to 64 µg/ml in the presence of 20 uM human apo-Transferrin (Sigma T-1147).

Compounds were evaluated against Gram-negative organisms selected from *Escherichia coli, Pseudomonas aeruginosa, Proteus mirabilis, Enterobacter cloacae, Enterobacter aerogenes, Klebsiella pneumoniae, Stenotrophomonas maltophilia, Acinetobacter baumanii, Serratia marascens, Citrobacter freundii*, and *Klebsiella oxytoca*.

The minimum inhibitory concentration (MIC) was determined as the lowest concentration of compound that inhibited visible growth. A mirror reader was used to assist in determining the MIC endpoint.

Each of the listed Examples 1 to 56 and 59 to 61 identified in the present application, were tested in at least one exemplified salt or free base form. Unless otherwise noted, the tested the aforementioned examples each had a MIC≤2 µg/ml for at least one strain of one organism listed above. Examples 5 and 47 had a MIC≤8 µg/ml for at least one strain of one organism listed above.

General

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at ambient temperature.

All temperatures are given in degrees Celsius, all solvents are highest available purity and all reactions run under anhydrous conditions in an argon (Ar) or nitrogen ($N_2$) atmosphere where necessary.

$^1$H NMR (hereinafter also "NMR") spectra were recorded on Brucker AVANCE-400 spectrometers. $CDCl_3$ is deuteriochloroform, DMSO-$D_6$ is hexadeuteriodimethylsulfoxide, $D_2O$ is Deuterium oxide, and $CD_3OD$ is tetradeuteriomethanol. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on open access LC-MS systems, either a PE Sciex Single Quadrupole LC/MS API-150 or a Waters. The compound is analyzed using a reverse phase column, e.g., Xbridge-C18, Sunfire-C18, Thermo Aquasil/Aquasil C18, Acquity HPLC C18, Thermo Hypersil Gold eluted using an acetonitrile and water gradient with a low percentage of an acid modifier such as 0.02% TFA.

Analytical HPLC was run using an Agilent system (1100 series) with variable wavelength UV detection using Sunfire-C18 analytical columns and reverse phase chromatography with acetonitrile and water gradient with a 0.05 or 0.1% TFA modifier (added to each solvent). Preparative HPLC was performed using a Gilson Preparative System with variable wavelength UV detection and SunFire☐ C18 preparative columns. The compounds are eluted using a gradient of acetonitrile and water. Neutral conditions used an acetonitrile and water gradient with no additional modifier, acidic conditions used an acid modifier, usually 0.05% or 0.1% TFA (added to both the acetonitrile and water).

Flash chromatography was run using a Teledyne Isco Combiflash RF or Companion, with normal or reverse phase, disposable Redi-Sep flash columns, and a detector with UV wavelength at 254 nm and a variety of solvents or solvent combinations.

Heating of reaction mixtures with microwave irradiations was carried out on a Biotage Microwave.

Compound Examples

Compound Examples

Example 1

1-(((6R,7R)-7-((Z)-2-(((((S)-4-(tert-butoxy)-1-((4-methoxybenzyl)oxy)-1,4-dioxobutan-2-yl)oxy)imino)-2-(2-(((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium Example 1a (E)-2-chloro-3,4-dimethoxy-1-(2-nitrovinyl)benzene

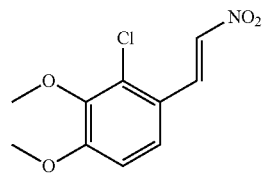 [SMILES: COc1ccc(/C=C/[N+](=O)[O-])c(Cl)c1OC]

The mixture of 2-chloro-3,4-dimethoxybenzaldehyde (5 g, 24.92 mmol) (Aldrich) and nitromethane (6.6 ml, 122 mmol) and ammonium acetate (1.921 g, 24.92 mmol) was reflux in glacial acetic acid (20 mL) for 4 h. Mixture was diluted with brine (300 ml) and extracted with ethyl acetate (2×150 ml), washed with water, dried over magnesium sulfate and evaporated to give (E)-2-chloro-3,4-dimethoxy-1-(2-nitrovinyl)benzene (6.07 g, 24.92 mmol, 100% yield). LCMS (M+H)+: 244.0

Example 1b 2-(2-Chloro-3,4-dimethoxyphenyl)ethanamine

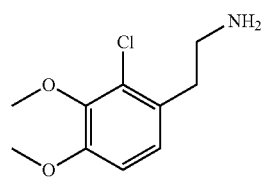

To tetrahydrofuran (THF) (60 mL) was added lithium aluminum hydride (1.822 g, 48.0 mmol) at 0° C. and aluminium chloride (6.40 g, 48.0 mmol) in tetrahydrofuran (THF) (80 mL) was added via syringe. The solution of (E)-2-chloro-3,4-dimethoxy-1-(2-nitrovinyl)benzene (5.85 g, 24 mmol) in tetrahydrofuran (THF) (100 mL) was added via addition funnel over 40 min. Stirred at rt for 16 h. Water (8 ml) was added dropwise followed by 5N hydrochloric acid (60 ml). The mixture was washed with ether (2×200 mL) and the aqueous phase was made basic with 6N sodium hydroxide. The aqueous layer was extracted with ether (3×200 mL). Dried over

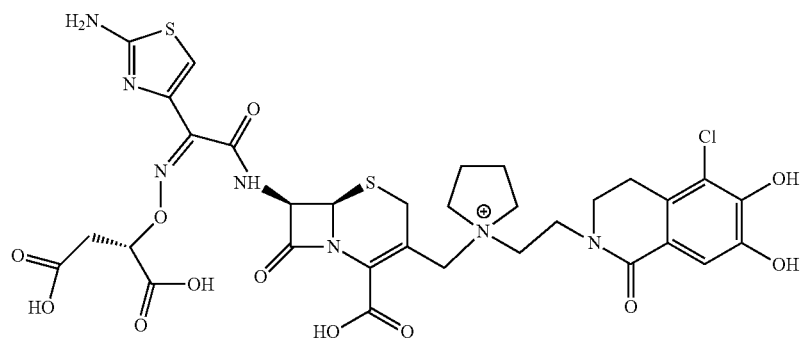

magnesium sulfate, evaporated to give 2-(2-chloro-3,4-dimethoxyphenyl)ethanamine (2.85 g, 13.21 mmol, 55.1% yield). LCMS (M+H)+: 216.0

Example 1c

Ethyl 2-chloro-3,4-dimethoxyphenethylcarbamate

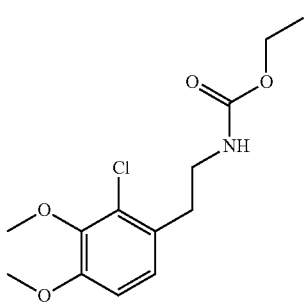 [SMILES: CCOC(=O)NCCc1ccc(OC)c(OC)c1Cl]

To the solution of 2-(2-chloro-3,4-dimethoxyphenyl)ethanamine (2.8 g, 12.98 mmol) in dichloromethane (DCM) (40 mL) at 0° C. was added triethylamine (1.990 mL, 14.28 mmol) and ethyl chloroformate (1.371 mL, 14.28 mmol). The reaction mixture was stirred at room temperature for 12 hours. The resulting mixture was washed with water, brine, dried over magnesium sulfate and chromatographed to give ethyl 2-chloro-3,4-dimethoxyphenethylcarbamate (1.7 g, 5.91 mmol, 97% yield). LCMS (M+H)+: 288.1

Example 1d

5-Chloro-6,7-dimethoxy-3,4-dihydroisoquinolin-1(2H)-one

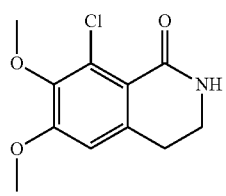 [SMILES: COc1cc2c(c(Cl)c1OC)C(=O)NCC2]

To ethyl 2-chloro-3,4-dimethoxyphenethylcarbamate 3 (2 g, 6.95 mmol) in 1,1,1,3,3,3-hexamethyldisiloxane (7.39 ml, 34.8 mmol) in a 20 ml microwave tube was added phosphorous oxichloride (6.48 ml, 69.5 mmol) and phosphorus pentoxide (4.93 g, 34.8 mmol). Microwaved at 150° C. (high absorption setting) for 1 hour. Solvent removed and poured on to the ice. Neutralized with 2M sodium hydroxide and extracted with dichloromethane. Dried over magnesium sulfate and chromotagraphed eluting with 0-20% methanol:dichloromethane to give 5-chloro-6,7-dimethoxy-3,4-dihydroisoquinolin-1(2H)-one (340 mg, 1.407 mmol, 20.24% yield).) LCMS (M+H)+: 242.1

Example 1e

5-Chloro-6,7-dihydroxy-3,4-dihydroisoquinolin-1(2H)-one

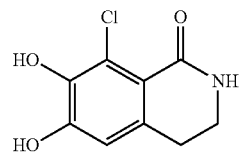 [SMILES: O=C1NCCc2cc(O)c(O)c(Cl)c21]

To the solution of 5-chloro-6,7-dimethoxy-3,4-dihydroisoquinolin-1(2H)-one (700 mg, 2.90 mmol) in dichloromethane (DCM) (2 mL) at −78° C. was added borontribromide (0.821 mL, 8.69 mmol). Mixture was allowed to warm up to room temperature and stirred at room temperature for 1 hour. Mixture was diluted with methanol and stripped several times to give 5-chloro-6,7-dihydroxy-3,4-dihydroisoquinolin-1(2H)-one (619 mg, 2.90 mmol, 100% yield) LCMS (M+H)+: 214.0

Example 1f

5-Chloro-6,7-bis((4-methoxybenzyl)oxy)-3,4-dihydroisoquinolin-1(2H)-one

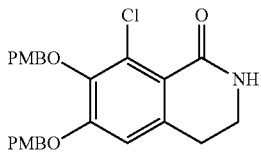

To the solution of 5-chloro-6,7-dihydroxy-3,4-dihydroisoquinolin-1(2H)-one (0.619 g, 2.9 mmol) in N,N-dimethylformamide (DMF) (10 mL) was added potassium carbonate (1.202 g, 8.70 mmol) followed by 1-(chloromethyl)-4-methoxybenzene (0.767 mL, 5.66 mmol). Stirred at room temperature for 4 hours. The mixture was extracted with ethyl acetate, washed with water, sodium chloride, and dried over magnesium sulfate. The crude mixture was chromatagraphed on silica ISCO column to give 5-chloro-6,7-bis((4-methoxybenzyl)oxy)-3,4-dihydroisoquinolin-1(2H)-one (1.017 g, 2.241 mmol, 77% yield). LCMS (M+H)+: 454.4

Example 1g

5-Chloro-6,7-bis((4-methoxybenzyl)oxy)-2-(2-(pyrrolidin-1-yl)ethyl)-3,4-dihydroisoquinolin-1(2H)-one

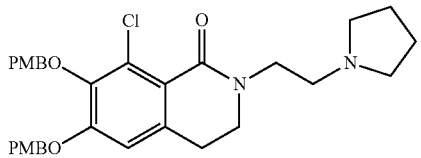

To the solution of 5-chloro-6,7-bis((4-methoxybenzyl)oxy)-3,4-dihydroisoquinolin-1(2H)-one (1.017 g, 2.241 mmol) in N,N-dimethylformamide (DMF) (10 ml) was added sodium hydride (0.179 g, 4.48 mmol). Stirred at rt for 10 min. 1-(2-Chloroethyl)pyrrolidine (0.329 g, 2.465 mmol) (first freed as free base with MP-carbonate resin) was added and the mixture was heated at 40° C. for 12 h. Mixture extracted with EtOAc, washed with water, NaCl, dried over magnesium sulfate. Chromatagraphed eluting with 0-10% methanol:dichloromethane to give 5-chloro-6,7-bis((4-methoxybenzyl) oxy)-2-(2-(pyrrolidin-1-yl)ethyl)-3,4-dihydroisoquinolin-1(2H)-one (420 mg, 0.762 mmol, 34.0% yield). LCMS (M+H)+: 551.0

Example 1h (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy) carbonyl)-5-oxido-8-oxo-5-thia-1-azabicyclo[4.2.0] oct-2-en-7-yl)amino)-2-oxoethylidene)amino)oxy) succinate

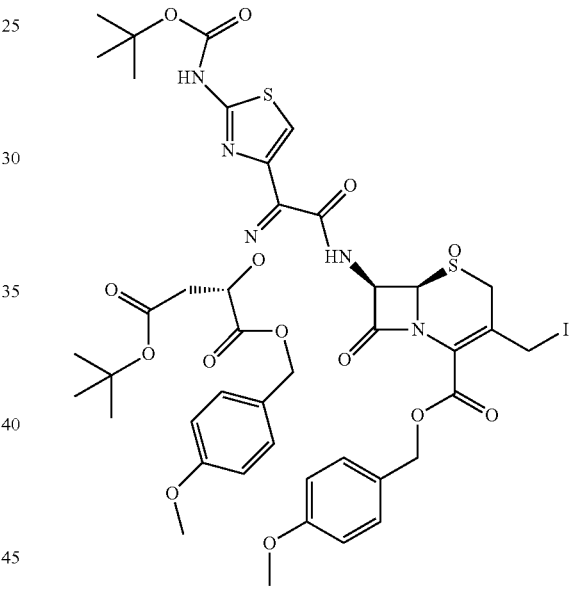

To the solution of (S)-4-tert-butyl 1-(4-methoxybenzyl) 2-(((Z)-(1-(2-((tert-butoxycarbonyl)amino)thiazol-4-yl)-2-(((5R,6R,7R)-3-(chloromethyl)-2-(((4-methoxybenzyl)oxy) carbonyl)-5-oxido-8-oxo-5-thia-1-azabicyclo[4.2.0]oct-2-en-7-yl)amino)-2-oxoethylidene)amino)oxy)succinate (1.183 g, 1.25 mmol) in acetone (50 mL) at room temperature was added sodium iodide (0.234 g, 1.563 mmol). The mixture stirred at room temperature for 2 hours. Filtered and evaporated to give (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy) carbonyl)-5-oxido-8-oxo-5-thia-1-azabicyclo[4.2.0]oct-2-en-7-yl)amino)-2-oxoethylidene)amino)oxy)succinate (1.1 g, 1.060 mmol, 85% yield). LCMS (M+H)+: 1038.9

Example 1i 1-((((6R,7R)-7-((Z)-2-(((((S)-4-(tert-butoxy)-1-((4-methoxybenzyl)oxy)-1,4-dioxobutan-2-yl)oxy)imino)-2-(2-(((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium

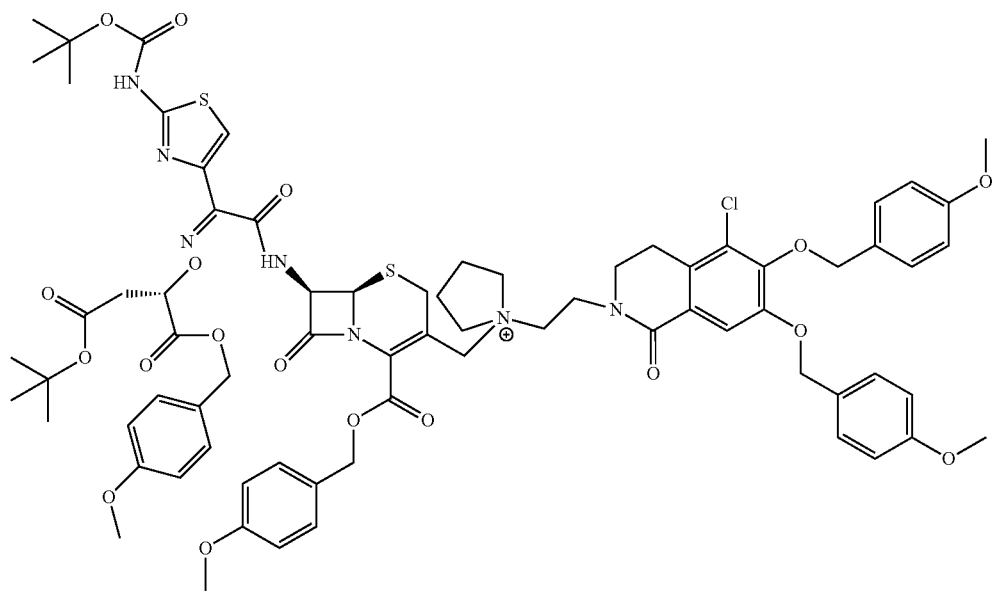 [SMILES: COc1ccc(COC(=O)[C@@H](O)CC(=O)OC(C)(C)C)cc1 ; COc1ccc(COC(=O)C2=C(C[N+]3(CCN4CCc5c(cc(OCc6ccc(OC)cc6)c(OCc6ccc(OC)cc6)c5Cl)C4=O)CCCC3)CS[C@@H]3[C@H](NC(=O)C(=N)c4csc(NC(=O)OC(C)(C)C)n4)C(=O)N23)cc1]

To the heat gun dried flask under nitrogen added 5-chloro-6,7-bis((4-methoxybenzyl)oxy)-2-(2-(pyrrolidin-1-yl)ethyl)-3,4-dihydroisoquinolin-1(2H)-one 7 (300 mg, 0.544 mmol) in N,N-dimethylacetamide (DMA) (10 mL) followed by (S)-4-tert-butyl 1-(4-methoxybenzyl) 2-(((Z)-(1-(2-(((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (565 mg, 0.544 mmol) in N,N-dimethylacetamide (DMA) (10 mL). The mixture was heated at 40° C. for 3 hours, and was then cooled and stored in refrigerator overnight. The mixture was cooled to −40° C. and N,N-dimethylformamide (DMF) (10 mL) was added followed by phosphorus tribromide (0.103 mL, 1.089 mmol) dropwise over 10 min. Stirred at −40° C. for 30 minutes. Poured into the cooled solution of 5% sodium chloride. The resulting solid was filtered and dried to give crude 1-((((6R,7R)-7-((Z)-2-(((((S)-4-(tert-butoxy)-1-((4-methoxybenzyl)oxy)-1,4-dioxobutan-2-yl)oxy)imino)-2-(2-(((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium (120 mg, 0.083 mmol, 15.24% yield). LCMS: (M+H)$^+$: 1447.5

Example 1j 1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium passed through plug of HP20ss on C18 ISCO column. Purified by Gilson HPLC (eluting with acetonitrile:water 0.1% trifluoroacetic acid). The acetonitrile evaporated. Resulting aqueous solution was basified to PH 6.0 with 0.2M sodium hydroxide. Lyophilized to give 1-(((6R,7R)-7-((Z)-2-(2-aminothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-6,7-dihydroxy-1-oxo-3,4-dihydroisoquinolin-2(1H)-yl)ethyl)pyrrolidin-1-ium, 2 Sodium salt (14 mg, 0.016 mmol, 13.37% yield). LCMS (M+H)$^+$: 809.5.

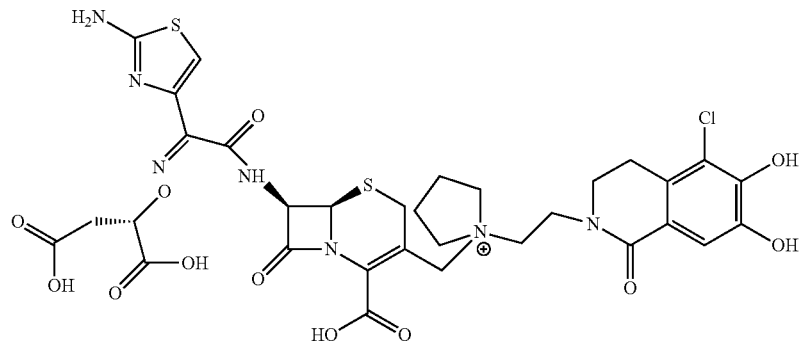 [SMILES: O=C(O)C[C@H](O)C(=O)O ; N=C(C(=O)N[C@@H]1C(=O)N2C(C(=O)O)=C(C[N+]3(CCN4CCc5c(cc(O)c(O)c5Cl)C4=O)CCCC3)CS[C@H]12)c1csc(N)n1]

To the solution of 1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium (170 mg, 0.118 mmol) in dichloromethane (DCM) (2 mL) was added anisole (0.385 mL, 3.53 mmol) followed by trifluoroacetic acid (0.543 mL, 7.05 mmol). Stirred at room temperature for 24 hours. Solvent removed and the mixture triturated with isopropyl ether. The resulting solid was filtered. The crude solid was dissolved in acetonitrile, water, hydrochloric acid. HP20ss resin was added and the mixture was concentrated to dryness. The compound absorbed on to the resin and $^1$H NMR (400 MHz, DEUTERIUM OXIDE) δ ppm 1.77-2.02 (m, 6 H) 2.12 (d, J=5.81 Hz, 4H) 2.48-2.73 (m, 3 H) 2.87 (br. s., 3 H)) 3.81 (br. s., 4 H) 3.92-4.03 (m, 2 H) 4.04 (br. s., 2 H) 4.78-4.90 (m, 3 H) 5.24 (d, J=4.55 Hz, 2 H) 5.73 (d, J=4.55 Hz, 2 H) 6.90 (s, 2H) 7.18 (br. s., 1 H)

Example 2

(6R,7R)-7-((Z)-2-(2-aminothiazol-4-yl)-2-(((S)-1,2-dicarboxyethoxy)imino)acetamido)-3-((1-(2-(5-hydroxy-1-methyl-4-oxo-1,4-dihydropyridine-2-carboxamido) ethyl)pyrrolidin-1-ium-1-yl)methyl)-8-oxo-5-thia-1-azabicyclo[4.2.0]oct-2-ene-2-carboxylate, 3 Sodium salt

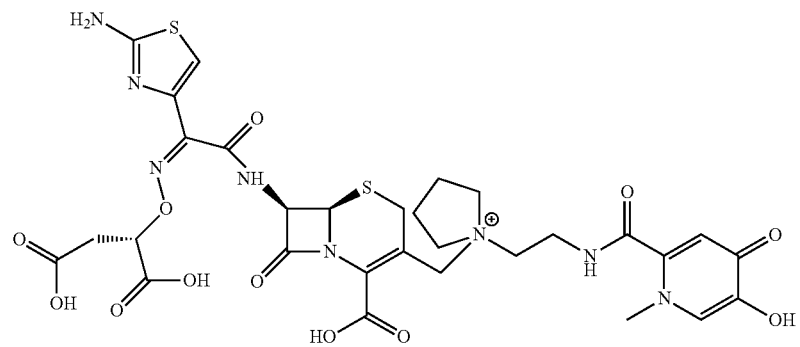 [SMILES: Cn1cc(O)c(=O)cc1C(=O)NCC[N+]1(CC2=C(C(=O)O)N3C(=O)[C@@H](NC(=O)/C(=N\O[C@@H](CC(=O)O)C(=O)O)c4csc(N)n4)[C@H]3SC2)CCCC1]

Example 2a 2-(hydroxymethyl)-5-((4-methoxybenzyl)oxy)-4H-pyran-4-one

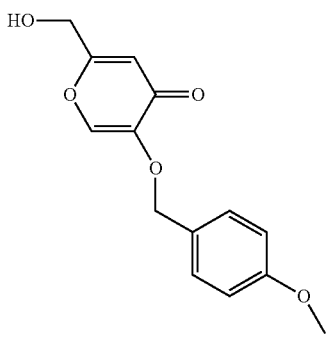 [SMILES: COc1ccc(COc2coc(CO)cc2=O)cc1]

To a solution of 5-hydroxy-2-(hydroxymethyl)-4H-pyran-4-one (13.35 g, 94 mmol) in N,N-dimethylformamide (160 ml) stirred under nitrogen at 0° C. was added a solution of potassium tert-butoxide (12.65 g, 113 mmol) in N,N-dimethylformamide (40.0 ml) dropwise over 10 min. The mixture was then stirred at room temperature for 90 minute and 4-methoxybenzyl chloride (15.5 ml, 114 mmol) was added dropwise over 15 min and allowed to stir at 50° C. for 3 days. The reaction was cooled and concentrated under vacuum. Water (400 mL) was added, the resulting precipitate was filtered, washed with water, collected and dried to afford 2-(hydroxymethyl)-5-((4-methoxybenzyl)oxy)-4H-pyran-4-one (18.17 g, 69.3 mmol, 73.8% yield) as tan solid. LCMS: $(M+H)^+$: 263.0

Example 2b 5-((4-methoxybenzyl)oxy)-4-oxo-4H-pyran-2-carboxylic acid

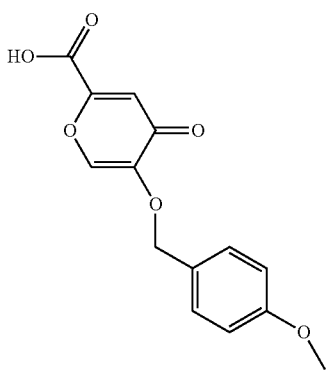 [SMILES: COc1ccc(COc2coc(C(=O)O)cc2=O)cc1]

To a solution of 2-(hydroxymethyl)-5-((4-methoxybenzyl)oxy)-4H-pyran-4-one (2.57 g, 9.80 mmol) in chloroform (45 ml) was added dimethyl sulfoxide (12 ml) and triethylamine (8.20 ml, 58.8 mmol). The mixture was cooled to 0° C., and sulfur trioxide, pyridine salt (3.96 ml, 49.0 mmol) was added. The mixture was allowed to warm to room temperature and stirred for 20 h. The resulting precipitate was filtered and washed with water. The filtrate was washed with water and the phases were separated. The organic layer was concentrated and combined with the precipitate. Water (20.0 ml), acetone (20.0 ml) and sulfamic acid (1.431 g, 14.74 mmol) were added, followed by sodium chlorite (1.332 g, 14.73 mmol) and the mixture was allowed to stir at room temperature for 70 h. The resulting precipitate was filtered, washed with water and acetone, and dried to give, 5-((4-methoxybenzyl)oxy)-4-oxo-4H-pyran-2-carboxylic acid (1.466 g, 5.31 mmol, 54.2% yield) as white solid. LCMS: $(M+Na)^+$: 299.0.

Example 2c 5-((4-methoxybenzyl)oxy)-1-methyl-4-oxo-1,4-dihydropyridine-2-carboxylic acid

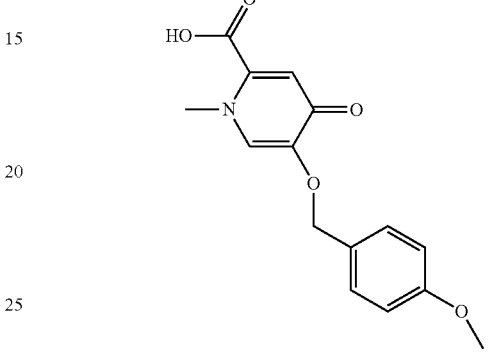

A mixture of 5-((4-methoxybenzyl)oxy)-4-oxo-4H-pyran-2-carboxylic acid (1.4627 g, 5.30 mmol) and methanamine (11.0 ml, 22.00 mmol) was stirred at room temperature for 20 h, The reaction was concentrated under reduced pressure, and the residue was dissolved in 15 mL of de-ionized water. The aqueous solution was cooled in an ice bath and treated dropwise with 2N hydrochloric acid (3.0 ml, 6.00 mmol). The resulting yellow solid was filtered, washed with water and acetone, and dried to give 5-((4-methoxybenzyl)oxy)-1-methyl-4-oxo-1,4-dihydropyridine-2-carboxylic acid (1.21 g, 4.18 mmol, 79% yield). LCMS: $(M+H)^+$: 290.1.

Example 2d 5-((4-methoxybenzyl)oxy)-1-methyl-4-oxo-N-(2-(pyrrolidin-1-yl)ethyl)-1,4-dihydropyridine-2-carboxamide

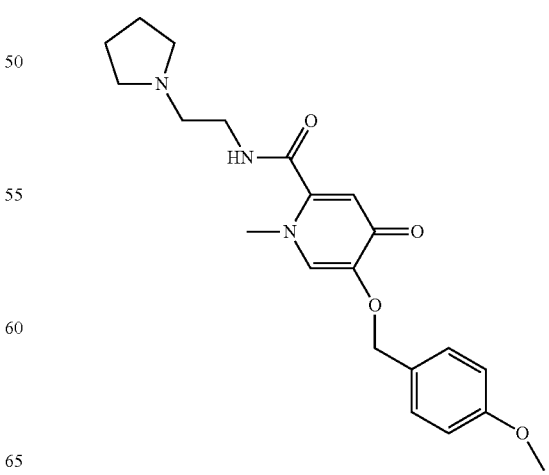

A mixture of 5-((4-methoxybenzyl)oxy)-1-methyl-4-oxo-1,4-dihydropyridine-2-carboxylic acid (1.21 g, 4.18 mmol), HATU (1.908 g, 5.02 mmol), diisopropylethyl amine (1.5 ml, 8.59 mmol) in N,N-dimethylformamide (15.0 ml) was stirred at room temperature for 30 min. at which time 2-(pyrrolidin-1-yl)ethanamine (0.58 ml, 4.61 mmol) was added and the reaction was allowed to stir for 3 h. The reaction was concentrated under vacuum, the residue was triturated with dichloromethane. The solid material was filtered and further washed with dichloromethane. The supernatant was collected, concentrated under reduced pressure and the residue was purified on silica gel eluting with methanol/dichloromethane/ammonium hydroxide. The fractions containing the desired product were concentrated, the residue was dissolved in dichloromethane, and washed with water. The organic phase was dried with anhydrous sodium sulfate, filtered, and concentrated to give 5-((4-methoxybenzyl)oxy)-1-methyl-4-oxo-N-(2-(pyrrolidin-1-yl)ethyl)-1,4-dihydropyridine-2-carboxamide (1.32 g, 3.42 mmol, 82% yield) as nearly white solid. LCMS: (M+H)$^+$: 386.2

Example 2e 1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-((4-methoxybenzyl)oxy)-1-methyl-4-oxo-1,4-dihydropyridine-2-carboxamido)ethyl)pyrrolidin-1-ium

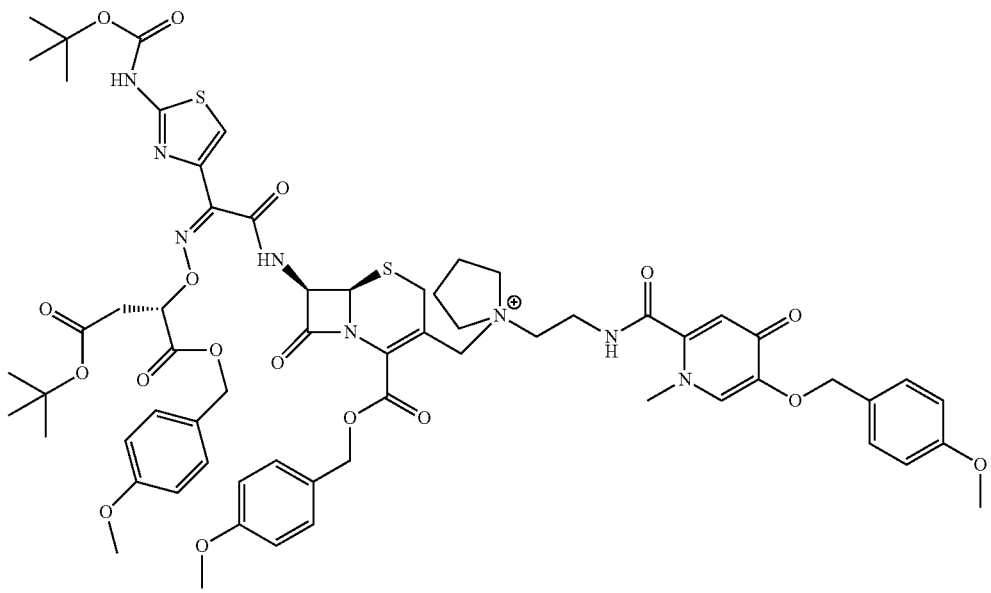 [SMILES: COc1ccc(COC(=O)C2=C(C[N+]3(CCNC(=O)c4cc(=O)c(OCc5ccc(OC)cc5)cn4C)CCCC3)CS[C@@H]3[C@H](NC(=O)/C(=N\O[C@@H](CC(=O)OC(C)(C)C)C(=O)OCc4ccc(OC)cc4)c4csc(NC(=O)OC(C)(C)C)n4)C(=O)N23)cc1]

To the solution of (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (Example 1h) (900 mg, 0.867 mmol) in N,N-dimethylacetamide (DMA) (20 mL) was added 5-((4-methoxybenzyl)oxy)-1-methyl-4-oxo-N-(2-(pyrrolidin-1-yl)ethyl)-1,4-dihydropyridine-2-carboxamide ((334 mg, 0.867 mmol). The mixture heated at 40° C. for 3 h, and was then coolled and stored in fridge overnight. The mixture was cooled to −40° C. and N,N-dimethylformamide (DMF) (20 mL) was added, followed by phosphorus tribromide (0.103 mL, 1.089 mmol) dropwise over 10 min. Stirred at −40° C. for 30 minutes. Poured into the coiled solution of 5% sodium chloride. The resulting solid filtered and dried to give crude 1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-((4-methoxybenzyl)oxy)-1-methyl-4-oxo-1,4-dihydropyridine-2-carboxamido)ethyl)pyrrolidin-1-ium (1110 mg, 0.867 mmol, 100% yield). Used in the next step without further purification. LCMS (M+H)$^+$: 1281.8

Example 2f (6R,7R)-7-((Z)-2-(2-aminothiazol-4-yl)-2-(((S)-1,2-dicarboxyethoxy)imino)acetamido)-3-((1-(2-(5-hydroxy-1-methyl-4-oxo-1,4-dihydropyridine-2-carboxamido)ethyl)pyrrolidin-1-ium-1-yl)methyl)-8-oxo-5-thia-1-azabicyclo[4.2.0]oct-2-ene-2-carboxylate, 3 Sodium salt

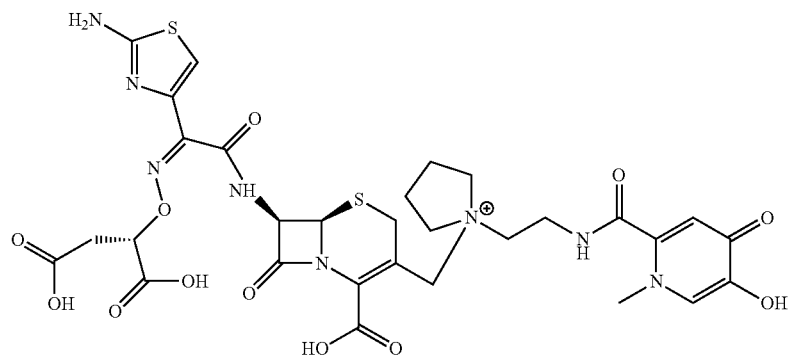 [SMILES: Cn1cc(O)c(=O)cc1C(=O)NCC[N+]1(CC2=C(C(=O)O)N3C(=O)[C@@H](NC(=O)/C(=N\O[C@@H](CC(=O)O)C(=O)O)c4csc(N)n4)[C@H]3SC2)CCCC1]

To the solution of 1-((((6R,7R)-7-((Z)-2-(((((S)-4-(tert-butoxy)-1-((4-methoxybenzyl)oxy)-1,4-dioxobutan-2-yl)oxy)imino)-2-(2-(((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-((4-methoxybenzyl)oxy)-1-methyl-4-oxo-1,4-dihydropyridine-2-carboxamido)ethyl)pyrrolidin-1-ium (1.1 g, 0.859 mmol) in dichloromethane (DCM) (20 mL) at 0° C. was added anisole (0.938 mL, 8.59 mmol) and trifloroacetic acid (1.324 mL, 17.18 mmol). The mixture was stirred at room temperature overnight. The solid was triturated with isopropyl ether and dissolved with acetonitrile, water, 2N hydrochloric acid. Compound was loaded onto HP20 resin and pased trough C18 ISCO column. Evaporated and the resulting aqueous solution was basified to PH 6.0 with 0.2M sodium hydroxide. Lyophilized to give (6R,7R)-7-((Z)-2-(2-aminothiazol-4-yl)-2-(((S)-1,2-dicarboxyethoxy)imino)acetamido)-3-((1-(2-(5-hydroxy-1-methyl-4-oxo-1,4-dihydropyridine-2-carboxamido)ethyl)pyrrolidin-1-ium-1-yl)methyl)-8-oxo-5-thia-1-azabicyclo[4.2.0]oct-2-ene-2-carboxylate, 3 Sodium salt (40 mg, 0.048 mmol, 5.60% yield). LCMS (M+H)$^+$: 763.3

$^1$H NMR (400 MHz, DEUTERIUM OXIDE) δ ppm 1.91-2.04 (m, 1 H) 2.14 (d, J=2.78 Hz, 3 H) 2.52-2.66 (m, 2 H) 2.80 (s, 1 H) 2.81-2.92 (m, 1 H) 2.96 (s, 1 H) 3.23-3.61 (m, 11 H) 3.61-3.78 (m, 4 H) 3.61-3.68 (m, 5 H) 3.75-3.90 (m, 2 H) 4.06 (d, J=−13.89 Hz, 1 H) 4.79-4.92 (m, 1 H) 5.25 (d, J=−4.55 Hz, 1 H) 5.72 (d, J=4.55 Hz, 1 H) 6.57 (s, 1 H) 6.90 (s, 1 H) 7.47 (s, 1 H)

Example 3

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate

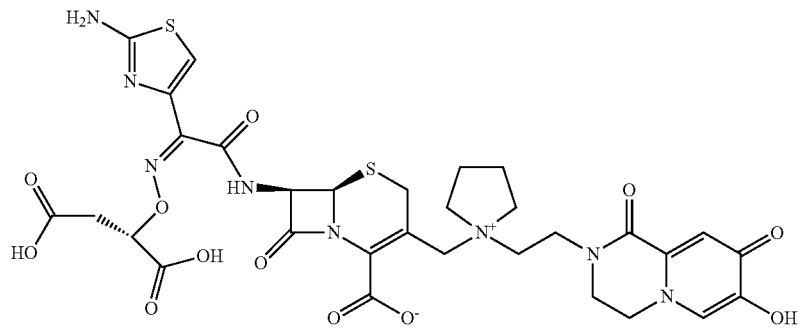 [SMILES: Nc1nc(/C(=N/O[C@@H](CC(=O)O)C(=O)O)C(=O)N[C@@H]2C(=O)N3C(C(=O)[O-])=C(C[N+]4(CCN5CCn6cc(O)c(=O)cc6C5=O)CCCC4)CS[C@H]23)cs1]

Example 3a 7-((4-methoxybenzyl)oxy)-3,4-dihydro-1H-pyrido[1,2-a]pyrazine-1,8(2H)-dione

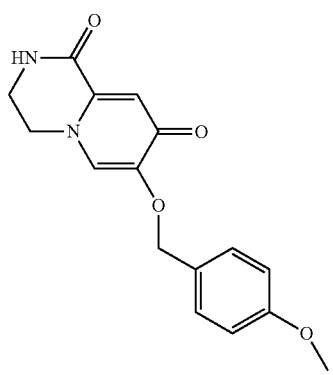 [SMILES: COc1ccc(COc2cn3c(cc2=O)C(=O)NCC3)cc1]

The mixture of 5-((4-methoxybenzyl)oxy)-4-oxo-4H-pyran-2-carboxylic acid (Example 2b) (5.24 g, 18.21 mmol), ethane-1,2-diamine (1.830 mL, 27.3 mmol) in water (80 mL) was stirred at 60° C. for 1 h and then 80° C. for 20 h. Yellow solid precipitated from the reaction when heating. After cooling, white precipitate was filtered off, washed with 20 mL of cold water/acetone (v:v=1:1) and dried to give 7-((4-methoxybenzyl)oxy)-3,4-dihydro-1H-pyrido[1,2-a]pyrazine-1,8(2H)-dione (4.15 g, 13.82 mmol, 76% yield) as white solid, which was used in the next step without further purification. LCMS (M+H)$^+$: 301.2

Example 3b 7-((4-methoxybenzyl)oxy)-2-(2-(pyrrolidin-1-yl)ethyl)-3,4-dihydro-1H-pyrido[1,2-a]pyrazine-1,8(2H)-dione

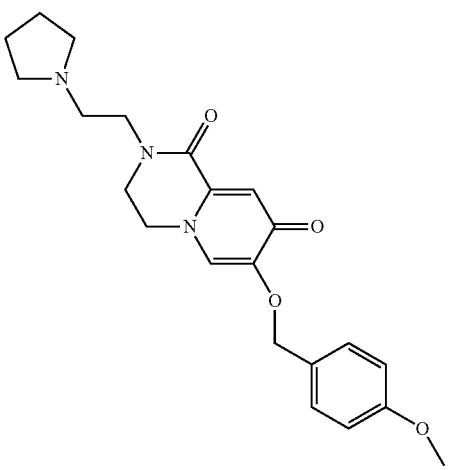 [SMILES: COc1ccc(COc2cn3c(cc2=O)C(=O)N(CCN2CCCC2)CC3)cc1]

To a solution of 7-((4-methoxybenzyl)oxy)-3,4-dihydro-1H-pyrido[1,2-a]pyrazine-1,8(2H)-dione (4.15 g, 13.82 mmol) in N,N-dimethylformamide (DMF) (50 mL) was added sodium hydride (1.382 g, 34.5 mmol) at 0° C., and the mixture was stirred at room temperature for 30 min. Then the mixture of 1-(2-chloroethyl)pyrrolidine, hydrochloride (Aldrich) (2.90 g, 17.03 mmol) and triethylamine (2.438 mL, 17.49 mmol) in N,N-dimethylformamide (DMF) (25.00 mL) was added. The reaction was stirred at 50° C. for 30 h. The solvent was evaporated and the residue was dissolved in water (50 mL) and extracted with dichloromethane (50 mL) three times. The organic phase was dried over anhydrous sodium sulfate, filtered and evaporated to afford light yellow crude product, which was then purified by normal phase automatic silica column chromatography (Combiflash RF), eluting with dichloromethane/methanol/ammonium hydroxide (v:v:v=80:20:2) over 16 min to afford 7-((4-methoxybenzyl)oxy)-2-(2-(pyrrolidin-1-yl)ethyl)-3,4-dihydro-1H-pyrido[1,2-a]pyrazine-1,8(2H)-dione (3 g, 7.55 mmol, 54.6% yield) as light yellow solid. LCMS (M+H)$^+$: 398.0.

Example 3c 1-(((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1 azabicyclo[4.2.0]oct-2-en-3-yl)methyl)-1-(2-(7-((4-methoxybenzyl)oxy)-1,8-dioxo-3,4-dihydro-1H-pyrido[1,2-a]pyrazin-2(8H)-yl)ethyl)pyrrolidin-1-ium, Iodide

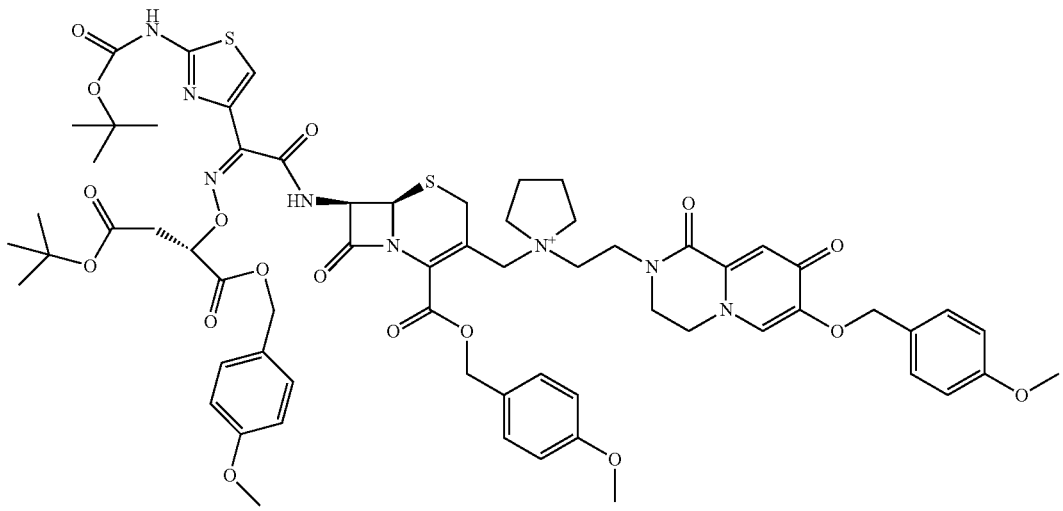 [SMILES: COc1ccc(COC(=O)C2=C(C[N+]3(CCN4CCn5cc(OCc6ccc(OC)cc6)c(=O)cc5C4=O)CCCC3)CS[C@@H]3[C@H](NC(=O)/C(=N\O[C@@H](CC(=O)OC(C)(C)C)C(=O)OCc4ccc(OC)cc4)c4csc(NC(=O)OC(C)(C)C)n4)C(=O)N23)cc1]

To the heat gun dried flask under nitrogen was added 7-((4-methoxybenzyl)oxy)-2-(2-(pyrrolidin-1-yl)ethyl)-3,4-dihydro-1H-pyrido[1,2-a]pyrazine-1,8(2H)-dione (700 mg, 1.761 mmol) in N,N-dimethylacetamide (DMA) (10 mL) followed by (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (Example 1h) (1828 mg, 1.761 mmol) in N,N-dimethylacetamide (DMA) (10 mL). Mixture was heated at 40° C. for 3 h. Cooled and stored in fridge overnight. The mixture was cooled to −40° C. and N,N-dimethylformamide (DMF) (10 mL) was added followed by phosphorus tribromide (0.332 mL, 3.52 mmol) dropwise over 10 min. Stirred at −40° C. for 30 min. Poured into the cooled solution of 5% sodium chloride. The resulting solid was filtered and dried to give crude 1-(((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(7-((4-methoxybenzyl)oxy)-1,8-dioxo-3,4-dihydro-1H-pyrido[1,2-a]pyrazin-2(8H)-yl)ethyl)pyrrolidin-1-ium, Iodide (2.6 g, 1.832 mmol, 104% yield). LCMS: (M+H)+: 1420.8

Example 3d (6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate

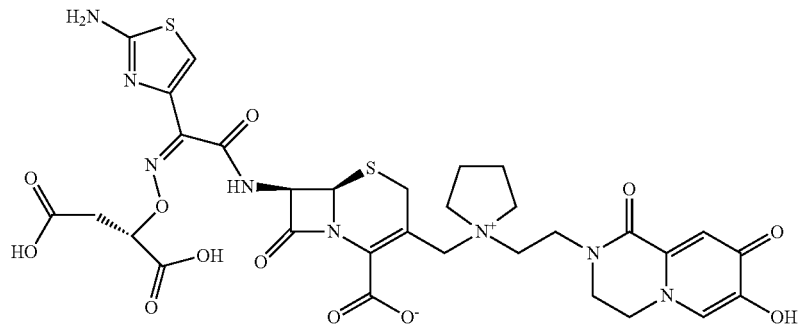 [SMILES: Nc1nc(/C(=N/O[C@@H](CC(=O)O)C(=O)O)C(=O)N[C@@H]2C(=O)N3C(C(=O)[O-])=C(C[N+]4(CCN5CCn6cc(O)c(=O)cc6C5=O)CCCC4)CS[C@H]23)cs1]

To a solution of 1-(((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(7-((4-methoxybenzyl)oxy)-1,8-dioxo-3,4-dihydro-1H-pyrido[1,2-a]pyrazin-2(8H)-yl)ethyl)pyrrolidin-1-ium (1.05 g, 0.812 mmol) in dichloromethane (15 mL) stirred under nitrogen at room temperature was added neat anisole (0.887 mL, 8.12 mmol) in one charge. The reaction mixture was stirred for one minute and trifluoroacetic acid (0.626 mL, 8.12 mmol) was then added. The reaction was allowed to stir at room temperature overnight and another 10 eq trifluoroacetic acid (0.626 mL, 8.12 mmol) was added and the reaction was allowed to stir for another 24 h. Diisopropyl ether (20 mL) and water (4 mL) were added and the suspension was allowed to stir for 5 min. then decanted off the supernate from the solid mass. The solid was dissolved in acetonitrile (10 mL), water (10 mL) and 2N hydrochloric acid (2.5 mL), absorbed onto HP20SS resin, and purified by dual HP20SS plug column and 26 g C18 column eluting with 0-20% acetonitrile in water. The fractions containing pure desired compound were collected and lyophilized to give (6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate (138 mg, 0.178 mmol, 21.92% yield) as an off white solid. LCMS: (M+H)$^+$: 775.4. $^1$H NMR (400 MHz, DEUTERIUM OXIDE) δ ppm 2.13 (br. s., 4 H) 2.54-2.71 (m, 2 H) 3.54 (br. s., 8 H) 3.74-3.87 (m, 8 H) 4.04 (br. s., 2 H) 4.27 (br. s., 2 H) 4.85 (br. s., 1 H) 5.23 (d, J=4.80 Hz, 1 H) 5.70 (d, J=4.80 Hz, 1 H) 6.90 (s, 1 H) 7.11 (s, 1 H) 7.57 (s, 1 H).

Example 4

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate, 2 Sodium salt The impure fractions of (6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate (Example 3) were absorbed onto HP20ss resin and purified using an HP20ss-C18 plug column followed by a 26 g C-18 column eluting with 0-20% acetonitrile in water. The fractions containing pure desired product were neutralized to pH 6 with 0.2 N sodium hydroxide. Quickly added a small cube of dry ice then frozen, lyophilized to give the desired product. Isolated (S)-2-(((Z)-(1-(2-aminothiazol-4-yl)-2-(((6R,7R)-2-carboxylato-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-en-7-yl)amino)-2-oxoethylidene)amino)oxy)succinate, 2 Sodium salt (45 mg, 0.055 mmol, 6.77% yield) as an off white solid. LCMS: (M+H)$^+$: 775.4. $^1$H NMR (400 MHz, DEUTERIUM OXIDE) δ ppm 2.11 (br. s, 4 H) 2.60-2.67 (m, 2 H) 3.32-3.65 (m, 9 H) 3.71-3.90 (m, 5 H) 4.05 (d, J=14.15 Hz, 2 H) 4.25 (br. s., 2 H) 4.84 (dd, J=8.59, 4.55 Hz, 1 H) 5.22 (d, J=4.80 Hz, 1 H) 5.69 (d, J=4.80 Hz, 1 H) 6.82-6.94 (m, 1 H) 7.10 (s, 1 H) 7.55 (s, 1 H).

Example 5

(6R,7R)-7-((Z)-2-(2-aminothiazol-4-yl)-2-(((S)-1,2-dicarboxyethoxy)imino)acetamido)-3-((1-((3-hydroxy-1-methyl-4-oxo-1,4-dihydroquinolin-6-yl)methyl)pyrrolidin-1-ium-1-yl)methyl)-8-oxo-5-thia-1-azabicyclo[4.2.0]oct-2-ene-2-carboxylate, 3 Sodium salt

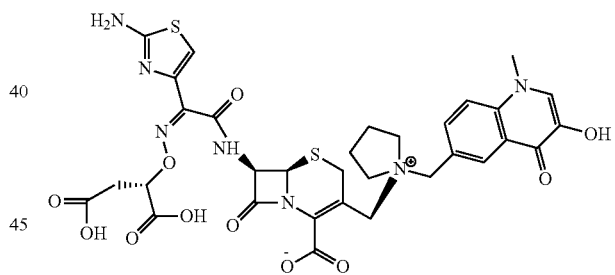

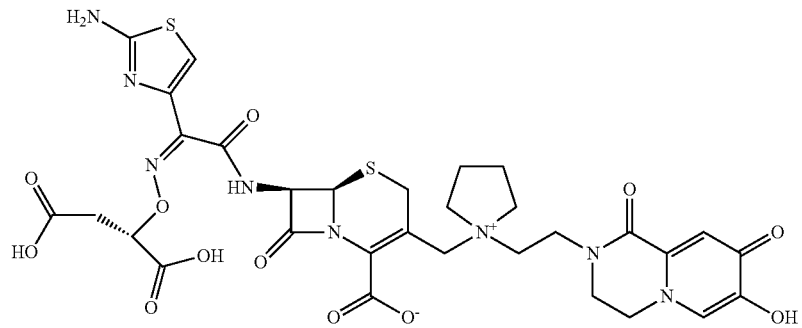 [SMILES: Nc1nc(/C(=N/O[C@@H](CC(=O)O)C(=O)O)C(=O)N[C@@H]2C(=O)N3C(C(=O)[O-])=C(C[N+]4(CCN5CCn6cc(O)c(=O)cc6C5=O)CCCC4)CS[C@H]23)cs1]

Example 5a

Ethyl 4-((2-(ethoxycarbonyl)-3-oxobut-1-en-1-yl)amino)benzoate

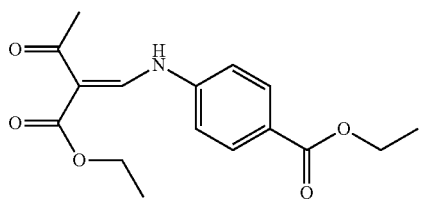 [SMILES: CCOC(=O)/C(=C/Nc1ccc(C(=O)OCC)cc1)C(C)=O]

To a solution of (Z/E)-ethyl 2-(ethoxymethylene)-3-oxobutanoate (4.95 g, 26.6 mmol) (commercially available from AK Scientific) in isopropanol (50 mL) was added ethyl 4-aminobenzoate (4.39 g, 26.6 mmol). The mixture was stirred at room temperature for 10 min, then heated to 65° C. and stirred for another 15 min. The reaction was allowed to cool and was then diluted with hexane. The suspension filtered, and the precipitate was washed with hexane, and dried to give ethyl 4-((2-(ethoxycarbonyl)-3-oxobut-1-en-1-yl)amino)benzoate (6.84 g, 22.40 mmol, 84% yield. LCMS: (M+H)$^+$: 306.0.

Example 5b

Ethyl 3-acetyl-4-oxo-1,4-dihydroquinoline-6-carboxylate

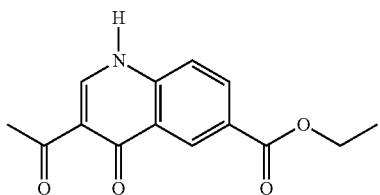 [SMILES: CCOC(=O)c1ccc2[nH]cc(C(C)=O)c(=O)c2c1]

Diphenyl ether (150 ml, 943 mmol) was heated to boiling and ethyl 4-((2-(ethoxycarbonyl)-3-oxobut-1-en-1-yl)amino)benzoate (6.84 g, 22.40 mmol) was added slowly. After the addition, the reaction was allowed to stir at 200-250° C. for another 30 min. After cooling, the reaction was diluted with hexane, filtered, and the precipitate was washed with hexane/diethyl ether, collected and dried to give ethyl 3-acetyl-4-oxo-1,4-dihydroquinoline-6-carboxylate (5.74 g, 22.14 mmol, 99% yield) as tan solid. LCMS: (M+H)$^+$: 260.0.

Example 5c

Ethyl 3-acetyl-1-methyl-4-oxo-1,4-dihydroquinoline-6-carboxylate

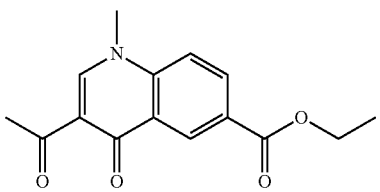 [SMILES: CCOC(=O)c1ccc2c(c1)c(=O)c(C(C)=O)cn2C]

To a suspension of ethyl 3-acetyl-4-oxo-1,4-dihydroquinoline-6-carboxylate (5.74 g, 22.14 mmol) in N,N-dimethylformamide (120 ml) was added potassium carbonate (9.18 g, 66.4 mmol) and methyl iodide (4.2 ml, 67.2 mmol). The mixture was stirred at 90° C. for 1 h. After cooling, the reaction was filtered, concentrated under high vacuum, diluted with dichloromethane/ethyl acetate, and filtered through a silica plug to afford ethyl 3-acetyl-1-methyl-4-oxo-1,4-dihydroquinoline-6-carboxylate (3.64 g, 13.32 mmol, 60.2% yield. LCMS: (M+H)$^+$: 274.0.

Example 5d

Ethyl 3-hydroxy-1-methyl-4-oxo-1,4-dihydroquinoline-6-carboxylate

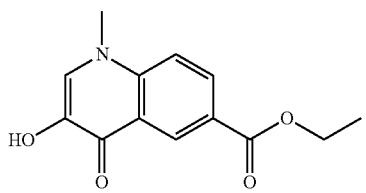 [SMILES: CCOC(=O)c1ccc2c(c1)c(=O)c(O)cn2C]

To a solution of ethyl 3-acetyl-1-methyl-4-oxo-1,4-dihydroquinoline-6-carboxylate (1.79 g, 6.55 mmol) in dichloromethane (40 ml) was added meta-chloroperbenzoic acid (2.2057 g, 9.84 mmol). The mixture was stirred at room temperature for 1 h, then concentrated under reduced pressure to roughly one half of the reaction volume. The resulting precipitate (O-acetate) was collected, added to methanol (20.0 ml), and heated at 65° C. overnight. After cooling, the reaction was filtered, and the precipitate was washed with dichloromethane to give ethyl 3-hydroxy-1-methyl-4-oxo-1, 4-dihydroquinoline-6-carboxylate (0.9956 g, 4.03 mmol, 61.5% yield) as white solid. LCMS: (M+H)$^+$: 248.0.

Example 5e 3-((4-methoxybenzyl)oxy)-1-methyl-4-oxo-1,4-dihydroquinoline-6-carboxylic acid

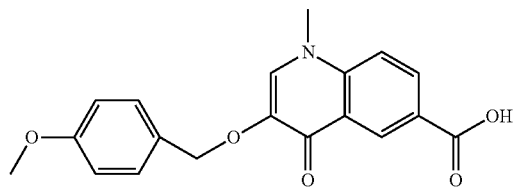 [SMILES: COc1ccc(COc2cn(C)c3ccc(C(=O)O)cc3c2=O)cc1]

To a suspension of ethyl 3-hydroxy-1-methyl-4-oxo-1,4-dihydroquinoline-6-carboxylate (6.7 g, 27.1 mmol) in N,N-dimethylformamide (18.0 ml) at 0° C. was added sodium hydride (2.168 g, 54.2 mmol), and the mixture was stirred for 20 min. At this time, 1-(chloromethyl)-4-methoxybenzene (3.7 ml, 27.3 mmol) was added and the reaction was heated to 75° C. and allowed to stir for 2 h. After cooling, the reaction was poured into ice, and the resulting precipitate was filtered, washed with water and diethyl ether, collected, and dried. Methanol (24.00 ml), water (8.00 ml) and lithium hydroxide (0.86 g, 35.9 mmol) were added, and the reaction was stirred at 60° C. for 2 h. The reaction was cooled and the pH was adjusted to 3-4 by addition of 2N hydrochloric acid (18.00 ml, 36 mmol). The resulting precipitate was filtered, washed with water and diethyl ether, and dried to give 3-((4-methoxybenzyl)oxy)-1-methyl-4-oxo-1,4-dihydroquinoline-6-carboxylic acid (6.1937 g, 18.25 mmol, 67.4% yield. LCMS: (M+H)$^+$: 340.1.

Example 5f 6-(Hydroxymethyl)-3-((4-methoxybenzyl)oxy)-1-methylquinolin-4(1H)-one

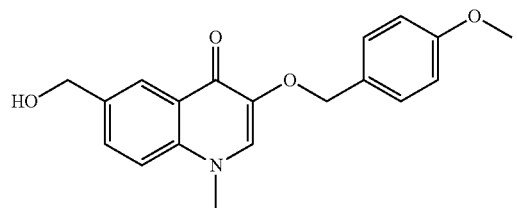 [SMILES: COc1ccc(COc2cn(C)c3ccc(CO)cc3c2=O)cc1]

To a suspension of 3-((4-methoxybenzyl)oxy)-1-methyl-4-oxo-1,4-dihydroquinoline-6-carboxylic acid (2.7 g, 7.96 mmol) in tetrahydrofuran (THF) (100 mL) was added triethylamine (3.88 mL, 27.8 mmol) and ethyl chloroformate (2.369 mL, 24.67 mmol). The resulting brown suspension was stirred at room temperature for 1.5 h. The crude carbonate solution was then added to a solution of sodium borohydride (3.61 g, 95 mmol) in ethanol (100 mL) at room temperature and the resulting mixture was stirred at room temperature, for 1.5 h.

The reaction was monitored by LCMS until completion. The reaction was quenched by addition of water (20 mL) and the organic volatiles were removed in vacuo. The residue was then diluted with water (100 mL) and extracted with dichloromethane (2×100 mL). The combined extracts were washed with water (4×15 mL), dried over sodium sulfate, filtered and concentrated in vacuo. The residue was purified by automatic silica gel column chromatography (Combiflash RF) eluting with methanol in dichloromethane (0-5%) to afford 6-(hydroxymethyl)-3-((4-methoxybenzyl)oxy)-1-methylquinolin-4(1H)-one (1.7 g, 4.81 mmol, 60.4% yield) as a light brown solid. LCMS: (M+H)$^+$: 326.3.

Example 5g 3-((4-methoxybenzyl)oxy)-1-methyl-4-oxo-1,4-dihydroquinoline-6-carbaldehyde

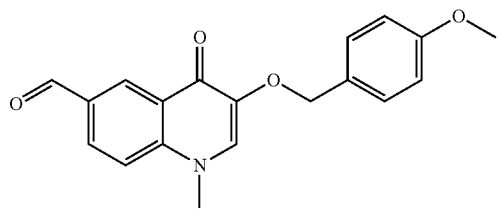 [SMILES: COc1ccc(COc2cn(C)c3ccc(C=O)cc3c2=O)cc1]

To a suspension of 6-(hydroxymethyl)-3-((4-methoxybenzyl)oxy)-1-methylquinolin-4(1H)-one (1.5 g, 4.61 mmol) in dichloromethane (DCM) (80 mL) at room temperature was added Dess-Martin periodinane (2.347 g, 5.53 mmol). The reaction mixture soon turned into a clear brown solution and was stirred at room temperature for 1 h. Saturated sodium bicarbonate solution was then added, and the mixture was extracted with dichloromethane. The combined organic layers were washed with brine, dried over sodium sulfate, filtered, and concentrated in vacuo. The residue was purified by automatic silica gel column chromatography (Combiflash RF) eluting with ethyl acetate/hexanes (0-100%) to afford 3-((4-methoxybenzyl)oxy)-1-methyl-4-oxo-1,4-dihydroquinoline-6-carbaldehyde (1.1 g, 3.40 mmol, 73.8% yield) as a yellow solid. LCMS: (M+H)$^+$: 324.0

Example 5h 3-((4-Methoxybenzyl)oxy)-1-methyl-6-(pyrrolidin-1-ylmethyl)quinolin-4(H)-one

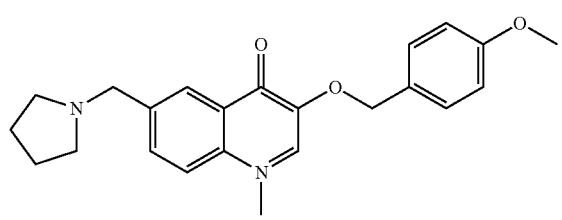

A solution of pyrrolidine (0.295 mL, 3.57 mmol) and 3-((4-methoxybenzyl)oxy)-1-methyl-4-oxo-1,4-dihydroquinoline-6-carbaldehyde (1.05 g, 3.25 mmol) in 1,2-dichloroethane (DCE) (50 mL) and 1 drop of acetic acid was treated with sodium triacetoxyborohydride (1.032 g, 4.87 mmol). The reaction mixture was stirred for 1.5 h, and was then concentrated under vacuum. The residue was taken in water (50 mL), and extracted with dichloromethane (2×50 mL). The organic layers were combined, washed with brine (50 mL), dried over sodium sulfate, and concentrated. The crude product was purified twice by automatic silica gel column chromatography (Combiflash RF), eluting with a mixture of [dichloromethane/methanol/ammonium hydroxide (80:20:2)]/dichlormethane (0-40%) to afford pure 3-((4-methoxybenzyl)oxy)-1-methyl-6-(pyrrolidin-1-ylmethyl)quinolin-4(1H)-one (1 g, 2.64 mmol, 81% yield) as a light yellow solid. LCMS: $(M+H)^+$: 379.5.

Example 5i 1-((((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((3-((4-methoxybenzyl)oxy)-1-methyl-4-oxo-1,4-dihydroquinolin-6-yl)methyl)pyrrolidin-1-ium

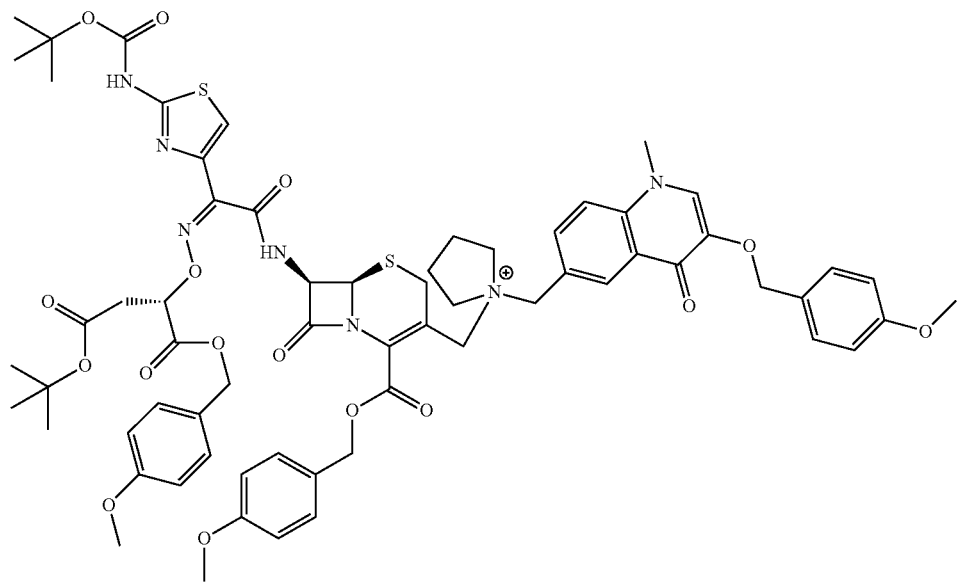 [SMILES: COc1ccc(COC(=O)C2=C(C[N+]3(Cc4ccc5c(c4)c(=O)c(OCc4ccc(OC)cc4)cn5C)CCCC3)CS[C@@H]3[C@H](NC(=O)/C(=N\O[C@@H](CC(=O)OC(C)(C)C)C(=O)OCc4ccc(OC)cc4)c4csc(NC(=O)OC(C)(C)C)n4)C(=O)N23)cc1]

To the heat gun dried flask under nitrogen was added 3-((4-methoxybenzyl)oxy)-1-methyl-6-(pyrrolidin-1-ylmethyl)quinolin-4(1H)-one (530 mg, 1.400 mmol) in N,N-dimethylacetamide (DMA) (10 mL) followed by (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (Example 1h) (1453 mg, 1.400 mmol) in N,N-dimethylacetamide (DMA) (10 mL). The mixture was heated at 40° C. for 3 h. Cooled and stored in the fridge overnight. The mixture was cooled to −40° C. and N,N-dimethylformamide (DMF) (10 mL) was added, followed by phosphorus tribromide (0.264 mL, 2.80 mmol) dropwise over 10 min. Stirred at −40° C. for 30 min. Poured into the cooled solution of 5% sodium chloride. The resulting solid filtered and dried. Chromatographed on ISCO silica gel column eluting with 0-20% methanol:dichloromethane to give 1-((((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-aza bicyclo[4.2.0]oct-2-en-3-yl)methyl)-1-((3-((4-methoxybenzyl)

oxy)-1-methyl-4-oxo-1,4-dihydroquinolin-6-yl)methyl) pyrrolidin-1-ium (400 mg, 0.314 mmol, 22% yield). LCMS: (M+H)+: 1274.8

Example 5j (6R,7R)-7-((Z)-2-(2-aminothiazol-4-yl)-2-(((S)-1,2-dicarboxyethoxy)imino)acetamido)-3-((1-((3-hydroxy-1-methyl-4-oxo-1,4-dihydroquinolin-6-yl)methyl)pyrrolidin-1-ium-1-yl)methyl)-8-oxo-5-thia-1-azabicyclo[4.2.0]oct-2-ene-2-carboxylate, 3 Sodium salt

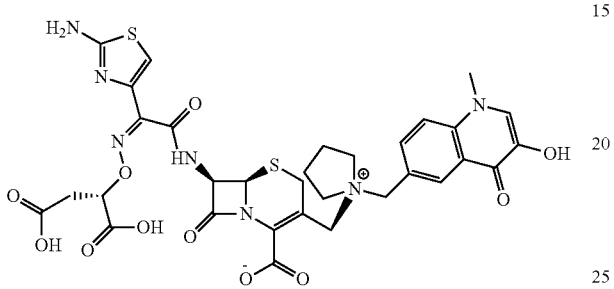

To the solution of 1-((((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((3-((4-methoxybenzyl)oxy)-1-methyl-4-oxo-1,4-dihydroquinolin-6-yl)methyl)pyrrolidin-1-ium (400 mg, 0.314 mmol) in Dichloromethane (DCM) (5 mL) was added anisole (0.343 mL, 3.14 mmol), followed by trifluoroacetic acid (1.210 mL, 15.71 mmol). The resulting mixture was stirred at room temperature for 18 h. Resulting mixture was triturated with isopropyl ether and filtered. The solid was redissolved in acetonitrile (2 mL), water (1 mL) plus 2 drops of hydrochloric acid. Loaded on to HP20ss resin and passed through HP20ss resin column. Evaporated the acetonitrile. Resulting aqueous solution was basified to PH 6.0 with 0.2M sodium hydroxide. Lyophilized to give (6R,7R)-7-((Z)-2-(2-aminothiazol-4-yl)-2-(((S)-1,2-dicarboxyethoxy)imino)acetamido)-3-((1-((3-hydroxy-1-methyl-4-oxo-1,4-dihydroquinolin-6-yl)methyl)pyrrolidin-1-ium-1-yl)methyl)-8-oxo-5-thia-1-azabicyclo[4.2.0]oct-2-ene-2-carboxylate, tri sodium salt (185 mg, 0.224 mmol, 71.4% yield). LCMS: (M+H)+: 756.4

1H NMR (400 MHz, DEUTERIUM OXIDE) δ ppm 0.98-1.04 (m, 1 H) 1.95 (br. s., 4 H) 2.07 (d. J=5.05 Hz, 3 H) 2.53-2.64 (m, 3 H) 3.22 (br. s., 1 H) 3.29-3.40 (m, 5 H) 3.40-3.48 (m, 2 H) 3.42-3.57 (m, 3 H) 3.75-3.86 (m, 3 H) 3.85-3.95 (m, 5 H) 4.08 (d, J=13.89 Hz, 2 H) 4.44-4.66 (m, 3 H) 4.79-4.94 (m, 2 H) 5.19-5.25 (m, 1 H) 5.72 (d, J=4.80 Hz, 1 H) 6.81-6.92 (m, 1 H) 7.74 (s, 2 H) 7.92 (s, 1 H) 8.29 (s, 1 H)

Example 6

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium

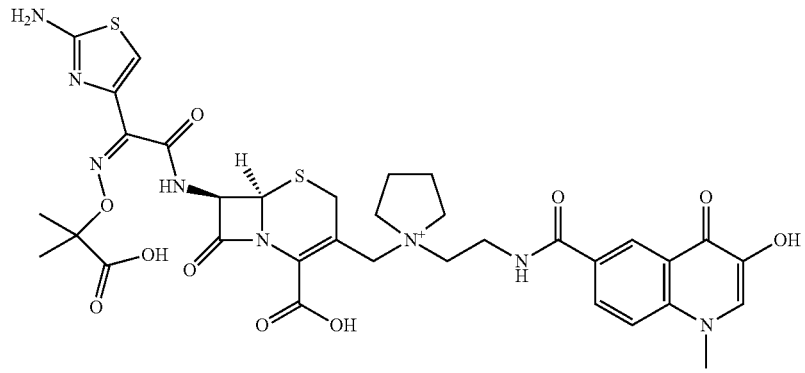 [SMILES: Cn1cc(O)c(=O)c2cc(C(=O)NCC[N+]3(CC4=C(C(=O)O)N5C(=O)[C@@H](NC(=O)/C(=N\OC(C)(C)C(=O)O)c6csc(N)n6)[C@H]5SC4)CCCC3)ccc21]

Example 6a 3-((4-methoxybenzyl)oxy)-1-methyl-4-oxo-N-(2-(pyrrolidin-1-yl)ethyl)-1,4-dihydroquinoline-6-carboxamide

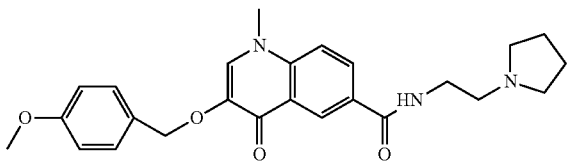 [SMILES: COc1ccc(COc2cn(C)c3ccc(C(=O)NCCN4CCCC4)cc3c2=O)cc1]

To a suspension of 3-((4-methoxybenzyl)oxy)-1-methyl-4-oxo-1,4-dihydroquinoline-6-carboxylic acid (Example 5e) (0.588 g, 1.733 mmol), 2-(pyrrolidin-1-yl)ethanamine (0.240 ml, 1.906 mmol), EDC (0.3865 g, 2.016 mmol), HOAt (0.1218 g, 0.895 mmol) in dichloromethane (16 ml) was added triethylamine (1.7 ml, 12.20 mmol), and the mixture was allowed to stir at 30° C. for 24 h. After cooling, the reaction was concentrated and the residue was purified on a silica gel column (24 g), eluting with 0-20% methanol/dichloroethane (2% ammonium hydroxide). The desired fractions were collected, concentrated. The solid was washed with water, filtered, and dried in vacuo to afford 3-((4-methoxybenzyl)oxy)-1-methyl-4-oxo-N-(2-(pyrrolidin-1-yl)ethyl)-1,4-dihydroquinoline-6-carboxamide (0.595 g, 1.366 mmol, 79% yield) as white solid. LCMS: (M+H)+: 436.2.

Example 6b 6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate

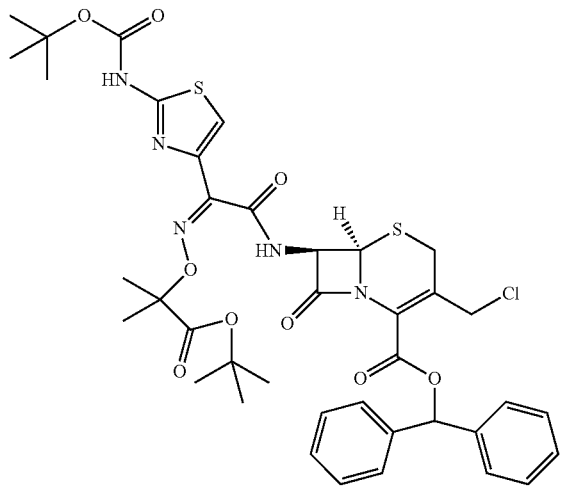 [SMILES: CC(C)(C)OC(=O)Nc1nc(/C(=N/OC(C)(C)C(=O)OC(C)(C)C)C(=O)N[C@@H]2C(=O)N3C(C(=O)OC(c4ccccc4)c4ccccc4)=C(CCl)CS[C@H]23)cs1]

To a solution of (Z)-2-(((1-(tert-butoxy)-2-methyl-1-oxopropan-2-yl)oxy)imino)-2-(2-((tert-butoxycarbonyl)amino)thiazol-4-yl)acetic acid (30.5 g, 71.0 mmol) and (6R,7R)-benzhydryl 7-amino-3-(chloromethyl)-8-oxo-5-thia-1-azabicyclo[4.2.0]oct-2-ene-2-carboxylate, hydrochloride (32.1 g, 71.0 mmol) in dichloromethane (500 mL), stirred under nitrogen at −30° C., was added neat phenyl phosphorodichloridate (12.93 mL, 85 mmol). The reaction mixture was cooled to −40° C. and N-methylmorpholine (23.42 mL, 213 mmol) was added dropwise over 30 min, and stirred for an additional 2 hours at −40° C. The reaction was then quenched by addition of 150 mL of a 10% aq. solution of citric acid, and the phases were separated. The organic phase was concentrated and the residue was then dissolved in 500 mL of ethyl acetate. The organic solution was washed with 100 mL of a 5% aq. sodium bicarbonate, 100 mL of brine, dried over sodium sulfate, concentrated under reduced pressure, and the residue was purified on a 330 g silica gel column eluting with 0-80% ethyl acetate in hexanes to afford (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate (42 g, 50.8 mmol, 71.6% yield). 1H NMR (400 MHz, CHLOROFORM-d) δ ppm 1.42 (s, 9 H) 1.55 (s, 9 H) 1.63 (s, 3 H) 1.66 (s, 3 H) 3.52 (d, J=18.19 Hz, 1 H) 3.66 (d, J=18.19 Hz, 1 H) 4.43 (d, J=4.29 Hz, 2 H) 5.12 (d, J=5.05 Hz, 1 H) 6.08 (dd. J=8.84, 5.05 Hz, 1 H) 6.99 (s, 1 H) 7.30-7.49 (m, 12 H) 8.25 (d, J=8.84 Hz, 1 H). LCMS: (M+H)+: 826.5.

Example 6c (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate 5-oxide

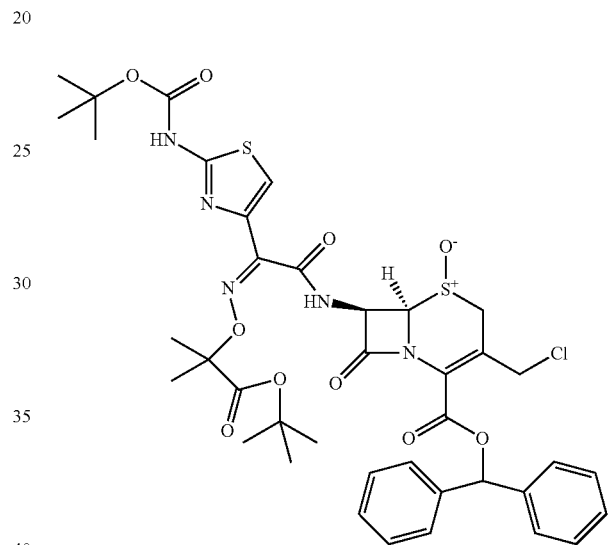

To a solution of (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate (3 g, 3.63 mmol) in dichloromethane (DCM) (100 mL) at −40° C. was added dropwise a solution of 3-chlorobenzoperoxoic acid (0.976 g, 4.36 mmol) in dichloromethane 20 mL) over 1 min. The mixture was stirred at the same temperature over 30 min. LCMS indicated completion of the reaction. Dichloromethane (60 mL) was added and the mixture was treated with 15% aqueous sodium thiosulfate (40 mL). The organic solution was separated and washed with 5% sodium bicarbonate (80 mL), brine (80 mL), dried over sodium sulfate, and concentrated. The residue was purified by ISCO automated silica gel chromatography (120 g column, 0-50% ethyl acetate/hexanes) to afford (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo

[4.2.0]oct-2-ene-2-carboxylate 5-oxide (2.44 g, 2.90 mmol, 53.2% yield) as a white solid. LCMS: (M+H)+: 842.2.

Example 6d (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide To a solution of (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate 5-oxide (2.68 g, 3.18 mmol) in acetone (40 mL) was added sodium iodide (0.715 g, 4.77 mmol). The mixture was stirred at room temperature over 3 h. LCMS indicated completion of the reaction. The solid was filtered off, the filtrate was concentrated under vacuum to afford (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (2.97 g, 3.18 mmol, 100% yield) as a dark red solid. LCMS: (M+H)+: 934.0.

Example 6e 1-(((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-6-carboxamido)ethyl)pyrrolidin-1-ium

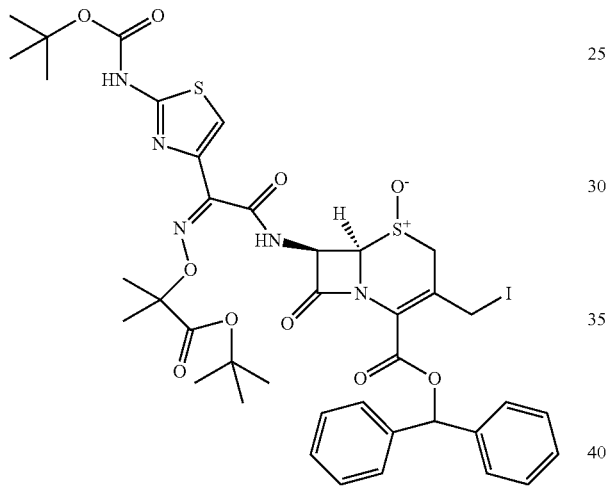

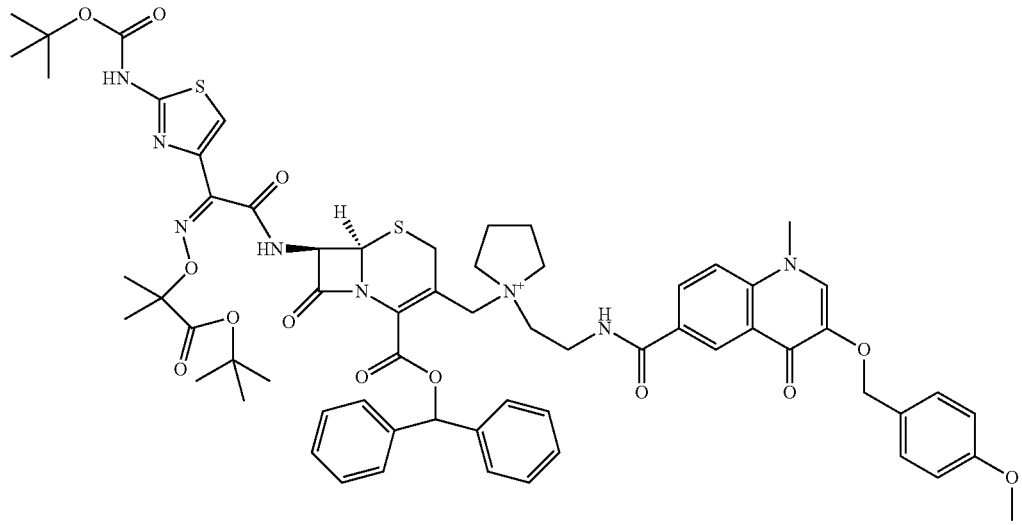 [SMILES: COc1ccc(COc2cn(C)c3ccc(C(=O)NCC[N+]4(CC5=C(C(=O)OC(c6ccccc6)c6ccccc6)N6C(=O)[C@@H](NC(=O)/C(=N\OC(C)(C)C(=O)OC(C)(C)C)c7csc(NC(=O)OC(C)(C)C)n7)[C@H]6SC5)CCCC4)cc3c2=O)cc1]

To a solution of 3-((4-methoxybenzyl)oxy)-1-methyl-4-oxo-N-(2-(pyrrolidin-1-yl)ethyl)-1,4-dihydroquinoline-6-carboxamide (Example 6a) (200 mg, 0.459 mmol) in N,N-dimethylacetamide (8 mL) stirred under nitrogen at room temperature was added solid (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (429 mg, 0.459 mmol) in one charge, and the reaction mixture was stirred at room temperature overnight. The reaction was diluted with N,N-dimethylformamide (16.00 mL), cooled to −60° C., and 1.1 eq (50 uL) phossphorous tribromide was added, and the reaction was allowed to warm to −40° C. LCMS showed little sulfoxide reduction so the reaction was again cooled to −60° C. and 3.3 eq PBr$_3$ (0.145 mL, 1.010 mmol) was added, and the reaction was allowed to warm to −40° C. The reaction was poured into 60 mL of a 5% sodium cloride solution at 0° C. and allowed to stir for approximately 15 min. The insoluble material was collected by filtration and the solid was placed under high vacuum on a lyophilizer. The crude 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-6-carboxamido)ethyl)pyrrolidin-1-ium was used without further purification. Isolated approximately 600 mg of crude material of unknown purity. LCMS: (M+H)$^+$: 1226.2.

Example 6f 1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium To 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-6-carboxamido)ethyl)pyrrolidin-1-ium (250 mg, 0.204 mmol) in dichloromethane at room temperature was added anisole (0.223 mL, 2.038 mmol) followed by trifluoroacetic acid (0.236 mL, 3.06 mmol). The reaction was allowed to stir under nitrogen for another 24 h at which time the reaction appeared to be completed. Added 10 mL diisopropyl ether and 2 mL of water and let stir at room temperature for 5 min. The solution was decanted away from the solid mass, which was then dissolved in water (5 mL), acetonitrile (5 mL), and 2N HCl (1 mL). Isopropanol (5 mL) was then added, the biphasic mixture was separated and the aqueous phase was treated with HP-20SS resin. This suspension was concentrated under vacuum and then purified on an HP20SS plug column followed by 26 g C-18 column. The fractions which contained desired product were concentrated to remove the acetonitrile and lyophilized to give 1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium (40 mg, 0.051 mmol, 25.03% yield) as an off white solid. LCMS: (M+H)$^+$: 783.5. $^1$H NMR (400 MHz, DEUTERIUM OXIDE) δ ppm 1.45 (s, 3 H), 1.46 (s, 3 H), 2.09 (br. s., 1 H) 3.48-3.67 (m, 7 H) 3.87 (s, 3 H), 3.89-4.0 (m, 2 H), 5.23 (d, J=4.55 Hz, 1 H) 6.73 (s, 1 H) 7.32 (s, 2 H) 7.76 (d, J=9.09 Hz, 1 H) 7.92 (s, 1 H) 8.10-8.17 (m, 1 H) 8.70 (br. s., 1 H) 8.79 (d, J=1.77 Hz, 1 H) 9.09 (br. s., 1 H) 9.47 (d. J=8.08 Hz, 1 H).

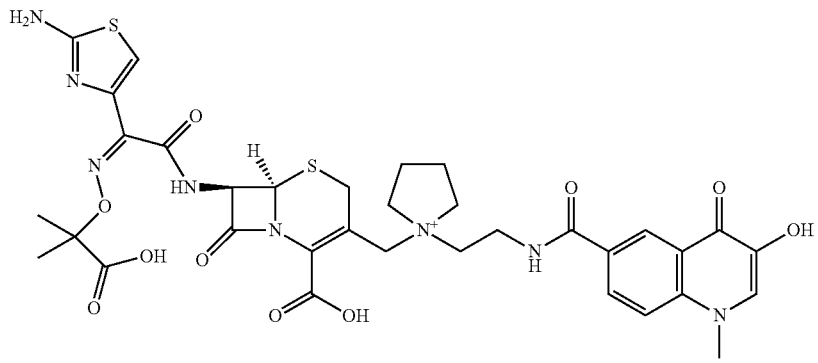 [SMILES: Cn1cc(O)c(=O)c2cc(C(=O)NCC[N+]3(CC4=C(C(=O)O)N5C(=O)[C@@H](NC(=O)/C(=N\OC(C)(C)C(=O)O)c6csc(N)n6)[C@H]5SC4)CCCC3)ccc21]

Example 7

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium, sodium salt

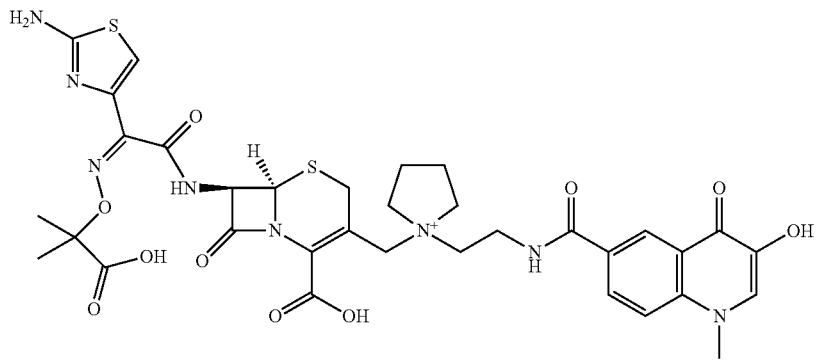 [SMILES: Cn1cc(O)c(=O)c2cc(C(=O)NCC[N+]3(CC4=C(C(=O)O)N5C(=O)[C@@H](NC(=O)/C(=N\OC(C)(C)C(=O)O)c6csc(N)n6)[C@H]5SC4)CCCC3)ccc21]

To 1-(((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-6-carboxamido)ethyl)pyrrolidin-1-ium (Example 6e) (175 mg, 0.143 mmol) in DCM at −30° C. was added anisole (0.156 mL, 1.427 mmol) followed by aluminium chloride (0.713 mL, 1.427 mmol) as a 2N solution in nitromethane. Let stir at −30° C. for 30 min. LCMS showed disappearance of starting material and conversion to product althrough product peak did not give a strong molecular ion. Added 10 mL of isopropyl ether and 2 mL of water and let stir at room temperature for 5 min. The solid mass was suspended in the solution mixture so decantation was not possible. The mixture was filtered and the solid product was collected and dissolved in water (5 mL), acetonitrile (5 mL) and 2N hydrochloric acid (1 mL). Isopropanol (5 mL) was then added, the biphasic mixture was separated and the aqueous phase was treated with HP-20SS resin. This suspension was concentrated under vacuum and then purified through a layer of HP20ss followed by a 26 g C-18 reversed phase column. Collected UV active peak and added NaOH (0.2N) until pH ~6 then quickly added dry ice. The solution was frozen and placed on high vacuum (lyophilizer) while frozen to afford 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium, Sodium salt (25 mg, 0.031 mmol, 21.72% yield) as an off white solid of ~82% purity. LCMS: (M+H)$^+$: 783.5. $^1$H NMR (400 MHz, DEUTERIUM OXIDE) δ ppm 1.31-1.39 (m, 6 H) 2.14 (br. s., 1 H) 3.44-3.55 (m, 5 H) 3.67-3.72 (m, 1 H) 3.89 (br. s., 3 H) 4.07 (br. s., 2 H) 5.24 (br. s., 1 H) 5.71 (d, J=4.29 Hz, 1 H) 6.73 (br. s., 1 H) 7.38 (br. s., 1 H) 7.66 (br. s., 2 H) 8.26 (br. s., 1 H). (M+H)$^+$: 783.4.

Example 8

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium, disodium salt

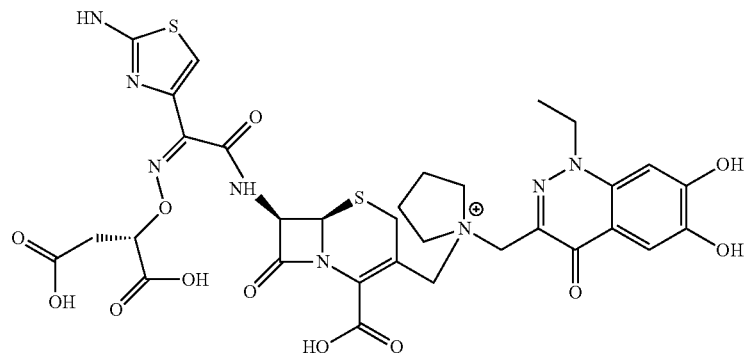 [SMILES: CCn1nc(C[N+]2(CC3=C(C(=O)O)N4C(=O)[C@@H](NC(=O)/C(=N\O[C@@H](CC(=O)O)C(=O)O)c5csc(N)n5)[C@H]4SC3)CCCC2)c(=O)c2cc(O)c(O)cc21]

Example 8a

Methyl 1-ethyl-6,7-dihydroxy-4-oxo-1,4-dihydrocinnoline-3-carboxylate

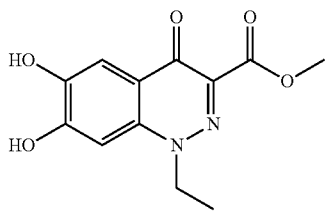 [SMILES: CCn1nc(C(=O)OC)c(=O)c2cc(O)c(O)cc21]

To a suspension of 1-ethyl-4-oxo-1,4-dihydro-[1,3]dioxolo[4,5-g]cinnoline-3-carboxylic acid (12.6 g, 48.1 mmol) in dichloromethane (DCM) (50 mL) stirred under nitrogen at −30° C. was added dropwise a solution of boron tribromide (168 mL, 168 mmol) in dichloromethane (140 mL). The white suspension turned yellowish. The mixture was kept at −30° C. for 1 h and then allowed to warm up to room temperature, and stirred for 40 h. The reaction mixture was again cooled to −30° C., methanol (100 mL) was added, and the resulting mixture was stirred at room temperature over the weekend. The organic solvents were partially removed to afford a light yellow suspension. The solid was collected by filtration and washed with dichloromethane (20 mL). The filtrate was concentrated again to provide more yellow solids that was collected and washed by dichloromethane (20 mL). The solids were combined to afford methyl 1-ethyl-6,7-dihydroxy-4-oxo-1,4-dihydrocinnoline-3-carboxylate (11 g, 35.8 mmol, 74.5% yield). LCMS: (M+H)$^+$: 265.0

Example 8b

Methyl 1-ethyl-6,7-bis((4-methoxybenzyl)oxy)-4-oxo-1,4-dihydrocinnoline-3-carboxylate

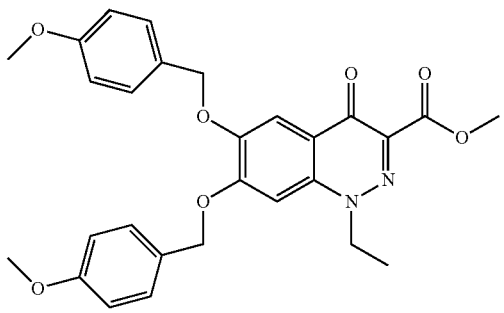

To a suspension of methyl 1-ethyl-6,7-dihydroxy-4-oxo-1,4-dihydrocinnoline-3-carboxylate (11 g, 35.8 mmol), potassium carbonate (16.33 g, 118 mmol) and potassium iodide (1.189 g, 7.16 mmol) in acetone (200 mL) at room temperature, was added 1-(chloromethyl)-4-methoxybenzene (16.82 g, 107 mmol). The mixture was then heated to reflux overnight. After cooling to room temperature, the mixture was concentrated in vacuo and the residue was partitioned between dichloromethane and brine. The organic phase was separated, and the aqueous phase was extracted with dichloromethane several times. The combined organic extracts were dried over sodium sulfate, filtered and concentrated. The residue was purified by automatic silica gel column chromatography (Combiflash RF) eluting with methanol/dichloromethane (0-20%) to afford methyl 1-ethyl-6,7-bis((4-methoxybenzyl)oxy)-4-oxo-1,4-dihydrocinnoline-3-carboxylate (15 g, 24.68 mmol, 68.9% yield) as a light yellow solid. LCMS: (M+H)$^+$: 505.1.

Example 8c

1-Ethyl-6,7-bis((4-methoxybenzyl)oxy)-4-oxo-1,4-dihydrocinnoline-3-carboxylic acid

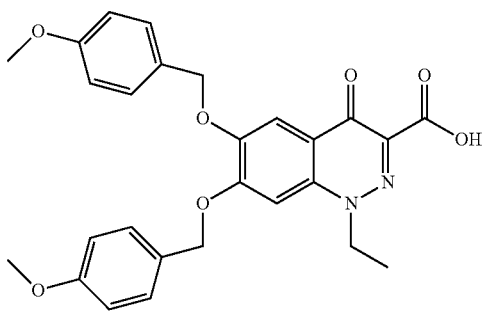 [SMILES: CCn1nc(C(=O)O)c(=O)c2cc(OCc3ccc(OC)cc3)c(OCc3ccc(OC)cc3)cc21]

To a suspension of methyl 1-ethyl-6,7-bis((4-methoxybenzyl)oxy)-4-oxo-1,4-dihydrocinnoline-3-carboxylate (3 g, 5.95 mmol) in a mixed solvent of water (25.00 mL) and methanol (75 mL) was added potassium hydtoxide (1.668 g, 29.7 mmol). The mixture was stirred at room temperature for 0.5 h and then heated to reflux for 1 h when the yellow suspension turned into a clear yellow solution. LCMS indicated completion of the reaction. The mixture was cooled to room temperature and concentrated. The residue was dissolved in water (100 mL), and was then acidified to ~pH 1 using aq. 6N hydrochloric acid. The white precipitates were collected by filtration, and the filtrate was extracted with ethyl acetate (2×100 mL). The combined organic layers were concentrated to provide more white solids that were combined with previous white precipitates and dried under high vacuum to afford 1-ethyl-6,7-bis((4-methoxybenzyl)oxy)-4-oxo-1,4-dihydrocinnoline-3-carboxylic acid (2.8 g, 5.71 mmol, 96% yield). LCMS: (M+H)$^+$: 491.4.

Example 8d 1-ethyl-3-(hydroxymethyl)-6,7-bis((4-methoxybenzyl)oxy)cinnolin-4(1H)-one

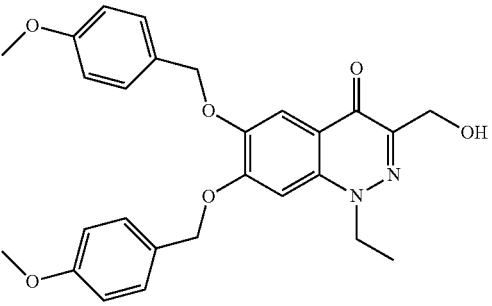 [SMILES: CCn1nc(CO)c(=O)c2cc(OCc3ccc(OC)cc3)c(OCc3ccc(OC)cc3)cc21]

To a suspension of 1-ethyl-6,7-bis((4-methoxybenzyl) oxy)-4-oxo-1,4-dihydrocinnoline-3-carboxylic acid (2.25 g, 4.59 mmol) in tetrahydrofuran (THF) (60 mL) was added triethylamine (2.110 mL, 15.14 mmol) and ethyl chloroformate (1.322 mL. 13.76 mmol). The resulting yellow solution was stirred at room temperature for 2 h, and was then added to a solution of sodium borohydride (2.083 g, 55.0 mmol) in ethanol (60 mL). After being stirred for 2 h, the reaction was quenched by addition of water (5 mL). The organic solvent was removed in vacuo, the residue was then taken in water (50 mL) and extracted with dichloromethane (2×50 mL). The combined extracts were dried over sodium sulfate, filtered and concentrated in vacuo. The crude product was purified by automatic silica gel column chromatography (Combiflash RF), eluting with methanol/dichloromethane (0-10%) to afford 1-ethyl-3-(hydroxymethyl)-6,7-bis((4-methoxybenzyl)oxy)cinnolin-4(1H)-one (1.97 g, 3.64 mmol, 79% yield) as a white solid. LCMS: (M+H)+: 477.1

Example 8e

1-Ethyl-6,7-bis((4-methoxybenzyl)oxy)-4-oxo-1,4-dihydrocinnoline-3-carbaldehyde

To a suspension of 1-ethyl-3-(hydroxymethyl)-6,7-bis((4-methoxybenzyl)oxy) cinnolin-4(1H)-one (1.6 g, 3.36 mmol) in dichloromethane (DCM) (50 mL) at room temperature was added Dess-Martin periodinane (1.709 g, 4.03 mmol). The white suspension turned into a dark green solution. The reaction was stirred at room temperature for 1 h, treated with sodium bicarbonate solution and extracted with dichloromethane. The combined organic extracts were washed with brine, dried over sodium sulfate, filtered, and concentrated. The residue was purified by automatic silica gel column chromatography (Combiflash RF), eluting with ethyl acetate/hexanes (0-100%) to afford 1-ethyl-6,7-bis((4-methoxybenzyl) oxy)-4-oxo-1,4-dihydrocinnoline-3-carbaldehyde (0.9 g, 1.897 mmol, 56.5% yield) as a yellow solid. LCMS: (M+H)+: 475.2

Example 8f

1-Ethyl-6,7-bis((4-methoxybenzyl)oxy)-3-(pyrrolidin-1-ylmethyl)cinnolin-4(1H)-one

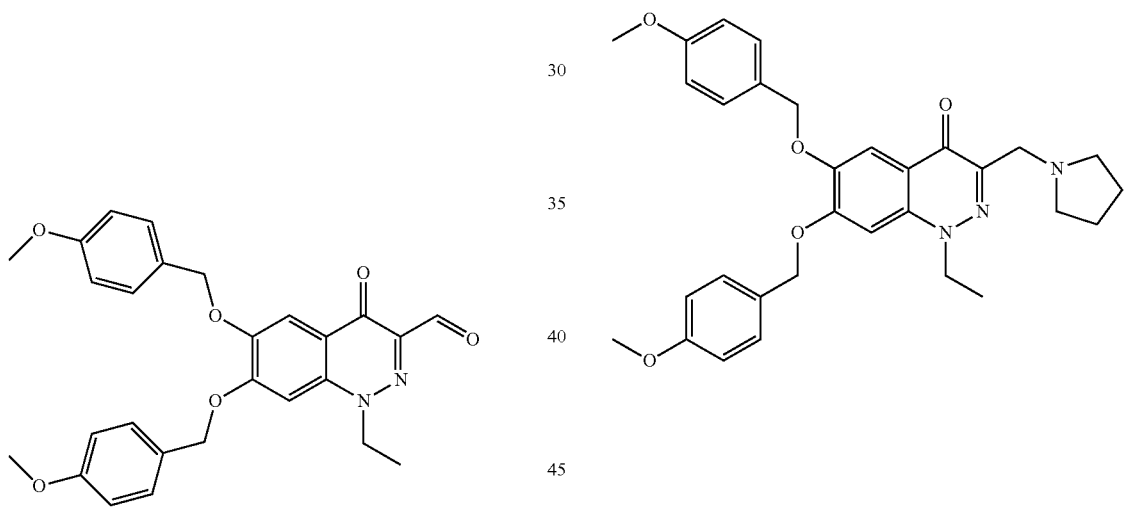

A solution of pyrrolidine (0.167 mL, 2.017 mmol) and 1-ethyl-6,7-bis((4-methoxybenzyl)oxy)-4-oxo-1,4-dihydrocinnoline-3-carbaldehyde (0.87 g, 1.833 mmol) in 1,2-dichloroethane (DCE) (19 mL) and 2 drops of acetic acid was treated with sodium triacetoxyborohydride (0.583 g, 2.75 mmol). The reaction mixture was stirred for 1.5 h and then concentrated. The residue was purified by automatic silica gel column chromatography (Combiflash RF), eluting with [dichloromethane/methanol/ammonium hydroxide (80:20:2)]/dichloromethane (0-60%) to afford 1-ethyl-6,7-bis((4-methoxybenzyl)oxy)-3-(pyrrolidin-1-ylmethyl)cinnolin-4 (1H)-one (750 mg, 1.416 mmol, 77% yield) as a light yellow gummy solid. LCMS: (M+H)+: 530.3

Example 8g 1-(((6R,7R)-7-((E)-3-((((R)-1-(tert-butoxy)-4-((4-methoxybenzyl)oxy)-1,4-dioxobutan-2-yl)oxy)imino)-3-(2-((tert-butoxycarbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)pyrrolidin-1-ium mmol) dropwise over 10 min. Stirred at −40° C. for 30 min. Poured into the cooled solution of 5% sodium chloride. The resulting solid was filtered and dried, and chromatographed on ISCO silica gel column eluting with 0-20% methanol:dichloromethane to give 1-(((6R,7R)-7-((E)-3-((((R)-1-(tert-butoxy)-4-((4-methoxybenzyl)oxy)-1,4-dioxobutan-2-yl)oxy)imino)-3-(2-((tert-butoxycarbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-

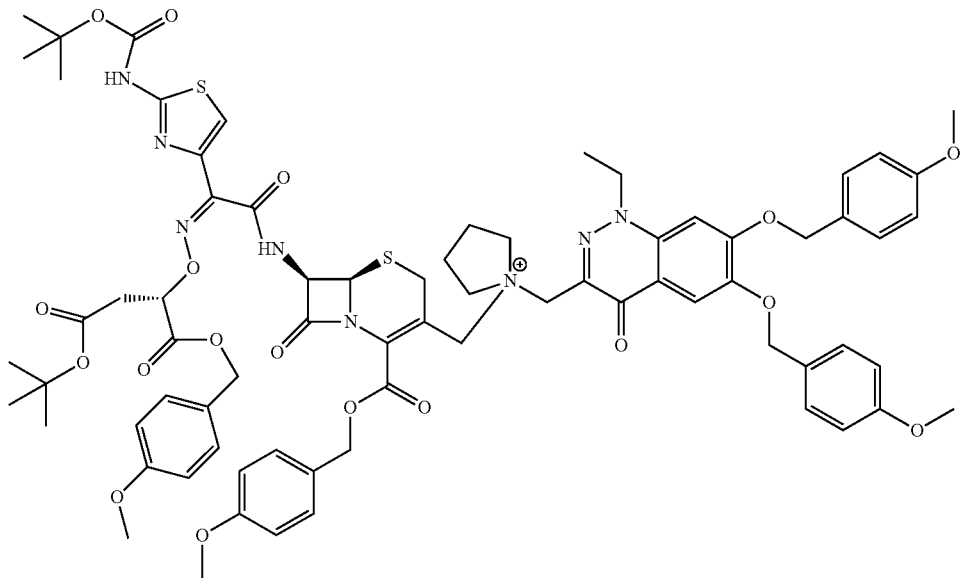 [SMILES: CCn1nc(C[N+]2(CC3=C(C(=O)OCc4ccc(OC)cc4)N4C(=O)[C@@H](NC(=O)/C(=N\O[C@@H](CC(=O)OC(C)(C)C)C(=O)OCc5ccc(OC)cc5)c5csc(NC(=O)OC(C)(C)C)n5)[C@H]4SC3)CCCC2)c(=O)c2cc(OCc3ccc(OC)cc3)c(OCc3ccc(OC)cc3)cc21]

To the heat gun dried flask under nitrogen was added 1-ethyl-6,7-bis((4-methoxybenzyl)oxy)-3-(pyrrolidin-1-ylmethyl)cinnolin-4(1H)-one (750 mg, 1.416 mmol) in N,N-dimethylacetamide (DMA) (10 mL) followed by (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (Example 1h) (1470 mg, 1.416 mmol) in N,N-dimethylacetamide (DMA) (10 mL). The mixture was heated at 40° C. for 3 h, then cooled and stored in fridge overnight. The mixture was cooled to −40° C. and N,N-dimethylformamide (DMF) (10 mL) was added, followed by phosphorus tribromide (0.267 mL, 2.83 dihydrocinnolin-3-yl)methyl)pyrrolidin-1-ium (1.35 g, 0.948 mmol, 66.9% yield). MS (M+H)+ 1426.4

Example 8h 1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium, disodium salt

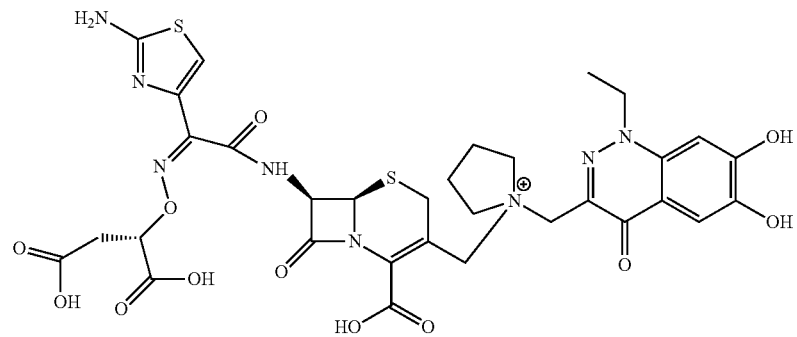

To a solution of 1-((((6R,7R)-7-((E)-3-((((R)-1-(tert-butoxy)-4-((4-methoxybenzyl)oxy)-1,4-dioxobutan-2-yl)oxy)imino)-3-(2-((tert-butoxycarbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)pyrrolidin-1-ium (1.35 g, 0.948 mmol) in dichloromethane (DCM) (10 mL) was added anisole (3.11 mL, 28.4 mmol) followed by trifluoroacetic acid (3.65 mL, 47.4 mmol). The resulting mixture was stirred at room temperature for 18 h. Resulting mixture was triturated with isopropyl ether and filtered, and chromatographed on preparative HPLC column eluting with isocratic solution of 10% acetonitrile and ammonium formate buffer to give desired Δ-3 isomer. Desired compound was lyophilized to constant weigh and acidified with 1M hydrochloric acid. The solution was allowed to pass through the HP 20-ss column and then converted to disodium salt by adjusting the pH to 6.2 with 0.2M sodium hydroxide, and lyophilized to give 1-((((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium, disodium salt (52 mg, 0.062 mmol, 6.58% yield). LCMS (M+H)$^+$ 788.4

$^1$H NMR (400 MHz, DEUTERIUM OXIDE) δ ppm 1.31-1.41 (m, 4 H) 2.02 (br. s., 5 H) 2.51-2.61 (m, 3 H) 3.52 (br. s., 5 H) 3.58-3.67 (m, 1 H) 3.87 (br. s., 1 H) 4.20 (br. s., 1 H) 4.36-4.48 (m, 2 H) 4.51 (br. s., 2 H) 4.76 (d, J=4.29 Hz, 1 H) 4.79-4.89 (m, 2 H) 5.26 (d, J=4.04 Hz, 1 H) 5.74 (d, J=4.55 Hz, 1 H) 6.73 (br. s., 1 H) 6.90 (s, 1 H) 7.25 (s, 1 H)

Example 9

1-((((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium, disodium salt Example 9a 1-Ethyl-6,7-bis((4-methoxybenzyl)oxy)-3-(pyrrolidin-1-ylmethyl)quinolin-4(1H)-one

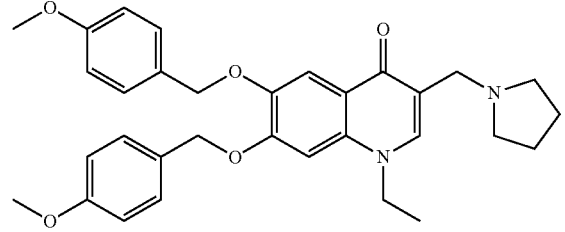 [SMILES: CCn1cc(CN2CCCC2)c(=O)c2cc(OCc3ccc(OC)cc3)c(OCc3ccc(OC)cc3)cc21]

The titled compound was prepared according to Example 8a-f, utilizing 1-ethyl-6,7-bis((4-methoxybenzyl)oxy)-4-oxo-1,4-dihydroquinoline-3-carboxylic acid in place of 1-ethyl-6,7-bis((4-methoxybenzyl)oxy)-4-oxo-1,4-dihydrocinnoline-3-carboxylic acid in Example 8a. LCMS: (M+H)$^+$: 529.3.

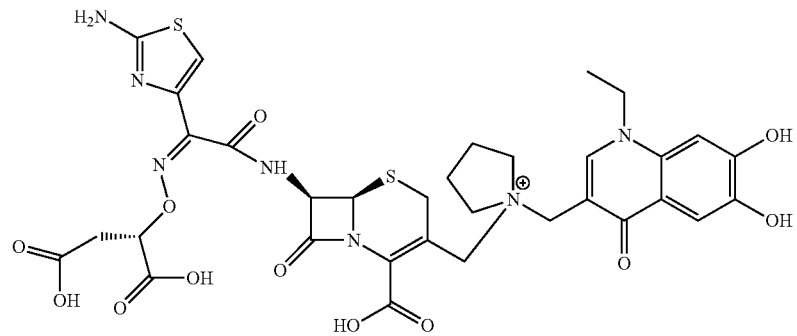

Example 9b 1-((((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydroquinolin-3-yl)methyl)pyrrolidin-1-ium

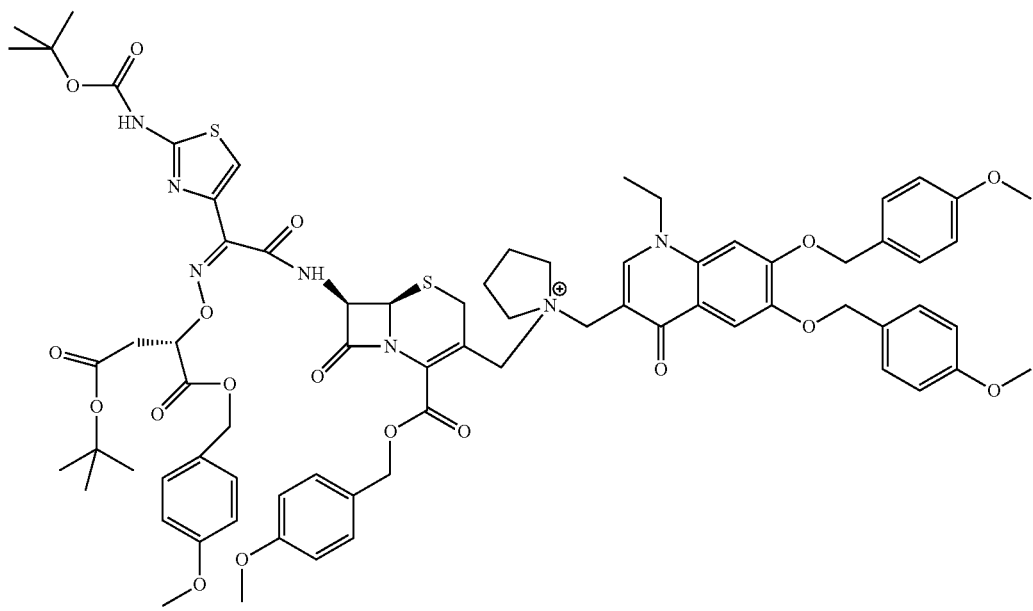

To the heat gun dried flask under nitrogen was added 1-ethyl-6,7-bis((4-methoxybenzyl)oxy)-3-(pyrrolidin-1-ylmethyl)quinolin-4(1H)-one (606 mg, 1.146 mmol) in N,N-dimethylacetamide (DMA) (10 mL), followed by (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (Example 1h) (1190 mg, 1.146 mmol) in N,N-dimethylacetamide (DMA) (10 mL). Mixture was heated at 40° C. for 3 h, then cooled and stored in fridge overnight. The mixture was cooled to −40° C. and N,N-dimethylformamide (DMF) (10 mL) was added, followed by phosphorus tribromide (0.216 mL, 2.293 mmol) dropwise over 10 min. Stirred at −40° C. for 30 min and poured into the cooled solution of 5% sodium chloride. The resulting solid was filtered and dried, and chromatographed on ISCO silica gel column eluting with 0-20% methanol:dichloromethane to give 1-((((6R,7R)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydroquinolin-3-yl)methyl)pyrrolidin-1-ium (270 mg, 0.190 mmol, 16.54% yield). LCMS (M+H)$^+$ 1424.4

Example 9c 1-((((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium, disodium salt

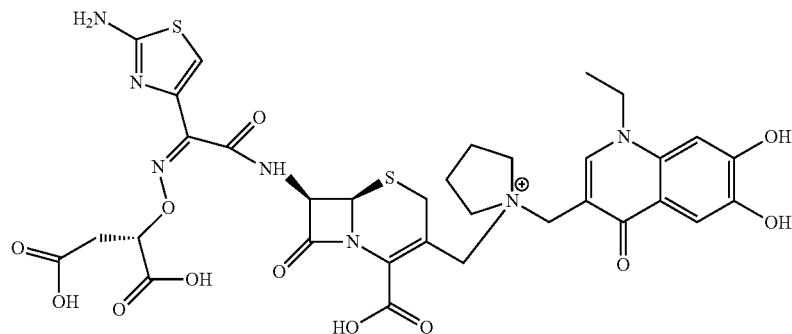

To the solution of 1-((((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-((((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydroquinolin-3-yl)methyl)pyrrolidin-1-ium (270 mg, 0.190 mmol) in dichloromethane (DCM) (2 ml) was added anisole (0.207 ml, 1.897 mmol), followed by trifluoroacetic acid (0.731 ml, 9.48 mmol) at room temperature. The mixture was stirred at room temperature for 18 h. Resulting mixture was triturated with isopropyl ether and filtered. Redissolved in acetonitrile (2 mL), water (1 mL) plus 2 drops of hydrochloric acid. Gilson HPLC eluting with 0-30% acetonitrile:water gave the fractions that were striped from acetonitrile and basified to pH 6.2 with 0.2M sodium hydroxide and lyophilized to give product 1-((((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium disodium salt (28 mg, 0.034 mmol, 17.73% yield) as yellow solid. LCMS: (M+H)$^+$: 787.2

$^1$H NMR (400 MHz, DEUTERIUM OXIDE) δ ppm 1.36 (d, J=6.57 Hz, 3 H) 2.00 (br. s., 4 H) 2.48-2.61 (m, 3 H) 3.34 (br. s., 5 H) 3.86 (s, 1 H) 3.97-4.06 (m, 1 H) 4.16-4.25 (m, 1 H) 4.30 (br. s., 2 H) 4.35-4.49 (m, 1 H) 4.78-4.89 (m, 2 H) 5.27 (d, J=4.80 Hz, 1 H) 5.74 (d, J=5.05 Hz, 1 H) 6.77 (br. s., 1 H) 6.84-6.93 (m, 1 H) 7.41 (s, 1 H) 8.06 (br. s., 1 H) 8.34 (s, 1 H)

Example 10

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium

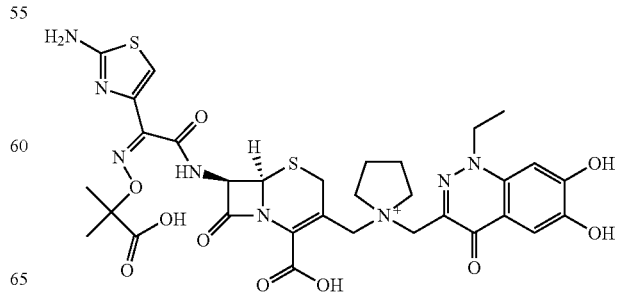

Example 10a 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)pyrrolidin-1-ium

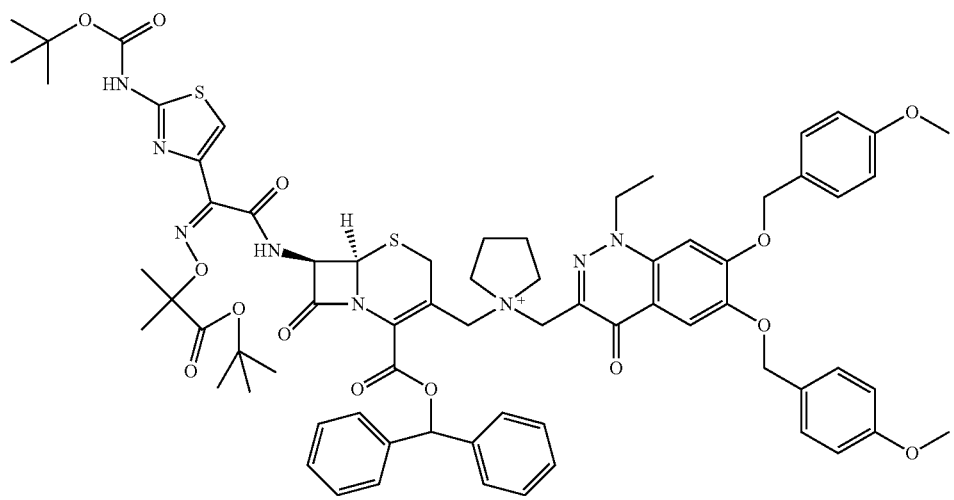

To a solution of 1-ethyl-6,7-bis((4-methoxybenzyl)oxy)-3-(pyrrolidin-1-ylmethyl)cinnolin-4(1H)-one (Example 8f) (384 mg, 0.725 mmol) in N,N-dimethylacetamide (12 mL) under $N_2$ at room temperature was added (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (Example 6d) (812 mg, 0.870 mmol) in N,N-dimethylacetamide (6 mL). The mixture was stirred at room temperature over 12 h. LCMS indicated ~31% desired product in the crude mixture. N,N-dimethylformamide (32.00 mL) was then added. The mixture was cooled to −70° C. and treated with phosphorous tribromide (0.150 mL, 1.595 mmol) dropwise. The mixture was allowed to warm up to −40° C. LCMS indicated complete reduction of the sulfoxide. The organic solution was poured into ice-cooled 5% sodium chloride (150 mL) and stirred for ~15 min. The solid was separated by filtration, washed with water and dried under high vacuum to afford 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)pyrrolidin-1-ium (1.45 g, 57% purity, 0.626 mmol, 86% yield) as a dark brown solid. LCMS: (M+H)$^+$: 1321.5.

Example 10b 1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium

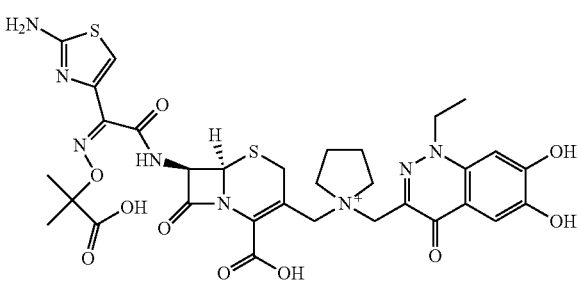

To a solution of 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)pyrrolidin-1-ium (1.45 g, 0.626 mmol) (57% purity by LCMS) in dichloromethane (10 mL) under N₂ at 0° C. was added anisole (0.684 mL, 6.26 mmol), followed by trifluoroacetic acid (3 mL, 38.9 mmol) dropwise. The mixture was warmed up to room temperature and stirred at room temperature overnight. LCMS indicated completion of the reaction. Diisopropyl ether (20 mL) and water (4 mL) were then added. The mixture was rapidly stirred for ~10 min and was then left standing for ~10 min. The solvents were decanted away. The solid (containing ~70% of desired product as shown by LCMS) was dissolved in a mixed solvents of water (10 mL), acetonitrile (10 mL) and 2N aqueous hydrochloric acid (2.5 mL), and was then absorbed onto HP20ss resin, and purified by reverse phase chromatography using HP20ss pre-column followed by 40 g C18 column, eluting with 0-20% acetonitrile/water. Only two fractions containing ~73% of desired product were obtained. The two fractions were combined, concentrated under reduced pressure to remove acetonitrile, frozen and placed on lyophilizer for 24 hours to provide 101 mg of product (~72% pure by LCMS). This product was dissolved in acetonitrile (5 mL) and 1 N hydrochloric acid (5 mL) and purified by Gilson automated HPLC (5-60% organic, 8 min gradient) to afford after lyophilization 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium (40 mg, 0.050 mmol, 7.93% yield) (100% pure by LCMS, 94% by HPLC). LCMS: (M+H)⁺: 758.4. ¹H NMR (400 MHz, DEUTERIUM OXIDE) δ ppm 1.30-1.48 (m, 9 H) 2.08 (br. s., 4 H) 3.35-3.70 (m, 6 H) 3.80-3.98 (m, 1 H) 4.11-4.28 (m, 1 H) 4.53 (br. s., 4 H) 5.30 (br. s., 1 H) 5.78 (d, J=4.04 Hz, 1 H) 6.89 (s, 1 H) 6.99-7.18 (m, 1 H) 7.28-7.45 (m, 1 H).

Example 11

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium

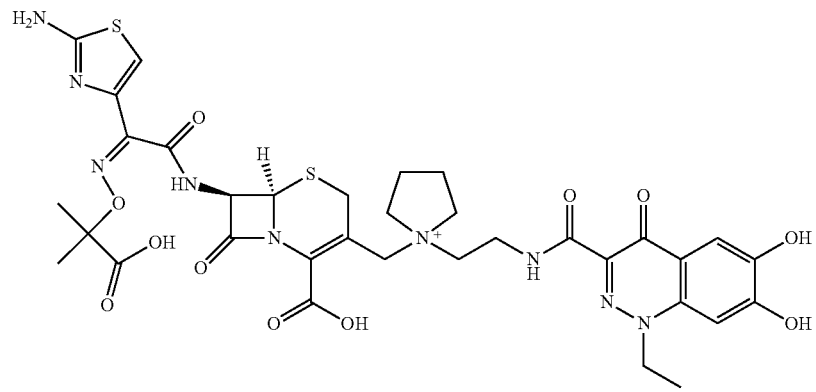

Example 11a

1-Ethyl-6,7-bis((4-methoxybenzyl)oxy)-4-oxo-N-(2-(pyrrolidin-1-yl)ethyl)-1,4-dihydrocinnoline-3-carboxamide

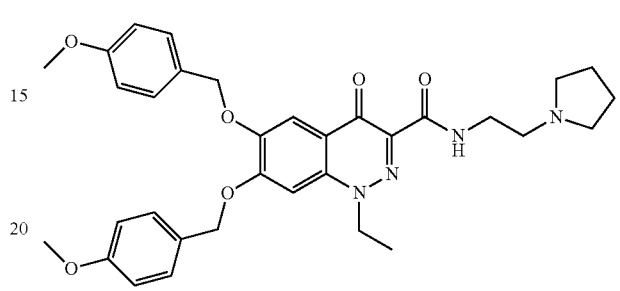

To a suspension of 1-ethyl-6,7-bis((4-methoxybenzyl)oxy)-4-oxo-1,4-dihydrocinnoline-3-carboxylic acid (Example 8c) (2.5 g, 5.10 mmol) in dichloromethane (50 mL) at room temperature was added thionyl chloride (0.446 mL, 6.12 mmol), and the mixture was heated to reflux for 1 h. After cooling to room temperature the mixture was added dropwise to a solution of 2-(pyrrolidin-1-yl)ethanamine (0.711 mL, 5.61 mmol) and triethylamine (1.066 mL, 7.65 mmol) in dichloromethane (50.0 mL) in an ice bath. The resulting mixture was then allowed to warm up to room temperature, and stirred for another 0.5 h. LCMS indicated completion of the reaction. The mixture was concentrated in vacuo, and the residue was purified twice by automatic silica gel column chromatography (Combiflash RF), eluting with a mixture of [dichloromethane/methanol/ammonium hydroxide (80:20:2)]/dichloromethane (0-50%) to afford 1-ethyl-6,7-bis((4-methoxybenzyl)oxy)-4-oxo-N-(2-(pyrrolidin-1-yl)ethyl)-1,4-dihydrocinnoline-3-carboxamide (2.2 g, 3.75 mmol, 73.6% yield) as a light yellow solid. LCMS: (M+H)⁺: 587.3.

Example 11b 1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium

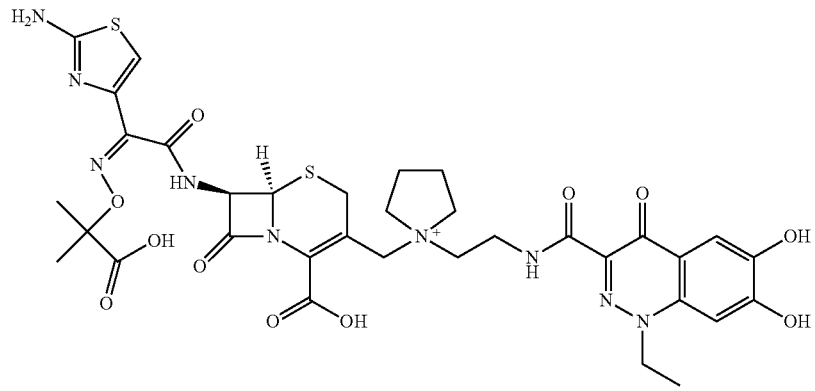

The compound was prepared according to the two-step sequence of Examples 10a-10b, utilizing the compound from Example 11a and the compound from Example 6d to afford 1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium (the combined yield for the two steps: 1.93%). LCMS: (M+H)$^+$: 814.7. $^1$H NMR (400 MHz, DEUTERIUM OXIDE) δ ppm 1.31-1.45 (m, 9 H) 2.13 (br. s., 4 H) 3.58 (br. s., 6 H) 3.75-4.16 (m, 4 H) 4.49 (d, J=7.58 Hz, 4 H) 5.28 (d, J=5.05 Hz, 1 H) 5.76 (s, 1 H) 6.93 (s, 1 H) 7.10 (s, 1 H) 7.37 (s, 1 H).

Example 12

1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydroquinoline-3-carboxamido)ethyl)pyrrolidin-1-ium

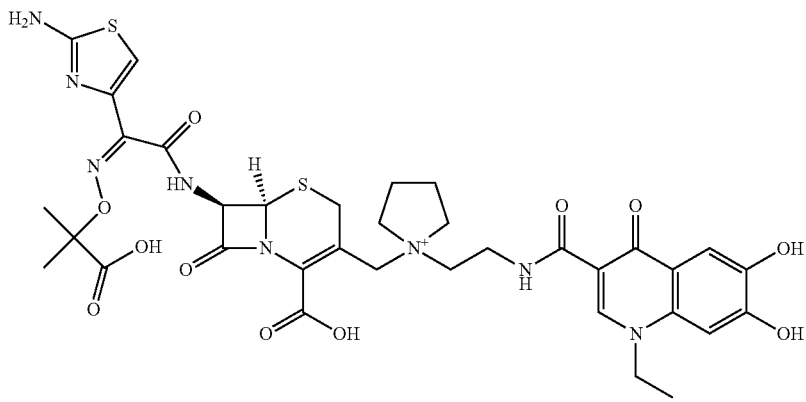 [SMILES: CCn1cc(C(=O)NCC[N+]2(CC3=C(C(=O)O)N4C(=O)[C@@H](NC(=O)/C(=N\OC(C)(C)C(=O)O)c5csc(N)n5)[C@H]4SC3)CCCC2)c(=O)c2cc(O)c(O)cc21]

Example 12a

1-Ethyl-6,7-bis((4-methoxybenzyl)oxy)-4-oxo-N-(2-(pyrrolidin-1-yl)ethyl)-1,4-dihydroquinoline-3-carboxamide

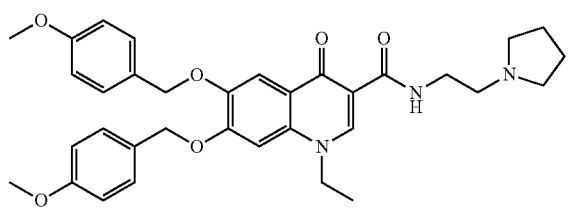 [SMILES: CCn1cc(C(=O)NCCN2CCCC2)c(=O)c2cc(OCc3ccc(OC)cc3)c(OCc3ccc(OC)cc3)cc21]

The compound was prepared according to Examples 8a-c and 11a, utilizing 5-ethyl-8-oxo-5,8-dihydro-[1,3]dioxolo[4,5-g]quinoline-7-carboxylic acid in place of 1-ethyl-4-oxo-1,4-dihydro-[1,3]dioxolo[4,5-g]cinnoline-3-carboxylic acid in Examples 8a. LCMS: (M+H)$^+$: 586.3.

Example 12b 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydroquinoline-3-carboxamido)ethyl)pyrrolidin-1-ium The compound was prepared according to the two-step sequence in Examples 10a-10b, utilizing the compound from Example 12a and the compound from Example 6d to provide 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydroquinoline-3-carboxamido)ethyl)pyrrolidin-1-ium (the combined yield for the two steps: 0.95%). LCMS: (M+H)$^+$: 814.2. $^1$H NMR (400 MHz, DEUTERIUM OXIDE) δ ppm 1.32 (br. s., 9 H) 2.03-2.22 (m, 4 H) 3.31-4.46 (m, 14 H) 5.19-5.33 (m, 1 H) 5.70-5.82 (m, 1 H) 6.80-6.92 (m, 2 H) 7.41-7.54 (m, 1 H) 8.44-8.60 (m, 1 H)

Example 13

1-((((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methy)-1-((1-ethyl-6,7-dihydroxy-4-oxo-1,4-dihydrocinnolin-3-yl)methyl)piperidin-1-ium, disodium salt

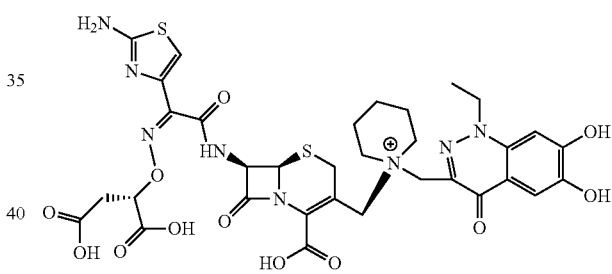

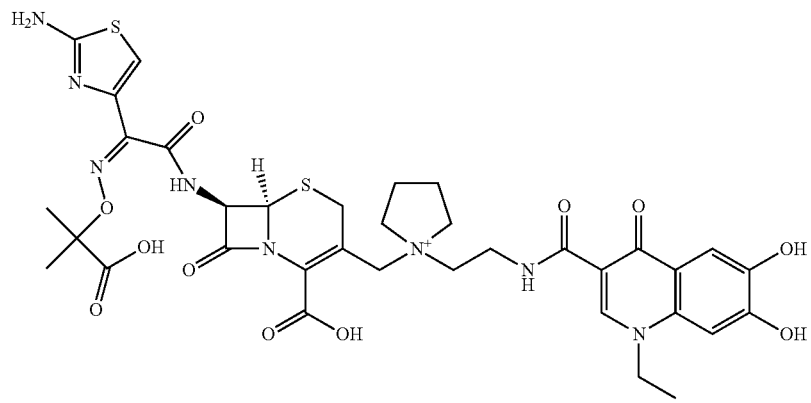 [SMILES: CCn1cc(C(=O)NCC[N+]2(CC3=C(C(=O)O)N4C(=O)[C@@H](NC(=O)/C(=N\OC(C)(C)C(=O)O)c5csc(N)n5)[C@H]4SC3)CCCC2)c(=O)c2cc(O)c(O)cc21]

Example 13a 1-ethyl-6,7-bis((4-methoxybenzyl)oxy)-3-(piperidin-1-ylmethyl)cinnolin-4(1H)-one

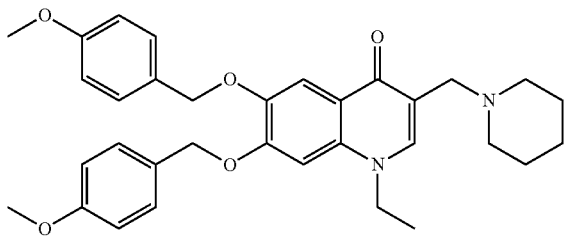 [SMILES: CCn1cc(CN2CCCCC2)c(=O)c2cc(OCc3ccc(OC)cc3)c(OCc3ccc(OC)cc3)cc21]

To a suspension of 1-ethyl-3-(hydroxymethyl)-6,7-bis((4-methoxybenzyl)oxy)cinnolin-4(1H)-one (Example 8d) (2.13 g, 4.47 mmol) in Dichloromethane (DCM) (40 mL) in an ice bath under $N_2$ was added TEA (1.495 mL, 10.73 mmol) followed by methanesulfonyl chloride (0.627 mL, 8.05 mmol) (white suspension turned into a light yellow clear solution). The mixture was stirred in an ice bath for 2 h, and then the above reaction mixture was added dropwise into a stirred solution of piperidine (1.195 mL, 12.07 mmol) in dichloromethane (DCM) (40.0 mL) at room temperature overnight. The reaction mixture was concentrated and purified through column chromatography eluting with dichloromethane and methanol/dichloromethane/ammonium hydroxide (from 0% to 100%) over 15 mins twice to afford 1-ethyl-6,7-bis((4-methoxybenzyl)oxy)-3-(piperidin-1-ylmethyl)cinnolin-4(1H)-one (1.54 g, 2.55 mmol, 57.0% yield). LCMS $(M+H)^+$: 544.0

Example 13b 1-((((6R,7R)-7-((E)-3-((((R)-1-(tert-butoxy)-4-((4-methoxybenzyl)oxy)-1,4-dioxobutan-2-yl)oxy)imino)-3-(2-((tert-butoxycarbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)piperidin-1-ium

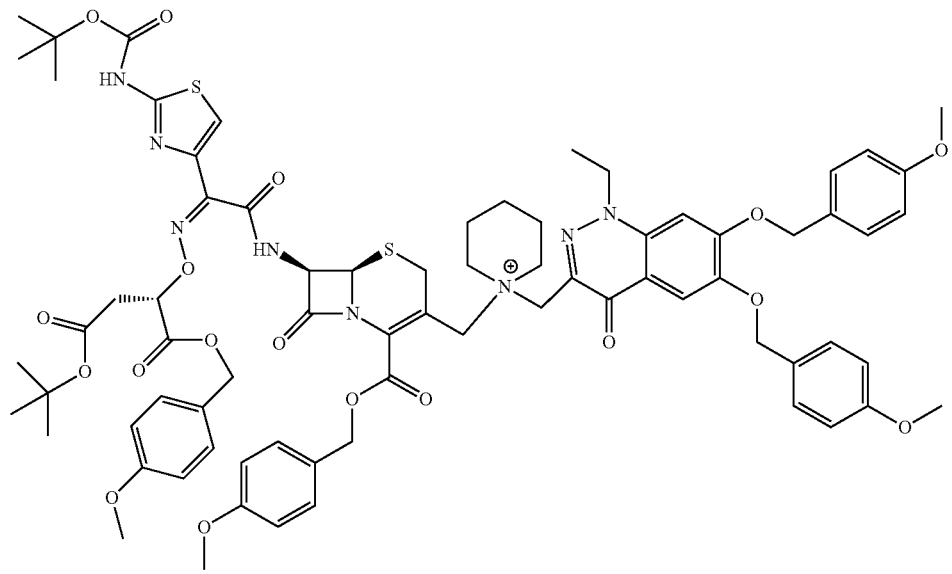 [SMILES: CCn1nc(C[N+]2(CC3=C(C(=O)OCc4ccc(OC)cc4)N4C(=O)[C@@H](NC(=O)/C(=N\O[C@@H](CC(=O)OC(C)(C)C)C(=O)OCc5ccc(OC)cc5)c5csc(NC(=O)OC(C)(C)C)n5)[C@H]4SC3)CCCCC2)c(=O)c2cc(OCc3ccc(OC)cc3)c(OCc3ccc(OC)cc3)cc21]

To the heat gun dried flask under nitrogen was added 1-ethyl-6,7-bis((4-methoxy benzyl)oxy)-3-(piperidin-1-ylmethyl)cinnolin-4(1H)-one (610 mg, 1.122 mmol) in N,N-dimethylacetamide (DMA) (10 mL) followed by (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (1165 mg, 1.122 mmol) in N,N-dimethylacetamide (DMA) (10 mL). Mixture was heated at 40° C. for 3 h, cooled and stored in fridge overnight. The mixture was cooled to −40° C. and N,N-dimethylformamide (DMF) (10 mL) was added followed by phosphorus tribromide (0.212 mL, 2.24 (mmol) dropwise over 10 min. Stirred at −40° C. for 30 min, and poured into the cooled solution of 5% sodium chloride. The resulting solid was filtered and dried, and chromatographed on ISCO silica gel column eluting with 0-20% methanol:

dichloromethane to give 1-((((6R,7R)-7-((E)-3-((((R)-1-(tert-butoxy)-4-((4-methoxybenzyl)oxy)-1,4-dioxobutan-2-yl)oxy)imino)-3-(2-((tert-butoxy carbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)piperidin-1-ium (640 mg, 0.445 mmol, 39.6% yield). LCMS (M+H)⁺:1439.4

Example 13c 1-((((6R,7R)-7-((E)-3-((((R)-1-(tert-butoxy)-4-((4-methoxybenzyl)oxy)-1,4-dioxobutan-2-yl)oxy)imino)-3-(2-((tert-butoxycarbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)piperidin-1-ium

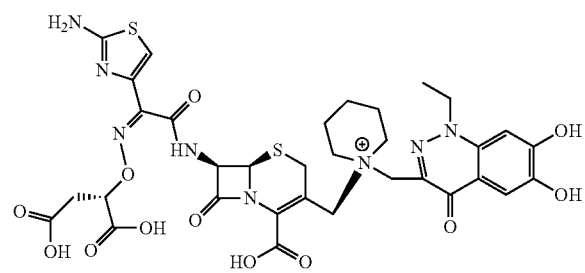

To the solution of 1-((((6R,7R)-7-((E)-3-((((R)-1-(tert-butoxy)-4-((4-methoxybenzyl)oxy)-1,4-dioxobutan-2-yl)oxy)imino)-3-(2-((tert-butoxycarbonyl)amino)thiazol-5-yl)-2-oxopropyl)-2-(((4-methoxybenzyl)oxy)carbonyl)-8-oxo-5-thia-1-azabicyclo[4.2.0]oct-2-en-3-yl)methyl)-1-((1-ethyl-6,7-bis((4-methoxybenzyl)oxy)-4-oxo-1,4-dihydrocinnolin-3-yl)methyl)piperidin-1-ium (640 mg, 0.445 mmol) in dichloromethane (DCM) (10 mL) was added anisole (1.458 mL, 13.35 mmol) and trifluoroacetic acid (1.714 mL, 22.24 mmol) at room temperature. The reaction mixture was stirred at room temperature for 18 h. Resulting mixture was triturated with isopropyl ether and filtered. The solid was redissolved in acetonitrile (2 mL), water (1 mL) plus 2 drops of hydrochloric acid and purified through ISCO C-18 column and HP-20ss pre-column eluting with 0-30% acetonitrile:water. The fractions were concentrated to remove acetonitrile and basified to pH 6.2 with 0.2M sodium hydroxide and lyophilized to give product 1-((((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)piperidin-1-ium, disodium salt (35 mg, 0.041 mmol, 9.28% yield) LCMS (M+H)⁺:802.3

¹H NMR (400 MHz, DEUTERIUM OXIDE) δ ppm 1.23-1.49 (m, 4 H) 1.53 (br. s., 2 H) 1.71-1.84 (m, 2 H) 1.82 (d, J=11.62 Hz, 2 H) 2.02 (br. s., 1 H) 2.40-2.71 (m, 4 H) 2.53-2.63 (m, 2 H) 3.07-3.20 (m, 1 H) 3.26 (br. s., 2 H) 3.43 (d, J=16.93 Hz, 2 H) 3.87 (d, J=16.93 Hz, 1 H) 4.15 (d, J=14.15 Hz, 1 H) 4.44 (d, J=7.07 Hz, 2 H) 4.57 (br. s., 1 H) 4.80 (br. s., 2 H) 4.85 (dd. J=9.09, 4.29 Hz, 2 H) 5.26 (d, J=5.05 Hz, 1 H) 5.75 (d, J=4.80 Hz, 1 H) 6.68 (s, 1 H) 6.83-6.93 (m, 1 H) 6.86-6.97 (m, 1 H) 7.27 (s, 1 H)

Example 14

1-((((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-8-carboxamido)ethyl)pyrrolidin-1-ium

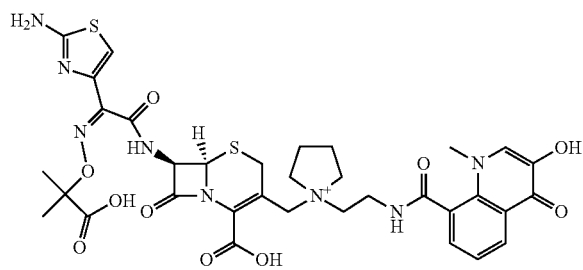 [SMILES: Cn1cc(O)c(=O)c2cccc(C(=O)NCC[N+]3(CC4=C(C(=O)O)N5C(=O)[C@@H](NC(=O)/C(=N\OC(C)(C)C(=O)O)c6csc(N)n6)[C@H]5SC4)CCCC3)c21]

Example 14a

Ethyl 2-(((2-bromophenyl)amino)methylene)-3-oxobutanoate

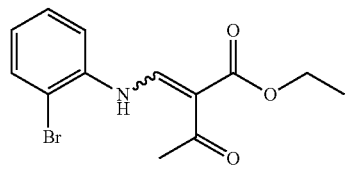 [SMILES: CCOC(=O)C(=CNc1ccccc1Br)C(C)=O]

To a solution of 2-bromoaniline (2 g, 11.63 mmol) in Isopropanol (15 mL) stirred under nitrogen at room temperature was added neat ethyl 2-(ethoxymethylene)-3-oxobutanoate (2.165 g, 11.63 mmol) in one charge. The reaction mixture was stirred at room temperature for 20 min, at which time LCMS showed only a trace amount of product. The reaction mixture was heated to 75° C. and stirred for 20 min. LCMS showed complete conversion. The mixture was cooled to room temperature and concentrated under vacuum, during which time a large amount of material precipitated out. Filtration followed by a hexanes wash afforded ethyl 2-(((2-bromophenyl)amino)methylene)-3-oxobutanoate (3.8 g, 10.96 mmol, 94% yield) that was apx. 90% pure to be used in the next step. LCMS: (M+H)+: 312.0.

Example 14b

3-Acetyl-8-bromoquinolin-4(1H)-one

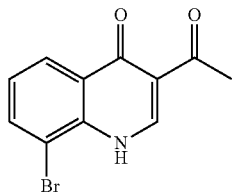

To Dowtherm (20 ml) at apx 200° C. was added solid ethyl 2-(((2-bromophenyl)amino) methylene)-3-oxobutanoate (3 g, 9.61 mmol). The reaction was heated to 250° C. and stirred for 1 h. LCMS showed consumption of starting material and formation of desired product along with an unknown biproduct of lower mass. The reaction was allowed to cool to room temperature and was them poured into 150 mL of hexanes. The mixture was stirred for 15 min, then the precipitate was collected by filtration and dried to afford 3-acetyl-8-bromoquinolin-4(1H)-one (1.77 g, 6.65 mmol, 69.2% yield) as a light brown solid. LCMS: (M+H)+: 265.9.

Example 14c

3-Acetyl-8-bromo-1-methylquinolin-4(1H)-one

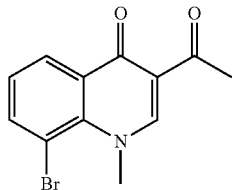 [SMILES: CC(=O)c1cn(C)c2c(Br)cccc2c1=O]

A mixture of 3-acetyl-8-bromoquinolin-4(1H)-one (5.35 g, 20.11 mmol) and K$_2$CO$_3$ (9.17 g, 66.3 mmol) in dry N,N-dimethylformamide (100 mL) was heated at 90° C. for 30 min. After cooling to room temperature, iodomethane (3.77 mL, 60.3 mmol) was added and the mixture was stirred again at 90° C. for 2 h. Then the reaction mixture was concentrated and diluted with water (50 mL), extracted with dichloromethane (4×50 mL), dried over sodium sulfate and absorbed onto silica gel. Purification by automatic silica gel column chromatography (Combiflash RF) eluting with ethyl acetate/hexanes (10-100%) afforded 3-acetyl-8-bromo-1-methylquinolin-4(1H)-one (3.4 g, 12.14 mmol, 60.4% yield) as a brown solid. LCMS: (M+H)+: 279.9.

Example 14d

8-Bromo-1-methyl-4-oxo-1,4-dihydroquinolin-3-yl acetate

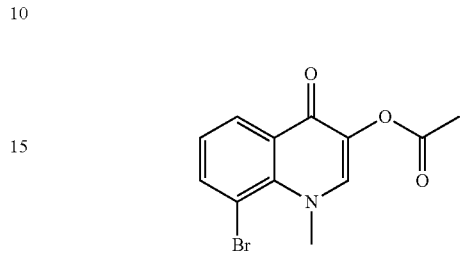

To a solution of 3-acetyl-8-bromo-1-methylquinolin-4 (1H)-one (3.4 g, 12.14 mmol) in dichloromethane (60 mL) at room temperature was added portionwise with stirring m-CPBA (4.08 g, 18.21 mmol). The resulting mixture was stirred at room temperature for 1 h. The excess m-CPBA was quenched via addition of 15% aqueous Na$_2$SO$_3$ (30 mL), and the resulting mixture was stirred at room temperature for 0.5 h. The layers were separated, and the organic layer was washed sequentially with water (100 mL), 5% aqueous NaHCO$_3$ (100 mL), and brine (100 mL). The organic layer was dried (Na$_2$SO$_4$), filtered, and concentrated in vacuo to afford crude 8-bromo-1-methyl-4-oxo-1,4-dihydroquinolin-3-yl acetate (3.68 g, 10.56 mmol, 87% yield) as brown solid, which was used in the next hydrolysis step without further purification. LCMS: (M+H)+: 295.9.

Example 14e

8-Bromo-3-hydroxy-1-methylquinolin-4(1H)-one

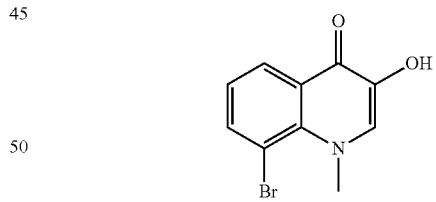

To a suspension of 8-bromo-1-methyl-4-oxo-1,4-dihydroquinolin-3-yl acetate (3.68 g, 10.56 mmol) in methanol (100 mL) was added aqueous 2 M KOH (15 mL), the mixture turned into a brown solution and was stirred at room temperature for 1 h. The reaction mixture was concentrated, and was then partitioned between dichloromethane and brine. The organic phase was separated, the aqueous phase was extracted with dichloromethane for several times. The combined organic extracts were dried (Na$_2$SO$_4$), filtered and the solvent was removed in vacuo. The residue was then absorbed onto silica gel and purified by automatic silica gel column chromatography (Combiflash RF), eluting with MeOH/dichloromethane (0-5%) to afford 8-bromo-3-hydroxy-1-methylquinolin-4(1H)-one (2.47 g, 9.24 mmol, 87% yield) as a brown solid. LCMS: (M+H)+: 254.1

Example 14f

8-Bromo-3-((4-methoxybenzyl)oxy)-1-methylquinolin-4(1H)-one

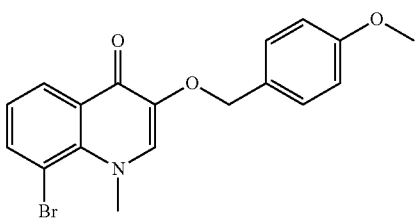 [SMILES: COc1ccc(COc2cn(C)c3c(Br)cccc3c2=O)cc1]

A suspension of 8-bromo-3-hydroxy-1-methylquinolin-4(1H)-one (2.4 g, 8.97 mmol) and potassium carbonate (1.488 g, 10.77 mmol) in N,N-dimethylformamide (50 mL) was heated at 90° C. for 0.5 h. Then 1-(chloromethyl)-4-methoxybenzene (1.442 mL, 9.87 mmol) and potassium iodide (0.149 g, 0.897 mmol) were added, and the mixture was heated at the same temperature for another 2 h. After cooling. N,N-dimethylformamide was removed in vacuo and the residue was partitioned between dichloromethane and brine. The organic phase was separated, the aqueous phase was extracted with dichloromethane for several times. The combined organic extracts were dried over sodium sulfate, filtered and concentrated, The residue was purified by automatic silica gel column chromatography (Combiflash RF), eluting with ethyl acetate/hexanes (0-100%) to afford 8-bromo-3-((4-methoxybenzyl)oxy)-1-methylquinolin-4(1H)-one (2.6 g, 6.95 mmol, 77% yield) as a light brown solid. LCMS: (M+H)+: 374.0.

Example 14g 3-((4-Methoxybenzyl)oxy)-1-methyl-4-oxo-1,4-dihydroquinoline-8-carbonitrile

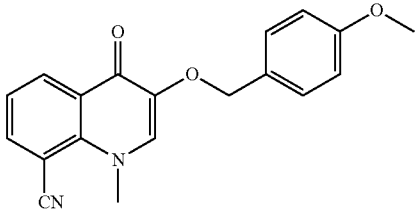

To a suspension of 8-bromo-3-((4-methoxybenzyl)oxy)-1-methylquinolin-4(1H)-one (2.6 g, 6.95 mmol), DPPF (0.462 g, 0.834 mmol), palladium tetrakis (0.482 g, 0.417 mmol) and Pd$_2$(dba)$_3$ (0.382 g, 0.417 mmol) in N,N-dimethylformamide (30 mL) at room temperature was added dicyanozinc (0.979 g, 8.34 mmol). The mixture was then heated at 110° C. under N$_2$ for 1 h. After cooled to room temperature, the mixture was concentrated in vacuo and then partitioned between EtOAc (80 mL) and conc. NH$_4$Cl (40 mL). The organic phase was separated, washed with brine (40 mL), dried over sodium sulfate, and concentrated. The residue was purified twice by automatic silica gel column chromatography (Combiflash RF), eluting with ethyl acetate/hexanes (0-100%) to afford 3-((4-methoxybenzyl)oxy)-1-methyl-4-oxo-1,4-dihydroquinoline-8-carbonitrile (1.87 g, 5.84 mmol, 84% yield) as a light brown solid. LCMS: (M+H)+: 321.1.

Example 14h 3-((4-Methoxybenzyl)oxy)-1-methyl-4-oxo-1,4-dihydroquinoline-8-carboxamide

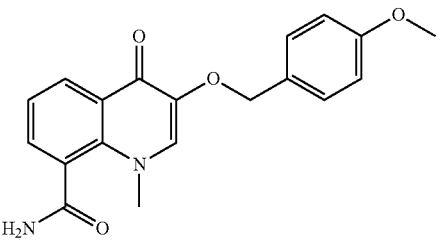 [SMILES: COc1ccc(COc2cn(C)c3c(C(N)=O)cccc3c2=O)cc1]

A solution of 3-((4-methoxybenzyl)oxy)-1-methyl-4-oxo-1,4-dihydroquinoline-8-carbonitrile (1.75 g, 5.46 mmol) and 25% aqueous sodium hydroxide (20 mL) in methanol (100 mL) was stirred at reflux for 3 h. After complete consumption of the nitrile, the mixture was concentrated to remove ~75% of the methanol. The mixture was acidified to pH 3 with 1 M HCl (aq), and partitioned between EtOAc and brine. The organic phase was separated, dried over sodium sulfate and concentrated in vacuo. The crude product was absorbed onto silica gel and purified by automatic silica gel column chromatography (Combiflash RF), eluting with methanol/dichloromethane (0-30%) to afford 3-((4-methoxybenzyl)oxy)-1-methyl-4-oxo-1,4-dihydroquinoline-8-carboxamide (1.21 g, 3.58 mmol, 65.5% yield) as light brown solid. LCMS (M+H)+: 339.3.

Example 14j 3-((4-methoxybenzyl)oxy)-1-methyl-4-oxo-N-(2-(pyrrolidin-1-yl)ethyl)-1,4-dihydroquinoline-8-carboxamide

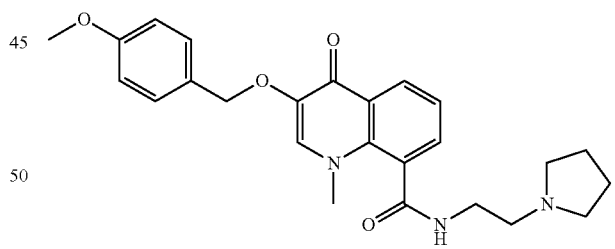

To a solution of 3-((4-methoxybenzyl)oxy)-1-methyl-4-oxo-1,4-dihydroquinoline-8-carboxamide (1.09 g, 3.22 mmol) in N,N-dimethylformamide (30 mL) was added sodium hydride (0.193 g, 4.83 mmol) and the mixture was stirred at room temperature for 1 h. Then the mixture of 1-(2-chloroethyl)pyrrolidine, Hydrochloride (0.548 g, 3.22 mmol) and triethylamine (0.494 mL, 3.54 mmol) in N,N-dimethylformamide (30.0 mL) was added in one portion. The resulting mixture was stirred at 50° C. for 3.5 h. Extra NaH (0.15 eq) was added, the mixture was stirred at 50° C. for another 0.5 h. The solvent was removed in vacuo, and the residue was partitioned between water (50 mL) and dichloromethane (50 mL), and extracted with DCM for three times. The combined organic phases were dried over sodium sulfate, filtered, and concentrated. The light yellow residue was purified by automatic silica gel column chromatography (Combiflash RF), eluting with [CH$_2$Cl$_2$/MeOH/NH$_4$OH (80:20:2)]/CH$_2$Cl$_2$ (0-50%) to afford 3-((4-methoxybenzyl)oxy)-1-methyl-4-oxo-N-(2-(pyrrolidin-1-yl)ethyl)-1,4-dihydroquinoline-8-carboxamide (0.3 g, 0.689 mmol, 21.38% yield) as a light brown oil. LCMS: (M+H)$^+$: 436.3.

Example 14k 1-(((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-8-carboxamido)ethyl)pyrrolidin-1-ium cooled to −70° C. and treated with tribromophosphine (0.096 mL, 1.020 mmol) dropwise. The mixture was allowed to warm up to −40° C. LCMS indicated complete reduction of sulfoxide. The organic solution was poured into ice-cooled 5% sodium chloride (80 mL) and stirred for ~15 min. The solid was separated by filtration, washed with water and dried under high vacuum to afford a dark brown solid (0.45 g, contained 42% of desired product by LCMS). The crude product was further purified by Combiflash automated silica gel chromatography (12 g Gold column, 0-15% MeOH in DCM) to provide 1-(((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-8-carboxamido)ethyl)pyrrolidin-1-

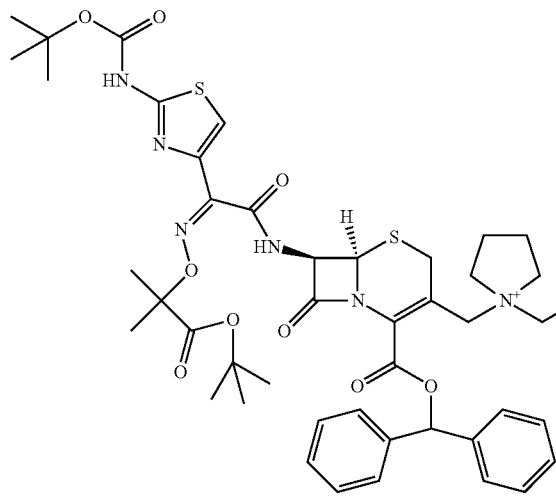

To a solution of 3-((4-methoxybenzyl)oxy)-1-methyl-4-oxo-N-(2-(pyrrolidin-1-yl)ethyl)-1,4-dihydroquinoline-8-carboxamide (0.202 g, 0.464 mmol) in N,N-dimethylacetamide (4 mL) under N$_2$ was added (6R,7R)-benzhydryl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (0.520 g, 0.557 mmol) in N,N-dimethylacetamide (4 mL). The mixture was stirred at room temperature over night. LCMS indicated ~18% of desired product in the reaction mixture. N,N-Dimethylformamide (16.00 mL) was then added. The mixture was ium (66 mg, 80% purity, 0.043 mmol, 9.28% yield) as a brown solid. LCMS: (M+H)$^+$: 1226.0.

Example 14l 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-8-carboxamido)ethyl)pyrrolidin-1-ium

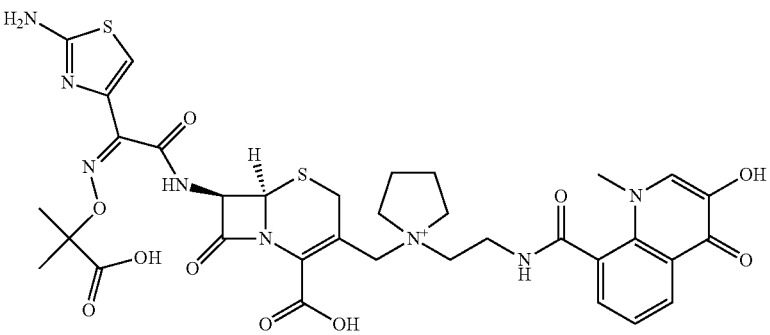 [SMILES: Cn1cc(O)c(=O)c2cccc(C(=O)NCC[N+]3(CC4=C(C(=O)O)N5C(=O)[C@@H](NC(=O)/C(=N\OC(C)(C)C(=O)O)c6csc(N)n6)[C@H]5SC4)CCCC3)c21]

To a solution of 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-8-oxo-5-thia-1-azabicyclo[4.2.0]oct-2-en-3-yl)methyl)-1-(2-(3-((4-methoxybenzyl)oxy)-1-methyl-4-oxo-1,4-dihydroquinoline-8-carboxamido)ethyl)pyrrolidin-1-ium (66 mg, 0.054 mmol) in dichloromethane (2 mL) under N₂ at 0° C. was added anisole (0.059 mL, 0.538 mmol), followed by trifluoroacetic acid (0.5 mL, 6.49 mmol). The mixture was warmed up to room temperature and stirred over night. LCMS indicated completion of the deprotection. Diisopropyl ether (5 mL) and water (1 mL) were then added. The mixture was stirred for 10 min and the solvents were decanted away from the solid. The solid was dissolved in acetonitrile (2 mL) and 1N HCl (2 mL), and purified by Gilson automated HPLC (acetonitrile/Water: 5-65%). The pure fractions were combined and concentrated under vacuum to ~15 mL (bath temperature 20° C.) and freeze-dried to afford 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-8-carboxamido)ethyl)pyrrolidin-1-ium (5 mg, 84% purity, 5.36 µmol, 9.96% yield) as a yellowish solid. LCMS: (M+H)⁺: 783.2. ¹H NMR (400 MHz, METHANOL-d4) δ ppm 1.56-1.70 (m, 6 H) 2.30 (br. s., 4 H) 3.62-4.31 (m, 14 H) 4.42-4.58 (m, 1 H) 5.38-5.50 (m, 1 H) 5.89-6.05 (m, 1 H) 7.12-7.28 (m, 1 H) 7.62-7.77 (m, 1 H) 7.89-8.05 (m, 1 H) 8.32-8.49 (m, 1 H) 8.54-8.69 (m, 1 H)

Example 15

(6R,7R)-7-((Z)-2-(2-aminothiazol-4-yl)-2-(((2-carboxypropan-2-yl)oxy)imino)acetamido)-3-((1-((1-ethyl-8-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

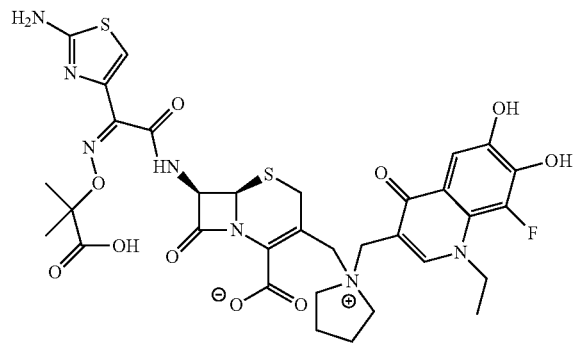 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)c(F)c21]

Example 15a

1-Fluoro-2,3-dimethoxybenzene

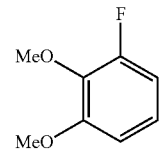

A mixture of 3-fluorobenzene-1,2-diol (145 g, 1132 mmol), potassium carbonate (313 g, 2264 mmol) and iodomethane (177 mL, 2830 mmol) in N,N-Dimethylformamide (DMF) (300 mL) was stirred at RT for 48 h. LCMS showed the complete consuption of starting material. The mixture was diluted with ethyl acetate (EA), filtered, washed with water, dried and evaporated in vacuo. The crude material was purified by normal phase automatic silica gel column chromatography (Combiflash RF, 220 g column), eluting with EA/Hexane (10%-80%) to afford 1-fluoro-2,3-dimethoxybenzene (149 g, 954 mmol, 84% yield) as a colorless oil. LCMS (M+H)⁺: 157.0.

Example 15b

2-Fluoro-3,4-dimethoxy-1-nitrobenzene

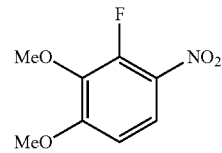

With stirring, to ice cold nitric acid (853 ml, 1.91 E+04 mmol) was added dropwise 1-fluor-2,3-dimethoxybenzene (149 g, 954 mmol). The mixture was stirred at 0° C. for another 15 mins and then warmed up to RT for 15 mins. The orange solution was poured onto ice and the resultant solid was filtered, washed with water and dried. LCMS showed the pale yellow solid was the mixture of 6-nitro and 5-nitro product (ratio=1/1.6). The crude material was purified by reverse phase automatic C18 column chromatography (Combiflash RF, 120 g column) for several times, eluting with Acetonitrile/Water (0-70%) to afford 2-fluoro-3,4-dimethoxy-1-nitrobenzene (53 g, 263 mmol, 27.6% yield) as a white solid. LCMS (M+H)⁺: 202.1.

Example 15c

2-Fluoro-3,4-dimethoxyaniline

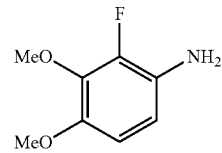

2-Fluoro-3,4-dimethoxy-1-nitrobenzene (52 g, 259 mmol) was hydrogenated on a Par shaker (30 psi) in Ethanol (300 mL) with platinum(IV) oxide (5 g, 22.02 mmol) at r.t. for 30 mins. LCMS indicated completion of the reaction. The catalyst was filtered off and the filtrate was concentrated to afford 2-fluoro-3,4-dimethoxyaniline (42 g, 245 mmol, 95% yield) as a brown oil. LCMS (M+H)$^+$: 172.0.

Example 15d 2-(((2-Fluoro-3,4-dimethoxyphenyl)amino)methylene)malonate

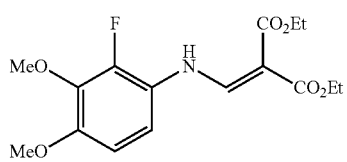 [SMILES: CCOC(=O)C(=CNc1ccc(OC)c(OC)c1F)C(=O)OCC]

To a solution of 2-fluoro-3,4-dimethoxyaniline (39 g, 228 mmol) in Ethanol (200 mL) was added diethyl 2-(ethoxymethylene)malonate (45.7 mL, 228 mmol), and the resulting mixture was heated at 80° C. for 1 h. LCMS indicated completion of the reaction. The mixture was concentrated in vacuo to remove ethanol and then washed with hexane to afford diethyl 2-(((2-fluoro-3,4-dimethoxyphenyl)amino)methylene)malonate (72 g, 211 mmol, 93% yield) as a brown solid. LCMS (M+H)$^+$: 342.1.

Example 15e

Ethyl 8-fluoro-6,7-dimethoxy-4-oxo-1,4-dihydroquinoline-3-carboxylate

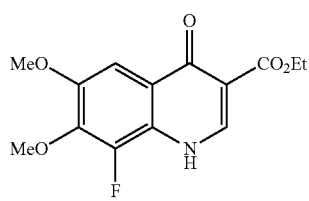 [SMILES: CCOC(=O)c1c[nH]c2c(F)c(OC)c(OC)cc2c1=O]

To Dowtherm (25 mL) heated at 250° C. was added diethyl 2-(((2-fluoro-3,4-dimethoxyphenyl)amino)methylene)malonate (10 g, 29.3 mmol). The mixture was stirred at the same temperature for 40 mins. LCMS indicated completion of the reaction. The reaction was allowed to cool at rt for 5 mins and was then poured into cold hexane, the yellow precipitate was collected by filtration, washed with hexane and dried in the air. This reaction was carried out in similar scale for several times. From a total of 72 g of diethyl 2-(((2-fluoro-3,4-dimethoxyphenyl)amino)methylene)malonate (211 mmol), ethyl 8-fluoro-6,7-dimethoxy-4-oxo-1,4-dihydroquinoline-3-carboxylate (38 g, 129 mmol, 61.0% yield) was obtained as a yellow solid. LCMS (M+H)$^+$: 296.0

Example 15f

Ethyl 1-ethyl-8-fluoro-6,7-dimethoxy-4-oxo-1,4-dihydroquinoline-3-carboxylate

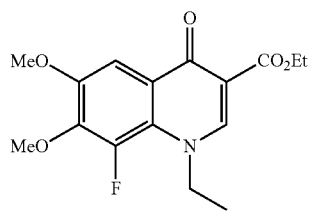 [SMILES: CCOC(=O)c1cn(CC)c2c(F)c(OC)c(OC)cc2c1=O]

A mixture of ethyl 8-fluoro-6,7-dimethoxy-4-oxo-1,4-dihydroquinoline-3-carboxylate (41 g, 139 mmol) and potassium carbonate (28.8 g, 208 mmol) in triethyl phosphate (118 ml, 694 mmol) was stirred at 120° C. for 5 h. LCMS indicated completion of the reaction. Then the reaction mixture was cooled down and diluted with water, extracted with DCM, dried over sodium sulfate and evaporated in vacuo. The crude material was purified by reverse phase automatic C-18 column chromatography (Combiflash RF, 130 g column), eluting with Acetonitrile/Water (10-80%) to afford ethyl 1-ethyl-8-fluoro-6,7-dimethoxy-4-oxo-1,4-dihydroquinoline-3-carboxylate (26 g, 80 mmol, 57.9% yield) as a white solid. LCMS (M+H)$^+$: 324.1.

Example 15g

1-Ethyl-8-fluoro-6,7-dihydroxy-4-oxo-1,4-dihydroquinoline-3-carboxylic acid

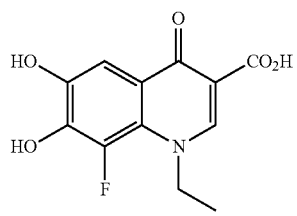 [SMILES: CCn1cc(C(=O)O)c(=O)c2cc(O)c(O)c(F)c21]

To a solution of ethyl 1-ethyl-8-fluoro-6,7-dimethoxy-4-oxo-1,4-dihydroquinoline-3-carboxylate (24 g, 74.2 mmol) in Dichloromethane (DCM) (300 mL) was added boron tribromide (35.1 mL, 371 mmol) at −78° C. The mixture was warmed up to rt and stirred at 25° C. overnight. LCMS indicated completion of the reaction. The mixture was diluted with EtOH and concentrated in vacuo. The same procedure was repeated several times to afford 1-ethyl-8-fluoro-6,7-dihydroxy-4-oxo-1,4-dihydroquinoline-3-carboxylic acid (18 g, 67.4 mmol, 91% yield) as a yellow solid. This product was used in next step reaction without further purification. LCMS (M+H)+: 268.0.

Example 15h

4-Methoxybenzyl 1-ethyl-8-fluoro-6,7-bis((4-methoxybenzyl)oxy)-4-oxo-1,4-dihydroquinoline-3-carboxylate

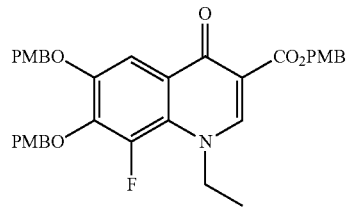

To a solution of 1-ethyl-8-fluoro-6,7-dihydroxy-4-oxo-1,4-dihydroquinoline-3-carboxylic acid (18 g, 67.4 mmol) in N,N-Dimethylformamide (DMF) (200 mL) was added $K_2CO_3$ (46.5 g, 337 mmol), followed by 1-(chloromethyl)-4-methoxybenzene (36.6 mL, 269 mmol). The reaction mixture was stirred at 50° C. overnight. LCMS indicated completion of the reaction. Water (500 ml) was added and the mixture was stirred at r.t for 15 mins. The precipitate was collected by filtration and washed with water to afford 4-methoxybenzyl 1-ethyl-8-fluoro-6,7-bis((4-methoxybenzyl)oxy)-4-oxo-1,4-dihydroquinoline-3-carboxylate (32 g, 51.0 mmol, 76% yield) as a yellow solid.

LCMS (M+H)+: 628.4.

Example 15i

1-Ethyl-8-fluoro-6,7-bis((4-methoxybenzyl)oxy)-4-oxo-1,4-dihydroquinoline-3-carboxylic acid

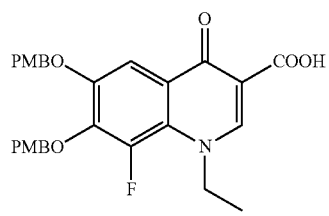

To a suspension of ethyl 1-ethyl-8-fluoro-6,7-bis((4-methoxybenzyl)oxy)-4-oxo-1,4-dihydroquinoline-3-carboxylate (32 g, 59.8 mmol) in a mixture of Methanol (250 mL) and Water (125 mL) was added KOH (6.70 g, 120 mmol) portionwise. The resulting mixture was stirred at 90° C. for 3 h. LCMS indicated completion of the reaction. The mixture was cooled down to r.t. and concentrated. Water was then added, and the mixture was adjusted to pH ~1 using 6 N aq. HCl. The precipitate was collected by filtration and dried to afford 1-ethyl-8-fluoro-6,7-bis((4-methoxybenzyl)oxy)-4-oxo-1,4-dihydroquinoline-3-carboxylic acid (28 g, 55.2 mmol, 92% yield) as a yellow solid. LCMS (M+H)+: 508.2.

Example 15j

1-Ethyl-8-fluoro-3-(hydroxymethyl)-6,7-bis((4-methoxybenzyl)oxy)quinolin-4(1H)-one

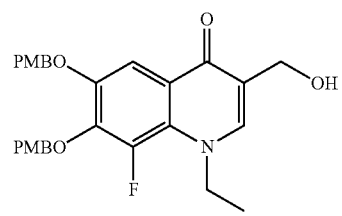

To a suspension of 1-ethyl-8-fluoro-6,7-bis((4-methoxybenzyl)oxy)-4-oxo-1,4-dihydroquinoline-3-carboxylic acid (15 g, 29.6 mmol) in Tetrahydrofuran (THF) (100 mL) was added TEA (6.18 mL, 44.3 mmol) and isobutyl chloroformate (5.82 mL, 44.3 mmol). The resulting mixture was stirred at r.t. for 1 h. The mixture was then cooled down to −40° C. and a solution of DIBAL-H (49.3 mL, 73.9 mmol) in toluene (1.5 M) was added. The mixture was stirred at the same temperature for 1.5 h, when LCMS indicated completion of the reaction. The reaction was quenched with sat. $NH_4Cl$ (aq.), warmed up to r.t. and concentrated. The mixture was diluted with sat. $NH_4Cl$ and extracted with dichloromethane (2×30 mL). The combined organic solution was then dried over sodium sulfate, filtered and concentrated in vacuo to afford 1-ethyl-8-fluoro-3-(hydroxymethyl)-6,7-bis((4-methoxybenzyl)oxy)quinolin-4(1H)-one (10 g, 20.26 mmol, 68.6% yield) as a yellow solid, which was used in the next oxidation step without further purification.

LCMS (M+H)+: 494.2.

Example 15k

1-Ethyl-8-fluoro-6,7-bis((4-methoxybenzyl)oxy)-4-oxo-1,4-dihydroquinoline-3-carbaldehyde

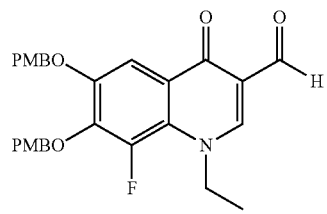

To a yellow solution of 1-ethyl-8-fluoro-3-(hydroxymethyl)-6,7-bis((4-methoxybenzyl)oxy)quinolin-4(1H)-one (10 g, 20.26 mmol) in Dichloromethane (DCM) (100 mL) was added manganese dioxide (17.62 g, 203 mmol), and the mixture was stirred at 25° C. for 6.5 h. LCMS indicated completion of the reaction. The solid was filtered off through Celite and washed with DCM, the filtrate was concentrated to afford 1-ethyl-8-fluoro-6,7-bis((4-methoxybenzyl)oxy)-4-oxo-1,4-dihydroquinoline-3-carbaldehyde (6.5 g, 13.22

Example 151

1-ethyl-8-fluoro-6,7-bis((4-methoxybenzyl)oxy)-3-(pyrrolidin-1-ylmethyl)quinolin-4(1H)-one

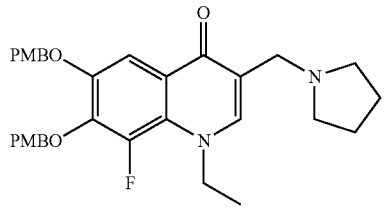

To a solution of 1-ethyl-8-fluoro-6,7-bis((4-methoxybenzyl)oxy)-4-oxo-1,4-dihydroquinoline-3-carbaldehyde (6.5 g, 13.22 mmol) in 1,2-Dichloroethane (DCE) (100 mL) was added pyrrolidine (1.637 mL, 19.84 mmol), sodium triacetoxyborohydride (5.61 g, 26.4 mmol) and AcOH (0.076 mL, 1.322 mmol). The reaction mixture was stirred at 25° C. for 3 h. LCMS indicated completion of the reaction. The mixture was diluted with DCM and washed with brine. The organic layer was dried over sodium sulfate and evaporated in vacuo. The crude material was purified by normal phase automatic silica column chromatography (Combiflash RF, 40 g golden column) eluting with MeOH/DCM (0-20%), and purified again with reverse phase automatic silica column chromatography (Combiflash RF, 150 g golden column) eluting with acetonitrile/Water (0-60%) to afford 1-ethyl-8-fluoro-6,7-bis((4-methoxybenzyl)oxy)-3-(pyrrolidin-1-ylmethyl)quinolin-4(1H)-one (4.3 g, 7.87 mmol, 59.5% yield) as a pale yellow solid.

mmol, 65.3% yield) as a yellow solid that was used in the next step without further purification. LCMS (M+H)$^+$: 492.2.

Example 15m (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide

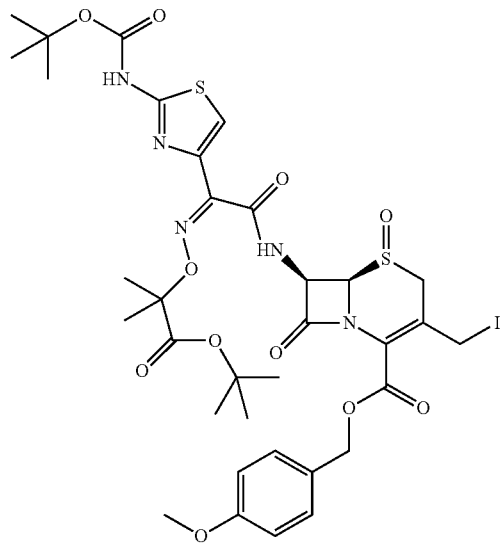

To the solution of (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate 5-oxide (5 g, 6.28 mmol) in Acetone (50 mL) was added sodium iodide (1.176 g, 7.85 mmol) and the mixture was stirred at rt for 2 h. Solvent was removed under vacuum, the residue was chromatographed to give (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (4.5 g, 5.07 mmol, 81% yield). LCMS: (M+H)$^+$: 887.6

Example 15n 1-((((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxy-5-thia-1-azabicyclo[4.2.0]oct-2-en-3-yl)methyl)-1-((1-ethyl-8-fluoro-6,7-bis((4-methoxybenzyl)oxy)-4-oxo-1,4-dihydroquinolin-3-yl)methyl)pyrrolidin-1-ium

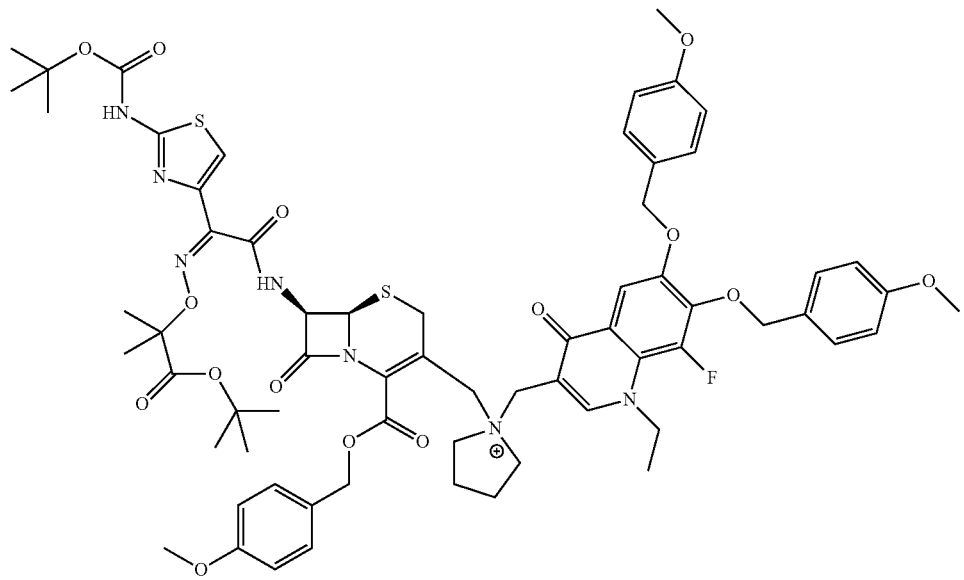 [SMILES: CCn1cc(C[N+]2(CC3=C(C(=O)OCc4ccc(OC)cc4)N4C(=O)[C@@H](NC(=O)/C(=N\OC(C)(C)C(=O)OC(C)(C)C)c5csc(NC(=O)OC(C)(C)C)n5)[C@H]4SC3)CCCC2)c(=O)c2cc(OCc3ccc(OC)cc3)c(OCc3ccc(OC)cc3)c(F)c21]

A solution of (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (1.624 g, 1.829 mmol) and 1-ethyl-8-fluoro-6,7-bis((4-methoxybenzyl)oxy)-3-(pyrrolidin-1-ylmethyl)quinolin-4(1H)-one (Example 15l) (1 g, 1.829 mmol) in N,N-dimethylacetamide (DMA) (10 mL) was stirred at room temperature for 3 h and was then left overnight in the refrigerator. N,N-dimethylformamide (DMF) (10.00 mL) was added and the mixture was cooled to −40° C. followed by addition of PBr₃ (0.345 mL, 3.66 mmol). Stirred at −40° C. for 30 min. Quenched with 5% sodium chloride solution. Filtered. Chromatographed on ISCO silica gel column eluting with 0-20% methanol: dichloromethane to give 1-((((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((1-ethyl-8-fluoro-6,7-bis((4-methoxybenzyl)oxy)-4-oxo-1,4-dihydroquinolin-3-yl)methyl)pyrrolidin-1-ium (2.67 g, 2.067 mmol, 113% yield). LCMS: (M+H)⁺: 1291.2

Example 15o (6R,7R)-7-((Z)-2-(2-aminothiazol-4-yl)-2-(((2-carboxypropan-2-yl)oxy)imino)acetamido)-3-((1-((1-ethyl-8-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

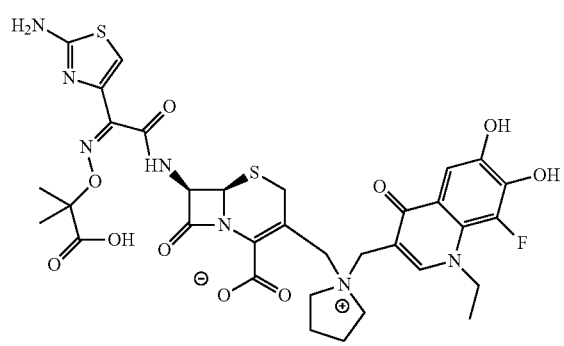 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)c(F)c21]

To the solution of 1-((((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((1-ethyl-8-fluoro-6,7-bis((4-methoxybenzyl)oxy)-4-oxo-1,4-dihydroquinolin-3-yl)methyl)pyrrolidin-1-ium (2.6 g, 2.013 mmol) in dichloromethane (DCM) (30 mL) was added anisole (2.199 mL, 20.13 mmol) followed by trifluoroacertic acid (4.65 mL, 60.4 mmol) at 0° C. The mixture was allowed to warm up to room temperature and stirred at room temperature for 18 h. Solvent was removed and residue triturated with isopropyl ether. Filtered. Dissolved in acetonitrile, water, 2N hydrochloric acid and HP-20-ss resin added. Solvent removed. Purified through HP-20-ss resin and C18 ISCO column. Desired fractions were stripped and lyophilized to constant weight. 1 eq of 0.2N sodium hydroxide was added, followed by dry ice. Lyophilized to give (6R,7R)-7-((Z)-2-(2-aminothiazol-4-yl)-2-(((2-carboxypropan-2-yl)oxy)imino)acetamido)-3-((1-((1-ethyl-8-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate. Sodium salt (442 mg, 0.555 mmol, 27.6% yield). LCMS: (M+H)+: 774.3; 1H NMR (400 MHz, DEUTERIUM OXIDE) δ ppm 1.31-1.45 (m, 9 H) 2.13 (br. s., 4 H) 3.58 (br. s, 6 H) 3.75-4.16 (m, 4 H) 4.49 (d. J=7.58 Hz, 4 H) 5.45 (d, J=5.05 Hz, 1 H) 5.80 (s, 1 H) 6.93 (s, 1 H) 7.35 (s, 1 H), 8.15 (s, 1 H).

Example 16

(6R,7R)-7-((Z)-2-(2-aminothiazol-4-yl)-2-(((S)-1,2-dicarboxyethoxy)imino) acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

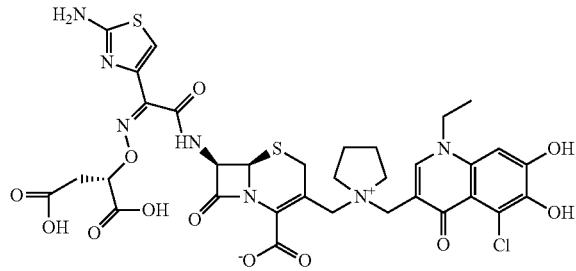

Example 16a

5-Ethyl-9-nitro-8-oxo-5,8-dihydro-[1,3]dioxolo[4,5-g]quinoline-7-carboxylic acid

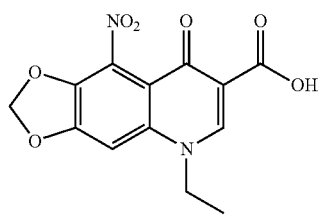

5-Ethyl-8-oxo-5,8-dihydro-[1,3]dioxolo[4,5-g]quinoline-7-carboxylic acid (50 g, 191 mmol) was dissolved in H$_2$SO$_4$ (112 ml, 2105 mmol) with stirring. The thick solution was cooled to 0° C. and potassium nitrate (21.29 g, 211 mmol) was added in small portions. The temperature of the reaction mixture was maintained below 10° C. by use of an iced water bath. After the addition, the mixture was kept under 10° C. for 1 h, and then was allowed to warm up to r.t. and stirred for overnight. It was poured into iced water (2 L). The yellow precipitates were collected by filtration, washed with water and ethanol, and dried in vacuo to afford 5-ethyl-9-nitro-8-oxo-5,8-dihydro-[1,3]dioxolo[4,5-g]quinoline-7-carboxylic acid (61 g, 187 mmol, 98% yield) as a light brown solid. LCMS: (M+H)+: 307.4.

Example 16b

9-Amino-5-ethyl-8-oxo-5,8-dihydro-[1,3]dioxolo[4,5-g]quinoline-7-carboxylic acid

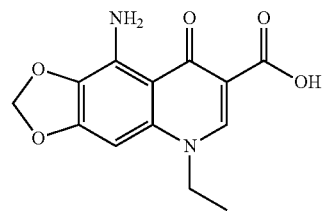 [SMILES: CCn1cc(C(=O)O)c(=O)c2c([N+](=O)[O-])c3c(cc21)OCO3]

A suspension of 5-Ethyl-9-nitro-8-oxo-5,8-dihydro-[1,3]dioxolo[4,5-g]quinoline-7-carboxylic acid (6 g, 19.59 mmol) and Pd/C (1 g, 0.940 mmol) in a mixture of acetic acid (150 mL) and con. HCl (50 mL) was hydrogenated on a Parr apparatus at 50 psi of H$_2$ for 1 h at r.t. LCMS indicated completion of the reaction. The catalyst was filtered off. The filtrate was added dropwise into water (675 mL). The light yellow precipitates were collected by filtration, washed with water and dried in vacuo to afford 9-amino-5-ethyl-8-oxo-5,8-dihydro-[1,3]dioxolo[4,5-g]quinoline-7-carboxylic acid (4.72 g, 17.09 mmol, 87% yield). LCMS: (M+H)+: 277.2.

Example 16c

7-Carboxy-5-ethyl-8-oxo-5,8-dihydro-[1,3]dioxolo[4,5-g]quinoline-9-diazonium chloride

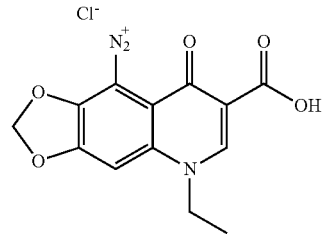

To a pale brown suspension of 9-amino-5-ethyl-8-oxo-5,8-dihydro-[1,3]dioxolo[4,5-g]quinoline-7-carboxylic acid (11 g, 39.8 mmol) in con. HCl (25 mL) stirred at r.t. was added dropwise sodium nitrite (3.57 g, 51.8 mmol) in water (9 mL) at such a rate that the temperature of the reaction mixture would not exceed 45° C. (Ice bath! Slow addition!). Stirring continued for 5 h. The solution was poured into 120 mL of water and allowed to stand overnight in the refrigerator. The precipitate was collected by filtration, washed with water and dried to afford 7-carboxy-5-ethyl-8-oxo-5,8-dihydro-[1,3]dioxolo[4,5-g]quinoline-9-diazonium, Chloride (5 g, 15.45 mmol, 38.8% yield). LCMS: $(M+H)^+$: 324.2.

Note: From LCMS and $^1H$ NMR, the solid was a mixture of the title compound and 5-chloro-1-ethyl-6,7-dihydroxy-4-oxo-1,4-dihydroquinoline-3-carboxylic acid (Example 16d).

Example 16d

5-Chloro-1-ethyl-6,7-dihydroxy-4-oxo-1,4-dihydroquinoline-3-carboxylic acid

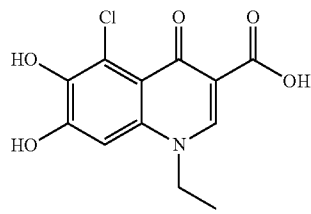 [SMILES: CCn1cc(C(=O)O)c(=O)c2c(Cl)c(O)c(O)cc21]

A solution of 7-carboxy-5-ethyl-8-oxo-5,8-dihydro-[1,3]dioxolo[4,5-g]quinoline-9-diazonium chloride (7.5 g, 23.17 mmol) (Mixture of 16c and 16d) in 50% $H_2SO_4$ (60 mL) was heated at 95° C. for 4 h. The reaction mixture was cooled down to r.t. and then poured into 450 mL of water. The precipitates were collected by filtration and dried to afford 5-chloro-1-ethyl-6,7-dihydroxy-4-oxo-1,4-dihydroquinoline-3-carboxylic acid (6 g, 18.61 mmol, 80% yield) as a yellow brown solid. LCMS: $(M+H)^+$: 284.1.

Example 16e

4-Methoxybenzyl 5-chloro-1-ethyl-6,7-bis((4-methoxybenzyl)oxy)-4-oxo-1,4-dihydroquinoline-3-carboxylate

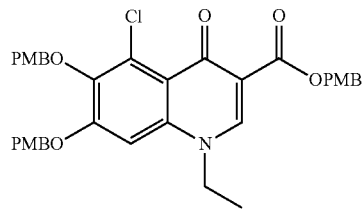

To a red suspension of 5-chloro-1-ethyl-6,7-dihydroxy-4-oxo-1,4-dihydroquinoline-3-carboxylic acid (12.2 g, 43.0 mmol), $K_2CO_3$ (23.78 g, 172 mmol) and KI (0.714 g, 4.30 mmol) in N,N-Dimethylformamide (DMF) (200 mL) at r.t. was added 1-(chloromethyl)-4-methoxybenzene (19.26 mL, 142 mmol). The mixture was heated at 90° C. for 4 h. After cooling, the mixture was concentrated and partitioned between water (200 mL) and DCM (200 mL), and extracted with DCM (150 mL) twice. The organic layers were combined, dried and concentrated. The crude product was purified twice through column chromatography eluting with EtOAc/hexanes (0-100%) to afford pure 4-methoxybenzyl 5-chloro-1-ethyl-6,7-bis((4-methoxybenzyl)oxy)-4-oxo-1,4-dihydroquinoline-3-carboxylate (14 g, 20.65 mmol, 48.0% yield) as a white solid. LCMS: $(M+H)^+$: 644.1.

Example 16f

5-Chloro-1-ethyl-6,7-bis((4-methoxybenzyl)oxy)-4-oxo-1,4-dihydroquinoline-3-carboxylic acid

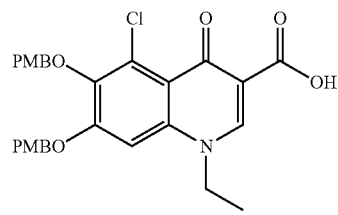

To a suspension of 4-methoxybenzyl 5-chloro-1-ethyl-6,7-bis((4-methoxybenzyl)oxy)-4-oxo-1,4-dihydroquinoline-3-carboxylate (8.4 g, 13.04 mmol) in a mixture of Methanol (90 mL) and Water (30.0 mL) was added KOH (1.463 g, 26.1 mmol) portionwise. The resulting mixture was stirred under reflux for 1.5 h. The mixture was then cooled down to r.t., concentrated, diluted with water (150 mL) and adjusted pH to 2-3 using 6 N HCl (aq.). The precipitates were collected by filtration and dried to afford 5-chloro-1-ethyl-6,7-bis((4-methoxybenzyl)oxy)-4-oxo-1,4-dihydroquinoline-3-carboxylic acid (6.7 g, 12.79 mmol, 98% yield) as a white solid. LCMS: $(M+H)^+$: 524.2.

Example 16g 5-chloro-1-ethyl-3-(hydroxymethyl)-6,7-bis((4-methoxybenzyl)oxy)quinolin-4(1H)-one

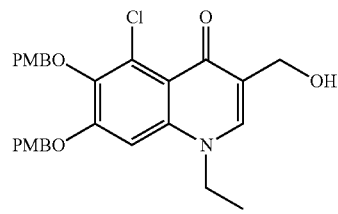

To a suspension of 5-chloro-1-ethyl-6,7-bis((4-methoxybenzyl)oxy)-4-oxo-1,4-dihydroquinoline-3-carboxylic acid (24 g, 41.7 mmol) in Tetrahydrofuran (THF) (450 mL) was added triethylamine (8.71 mL, 62.5 mmol), followed by careful addition of isobutyl chloroformate (7.66 mL, 58.4 mmol). The resulting mixture was stirred at r.t. for 2.5 h. Then the mixture was cooled down to −40° C. and a solution of DIBAL-H (69.5 mL, 104 mmol) in toluene (1.5 M) was added. The mixture was stirred at the same temperature for 3.5 h. After completion, the reaction was quenched with sat. $NH_4Cl$ (aq.), warmed up to r.t., diluted with sat. $NH_4Cl$ (aq.), filtered through Celite to remove gummy precipitate, and extracted with dichloromethane twice. The combined organic extracts were then saturated with brine and then dried over sodium sulfate, filtered and the resulting filtrate was concentrated in vacuo to afford 5-chloro-1-ethyl-3-(hydroxymethyl)-6,7-bis((4-methoxybenzyl)oxy)quinolin-4(1H)-one (19 g, 30.9 mmol, 74.2% yield) as a yellow solid, which was used in the next oxidation step. LCMS: (M+H)+: 510.0.

Example 16h 5-chloro-1-ethyl-6,7-bis((4-methoxybenzyl)oxy)-4-oxo-1,4-dihydroquinoline-3-carbaldehyde

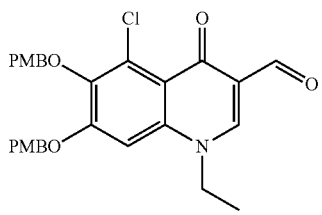

To a yellow solution of 5-chloro-1-ethyl-3-(hydroxymethyl)-6,7-bis((4-methoxybenzyl)oxy) quinolin-4(1H)-one (19 g, 30.9 mmol) in Dichloromethane (DCM) (250 mL) was added manganese dioxide (41.1 g, 402 mmol), and the mixture was stirred at r.t. for overnight. The mixture was then filtered through Celite and washed with DCM. The filtrate was concentrated to afford 5-chloro-1-ethyl-6,7-bis((4-methoxybenzyl)oxy)-4-oxo-1,4-dihydroquinoline-3-carbaldehyde (17 g, 27.4 mmol, 89% yield) as a yellow solid, which was used in the next step without further purification. LCMS: (M+H)+: 508.1.

Example 16i 5-chloro-1-ethyl-6,7-bis((4-methoxybenzyl)oxy)-3-(pyrrolidin-1-ylmethyl)quinolin-4(1H)-one

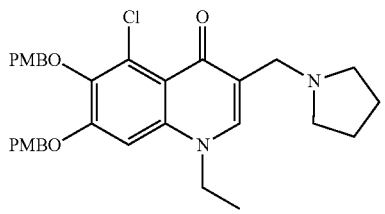

To a solution of 5-chloro-1-ethyl-6,7-bis((4-methoxybenzyl)oxy)-4-oxo-1,4-dihydro quinoline-3-carbaldehyde (21.3 g, 34.4 mmol) in 1,2-Dichloroethane (DCE) (200 mL) was added pyrrolidine (3.13 mL, 37.8 mmol) and sodium triacetoxyborohydride (10.93 g, 51.6 mmol). The mixture was stirred at r.t. for 3 h. Then reaction mixture was concentrated, partitioned between DCM and brine, and extracted with DCM twice. The combined organic extracts were dried over sodium sulfate and the solvent was removed in vacuo. The crude product was then purified through normal phase chromatography (CombiFlash Rf), eluting with [DCM/MeOH/NH4OH (v:v:v=80:20:2)]:DCM (0% to 60%) to afford 5-chloro-1-ethyl-6,7-bis((4-methoxybenzyl)oxy)-3-(pyrrolidin-1-ylmethyl)quinolin-4(1H)-one (17 g, 30.2 mmol, 88% yield) as a light yellow solid. LCMS: (M+H)+: 563.2.

Example 16j (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate

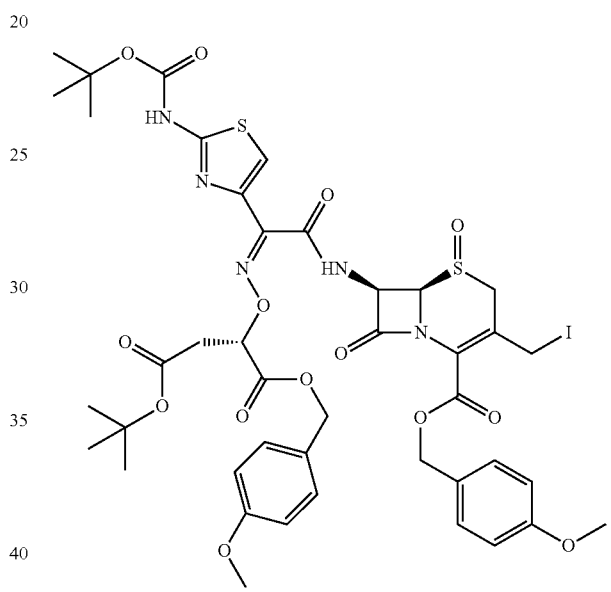

To a solution of (S)-4-tert-butyl 1-(4-methoxybenzyl) 2-(((Z)-(1-(2-((tert-butoxycarbonyl)amino)thiazol-4-yl)-2-(((5R,6R,7R)-3-(chloromethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy)succinate (10.60 g, 11.20 mmol) (from Shionogi) in Acetone (100 mL) at rt was added sodium iodide (2.52 g, 16.80 mmol). The mixture was stirred at the same temperature over 2 h. LCMS indicated completion of the reaction. The solid was filtered off, the filtrate was concentrated under vacuum, and the residue was purified by Combiflash automated silica gel chromatography (120 g Gold column), eluting with ethyl acetate/hexanes (0-50%) to afford (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxybenzyl)oxy)carbonyl)-5-oxido-8-oxo-5-thia-1-azabicyclo[4.2.0]oct-2-en-7-yl)amino)-2-oxoethylidene)amino)oxy) succinate (9.7 g, 9.35 mmol, 83% yield) as a yellow solid. LCMS: (M+H)+: 1037.8.

Example 16k 1-((((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium

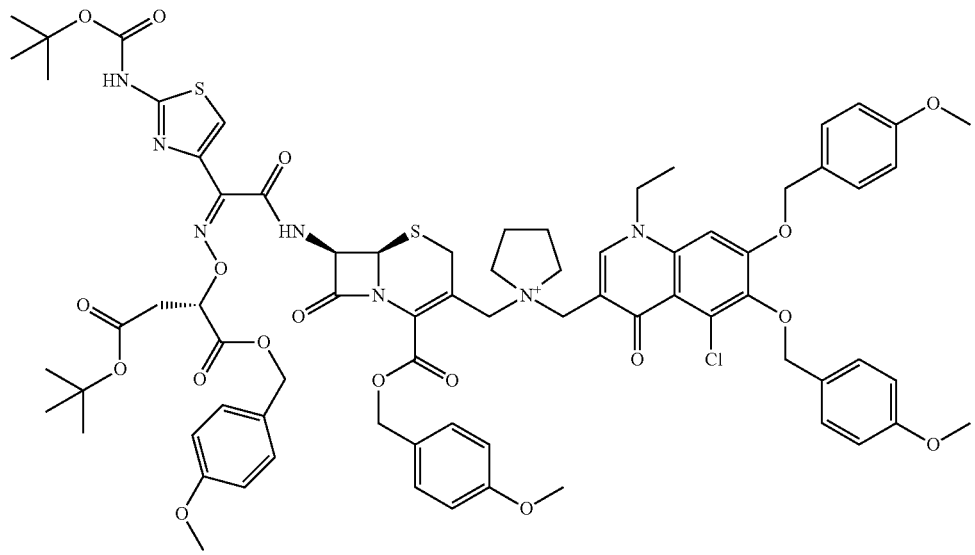 [SMILES: CCn1cc(C[N+]2(CC3=C(C(=O)OCc4ccc(OC)cc4)N4C(=O)[C@@H](NC(=O)/C(=N\O[C@@H](CC(=O)OC(C)(C)C)C(=O)OCc5ccc(OC)cc5)c5csc(NC(=O)OC(C)(C)C)n5)[C@H]4SC3)CCCC2)c(=O)c2c(Cl)c(OCc3ccc(OC)cc3)c(OCc3ccc(OC)cc3)cc21]

To a suspension of 5-chloro-1-ethyl-6,7-bis((4-methoxybenzyl)oxy)-3-(pyrrolidin-1-ylmethyl)quinolin-4(1H)-one (Example 16i) (2.0 g, 3.55 mmol) in DMA (20 mL) at 15° C. under $N_2$ was added (S)-4-tert-butyl 1-(4-methoxybenzyl) 2-(((Z)-(1-(2-((tert-butoxycarbonyl)amino)thiazol-4-yl)-2-(((5R,6R,7R)-3-(iodomethyl)-2-(((4-methoxy benzyl)oxy)carbonyl)-5-oxido-8-oxo-5-thia-1-azabicyclo[4.2.0]oct-2-en-7-yl)amino)-2-oxoethylidene)amino)oxy)succinate (3.69 g, 3.55 mmol) in DMA (8 mL). The mixture became clear solution after a few minutes and stirring continued at the same temperature over 2 h. N,N-Dimethylformamide (DMF) (56.00 mL) was then added. The mixture was cooled to −70° C. and treated with $PBr_3$ (0.737 mL, 7.81 mmol) dropwise. The mixture was allowed to warm up to −40° C. LCMS indicated complete reduction of sulfoxide. The organic solution was poured into ice-cooled 5% NaCl (250 mL, containing 0.05M HCl) and stirred for ~15 min. The solid was separated by filtration, washed with water and dried under high vacuum to afford 1-((((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino) thiazol-4-yl)acetamido)-2-(((4-methoxybenzyl)oxy)carbonyl)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (5.99 g, 84% purity, 3.45 mmol, 97% yield) as a brown solid. LCMS: (M+H)$^+$: 1456.5.

Example 16l (6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

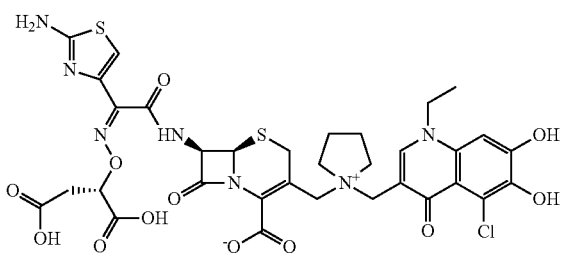

To a solution of 1-((((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (5.99 g, 3.45 mmol) in Dichloromethane (DCM) (30 mL) under N₂ at 0° C. was added anisole (3.77 mL, 34.5 mmol), followed by 2,2,2-trifluoroacetic acid (10.0 mL, 130 mmol). The mixture was warmed up to rt and stirred at rt over night. LCMS indicated completion of the deprotection. The mixture was cooled to 0° C., Diisopropyl ether (100 mL) was then added. The mixture was stirred for 10 min and the solid was collected by filtration, and washed twice with diisopropyl ether (2×20 mL). The solid (~4.4 g) was dissolved in a mixture of CH₃CN (25 mL)/water (25 mL)/2M HCl (10 mL), HP20SS resin (30 g) was then added. The mixture was concentrated to dryness, and the resin was loaded in a pre-column containing HP20SS resin (45 g), and was then purified by reverse phase Combiflash using C18 column and eluting with 0-30% CH₃CN/water to afford (6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (F1: 0.975 g, 1.189 mmol, 34.4%) as a slightly brown solid. LCMS: (M+H)⁺: 820.2. ¹H NMR (400 MHz, METHANOL-d4) δ ppm 1.50 (t, J=7.07 Hz, 3 H) 2.22 (br. s., 4 H) 2.93-2.99 (m, 2 H) 3.44-3.65 (m, 6 H) 3.89-3.98 (m, 1 H) 4.09-4.21 (m, 1 H) 4.27-4.41 (m, 3 H) 4.46-4.55 (m, 1 H) 5.09-5.16 (m, 1 H) 5.25-5.33 (m, 1 H) 5.85-5.90 (m, 1 H) 6.93 (s, 1 H) 7.04-7.11 (m, 1 H) 8.19-8.26 (m, 1 H)

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (Example 16l) (0.233 g, 0.284 mmol) was suspended in pure water (HPLC grade, 15 mL) with the help of sonication, and cooled to 0° C. With vigorous stirring, aq NaOH (0.2 N, 1.42 mL, 0.284 mmol) was added slowly into the suspension from an Eppendorf Pipette. After the addition a small piece of dry ice was added to quench any extra NaOH. The pale yellow solution was then frozen and lyophilized to afford (6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate. Sodium salt (0.239 g, 0.278 mmol, 8.05% yield) as an off-white solid. LCMS: (M+H)⁺: 820.3. ¹H NMR (400 MHz, DEUTERIUM OXIDE) δ ppm 1.30 (t, J=7.07 Hz, 3 H) 2.01 (br. s., 4 H) 2.59-2.68 (m, 2 H) 3.18-3.47 (m, 6 H) 3.87 (d, J=-16.67 Hz, 1 H) 3.94-4.36 (m, 5 H) 4.78-4.88 (m, 1 H) 5.28 (d, J=5.05 Hz, 1 H) 5.72 (d, J=5.05 Hz, 1 H) 6.88 (s, 2 H) 7.98-8.09 (m, 1 H).

Example 17

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt Example 18

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

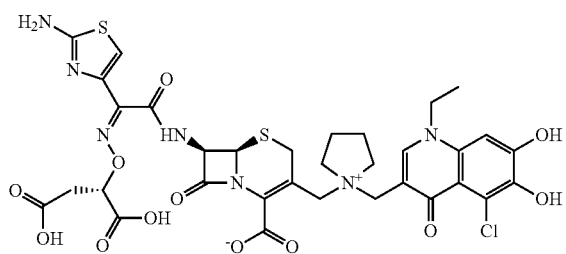

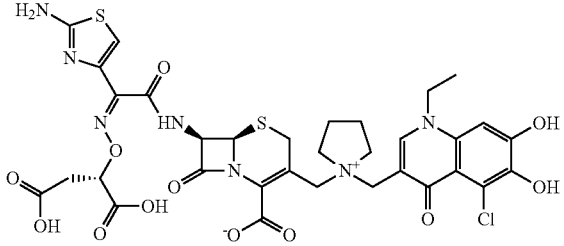

A suspension of (6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (Example 16l) (0.601 g, 0.733 mmol) was cooled to −5-0° C. using an acetone-dry ice bath. With vigorous stirring, aq NaOH (0.2 N) was added slowly into the suspension from an Eppendorf Pipette until pH of the mixture reached 6.5 (~7.2 mL of NaOH added). After the addition a small piece of dry ice was added to quench any extra NaOH. The solution was then frozen and lyophilized to afford (6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt (0.633 g, 0.687 mmol, 94% yield) as an off-white solid. LCMS: $(M+H)^+$: 820.3. $^1$H NMR (400 MHz, DEUTERIUM OXIDE) 56 ppm 1.33 (t, J=6.69 Hz, 3 H) 2.02 (br. s., 4 H) 2.60 (s, 2 H) 3.22-3.50 (m, 6 H) 3.82-3.93 (m, 1 H) 3.96-4.07 (m, 1 H) 4.10-4.40 (m, 4 H) 4.81-4.90 (m, 1 H) 5.26-5.32 (m, 1 H) 5.70-5.78 (m, 1 H) 6.90 (s, 2 H) 8.01-8.12 (m, 1 H).

Example 19

(6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

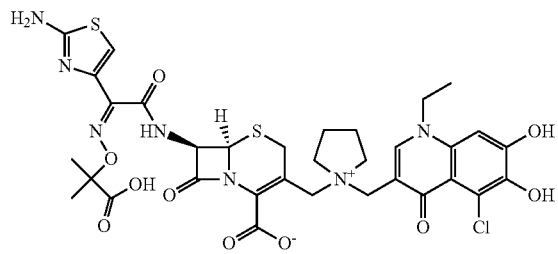 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2c(Cl)c(O)c(O)cc21]

Example 19a (6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide

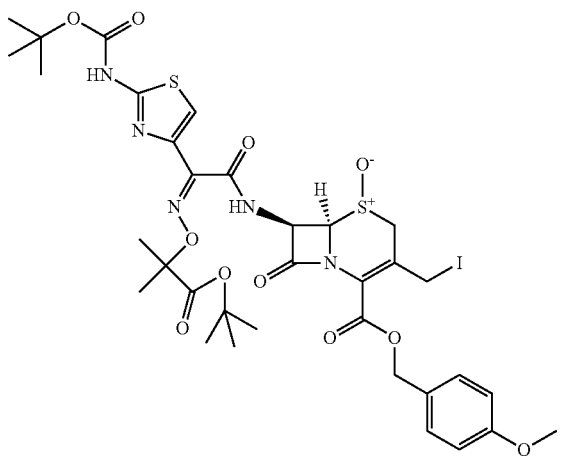 [SMILES: COc1ccc(COC(=O)C2=C(CI)C[S+]([O-])[C@@H]3[C@H](NC(=O)/C(=N\OC(C)(C)C(=O)OC(C)(C)C)c4csc(NC(=O)OC(C)(C)C)n4)C(=O)N23)cc1]

To a solution of (6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate 5-oxide (10.00 g, 12.56 mmol) in Acetone (100 mL) at rt was added sodium iodide (2.82 g, 18.84 mmol). The mixture was stirred at the same temperature over 2 h. LCMS indicated completion of the reaction. The solid was filtered off, the filtrate was concentrated under vacuum, and the residue was purified by Combiflash automated silica gel chromatography (120 g Gold column), eluting with ethyl acetate/hexanes (0-50%) to afford (6R,7R)-4-methoxybenzyl 7-((Z)-2-(((1-(tert-butoxy)-2-methyl-1-oxopropan-2-yl)oxy)imino)-2-(2-((tert-butoxy carbonyl)amino)thiazol-4-yl)acetamido)-3-(iodomethyl)-8-oxo-5-thia-1-azabicyclo[4.2.0]oct-2-ene-2-carboxylate 5-oxide (10.86 g, 12.23 mmol, 97% yield) as a yellow solid. LCMS: $(M+H)^+$: 887.9.

Example 19b 1-((((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium

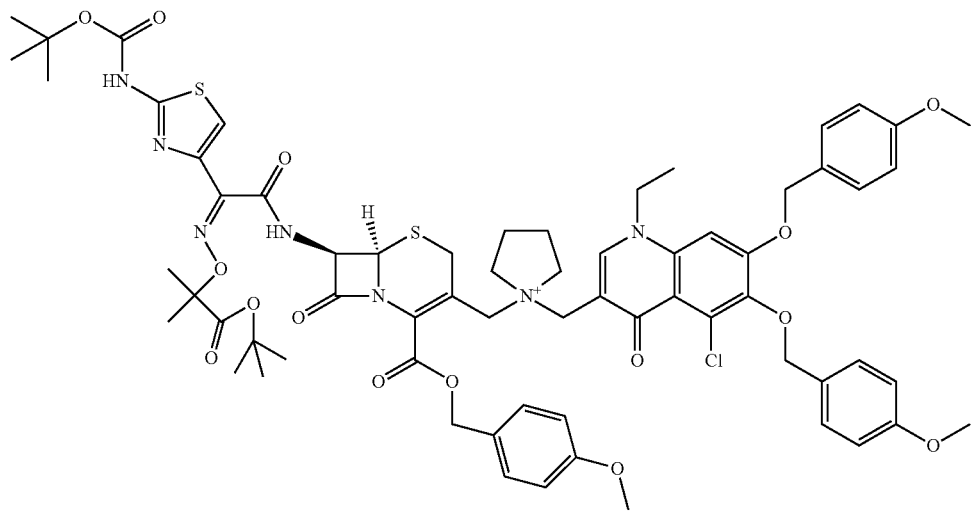 [SMILES: CCn1cc(C[N+]2(CC3=C(C(=O)OCc4ccc(OC)cc4)N4C(=O)[C@@H](NC(=O)/C(=N\OC(C)(C)C(=O)OC(C)(C)C)c5csc(NC(=O)OC(C)(C)C)n5)[C@H]4SC3)CCCC2)c(=O)c2c(Cl)c(OCc3ccc(OC)cc3)c(OCc3ccc(OC)cc3)cc21]

To a suspension of 5-chloro-1-ethyl-6,7-bis((4-methoxybenzyl)oxy)-3-(pyrrolidin-1-ylmethyl)quinolin-4(1H)-one (Example 16i) (0.982 g, 1.744 mmol) in DMA (10 mL) under N₂ at 10° C. was added (6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (1.548 g, 1.744 mmol) in DMA (5 mL). The mixture became clear solution after a few minutes and stirring continued at 10-15° C. over 2.5 h. N,N-Dimethylformamide (DMF) (30.00 mL) was then added. The mixture was cooled to −70° C. and treated with tribromophosphine (0.362 mL, 3.84 mmol) dropwise. The mixture was allowed to warm up to −40° C. over 30 min. LCMS indicated complete reduction of sulfoxide. The organic solution was poured into ice-cooled 5% NaCl (150 mL, containing 0.05M HCl) and stirred for ~15 min. The solid was separated by filtration, washed with water and dried under high vacuum to afford 1-(((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((5-chlor-1-ethyl-6,7-bis((4-methoxybenzyl)oxy)-4-oxo-1,4-dihydroquinolin-3-yl)methyl)pyrrolidin-1-ium (2.668 g, 80% purity, 1.632 mmol, 94% yield) as a dark brown foamy solid. LCMS: (M+H)⁺: 1306.1.

Example 19c (6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

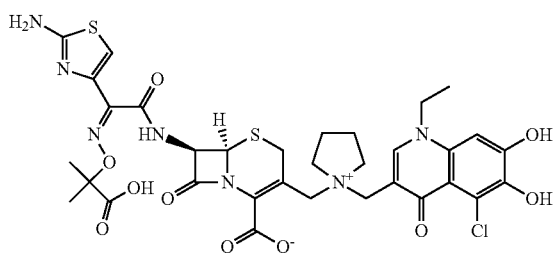 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2c(Cl)c(O)c(O)cc21]

To a solution of 1-(((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (2.668 g, 80% purity, 1.632 mmol) in Dichloromethane (DCM) (15 mL) under N₂ at 0° C. was added anisole (1.783 mL, 16.32 mmol), followed by TFA (5.0 mL, 64.9 mmol). The mixture was warmed up to rt and stirred at rt over night. LCMS indicated completion of the deprotection. The mixture was cooled to 0° C. Diisopropyl ether (50 mL) was then added. The mixture was stirred for 10 min and the solid was collected by filtration, and washed twice with diisopropyl ether (2×10 mL). The solid (~2.0 g) was dissolved in a mixture of $CH_3CN$ (10 mL)/water (10 mL)/2M HCl (2.5 mL), HP20SS resin (12 g) was then added. The mixture was concentrated to dryness, and the resin was loaded in a pre-column containing HP20SS resin (15 g), and was then purified by reverse phase Combiflash using C18 column and eluting with 0-30% $CH_3CN$/water to afford (6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (0.66 g, 0.793 mmol, 48.6% yield) as a slightly brown solid. LCMS: $(M+H)^+$: 790.1. $^1H$ NMR (400 MHz, METHANOL-d4) δ ppm 1.50 (s, 3 H) 1.62 (d, J=6.57 Hz, 6 H) 2.12-2.28 (m, 4 H) 3.42-3.63 (m, 6 H) 3.95-4.05 (m, 1 H) 4.07-4.16 (m, 1 H) 4.26-4.40 (m, 3 H) 4.47-4.55 (m, 1 H) 5.30-5.37 (m, 1 H) 5.89-5.97 (m, 1 H) 6.91 (s, 1 H) 7.04-7.10 (m, 1 H) 8.17-8.24 (m, 1 H).

Example 20

(6R,7R)-7-((Z)-2-(2-aminothiazol-4-yl)-2-(((2-carboxylatopropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

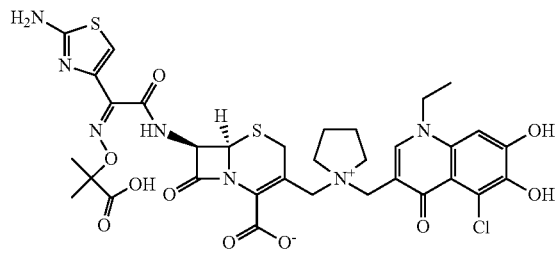 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2c(Cl)c(O)c(O)cc21]

To a suspension of (6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (Example 19c) (0.361 g, 0.457 mmol) in Water (20 mL) at 0° C. was added 0.2 N sodium hydroxide (2.284 mL, 0.457 mmol) dropwise, followed by a small cube of dry ice. The mixture was then frozen and lyophilized to afford (6R,7R)-7-((Z)-2-(2-amino thiazol-4-yl)-2-(((2-carboxylatopropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt (0.371 g, 0.411 mmol, 90% yield) as a light brown solid. LCMS: $(M+H)^+$: 790.1. $^1H$ NMR (400 MHz, DEUTERIUM OXIDE) δ ppm 1.20-1.48 (m, 9 H) 2.03 (br. s., 4 H) 3.18-3.52 (m, 6 H) 3.81-4.09 (m, 4 H) 4.11-4.34 (m, 2 H) 5.30 (d, J=5.05 Hz, 1 H) 5.76 (d, J=4.80 Hz, 1 H) 6.69 (s, 1 H) 6.82 (s, 1 H) 7.94 (br. s., 1 H).

Example 21

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

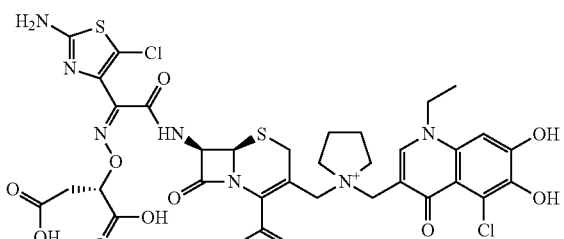

Example 21a 2-(2-((tert-butoxycarbonyl)amino)thiazol-4-yl)-2-oxoacetic acid

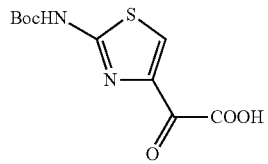

To a suspension of ethyl 2-(2-aminothiazol-4-yl)-2-oxoacetate (30 g, 150 mmol) in Dichloromethane (DCM) (500 mL) was added $(Boc)_2O$ (48.7 mL, 210 mmol) and DABCO (16.81 g, 150 mmol). The mixture was stirred at rt overnight. LCMS indicated completion of the reaction. Solvent was removed under vacuum, and to the resulting residue was added a pre-cooled solution of 2M NaOH (300 mL, 599 mmol) and the mixture was stirred in ice bath for 2 h. Iced Water (250 mL) was added, and the mixture was carefully acidified with 6N HCl (aq) to pH=1. The precipitated material was collected by filtration, washed with water, and dried in vacuo to afford 2-(2-((tert-butoxycarbonyl)amino)thiazol-4- yl)-2-oxoacetic acid (33.5 g, 123 mmol, 82% yield) as pale yellow solid. LCMS: (M+Na)+: 295.0

Example 21b 2-(2-((tert-butoxycarbonyl)amino)-5-chlorothiazol-4-yl)-2-oxoacetic acid

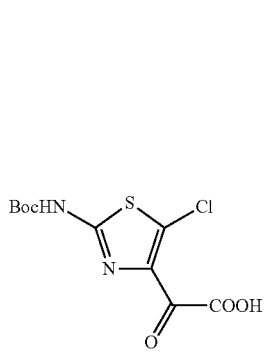

To a suspension of 2-(2-((tert-butoxycarbonyl)amino)thiazol-4-yl)-2-oxoacetic acid (23.5 g, 86 mmol) in 1,4-Dioxane (200 mL) was added NCS (12.22 g, 91 mmol) portionwise. The mixture was stirred at 40° C. for 2.5 h. The mixture was cooled to r.t. and filtered to remove the insoluable material. The filtrate was concentrated under vacuum. The residue was taken with Et₂O and filtered. The filtrate was diluted with EtOAc and washed with water and brine. The organic solution was dried over sodium sulfate, filtered and concentrated. To the oily residue was added n-hexane and Et₂O, and the mixture was concentrated in vacuo. After trituration, 2-(2-((tert-butoxycarbonyl)amino)-5-chlorothiazol-4-yl)-2-oxoacetic acid (22.8 g, 74.3 mmol, 86% yield) was obtained as a light yellow solid. LCMS: (M+Na)+: 329.0.

Example 21c (R)-2,5-dioxotetrahydrofuran-3-yl 2,2,2-trifluoroacetate

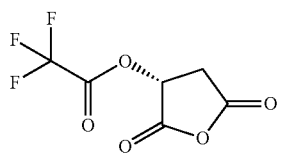

To neat (R)-2-hydroxysuccinic acid (60 g, 447 mmol) being stirred in ice bath was added TFAA (145 ml, 1029 mmol). The mixture was stirred for 1 h and then at room temperature for 3 h. Toluene was added and the mixture was concentrated under vacuum to afford (R)-2,5-dioxotetrahydrofuran-3-yl 2,2,2-trifluoroacetate (94.7 g, 447 mmol, 100% yield) as a white solid which was used for the next step without further purification. $^1$H NMR (400 MHz, DMSO-d6) δ ppm 3.35-3.59 (m, 2 H) 6.10 (dd, 1 H)

Example 21d (E)-tert-butyl N,N'-diisopropylcarbamimidate

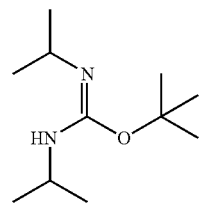

To a solution of N,N'-methanediylidenebis(propan-2-amine) (307 ml, 1981 mmol) in t-BuOH (227 ml, 2377 mmol) at r.t. was added copper(I) chloride (1.961 g, 19.81 mmol). The reaction was stirred at room temperature for 24 h and the resulting mixture was distilled under reduced pressure to afford (E)-tert-butyl N,N'-diisopropylcarbamimidate (279 g, 1393 mmol, 70.3% yield) as a colorless liquid. $^1$H NMR (400 MHz, CHLOROFORM-d4) δ ppm 1.04 (d, J=−6.06 Hz, 6 H) 1.08 (d, J=6.57 Hz, 6 H) 1.46 (s, 9 H) 2.98-3.19 (m, 1 H) 3.25 (m, 1 H) 3.64 (s, 1 H)

Example 21e (R)-4-tert-butyl 1-(4-methoxybenzyl) 2-hydroxysuccinate

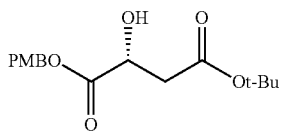

To a solution of (R)-2,5-dioxotetrahydrofuran-3-yl 2,2,2-trifluoroacetate (85 g, 401 mmol) in Dichloromethane (DCM) (600 mL) was added (4-methoxyphenyl)methanol (150 mL, 1202 mmol). The mixture was stirred at rt for 3 h and then extracted three times with 10% aqueous solution of NaHCO₃. The combined aqueous extracts were washed with DCM, acidified to pH 2 with 2 N HCl, and then extracted with DCM. The organic layer was dried over sodium sulfate and filtered. To the filtrate was added (E)-tert-butyl N,N'-diisopropylcarbamimidate (161 g, 802 mmol) dropwise over 1 h. The mixture was stirred at rt overnight. The precipitate was removed by filtration and the filtrate was purified by normal phase automatic silica column chromatography (Combiflash RF), eluting with EA/Hexane (10-80%) to afford (R)-4-tertbutyl 1-(4-methoxybenzyl) 2-hydroxysuccinate (62.5 g, 201 mmol, 50.2% yield) as a colorless oil. LCMS: (M+Na)+: 333.1

Example 21f (S)-4-tert-butyl 1-(4-methoxybenzyl) 2-((1,3-dioxoisoindolin-2-yl)oxy)succinate

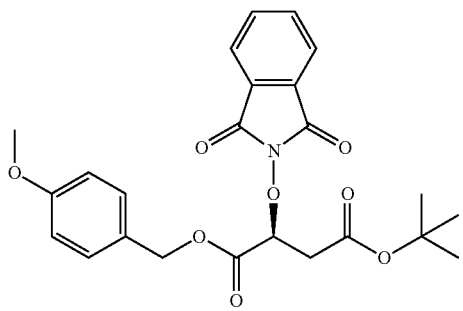 [SMILES: COc1ccc(COC(=O)[C@H](CC(=O)OC(C)(C)C)ON2C(=O)c3ccccc3C2=O)cc1]

To a mixture of (R)-4-tert-butyl 1-(4-methoxybenzyl) 2-hydroxysuccinate (61 g, 197 mmol), N-Hydroxyphthalimide (38.5 g, 236 mmol) and triphenylphosphine (61.9 g, 236 mmol) in Tetrahydrofuran (THF) (1000 mL) was added DIAD (45.9 mL, 236 mmol) dropwise at 0° C. over 30 min. The mixture was stirred at room temperature for 1 h. The solvent was removed under vacuum, and the residue was purified by normal phase automatic silica column chromatography (Combiflash RF), eluting with EA/Hexane (0-90%) to afford (S)-4-tert-butyl 1-(4-methoxybenzyl) 2-((1,3-dioxoisoindolin-2-yl)oxy) succinate (88 g, 193 mmol, 98% yield) as a pale yellow oil. LCMS: (M+Na)+: 478.3

Example 21g (S)-4-tert-butyl 1-(4-methoxybenzyl) 2-(aminooxy)succinate

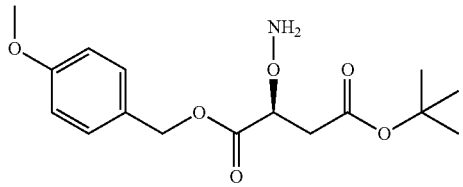 [SMILES: COc1ccc(COC(=O)[C@H](CC(=O)OC(C)(C)C)ON)cc1]

To a solution of (S)-4-tert-butyl 1-(4-methoxybenzyl) 2-((1,3-dioxoisoindolin-2-yl)oxy)succinate (68 g, 149 mmol) in Dichloromethane (DCM) (500 mL) was added methylhydrazine (7.86 mL, 149 mmol) dropwise at 0° C. over 30 min. The mixture was allowed to warm to rt and stirred at rt for 1 h. LCMS indicated completion of the reaction. The insoluble material was removed by filtration and the filtrate was concentrated and diluted with toluene. The resulting precipitate was removed by filtration again and the filtrate was concentrated to afford crude (S)-4-tert-butyl 1-(4-methoxybenzyl) 2-(aminooxy)succinate (47 g, 144 mmol, 97% yield) as a pale yellow oil. The product was used in next step without further purification. LCMS: (M+H)+: 326.1

Example 21h (S,Z)-2-(((4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetic acid

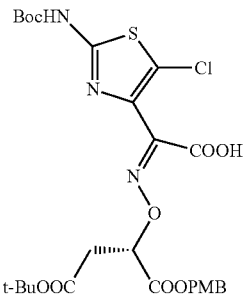

To a solution of (S)-4-tert-butyl 1-(4-methoxybenzyl) 2-(aminooxy)succinate (39.7 g, 122 mmol) in Methanol (300 mL) was added a solution of 2-(2-((tert-butoxycarbonyl)amino)-5-chlorothiazol-4-yl)-2-oxoacetic acid (Example 21b) (34 g, 111 mmol) at 0° C. Then the mixture was allowed to warm up to rt and stirred for 2 h. LCMS indicated completion of the reaction and the product as a mixture of Z/E isomer (19:1). The reaction mixture was concentrated and the residue was purified by reverse phase automatic C18 column chromatography (Combinflash RF, 150 g column, six runs), eluting with Acetonitrile/Water (0-90%) to afford (S,Z)-2-(((4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetic acid (46 g, 74.9 mmol, 67.6% yield) as pale yellow solid. LCMS: (M+H)+: 614.4. ¹H NMR (400 MHz, METHANOL-d4) δ ppm 1.44 (s, 9 H) 1.55 (s, 9 H)

2.74-2.96 (m, 2 H) 3.78 (s, 3 H) 5.06-5.13 (m, 1 H) 5.17 (s, 2 H) 6.86 (d, J=8.84 Hz, 2 H) 7.32 (d. J=8.59 Hz, 2 H)

Example 21i (S)-4-tert-butyl 1-(4-methoxybenzyl) 2-(((Z)-(2-(((6R,7R)-2-((benzhydryl oxy)carbonyl)-3-(chloromethyl)-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy) succinate

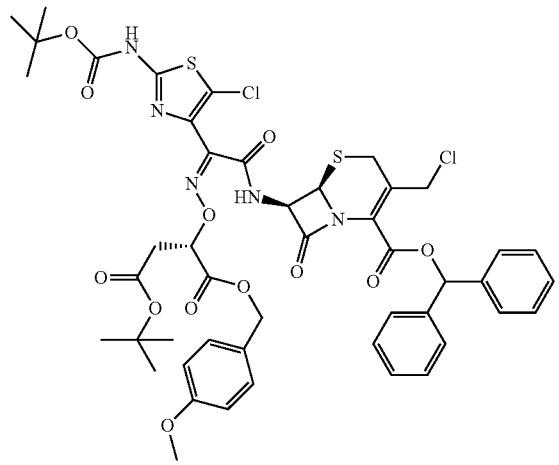 [SMILES: COc1ccc(COC(=O)[C@H](CC(=O)OC(C)(C)C)O/N=C(\C(=O)N[C@@H]2C(=O)N3C(C(=O)OC(c4ccccc4)c4ccccc4)=C(CCl)CS[C@H]23)c2nc(NC(=O)OC(C)(C)C)sc2Cl)cc1]

To a suspension of (S,Z)-2-(((4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetic acid (16.7 g, 27.2 mmol) and (6R,7R)-benzhydryl 7-amino-3-(chloromethyl)-8-oxo-5-thia-1-azabicyclo[4.2.0]oct-2-ene-2-carboxylate, Hydrochloride (12.89 g, 28.6 mmol) in Dichloromethane (DCM) (210 mL) at −30° C. was added phenyl phosphorodichloridate (4.95 mL, 32.6 mmol), followed by dropwise N-methylmorpholine (8.97 mL, 82 mmol) over 15 mins. The mixture was stirred at the same temperature over 3 h. LCMS indicated completion of the reaction. The reaction was quenched by addition of 10% aq. citric acid (85 mL), the organic solution was separated and washed with 5% NaHCO₃, brine, and dried (Na₂SO₄), filtered, and concentrated. The residue was purified by CombiFlash automated silica gel chromatography (330 g column, 0-50% EtOAc/Hexanes) to afford (S)-4-tert-butyl 1-(4-methoxybenzyl) 2-(((Z)-(2-(((6R,7R)-2-((benzhydryloxy)carbonyl)-3-(chloromethyl)-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy)succinate (26 g, 25.7 mmol, 95% yield) as a light yellow foaming solid. LCMS: $(M+H)^+$: 1010.6

Example 21j (S)-4-tert-butyl 1-(4-methoxybenzyl) 2-(((Z)-(2-(((5R,6R,7R)-2-((benzhydryl oxy)carbonyl)-3-(chloromethyl)-5-oxido-8-oxo-5-thia-1-azabicyclo[4.2.0] oct-2-en-7-yl)amino)-1-(2-((tert-butoxycarbonyl) amino)-5-chlorothiazol-4-yl)-2-oxoethylidene) amino)oxy)succinate

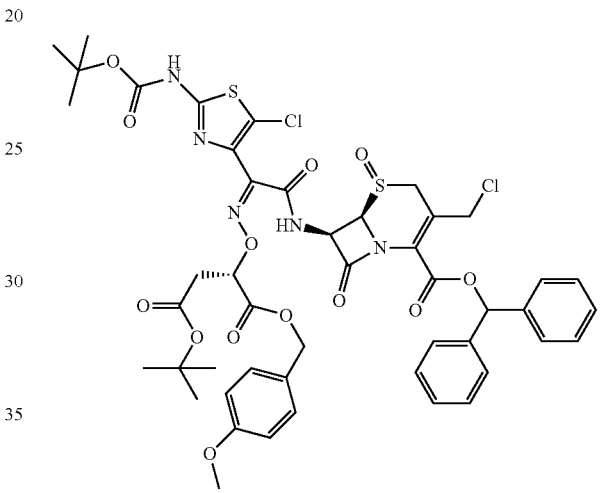

To a solution of (S)-4-tert-butyl 1-(4-methoxybenzyl) 2-(((Z)-(2-(((6R,7R)-2-((benzhydryl oxy)carbonyl)-3-(chloromethyl)-8-oxo-5-thia-1-azabicyclo[4.2.0]oct-2-en-7-yl) amino)-1-(2-((tert-butoxycarbonyl)amino)-5-chlorothiazol-4-yl)-2-oxoethylidene)amino)oxy)succinate (27.5 g, 27.2 mmol) in Dichloromethane (DCM) (IL) at −40° C. was added dropwise a solution of m-CPBA (6.40 g, 28.6 mmol) in Dichloromethane (DCM) (200 mL) over 10 min. The mixture was stirred at the same temperature over 30 min. LCMS indicated completion of the reaction. The mixture was treated with 15% aq. Na₂S₂O₃ (200 mL). The organic solution was separated and washed with 5% NaHCO₃ (400 mL), brine (400 mL), dried (Na₂SO₄), filtered, and concentrated (temperature of the water bath should not be too high—apx. 25° C.). The residue was purified by CombiFlash automated silica gel chromatography (220 g column), eluting with EtOAc/Hexanes (0-60%) to afford (S)-4-tert-butyl 1-(4-methoxybenzyl) 2-(((Z)-(2-(((5R,6R,7R)-2-((benzhydryloxy)carbonyl)-3-(chloromethyl)-5-oxido-8-oxo-5-thia-1-azabicyclo[4.2.0] oct-2-en-7-yl)amino)-1-(2-((tert-butoxycarbonyl)amino)-5-chlorothiazol-4-yl)-2-oxoethylidene)amino)oxy)succinate (27.5 g, 25.4 mmol, 94% yield) as a light yellow foaming solid. LCMS: $(M+H)^+$: 1026.3

Example 21k (S)-4-tert-butyl 1-(4-methoxybenzyl) 2-(((Z)-(2-(((5R,6R,7R)-2-((benzhydryl oxy)carbonyl)-3-(iodomethyl)-5-oxido-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy)succinate

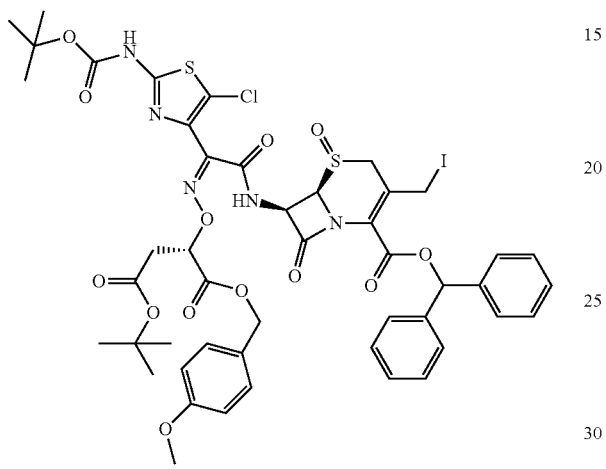

To a solution of (S)-4-tert-butyl 1-(4-methoxybenzyl) 2-(((Z)-(2-(((5R,6R,7R)-2-((benzhydryloxy)carbonyl)-3-(chloromethyl)-5-oxido-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy)succinate (27 g, 24.98 mmol) in Acetonitrile (300 mL) was added sodium iodide (5.62 g, 37.5 mmol). The mixture was stirred at room temperature over 1.5 h. LCMS indicated completion of the reaction. The solid was filtered off, the filtrate was concentrated under vacuum, and the residue was purified by CombiFlash Rf automated silica gel chromatography (330 g column), eluting with EtOAc/Hexanes (0-50%) to afford (S)-4-tert-butyl 1-(4-methoxybenzyl) 2-(((Z)-(2-(((5R,6R,7R)-2-((benzhydryloxy)carbonyl)-3-(iodomethyl)-5-oxido-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy)succinate (18 g, 14.97 mmol, 59.9% yield) as a red-brown solid. LCMS: (M+H)$^+$: 1118.1

Example 21l 1-((((6R,7R)-2-((benzhydryloxy)carbonyl)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium

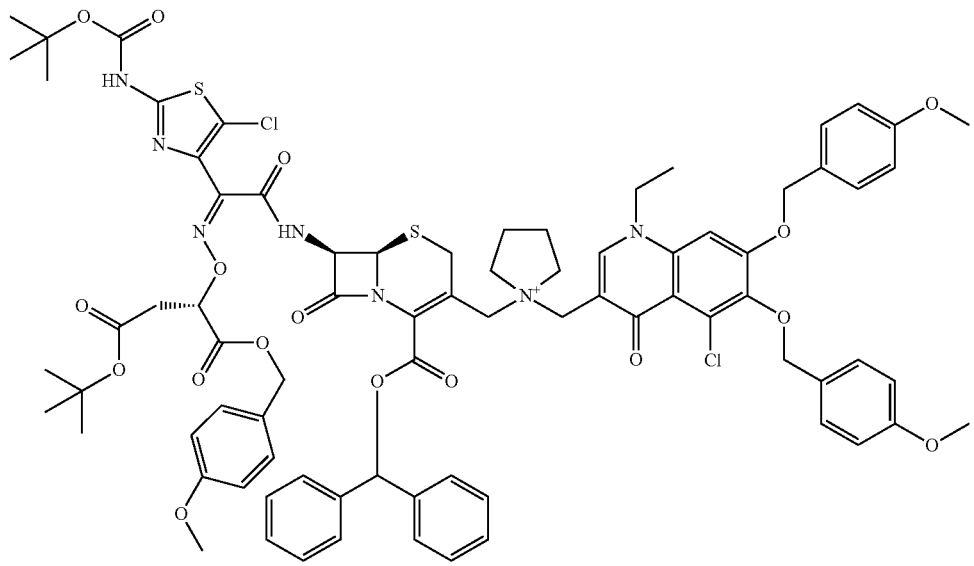 [SMILES: CCn1cc(C[N+]2(CC3=C(C(=O)OC(c4ccccc4)c4ccccc4)N4C(=O)[C@@H](NC(=O)/C(=N\O[C@@H](CC(=O)OC(C)(C)C)C(=O)OCc5ccc(OC)cc5)c5nc(NC(=O)OC(C)(C)C)sc5Cl)[C@H]4SC3)CCCC2)c(=O)c2c(Cl)c(OCc3ccc(OC)cc3)c(OCc3ccc(OC)cc3)cc21]

To a solution of 5-chloro-1-ethyl-6,7-bis((4-methoxybenzyl)oxy)-3-(pyrrolidin-1-ylmethyl) quinolin-4(1H)-one (Example 16i) (0.736 g, 1.307 mmol) in DMA (5 mL) at 15° C. under N$_2$ was added (S)-4-tert-butyl 1-(4-methoxybenzyl) 2-(((Z)-(2-(((5R,6R,7R)-2-((benzhydryl oxy)carbonyl)-3-

(iodomethyl)-5-oxido-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy)succinate (1.462 g, 1.307 mmol) in DMA (5 mL). The mixture was stirred at the same temperature over 3 h. N,N-Dimethylformamide (DMF) (20.00 mL) was then added. The mixture was cooled to −70° C. and treated with PBr$_3$ (0.271 mL, 2.88 mmol) dropwise. The mixture was allowed to warm up to −40° C. LCMS indicated complete reduction of sulfoxide. The organic solution was poured into ice-cooled 5% NaCl (120 mL, containing 0.05M HCl) and stirred for ~15 min. The solid was separated by filtration, washed with water (2×10 mL) and dried under high vacuum to afford 1-((((6R,7R)-2-((benzhydryloxy)carbonyl)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (2.41 g, 1.018 mmol, 65% purity, 78% yield) as a dark brown solid. LCMS: (M+H)$^+$: 1538.1

Example 21m (6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

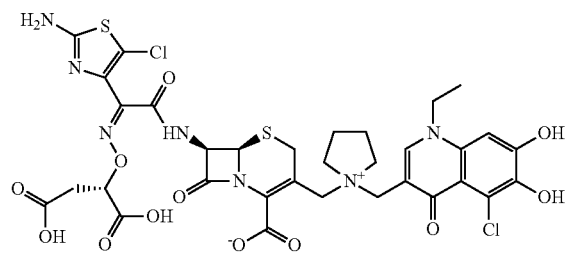

To a solution of 1-((((6R,7R)-2-((benzhydryloxy)carbonyl)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (2.41 g, 1.018 mmol) in Dichloromethane (DCM) (15 mL) under N$_2$ at 0° C. was added anisole (1.112 mL, 10.18 mmol), followed by TFA (5.0 mL, 64.9 mmol). The mixture was warmed up to rt and stirred at rt over night. LCMS indicated completion of the deprotection. The mixture was cooled to 0° C., Diisopropyl ether (50 mL) was then added. The mixture was stirred for 10 min and the solid was collected by filtration, and washed twice with diisopropyl ether (2×10 mL). The crude product was dissolved in a mixture of CH$_3$CN (10 mL)/water (10 mL)/2M HCl (2.5 mL), HP20SS resin (10 g) was then added. The mixture was concentrated to dryness, and the resin was loaded in a pre-column containing HP20SS resin (15 g), and was then purified by reverse phase Combiflash using C18 column and eluting with 0-30% CH$_3$CN/water to afford (6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (0.504 g, 0.59 mmol, 43.3% yield) as a slightly brown solid. Portion of this product (0.283 g, 0.331 mmol) was suspended in pure water (HPLC grade, 20 mL) with the help of sonication, and cooled to 0° C. With vigorous stirring, aq NaOH (0.2 N, 1.655 mL, 0.331 mmol) was added slowly into the suspension from an Eppendorf Pipette. After the addition a small piece of dry ice was added to quench any extra NaOH. The mixture was then frozen and lyophilized to afford (6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt (0.291 g, 0.315 mmol, 95.2% yield) as a slightly brown solid. LCMS: (M+H)$^+$: 854.0. $^1$H NMR (400 MHz, DEUTERIUM OXIDE) δ ppm 1.30 (t, J=6.95 Hz, 3 H) 2.01 (br. s., 4 H) 2.69 (d, J=6.57 Hz, 2 H) 3.23-3.47 (m, 6 H) 3.83-3.92 (m, 1 H) 3.96-4.04 (m, 1 H) 4.07-4.17 (m, 2 H) 4.18-4.37 (m, 2 H) 4.86 (t, J=6.57 Hz, 1H) 5.27 (d, J=4.80 Hz, 1 H) 5.67-5.76 (m, 1 H) 6.83-6.91 (m, 1 H) 7.97-8.06 (m, 1 H)

Example 22

(6R,7R)-7-((Z)-2-(2-amino-5-chlorothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

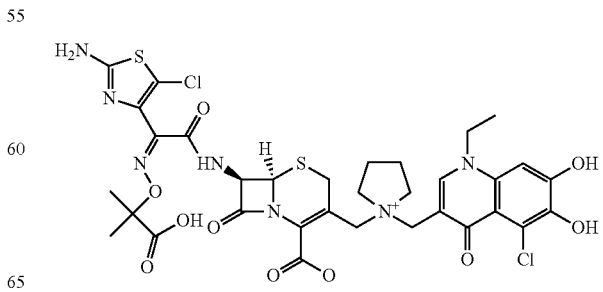

Example 22a (Z)-2-(((1-(tert-butoxy)-2-methyl-1-oxopropan-2-yl)oxy)imino)-2-(2-((tert-butoxycarbonyl)amino)thiazol-4-yl)acetic acid

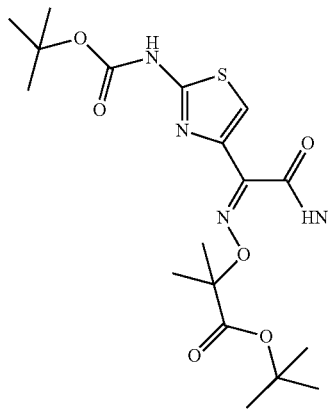 [SMILES: CC(C)(C)OC(=O)Nc1nc(/C(=N/OC(C)(C)C(=O)OC(C)(C)C)C(N)=O)cs1]

To a solution of (Z)-2-(2-aminothiazol-4-yl)-2-(((1-(tert-butoxy)-2-methyl-1-oxopropan-2-yl)oxy)imino)acetic acid (120 g, 364 mmol) in Dichloromethane (DCM) (840 mL) in an ice bath was added TEA (76 mL, 546 mmol), a solution of Boc-anhydride (110 mL, 474 mmol), and DMAP (8.90 g, 72.9 mmol). The mixture was stirred at r.t. over night. The solvent was then removed under vacuum. Water (1 L) and diisopropylether (700 mL) were added to the mixture. The aqueous layer was separated, washed with toluene and was adjusted to pH ~2 with 2N HCl. The aqueous layer was extracted with toluene. The organic layer was concentrated. IPE was added and the insoluble material was triturated. The material was collected by filtration and dried to afford (Z)-2-(((1-(tert-butoxy)-2-methyl-1-oxopropan-2-yl)oxy)imino)-2-(2-((tert-butoxycarbonyl)amino)thiazol-4-yl)acetic acid (69 g, 145 mmol, 39.7% yield) as a white powder. LCMS: (M+H)$^+$: 430.0

Example 22b (Z)-2-(((1-(tert-butoxy)-2-methyl-1-oxopropan-2-yl)oxy)imino)-2-(2-((tert-butoxycarbonyl)amino)-5-chlorothiazol-4-yl)acetic acid

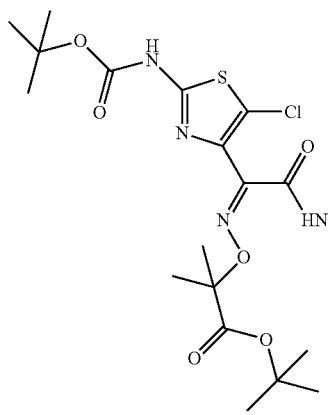 [SMILES: CC(C)(C)OC(=O)Nc1nc(/C(=N/OC(C)(C)C(=O)OC(C)(C)C)C(N)=O)c(Cl)s1]

A solution of (Z)-2-(((1-(tert-butoxy)-2-methyl-1-oxopropan-2-yl)oxy)imino)-2-(2-((tert-butoxycarbonyl)amino)thiazol-4-yl)acetic acid (70 g, 147 mmol) and NCS (23.50 g, 176 mmol) in N,N-Dimethylformamide (DMF) (735 mL) was stirred at 40° C. for 2.5 h. The reaction was quenched by addition of H$_2$O (2 L), EtOAc (1 L) and 5% aq. sodium thiosulfate soln (400 mL). The organic layer was separated, and washed with H$_2$O (2×), brine, dried and evaporated to afford (Z)-2-(((1-(tert-butoxy)-2-methyl-1-oxopropan-2-yl)oxy)imino)-2-(2-((tert-butoxycarbonyl)amino)-5-chlorothiazol-4-yl)acetic acid (69 g, 91% purity, 135 mmol, 92% yield) as a light yellow foaming solid. LCMS: (M+H)$^+$: 464.2

Example 22c (6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(chloromethyl)-8-oxo-5-thia-1-azabicyclo[4.2.0]oct-2-ene-2-carboxylate

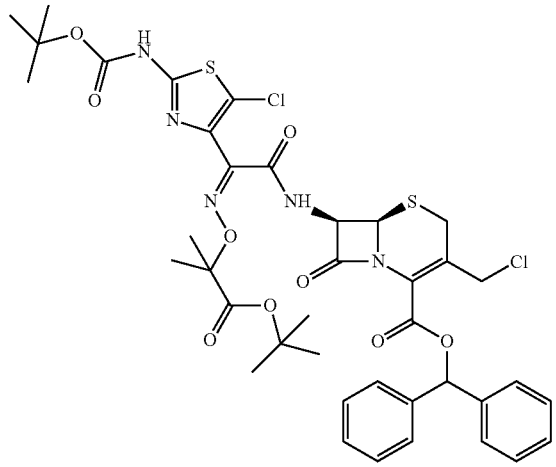 [SMILES: CC(C)(C)OC(=O)Nc1nc(/C(=N/OC(C)(C)C(=O)OC(C)(C)C)C(=O)N[C@@H]2C(=O)N3C(C(=O)OC(c4ccccc4)c4ccccc4)=C(CCl)CS[C@H]23)c(Cl)s1]

To a suspension of (Z)-2-(((1-(tert-butoxy)-2-methyl-1-oxopropan-2-yl)oxy)imino)-2-(2-((tert-butoxycarbonyl)amino)-5-chlorothiazol-4-yl)acetic acid (20 g, 39.2 mmol) and (6R,7R)-benzhydryl 7-amino-3-(chloromethyl)-8-oxo-5-thia-1-azabicyclo[4.2.0]oct-2-ene-2-carboxylate, Hydrochloride (18.59 g, 41.2 mmol) in Dichloromethane (DCM) (300 mL) at −30° C. was added phenyl phosphorodichloridate (7.15 mL, 47.1 mmol), followed by dropwise 4-methylmorpholine (12.94 mL, 118 mmol) over 15 mins. The mixture was stirred at the same temperature over 3 h. LCMS indicated completion of the reaction. The reaction was quenched by addition of 10% aq. citric acid (120 mL), the organic solution was separated and washed with 5% NaHCO$_3$, brine, and dried (Na$_2$SO$_4$), filtered, and concentrated. The residue was purified by CombiFlash automated silica gel chromatography (330 g column, 0-45% EtOAc/Hexanes) to afford (6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(chloromethyl)-8-oxo-5- thia-1-azabicyclo[4.2.0]oct-2-ene-2-carboxylate (29.9 g, 34.7 mmol, 89% yield) as a light yellow foaming solid. LCMS: (M+H)⁺: 860.3

Example 22d (5R,6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(chloromethyl)-8-oxo-5-thia-1-azabicyclo[4.2.0]oct-2-ene-2-carboxylate 5-oxide

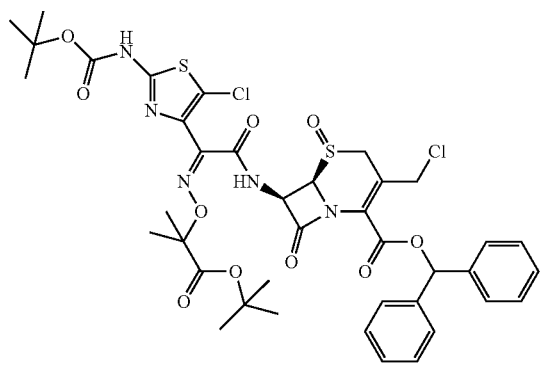

To a solution of (6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(chloromethyl)-8-oxo-5-thia-1-azabicyclo[4.2.0]oct-2-ene-2-carboxylate (29.9 g, 34.7 mmol) in Dichloromethane (DCM) (1.1 L) at −40° C. was added dropwise a solution of m-CPBA (8.17 g, 36.5 mmol) in Dichloromethane (DCM) (220 mL) over 10 min. The mixture was stirred at the same temperature over 30 min. LCMS indicated completion of the reaction. The mixture was treated with 15% aq. Na₂S₂O₃ (200 mL). The organic phase was separated and washed with 5% NaHCO₃ (400 mL), brine (400 mL), dried (Na₂SO₄), filtered, and concentrated. The residue was purified by CombiFlash automated silica gel chromatography (330 g column, 0-50% EtOAc/Hexanes) to afford (5R,6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(chloromethyl)-8-oxo-5-thia-1-azabicyclo[4.2.0]oct-2-ene-2-carboxylate 5-oxide (29 g, 31.8 mmol, 91% yield) as a light yellow solid. LCMS: (M+H)⁺: 876.3

Example 22e (5R,6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(iodomethyl)-8-oxo-5-thia-1-azabicyclo[4.2.0]oct-2-ene-2-carboxylate 5-oxide

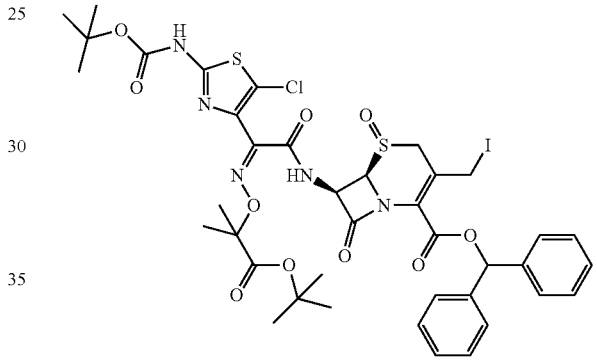

To a solution of (5R,6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(chloromethyl)-8-oxo-5-thia-1-azabicyclo[4.2.0]oct-2-ene-2-carboxylate 5-oxide (10.5 g, 11.50 mmol) in acetone (120 mL) was added sodium iodide (2.58 g, 17.24 mmol). The mixture was stirred at room temperature over 1.5 h. LCMS indicated completion of the reaction. The solid was filtered off, the filtrate was concentrated under vacuum, the residue was purified twice by CombiFlash Rf automated silica gel chromatography (120 g column), eluting with EtOAc/Hexanes (0-45%) to afford (5R,6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(iodomethyl)-8-oxo-5-thia-1-azabicyclo[4.2.0]oct-2-ene-2-carboxylate 5-oxide (7.5 g, 7.75 mmol, 67.4% yield) as a light brown foaming solid. LCMS: (M+H)⁺: 967.9.

Example 22f 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-((5-chloro-1-ethyl-6,7-bis((4-methoxybenzyl oxy)-4-oxo-1,4-dihydroquinolin-3-yl)methyl)pyrrolidin-1-ium

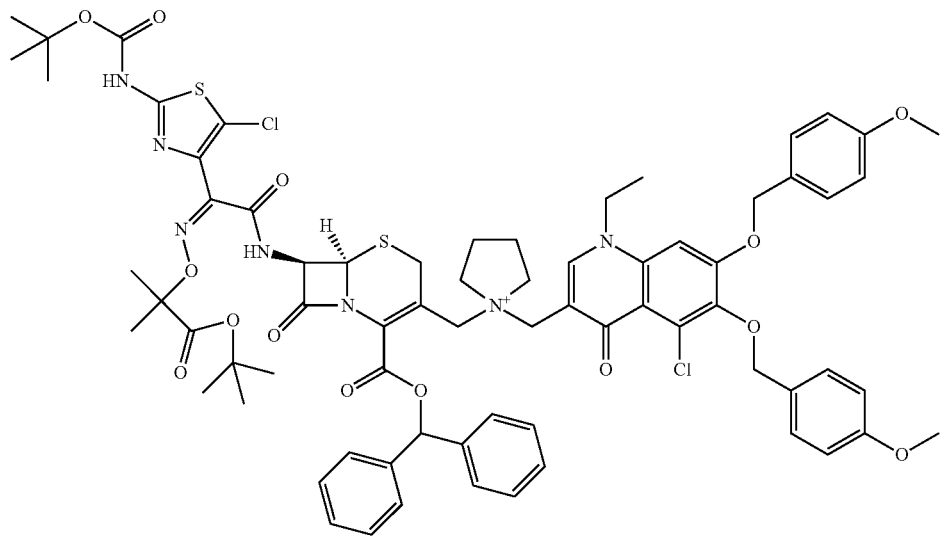 [SMILES: CCn1cc(C[N+]2(CC3=C(C(=O)OC(c4ccccc4)c4ccccc4)N4C(=O)[C@@H](NC(=O)/C(=N\OC(C)(C)C(=O)OC(C)(C)C)c5nc(NC(=O)OC(C)(C)C)sc5Cl)[C@H]4SC3)CCCC2)c(=O)c2c(Cl)c(OCc3ccc(OC)cc3)c(OCc3ccc(OC)cc3)cc21]

To a solution of 5-chloro-1-ethyl-6,7-bis((4-methoxybenzyl)oxy)-3-(pyrrolidin-1-ylmethyl)quinolin-4(1H)-one (Example 16i) (0.734 g, 1.304 mmol) in DMA (5 mL) at 15° C. under N₂ was added (6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(iodomethyl)-8-oxo-5-thia-1-azabicyclo[4.2.0]oct-2-ene-2-carboxylate 5-oxide (1.262 g, 1.304 mmol) in DMA (5 mL). The mixture was stirred at the same temperature over 3 h. N,N-Dimethylformamide (DMF) (20.00 mL) was then added. The mixture was cooled to −70° C. and treated with tribromophosphine (0.270 mL, 2.87 mmol) dropwise. The mixture was allowed to warm up to −40° C. LCMS indicated complete reduction of sulfoxide. The organic solution was poured into ice-cooled 5% NaCl (120 mL, containing 0.05M HCl) and stirred for ~15 min. The solid was separated by filtration, washed with water (2×10 mL) and dried under high vacuum to afford 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (2.19 g, 1.136 mmol, 87% yield) as a dark brown solid. LCMS: (M+H)⁺: 1388.1.

Example 22g (6R,7R)-7-((Z)-2-(2-amino-5-chlorothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

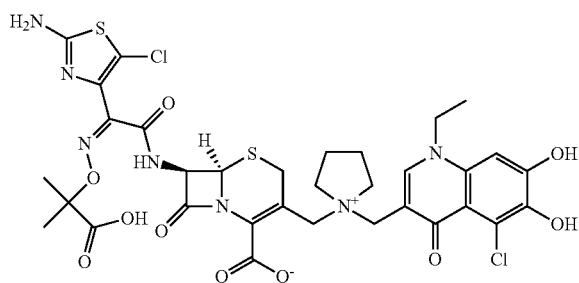 [SMILES: CCn1cc(C[N+]2(CC3=C(C(=O)[O-])N4C(=O)[C@@H](NC(=O)/C(=N\OC(C)(C)C(=O)O)c5nc(N)sc5Cl)[C@H]4SC3)CCCC2)c(=O)c2c(Cl)c(O)c(O)cc21]

To a solution of 1-((((6R,7R)-2-((benzhydryloxy)carbonyl)-7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-((5-chloro-1-ethyl-6,7-bis((4-methoxybenzyl)oxy)-4-oxo-1,4-dihydroquinolin-3-yl)methyl)pyrrolidin-1-ium (2.19 g, 1.136 mmol) in Dichloromethane (DCM) (12 mL) under N₂ at 0° C. was added anisole (1.240 mL, 11.36 mmol), followed by TFA (4.0 mL, 51.9 mmol). The mixture was warmed up to rt and stirred at rt over night. LCMS indicated completion of the deprotection. The mixture was cooled to 0° C., Diisopropyl ether (50 mL) was then added. The mixture was stirred for 10 min and the solid was collected by filtration, and washed twice with diisopropyl ether (2×10 mL). The crude product was dissolved in a mixture of CH₃CN (10 mL)/water (10 mL)/2M HCl (2.5 mL), HP20SS resin (10 g) was then added. The mixture was concentrated to dryness, and the resin was loaded in a pre-column containing HP20SS resin (15 g), and was then purified by reverse phase Combiflash using C18 column and eluting with 0-30% CH₃CN/water to afford (6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate (0.440 g, 0.534 mmol, 47.0% yield) as an off-white solid. Portion of this product (0.246 g, 0.298 mmol) was suspended in pure water (HPLC grade, 20 mL) with the help of sonication, and cooled to 0° C. With vigorous stirring, aq NaOH (0.2 N, 1.49 mL, 0.298 mmol) was added slowly into the suspension from an Eppendorf Pipette. After the addition a small piece of dry ice was added to quench any extra NaOH. The mixture was then frozen and lyophilized to afford (6R,7R)-7-((Z)-2-(2-amino-5-chlorothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt (0.253 g, 0.278 mmol, 93.3% yield) as a pale yellow foamy solid. LCMS: (M+H)⁺: 824.2. ¹H NMR (400 MHz, DEUTERIUM OXIDE) δ ppm 1.27 (t, J=6.82 Hz, 3 H) 1.39 (d, J=6.82 Hz, 6 H) 1.90-2.09 (m, 4 H) 3.34 (br. s., 6 H) 3.84-4.11 (m, 4 H) 4.15-4.36 (m, 2 H) 5.30 (s, 1 H) 5.72-5.82 (m, 1 H) 6.69-6.80 (m, 1 H) 7.96 (s, 1 H).

Example 23

(6R,7R)-7-((Z)-2-(2-aminothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

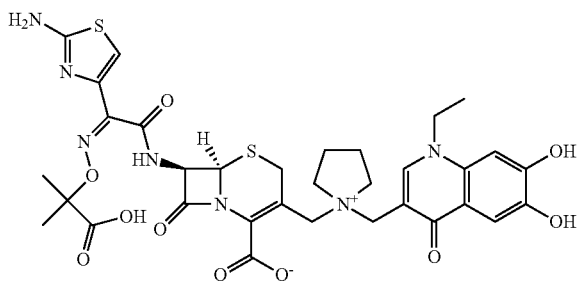 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)cc21]

The compound was prepared according to the procedures in Examples 19b-19c and Example 20, utilizing 1-ethyl-6,7-bis((4-methoxybenzyl)oxy)-3-(pyrrolidin-1-ylmethyl)quinolin-4(1H)-one (Example 9a) in place of 5-chloro-1-ethyl-6,7-bis((4-methoxybenzyl)oxy)-3-(pyrrolidin-1-ylmethyl)quinolin-4(1H)-one in Example 19b. LCMS: (M+H)⁺: 756.2. ¹H NMR (400 MHz, DEUTERIUM OXIDE) δ ppm 1.24-1.43 (m, 9 H) 2.00 (br. s., 4 H) 3.29 (br. s., 6 H) 3.84-4.03 (m, 2 H) 4.12 (d, J=7.33 Hz, 2H) 4.19-4.28 (m, 1 H) 4.30-4.40 (m, 1 H) 5.29 (d, J=5.05 Hz, 1 H) 5.76 (d, J=4.80 Hz, 1 H) 6.82 (s, 1H) 6.86 (s, 1 H) 7.33 (s, 1 H) 8.03 (s, 1 H)

Example 24

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

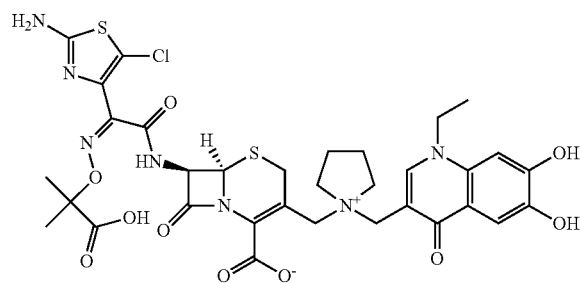 [SMILES: CCn1cc(C[N+]2(CC3=C(C(=O)[O-])N4C(=O)[C@@H](NC(=O)/C(=N\OC(C)(C)C(=O)O)c5nc(N)sc5Cl)[C@H]4SC3)CCCC2)c(=O)c2cc(O)c(O)cc21]

The compound was prepared according to the two-step sequence of Examples 22f-22g, utilizing 1-ethyl-6,7-bis((4-methoxybenzyl)oxy)-3-(pyrrolidin-1-ylmethyl)quinolin-4(1H)-one (Example 9a) in place of 5-chloro-1-ethyl-6,7-bis((4-methoxybenzyl)oxy)-3-(pyrrolidin-1-ylmethyl)quinolin-4(1H)-one in Example 22f. LCMS: (M+H)⁺:790.1. ¹H NMR (400 MHz, METHANOL-d₄) δ ppm 1.52 (s, 3 H) 1.61 (d, J=1.52 Hz, 6 H) 2.19 (d, J=9.85 Hz, 4 H) 3.40-3.68 (m, 6 H) 3.92-4.02 (m, 1 H) 4.07-4.17 (m, 1 H) 4.31-4.44 (m, 3 H) 4.50-4.58 (m, 1 H) 4.98-5.05 (m, 1 H) 5.25-5.32 (m, 1 H) 5.86-5.92 (m, 1 H) 7.12 (s, 1 H) 7.66 (s, 1 H) 8.25 (s, 1 H)

Example 25

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

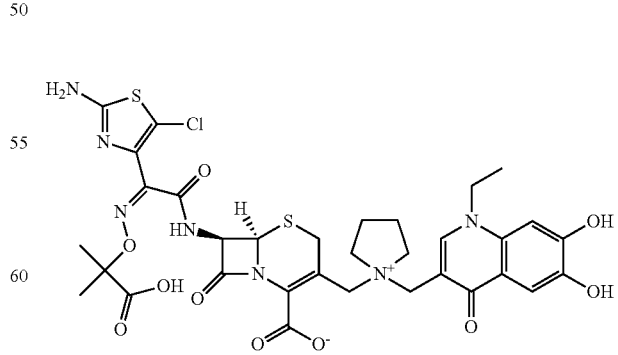

The compound was prepared according to the procedure from Examples 20, utilizing (6R,7R)-7-((Z)-2-(2-amino-5-chlorothiazol-4-yl)-2-(((2-carboxypropan-2-yl)oxy)imino)

acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate (Example 24) in place of (6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate. LCMS: (M+H)$^+$:790.1. $^1$H NMR (400 MHz, DEUTERIUM OXIDE) δ ppm 1.32 (s, 3 H) 1.39 (d, J=6.82 Hz, 6 H) 1.88-2.09 (m, 4 H) 3.24-3.50 (m, 6 H) 3.84-3.94 (m, 1 H) 3.94-4.04 (m, 1 H) 4.05-4.21 (m, 2 H) 4.20-4.31 (m, 1 H) 4.31-4.43 (m, 1 H) 5.28 (d, J=4.80 Hz, 1 H) 5.77 (d, J=4.80 Hz, 1 H) 6.90 (s, 1 H) 7.38 (s, 1 H) 8.05 (s, 1 H)

Example 26

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

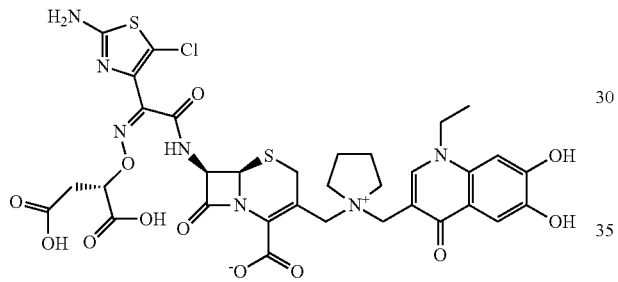

The compound was prepared according to the two-step sequence of Examples 21l-21m, utilizing 1-ethyl-6,7-bis((4-methoxybenzyl)oxy)-3-(pyrrolidin-1-ylmethyl)quinolin-4 (1H)-one (Example 9a) in place of 5-chloro-1-ethyl-6,7-bis((4-methoxybenzyl)oxy)-3-(pyrrolidin-1-ylmethyl)quinolin-4(1H)-one in Example 21l. LCMS: (M+H)$^+$: 820.2. $^1$H NMR (400 MHz, DEUTERIUM OXIDE) δ ppm 1.33 (t, J=7.07 Hz, 3 H) 2.00 (br. s., 4 H) 2.69-2.79 (m, 2 H) 3.23-3.49 (m, 6 H) 3.82-3.93 (m, 1 H) 3.95-4.05 (m, 1 H) 4.12-4.24 (m, 2 H) 4.25-4.42 (m, 2 H) 4.82-4.92 (m, 1 H) 4.87 (dd, J=7.83, 5.31 Hz, 2 H) 5.27 (s, 1 H) 5.67-5.77 (m, 1 H) 6.96-7.06 (m, 1 H) 7.42 (s, 1 H) 8.09 (s, 1 H)

Example 27

(6R,7R)-7-((Z)-2-(2-aminothiazol-4-yl)-2-(((S)-1,2-dicarboxyethoxy)imino)acetamido)-3-((1-(2-(5-chloro-1-ethyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate sodium salt

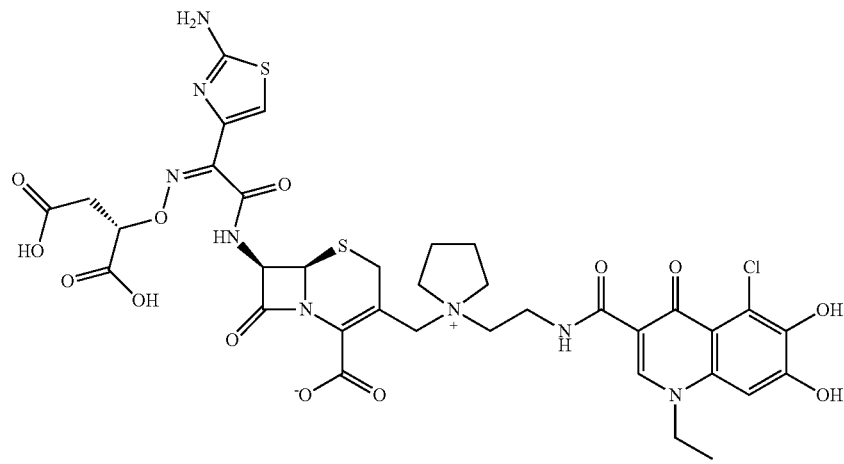

Example 27a

5-Chloro-1-ethyl-6,7-bis((4-methoxybenzyl)oxy)-4-oxo-N-(2-(pyrrolidin-1-yl)ethyl)-1,4-dihydroquinoline-3-carboxamide

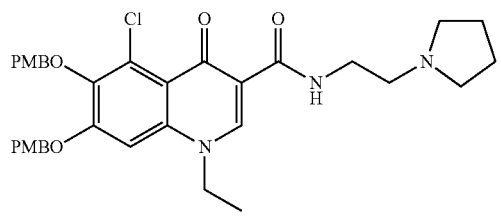

To a solution of 5-chloro-1-ethyl-6,7-bis((4-methoxybenzyl)oxy)-4-oxo-1,4-dihydroquinoline-3-carboxylic acid (Example 16f) (5 g, 8.68 mmol) in N,N-Dimethylformamide (DMF) (75 mL) was added HATU (3.96 g, 10.42 mmol) and DIPEA (4.55 mL, 26.1 mmol), the resulting mixture was stirred at r.t. for 15 min. Then 2-(pyrrolidin-1-yl)ethanamine (1.502 mL, 9.55 mmol) was added and the resulting mixture was stirred at r.t. for 1 h. The mixture was concentrated and partitioned between water and DCM. The organic layer was separated and washed with water (2×), sat. $NaHCO_3$ (aq.) and brine. The organic solution was dried over $Na_2SO_4$, and concentrated. The residue was purified by automated silica gel chromatography (CombiFlash Rf) eluting with MeOH/DCM (0-25%), followed by reverse phase chromatography (CombiFlash Rf) eluting with ACN/water (0-100%) to afford 5-chloro-1-ethyl-6,7-bis((4-methoxybenzyl)oxy)-4-oxo-N-(2-(pyrrolidin-1-yl)ethyl)-1,4-dihydroquinoline-3-carboxamide (3.6 g, 5.81 mmol, 66.9% yield) as a white solid. LCMS: $(M+H)^+$: 620.5

Example 27b (6R,7R)-7-((Z)-2-(2-aminothiazol-4-yl)-2-(((S)-1,2-dicarboxyethoxy)imino)acetamido)-3-((1-(2-(5-chloro-1-ethyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, sodium salt

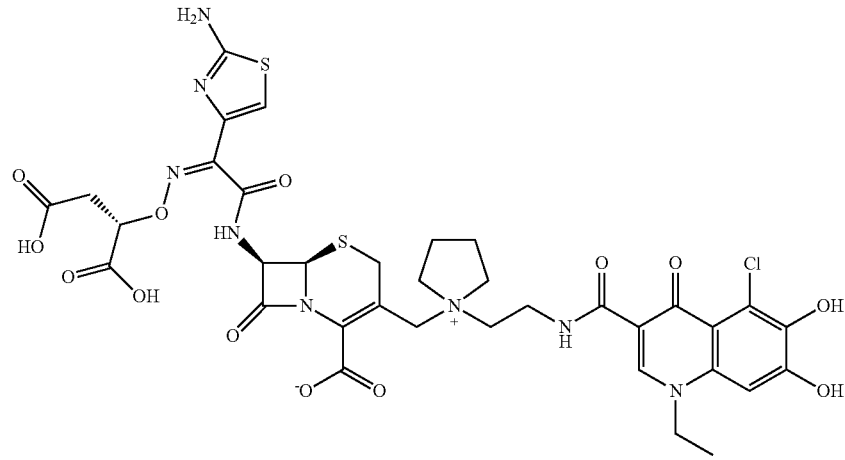

The compound was prepared according to the procedure described in Examples 16k-16l and 17, utilizing 5-chloro-1-ethyl-6,7-bis((4-methoxybenzyl)oxy)-4-oxo-N-(2-(pyrrolidin-1-yl)ethyl)-1,4-dihydroquinoline-3-carboxamide in place of 5-chloro-1-ethyl-6,7-bis((4-methoxybenzyl)oxy)-3-(pyrrolidin-1-ylmethyl)quinolin-4(1H)-one in Example 16k. LCMS: $(M+H)^+$: 877.6. $^1$H NMR (400 MHz, DEUTERIUM OXIDE) δ ppm 1.27 (t, J=7.07 Hz, 3 H) 2.11 (br. s., 4 H) 2.65 (br. s., 2 H) 3.37-3.72 (m, 8 H) 3.76-3.89 (m, 2 H) 3.92-4.15 (m, 4 H) 4.80-4.86 (m, 1 H) 5.20-5.29 (m, 1 H) 5.74 (d, J=4.55 Hz, 1 H) 6.67-6.75 (m, 1 H) 6.80 (s, 1 H) 8.20-8.29 (m, 1 H)

Example 28

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt

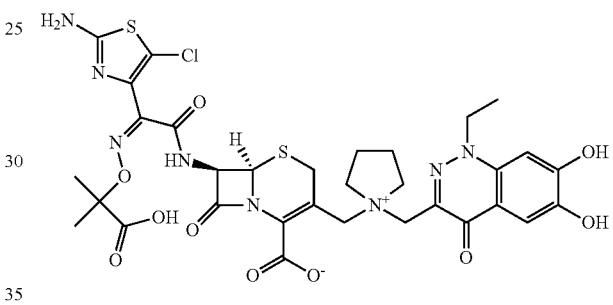

The compound was prepared according to the procedure from Examples 22f-22g, utilizing 1-ethyl-6,7-bis((4-methoxybenzyl)oxy)-3-(pyrrolidin-1-ylmethyl)cinnolin-4(1H)-one (Example 8f) in place of 5-chloro-1-ethyl-6,7-bis((4-methoxybenzyl)oxy)-3-(pyrrolidin-1-ylmethyl)quinolin-4(1H)-one in Example 22f. LCMS: $(M+H)^+$:791.9. $^1$H NMR (400 MHz, DEUTERIUM OXIDE) δ ppm 1.28-1.47 (m, 9 H) 2.04 (br. s., 4 H) 3.33-3.63 (m, 6 H) 3.81-3.92 (m, 1 H) 4.10-4.22 (m, 1 H) 4.34 (br. s., 2 H) 4.47 (br. s., 2 H) 5.27 (d, J=5.05 Hz, 1 H) 5.73-5.80 (m, 1 H) 6.83 (s, 1 H) 7.17 (s, 1 H)

Example 29

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt

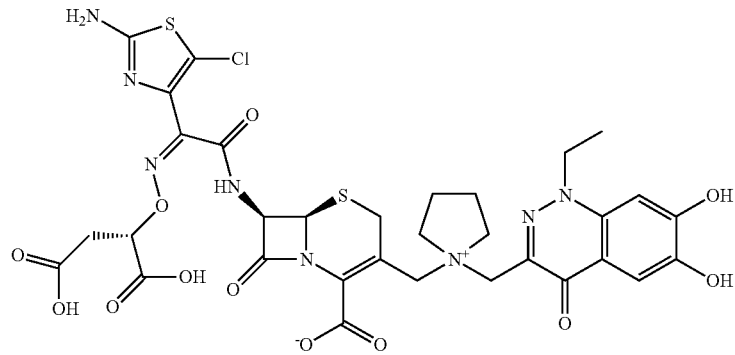

The compound was prepared according to the procedure from Examples 21l-21m, utilizing 1-ethyl-6,7-bis((4-methoxybenzyl)oxy)-3-(pyrrolidin-1-ylmethyl)cinnolin-4(1H)-one (Example 8f) in place of 5-chloro-1-ethyl-6,7-bis((4-methoxybenzyl)oxy)-3-(pyrrolidin-1-ylmethyl)quinolin-4(1H)-one in Example 21l. LCMS: (M+H)$^+$:821.2. $^1$H NMR (400 MHz, DEUTERIUM OXIDE) δ ppm 1.37 (t, J=7.07 Hz, 3 H) 2.05 (br. s., 4 H) 2.73-2.84 (m, 2H) 3.49 (d, J=16.42 Hz, 6 H) 3.85 (d, J=16.93 Hz, 1 H) 4.18 (s, 1 H) 4.38 (d, J=7.07 Hz, 2 H) 4.48 (br. s., 2 H) 4.84-4.90 (m, 1 H) 5.25 (d, J=4.80 Hz, 1 H) 5.70 (d, J=4.80 Hz, 1 H) 6.94 (s, 1 H) 7.21 (s, 1 H)

Example 30

(6R,7R)-7-((Z)-2-(2-aminothiazol-4-yl)-2-(((S)-1,2-dicarboxyethoxy)imino)acetamido)-3-((1-(2-(1-ethyl-6,7-dihydroxy-4-oxo-1,4-dihydrocinnoline-3-carboxamido)ethyl)pyrrolidin-1-ium-1-yl)methyl)-8-oxo-5-thia-1-azabicyclo[4.2.0]oct-2-ene-2-carboxylate, sodium salt

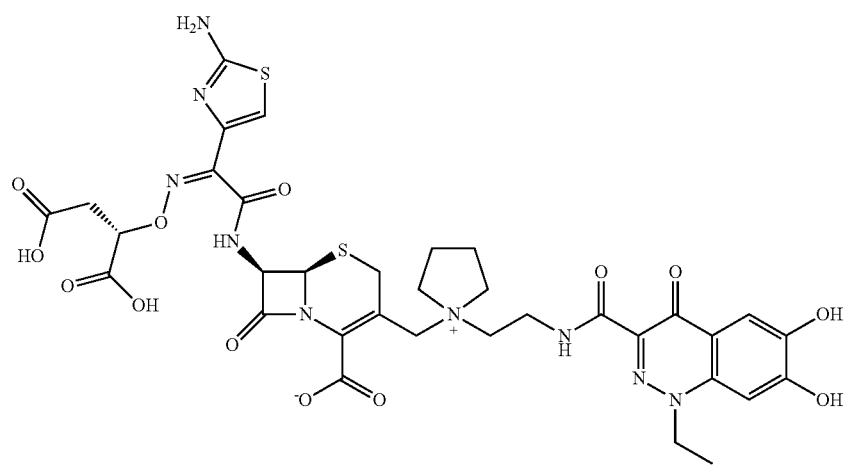

The compound was prepared according to the procedure described in Examples 16k-16l and 17, utilizing 1-Ethyl-6,7-bis((4-methoxybenzyl)oxy)-4-oxo-N-(2-(pyrrolidin-1-yl)ethyl)-1,4-dihydrocinnoline-3-carboxamide (Example 11a) in place of 5-chloro-1-ethyl-6,7-bis((4-methoxybenzyl)oxy)-3-(pyrrolidin-1-ylmethyl)quinolin-4(1H)-one in Example 16k. LCMS: (M+H)$^+$: 844.1. $^1$H NMR (400 MHz, DEUTERIUM OXIDE) δ ppm 1.35 (t, J=7.20 Hz, 3 H) 2.12 (d, J=3.79 Hz, 4 H) 2.58-2.65 (m, 2 H) 3.36-3.64 (m, 8 H) 3.69-3.96 (m, 3 H) 4.03-4.13 (m, 1 H) 4.32-4.45 (m, 2 H) 4.79-4.86 (m, 1 H) 5.24 (d, J=5.05 Hz, 1 H) 5.71 (s, 1 H) 6.82 (s, 1 H) 6.94 (s, 1 H) 7.19 (s, 1 H)

Example 31

(6R,7R)-7-(((Z)-2-(2-aminothiazol-4-yl)-2-(((2-carboxypropan-2-yl)oxy)imino)acetamido)-3-(((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate, Sodium salt

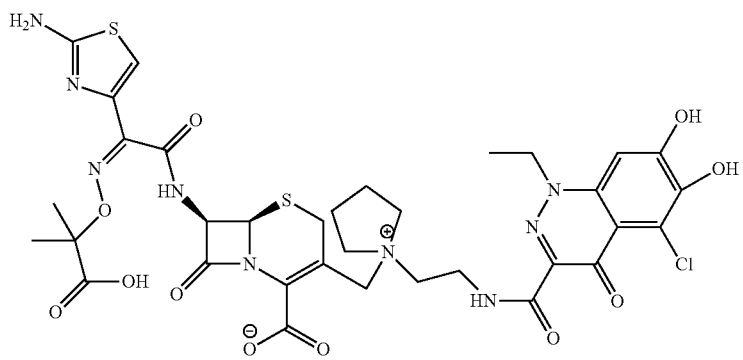 [SMILES: CCn1nc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2c(Cl)c(O)c(O)cc21]

Example 31a

1-Ethyl-5-nitro-4-oxo-1,4-dihydro-[1,3]dioxolo[4,5-g]cinnoline-3-carboxylic acid

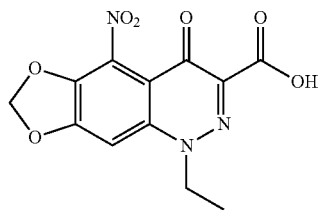

To a solution of 1-ethyl-4-oxo-1,4-dihydro-[1,3]dioxolo[4,5-g]cinnoline-3-carboxylic acid (5 g, 19.07 mmol) in sulfuric acid (15 mL) cooled to 0° C. was added potassium nitrate (2.121 g, 20.97 mmol) in small portions to maintain temperature bellow 10° C. with ice water. The mixture was stirred at 10° C. for 1 h and at room temperature for 12 h, and was then poured into ice cold water (200 ml). The mixture was filtered, the solid was washed with water and ethanol to afford 1-ethyl-5-nitro-4-oxo-1,4-dihydro-[1,3]dioxolo[4,5-g]cinnoline-3-carboxylic acid (4.4 g, 14.32 mmol, 75% yield). LCMS: (M+H)$^+$: 308.2

Example 31b

5-Amino-1-ethyl-4-oxo-1,4-dihydro-[1,3]dioxolo[4,5-g]cinnoline-3-carboxylic acid

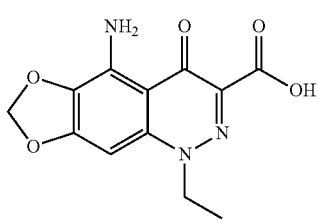 [SMILES: CCn1nc(C(=O)O)c(=O)c2c([N+](=O)[O-])c3c(cc21)OCO3]

To a suspension of 1-ethyl-5-nitro-4-oxo-1,4-dihydro-[1,3]dioxolo[4,5-g]cinnoline-3-carboxylic acid (4.25 g, 13.83 mmol) in Acetic Acid (100 mL) and hydrochloric acid (30 mL) in parr shaker bottle was added Pd/C (0.6 g, 5.64 mmol) and the mixture was hydrogenated at 50 psi on a parr shaker for 5 h. The mixture was filtered. The filtrate was allowed to drop into 500 ml of water and the precipitate was collected by filtration, dried to afford 5-amino-1-ethyl-4-oxo-1,4-dihydro-[1,3]dioxolo[4,5-g]cinnoline-3-carboxylic acid (3.6 g, 12.99 mmol, 94% yield). LCMS: (M+H)+: 278.2

Example 31c

3-Carboxy-1-ethyl-4-oxo-1,4-dihydro-[1,3]dioxolo[4,5-g]cinnoline-5-diazonium chloride

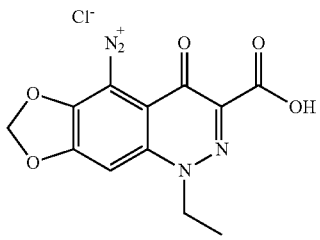

A mixture of 5-amino-1-ethyl-4-oxo-1,4-dihydro-[1,3]dioxolo[4,5-g]cinnoline-3-carboxylic acid (3.6 g, 12.99 mmol) in hydrochloric acid (conc) (20 ml) was stirred at room temperature and sodium nitrite (0.986 g, 14.28 mmol) in water (7 mL) was added dropwise to maintain the temperature bellow 45° C. Stirring continued for 5 h. The solution was poured into 50 ml of water and was allowed to stand overnight in the refrigerator. Precipitate was collected by filtration and dried over drierite in a desiccator to yield 3-Carboxy-1-ethyl-4-oxo-1,4-dihydro-[1,3]dioxolo[4,5-g]cinnoline-5-diazonium chloride (3.15 g, 9.67 mmol, 74.5% yield). LCMS: (M+H)+: 326.2

Example 31d

5-Chloro-1-ethyl-6,7-dihydroxy-4-oxo-1,4-dihydrocinnoline-3-carboxylic acid

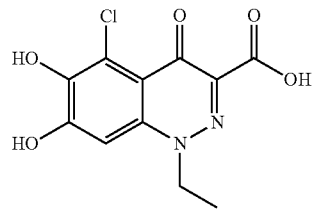 [SMILES: CCn1nc(C(=O)O)c(=O)c2c(Cl)c(O)c(O)cc21]

A solution of 3-Carboxy-1-ethyl-4-oxo-1,4-dihydro-[1,3]dioxolo[4,5-g]cinnoline-5-diazonium chloride (1.85 g, 5.68 mmol) in sulfuric acid (19.98 ml, 187 mmol) was heated at 95° C. for 20 h. Water was added, the precipitates were collected to provide 5-chloro-1-ethyl-6,7-dihydroxy-4-oxo-1,4-dihydrocinnoline-3-carboxylic acid (1.46 g, 5.13 mmol, 90% yield). LCMS: (M+H)+: 285.2

Example 31e

4-Methoxybenzyl 5-chloro-1-ethyl-6,7-bis((4-methoxybenzyl)oxy)-4-oxo-1,4-dihydrocinnoline-3-ca

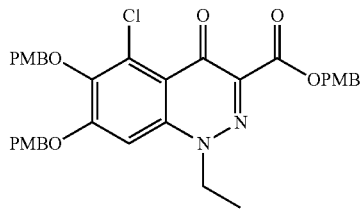

To a solution of 5-chloro-1-ethyl-6,7-dihydroxy-4-oxo-1,4-dihydrocinnoline-3-carboxylic acid (1.46 g, 5.13 mmol) in N,N-dimethylformamide (DMF) (20 mL) was added potassium carbonate (1.772 g, 12.82 mmol) followed by 1-(chloromethyl)-4-methoxybenzene (1.392 mL, 10.26 mmol). The mixture was heated at 50° C. for 12 h, extracted with ethyl acetate and washed with water, brine, dried over magnesium sulfate. The solvent was removed under vacuum and the residue was chromatographed on ISCO silica column eluting with 0-10% methanol:dichloromethane to afford 4-methoxybenzyl 5-chloro-1-ethyl-6,7-bis((4-methoxybenzyl)oxy)-4-oxo-1,4-dihydrocinnoline-3-carboxylate (1.4 g, 2.170 mmol, 42.3% yield). LCMS: (M+H)+: 645.2

Example 31f

5-Chloro-1-ethyl-6,7-bis((4-methoxybenzyl)oxy)-4-oxo-1,4-dihydrocinnoline-3-carboxylic acid

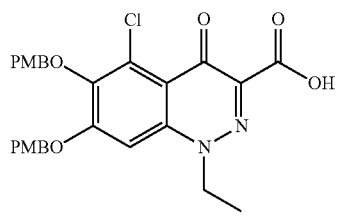

To the solution of 4-methoxybenzyl 5-chloro-1-ethyl-6,7-bis((4-methoxybenzyl)oxy)-4-oxo-1,4-dihydrocinnoline-3-carboxylate (24 g, 37.2 mmol) in methanol (400 mL) and water (133 mL) was added potassium hydroxide (8.35 g, 149 mmol). The reaction mixture was heated to reflux for 3 h. Solvent was removed under vacuum. The residue was suspended in water and the resulting mixture was acidified to pH4 with 2N hydrochloric acid. The precipitated solid was filtered and dried to afford 5-chloro-1-ethyl-6,7-bis((4-methoxybenzyl)oxy)-4-oxo-1,4-dihydrocinnoline-3-carboxylic acid (12.6 g, 24.00 mmol, 64.5% yield). LCMS: (M+H)+: 525.2

Example 31g

5-Chloro-1-ethyl-6,7-bis((4-methoxybenzyl)oxy)-4-oxo-N-(2-(pyrrolidin-1-yl)ethyl)-1,4-dihydrocinnoline-3-carboxamide

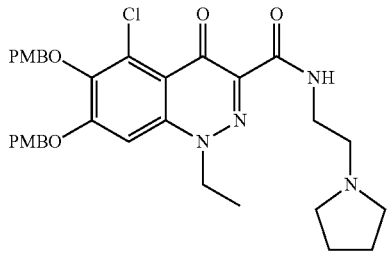

To a suspension of 5-chloro-1-ethyl-6,7-bis((4-methoxybenzyl)oxy)-4-oxo-1,4-dihydrocinnoline-3-carboxylic acid (3 g, 5.71 mmol) in tetrahydrofuran (THF) (25 mL) was added triethylamine (0.876 mL, 6.29 mmol), followed by isobutyl chloroformate (0.826 mL, 6.29 mmol). The reaction mixture was stirred at 0° C. for 30 min. 2-(Pyrrolidin-1-yl)ethanamine (0.979 g, 8.57 mmol) was added and the mixture was stirred at 0° C. for 30 min and warmed up to room temperature for 2 h. Solvent was removed and the residue was chromatographed to afford 5-chloro-1-ethyl-6,7-bis((4-methoxybenzyl)oxy)-4-oxo-N-(2-(pyrrolidin-1-yl)ethyl)-1,4-dihydrocinnoline-3-carboxamide (1.2 g, 1.932 mmol, 33.8% yield). LCMS: (M+H)+: 621.2

Example 31h 1-(((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-1-ethyl-6,7-bis((4-methoxybenzyl)oxy)-4-oxo-1,4-dihydrocinnoline-3-carboxamido)ethan-1-ylium-1-yl)pyrrolidin-1-ium

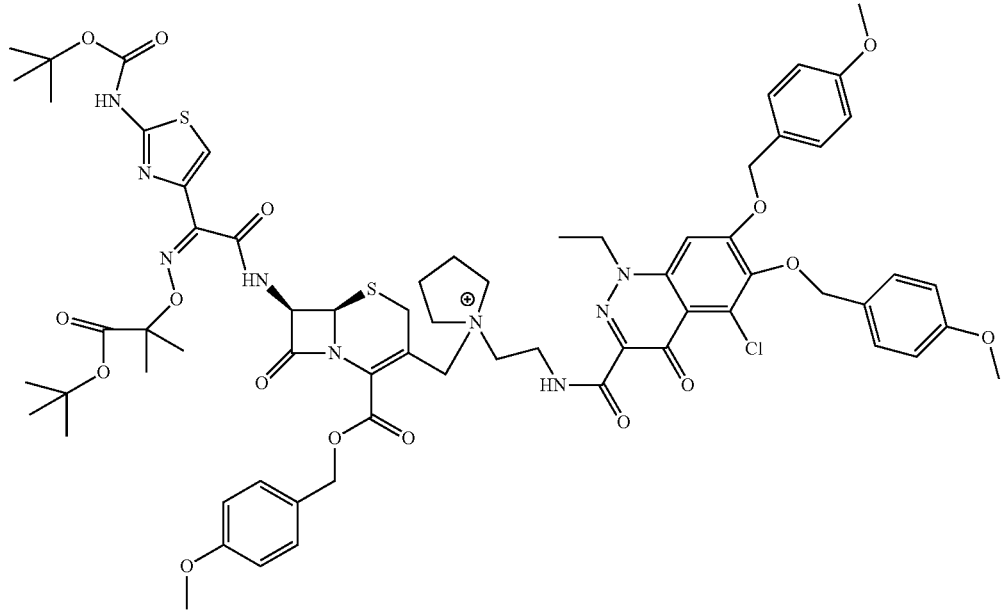 [SMILES: CCn1nc(C(=O)NCC[N+]2(CC3=C(C(=O)OCc4ccc(OC)cc4)N4C(=O)[C@@H](NC(=O)/C(=N\OC(C)(C)C(=O)OC(C)(C)C)c5csc(NC(=O)OC(C)(C)C)n5)[C@H]4SC3)CCCC2)c(=O)c2c(Cl)c(OCc3ccc(OC)cc3)c(OCc3ccc(OC)cc3)cc21]

A solution of (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide (Example 19a) (0.858 g, 0.966 mmol) and 5-chloro-1-ethyl-6,7-bis((4-methoxybenzyl)oxy)-4-oxo-N-(2-(pyrrolidin-1-yl)ethyl)-1,4-dihydrocinnoline-3-carboxamide (0.6 g, 0.966 mmol) in N,N-dimethylacetamide (DMA) (10 mL) was heated at 40° C. for 3 h, and was then left overnight in the refrigerator. N,N-dimethylformamide (DMF) (10 mL) was added and the mixture was cooled to −40° C., followed by addition of PBr₃ (0.182 mL, 1.932 mmol). The mixture was stirred at −40° C. for 30 min, and the reaction was then quenched with 5% NaCl solution. The solid was collected by filtration and purified on ISCO silica gel column eluting with 0-20% methanol:dichloromethane to afford 1-(((6R,7R)-7-((Z)-2-(((1-(tert-butoxy)-2-methyl-1-oxopropan-2-yl)oxy)imino)-2-(2-((tert-butoxycarbonyl) amino)thiazol-4-yl)acetamido)-2-(((4-methoxybenzyl)oxy) carbonyl)-8-oxo-5-thia-1-azabicyclo[4.2.0]oct-2-en-3-yl) methyl)-1-(2-(5-chloro-1-ethyl-6,7-bis((4-methoxybenzyl) oxy)-4-oxo-1,4-dihydrocinnoline-3-carboxamido)ethan-1- ylium-1-yl)pyrrolidin-1-ium (1.08 g, 0.791 mmol, 82% yield). LCMS: (M+H)+: 1364.2.

Example 31i (6R,7R)-7-((Z)-2-(2-aminothiazol-4-yl)-2-(((2-carboxypropan-2-yl)oxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate, Sodium salt

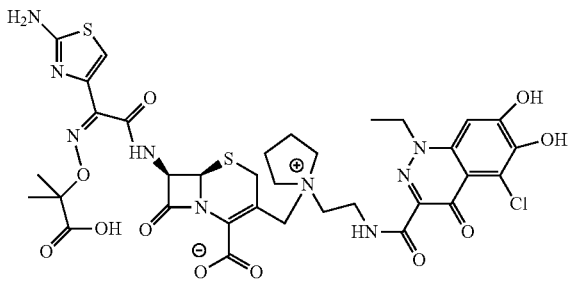 [SMILES: CCn1nc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2c(Cl)c(O)c(O)cc21]

To a solution of 1-(((6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-1-ethyl-6,7-bis((4-methoxybenzyl)oxy)-4-oxo-1,4-dihydrocinnoline-3-carboxamido)ethyl)pyrrolidin-1-ium-2-ylium (1.08 g, 0.791 mmol) in dichloromethane (DCM) (20 mL) at room temperature was added anisole (2.59 mL, 23.74 mmol) followed by trifluoroacetic acid (3.05 mL, 39.6 mmol). The resulting mixture stirred at room temperature for 18 hours, and was then triturated with isopropyl ether. Resulting solid was redissolved in acetonitrile, water and 1N hydrochloric acid, and HP20ss resin was added. The mixture was concentrated and loaded onto the cartridge containing HP20ss resin. The cartridge was connected to C18 reverse phase ISCO column and eluted with 0-95% acetonitrile:water. The fractions with pure desired product were concentrated and lyophilized to constant weight, and was then converted to sodium salt by addition of 1 eq of 0.2N sodium hydroxide, followed by lyophilization to afford (6R,7R)-7-((Z)-2-(2-aminothiazol-4-yl)-2-(((2-carboxypropan-2-yl)oxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate, Sodium salt (150 mg, 0.172 mmol, 21.78% yield). LCMS: (M+H)+: 847.3; $^1$H NMR (400 MHz, DEUTERIUM OXIDE) δ ppm 1.31-1.45 (m, 9 H) 2.13 (br. s., 4 H) 3.58 (br. s., 6 H) 3.75-4.16 (m, 4 H) 4.49 (d, J=7.58 Hz, 4 H) 5.35 (d, J=5.05 Hz, 1 H) 5.67 (s, 1 H), 6.72 (s, 1 H) 6.93 (s, 1 H)

Example 32

1-(((6R,7R)-7-((Z)-2-(2-amino-5-chlorothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydrocinnoline-3-carboxamido)ethan-1-ylium-1-yl)pyrrolidin-1-ium, Sodium salt

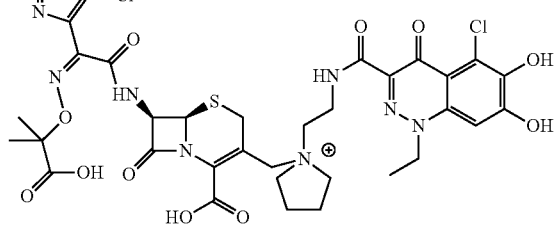

The compound was prepared according to the procedure described in Examples 31h-31i, utilizing (5R,6R,7R)-benzhydryl 7-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-3-(iodomethyl)-8-oxo-5-thia-1-azabicyclo[4.2.0]oct-2-ene-2-carboxylate 5-oxide (Example 22e) in place of (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide in Example 31h. LCMS: (M+H)$^+$: 882.6. $^1$H NMR (400 MHz, DEUTERIUM OXIDE) δ ppm 1.31-1.45 (m, 9 H) 2.13 (br. s., 4 H) 3.58 (br. s., 6 H) 3.75-4.16 (m, 4 H) 4.49 (d, J=7.58 Hz, 4H) 5.35 (d, J=5.05 Hz, 1 H) 5.67 (s, 1 H) 6.93 (s, 1 H)

Example 33

(6R,7R)-7-((Z)-2-(2-amino-5-chlorothiazol-4-yl)-2-(((S)-1,2-dicarboxyethoxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate

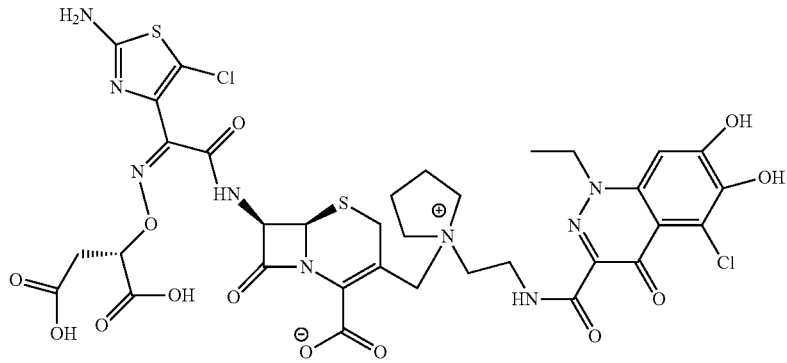 [SMILES: CCn1nc(C(=O)NCC[N+]2(CC3=C(C(=O)[O-])N4C(=O)[C@@H](NC(=O)/C(=N\O[C@@H](CC(=O)O)C(=O)O)c5nc(N)sc5Cl)[C@H]4SC3)CCCC2)c(=O)c2c(Cl)c(O)c(O)cc21]

The compound was prepared according to the procedure described in Examples 31h-31i, utilizing (S)-4-tert-butyl 1-(4-methoxybenzyl) 2-(((Z)-(2-(((5R,6R,7R)-2-((benzhydryloxy)carbonyl)-3-(iodomethyl)-5-oxido-8-oxo-5-thia-1-azabicyclo[4.2.0]oct-2-en-7-yl)amino)-1-(2-((tert-butoxycarbonyl)amino)-5-chlorothiazol-4-yl)-2-oxoethylidene)amino)oxy)succinate (Example 21k) in place of (5R,6R,7R)-4-methoxybenzyl 7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(iodomethyl)-8-oxo-5-thia-1-azabicyclo[4.2.0]oct-2-ene-2-carboxylate 5-oxide in step 31h. LCMS: (M+H)⁺: 911.2. 1H NMR (400 MHz, DEUTERIUM OXIDE) δ ppm 1.31-1.45 (m, 9 H) 2.13 (br. s., 4 H) 3.58 (br. s., 6 H) 3.75-4.16 (m, 4 H) 4.49 (d, J=7.58 Hz, 4 H) 5.28 (d, J=5.05 Hz, 1 H) 5.82 (s, 1 H) 7.4 (s, 1 H)

Example 34

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt

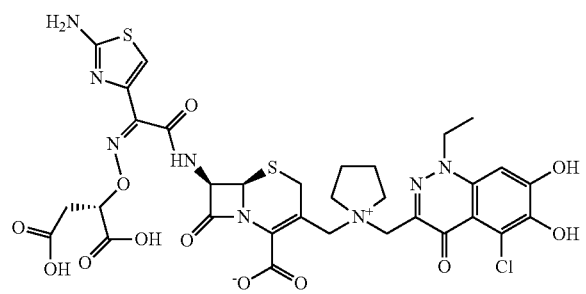

Example 34a

5-Chloro-1-ethyl-3-(hydroxymethyl)-6,7-bis((4-methoxybenzyl)oxy)cinnolin-4(1H)-one

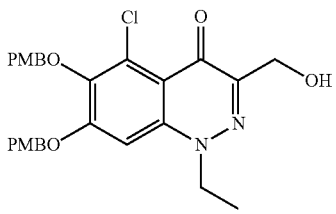

To a yellow suspension of 5-chloro-1-ethyl-6,7-bis((4-methoxybenzyl)oxy)-4-oxo-1,4-dihydrocinnoline-3-carboxylic acid (Example 31f) (6.7 g, 12.25 mmol) in Tetrahydrofuran (THF) (250 mL) was added TEA (3.42 mL, 24.51 mmol), followed by careful addition of isobutyl chloroformate (2.57 mL, 19.60 mmol). The resulting mixture was stirred at r.t. for 3 h. The crude carbonate solution was then slowly added to NaBH₄ (3.01 g, 80 mmol) in Ethanol (150 mL) in an ice bath over 15 min and the resulting mixture was stirred at r.t. for 1 h. The reaction was quenched by addition of H₂O (10 mL) and evaporated in vacuo. The residue was then diluted with water (200 mL) and extracted with dichloromethane (200 mL) twice. The organic extracts were washed with brine and then dried over sodium sulfate, filtered and the resulting filtrate was concentrated in vacuo to afford 5-chloro-1-ethyl-3-(hydroxymethyl)-6,7-bis((4-methoxybenzyl)oxy)cinnolin-4(H)-one (6.5 g, 9.16 mmol, 74.8% yield) as a yellow solid, which was used in the next oxidation step without further purification. LCMS: (M+H)+: 511.4.

Example 34b

5-Chloro-1-ethyl-6,7-bis((4-methoxybenzyl)oxy)-4-oxo-1,4-dihydrocinnoline-3-carbaldehyde

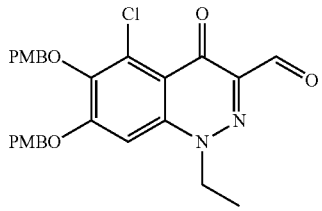

To a yellow solution of 5-chloro-1-ethyl-3-(hydroxymethyl)-6,7-bis((4-methoxybenzyl)oxy)cinnolin-4(1H)-one (6 g, 8.45 mmol) in Dichloromethane (DCM) (100 mL) was added manganese dioxide (12.11 g, 118 mmol), and the mixture was stirred at r.t. overnight. Solid was filtered off and washed with DCM. The filtrate was concentrated to afford 5-chloro-1-ethyl-6,7-bis((4-methoxybenzyl)oxy)-4-oxo-1,4-dihydrocinnoline-3-carbaldehyde (4 g, 4.79 mmol, 56.7% yield) as a crude dark brown solid. LCMS: (M+H)+: 509.3.

Example 34c

5-Chloro-1-ethyl-6,7-bis((4-methoxybenzyl)oxy)-3-(pyrrolidin-1-ylmethyl)cinnolin-4(1H)-one

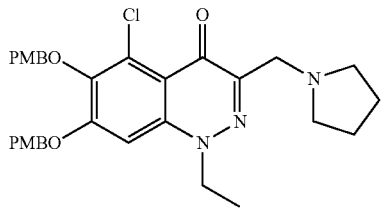

To a solution of 5-chloro-1-ethyl-6,7-bis((4-methoxybenzyl)oxy)-4-oxo-1,4-dihydrocinnoline-3-carbaldehyde (3.5 g, 4.26 mmol) in Dichloromethane (DCM) (80 mL) was added pyrrolidine (0.370 mL, 4.48 mmol) and sodium triacetoxyborohydride (1.355 g, 6.40 mmol). The mixture was stirred at r.t. for 1 h. Then reaction mixture was washed with sat. NaHCO$_3$ (aq.) and brine, dried over sodium sulfate and the solvent was removed in vacuo. The crude product was then purified through normal phase chromatography (CombiFlash Rf), eluting with MeOH/DCM (0-20%) to afford 5-chloro-1-ethyl-6,7-bis((4-methoxybenzyl)oxy)-3-(pyrrolidin-1-ylmethyl)cinnolin-4(1H)-one (1.9 g, 3.37 mmol, 79% yield) as an orange solid. The desired product was dissolved in DCM and washed with sat. NaHCO$_3$ (aq.) and brine, concentrated and passed through a flash column chromatography before being used for the next step. LCMS: (M+H)+: 564.4.

Example 34d (6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt

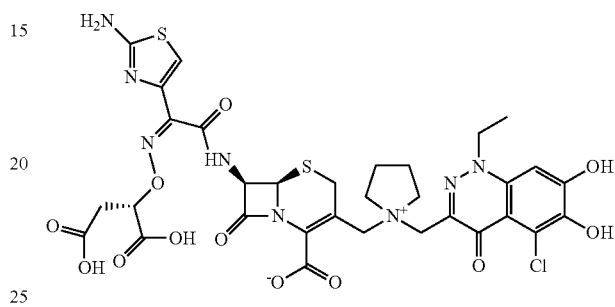

The compound was prepared according to the procedure described in Examples 16k-16l and 17, utilizing 5-chloro-1-ethyl-6,7-bis((4-methoxybenzyl)oxy)-3-(pyrrolidin-1-ylmethyl)cinnolin-4(1H)-one (Example 34c) in place of 5-chloro-1-ethyl-6,7-bis((4-methoxybenzyl)oxy)-3-(pyrrolidin-1-ylmethyl)quinolin-4(1H)-one in step 16k. LCMS: (M+H)+: 821.0. $^1$H NMR (400 MHz, DEUTERIUM OXIDE) δ ppm 1.33 (s, 3 H) 2.10 (br. s., 4 H) 2.74 (br. s., 2 H) 3.37-3.70 (m, 6 H) 3.80-3.94 (m, 1 H) 4.09-4.48 (m, 5 H) 4.84-4.92 (m, 1 H) 5.24-5.33 (m, 1 H) 5.72 (d, J=4.80 Hz, 1 H) 6.63-6.74 (m, 1 H) 6.83-6.95 (m, 1 H)

Example 35

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate, Sodium salt

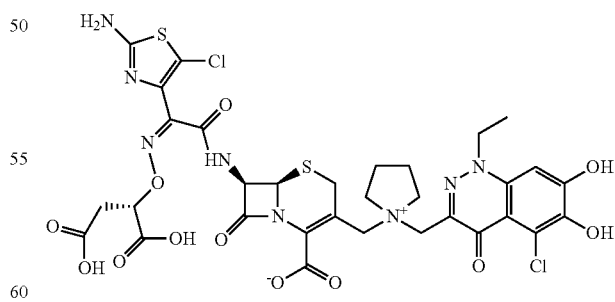

The compound was prepared according to the procedure described in Examples 21l-21m, utilizing 5-chloro-1-ethyl-6,7-bis((4-methoxybenzyl)oxy)-3-(pyrrolidin-1-ylmethyl) cinnolin-4(1H)-one (Example 34c) in place of 5-chloro-1-ethyl-6,7-bis((4-methoxybenzyl)oxy)-3-(pyrrolidin-1-ylmethyl)quinolin-4(1H)-one in step 21l. LCMS: (M+H)+:

855.0. $^1$H NMR (400 MHz, DEUTERIUM OXIDE) δ ppm 1.36 (s, 3 H) 2.10 (br. s., 4 H) 2.74-2.85 (m, 2 H) 3.49 (br. s., 6 H) 3.81-3.92 (m, 1 H) 4.13-4.24 (m, 1 H) 4.25-4.36 (m, 2 H) 4.44 (br. s., 2 H) 4.85-4.92 (m, 1 H) 5.23-5.32 (m, 1 H) 5.73 (d, J=4.80 Hz, 1 H) 6.79 (s, 1 H)

Example 36

(6R,7R)-7-(((Z)-2-(2-amino-5-chlorothiazol-4-yl)-2-(((S)-1,2-dicarboxyethoxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

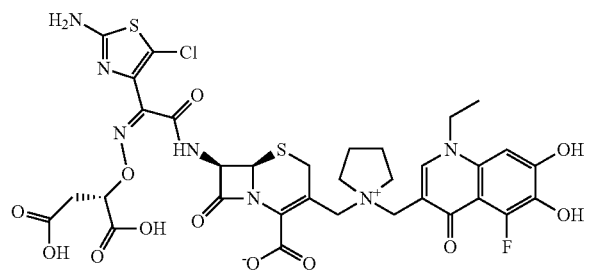

Example 36a

1-Fluoro-2,3-dimethoxy-5-nitrobenzene and 2-fluoro-3,4-dimethoxy-1-nitrobenzene

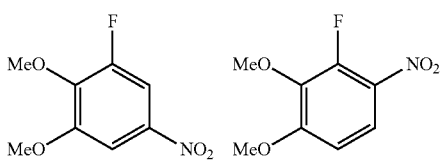 [SMILES: COc1cc([N+](=O)[O-])cc(F)c1OC ; COc1ccc([N+](=O)[O-])c(F)c1OC]

To a solution of nitric acid (853 ml, 1.91E+04 mmol) stirred at 0° C. was added dropwise 1-fluoro-2,3-dimethoxybenzene (149 g, 954 mmol). The mixture was stirred at the same temperature for 15 min, and then was allowed to warm up to RT for 15 min. The orange solution was poured into ice and the resultant solid was filtered, washed with water and dried. LCMS showed that the pale yellow solid was the mixture of two products (ratio 1/1.8). The crude material was purified by reverse phase automatic C18 column chromatography (Combiflash RF, 120 g column), eluting with Acetonitrile/Water (0-90%) over 35 min to afford 2-fluoro-3,4-dimethoxy-1-nitrobenzene (53 g, 263 mmol, 28% yield) and 1-fluoro-2,3-dimethoxy-5-nitrobenzene (94 g, 467 mmol, 49% yield) as white solids. LCMS: (M+H)$^+$: 202.1.

Example 36b

3-Fluoro-4,5-dimethoxyaniline

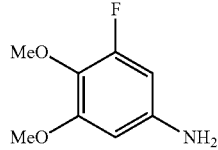

A mixture of 1-fluoro-2,3-dimethoxy-5-nitrobenzene (91 g, 452 mmol) and platinum(IV) oxide (9 g, 39.6 mmol) in ethanol (500 mL) was hydrogenated with a Par shaker (40 psi) at r.t. for 30 min. LCMS indicated completion of the reaction. The mixture was filtered and the filtrate was concentrated to afford 3-fluoro-4,5-dimethoxyaniline (73 g, 426 mmol, 94% yield) as a brown oil that was directly used in next step. LCMS: (M+H)$^+$:171.9.

Example 36c

Diethyl 2-(((3-fluoro-4,5-dimethoxyphenyl)amino)methylene)malonate

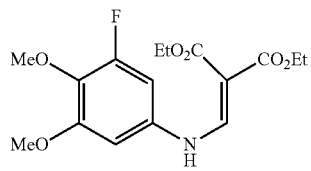

To the suspension of 3-fluoro-4,5-dimethoxyaniline (73 g, 426 mmol) in Ethanol (100 mL) was added diethyl 2-(ethoxymethylene)malonate (85 mL, 426 mmol), and the resulting mixture was heated at 80° C. for 1 h. LCMS indicated completion of the reaction. The mixture was concentrated in vacuo to remove ethanol, and the residue was washed with hexane to afford diethyl 2-(((3-fluoro-4,5-dimethoxyphenyl)amino)methylene)malonate (142 g, 416 mmol, 98% yield) as a yellow solid. LCMS: (M+H)$^+$: 342.1.

Example 36d

Ethyl 5-fluoro-6,7-dimethoxy-4-oxo-1,4-dihydroquinoline-3-carboxylate (6a) and ethyl 7-fluoro-5,6-dimethoxy-4-oxo-1,4-dihydroquinoline-3-carboxylate (6b)

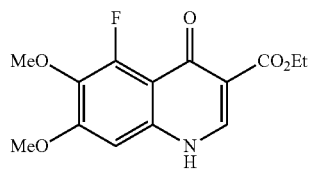 [SMILES: CCOC(=O)c1c[nH]c2cc(OC)c(OC)c(F)c2c1=O]

To Dowtherm (150 mL) heated at 250° C. was added diethyl 2-(((3-fluoro-4,5-dimethoxyphenyl)amino)methylene)malonate (30 g, 87 mmol). The mixture was stirred at 250° C. for 30 min. LCMS indicated completion of the reaction. The reaction mixture was allowed to cool a bit and was then added to cold hexane, the precipitates were collected by filtration, washed with hexane and then allowed to dry in the air. Similar scale reactions were repeated several times. From a total amount of the malonate (148 g, 434 mmol), a mixture of ethyl 5-fluoro-6,7-dimethoxy-4-oxo-1,4-dihydroquinoline-3-carboxylate and ethyl 7-fluoro-5,6-dimethoxy-4-oxo-1,4-dihydroquinoline-3-carboxylate was obtained as brown solid without further purification (103 g, 349 mmol, 80% yield). LCMS: (M+H)+: 296.1.

Example 36e

Ethyl 1-ethyl-5-fluoro-6,7-dimethoxy-4-oxo-1,4-dihydroquinoline-3-carboxylate

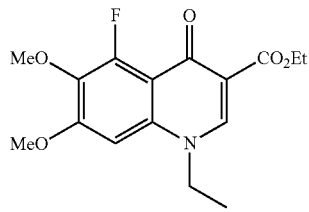 [SMILES: CCOC(=O)c1cn(CC)c2cc(OC)c(OC)c(F)c2c1=O]

A mixture of ethyl 5-fluoro-6,7-dimethoxy-4-oxo-1,4-dihydroquinoline-3-carboxylate and ethyl 7-fluoro-5,6-dimethoxy-4-oxo-1,4-dihydroquinoline-3-carboxylate (103 g, 349 mmol), and potassium carbonate (72.3 g, 523 mmol) in triethyl phosphate (297 ml, 1744 mmol) was stirred at 120° C. for 8 h. LCMS indicated completion of the reaction. The reaction mixture was cooled down to rt and diluted with water, extracted with DCM, dried over sodium sulfate and concentrated in vacuo. The crude material was recrystallized in EtOH, the precipitate was collected by filtration and washed by cold EtOH and dried in air. Another recrystallization afforded pure ethyl 1-ethyl-5-fluoro-6,7-dimethoxy-4-oxo-1,4-dihydroquinoline-3-carboxylate (65 g, 201 mmol, 57.6% yield) as a brown solid. LCMS: (M+H)+: 324.1.

Example 36f

1-Ethyl-5-fluoro-6,7-dihydroxy-4-oxo-1,4-dihydroquinoline-3-carboxylic acid

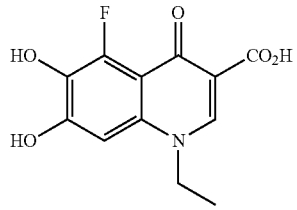 [SMILES: CCn1cc(C(=O)O)c(=O)c2c(F)c(O)c(O)cc21]

To a solution of ethyl 1-ethyl-5-fluoro-6,7-dimethoxy-4-oxo-1,4-dihydroquinoline-3-carboxylate (65 g, 201 mmol) in Dichloromethane (DCM) (300 mL) was added BBr3 (95 mL, 1005 mmol) at −78° C. The mixture was allowed to warm up to rt, and stirred at 25° C. overnight. LCMS indicated completion of the reaction. The mixture was diluted with MeOH and concentrated to dryness. The same process was repeated several times to afford 1-ethyl-5-fluoro-6,7-dihydroxy-4-oxo-1,4-dihydroquinoline-3-carboxylic acid (48 g, 180 mmol, 89% yield) as yellow solid. The crude product was a mixture of acid and small amount of methyl ester, which was used in next step reaction without further purification. LCMS: (M+H)+: 268.0.

Example 36g

4-Methoxybenzyl 1-ethyl-5-fluoro-6,7-bis((4-methoxybenzyl)oxy)-4-oxo-1,4-dihydroquinoline-3-carboxylate

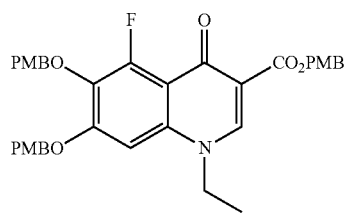

To a solution of 1-ethyl-5-fluoro-6,7-dihydroxy-4-oxo-1,4-dihydroquinoline-3-carboxylic acid (48 g, 180 mmol) in N,N-Dimethylformamide (DMF) (500 mL) was added K2CO3 (124 g, 898 mmol), followed by 1-(chloromethyl)-4-methoxybenzene (98 mL, 719 mmol). The reaction mixture was stirred at 50° C. overnight. LCMS indicated completion of the reaction. Water was added and the mixture was stirred at r.t for 15 mins. The yellow precipitates were collected by filtration and washed with water to afford 4-methoxybenzyl 1-ethyl-5-fluoro-6,7-bis((4-methoxybenzyl)oxy)-4-oxo-1,4-dihydroquinoline-3-carboxylate (68 g, 108 mmol, 60.3% yield) as a yellow solid. LCMS: (M+H)+: 628.4.

Example 36h

1-Ethyl-5-fluoro-6,7-bis((4-methoxybenzyl)oxy)-4-oxo-1,4-dihydroquinoline-3-carboxylic acid

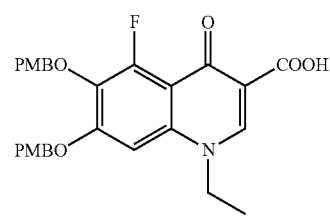

To a suspension of 4-methoxybenzyl 1-ethyl-5-fluoro-6,7-bis((4-methoxybenzyl)oxy)-4-oxo-1,4-dihydroquinoline-3-carboxylate (68 g, 108 mmol) in a mixture of Methanol (250 mL) and Water (125 mL) was added KOH (12.16 g, 217 mmol) portionwise. The resulting mixture was stirred at 90° C. for 3 h. LCMS indicated completion of the reaction. The reaction mixture was cooled down to r.t. and concentrated, and was then diluted with water and adjusted pH to 1 using 6 N HCl (aq.). The precipitates were collected by filtration and dried to afford 1-ethyl-5-fluoro-6,7-bis((4-methoxybenzyl)

oxy)-4-oxo-1,4-dihydroquinoline-3-carboxylic acid (50 g, 99 mmol, 91% yield) as a brown solid. LCMS: (M+H)+: 508.2.

Example 36i

1-Ethyl-5-fluoro-3-(hydroxymethyl)-6,7-bis((4-methoxybenzyl)oxy)quinolin-4(1H)-one

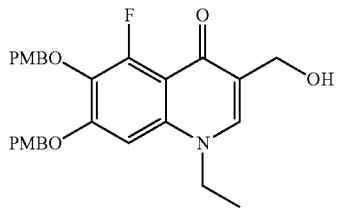

To a suspension of 1-ethyl-5-fluoro-6,7-bis((4-methoxybenzyl)oxy)-4-oxo-1,4-dihydroquinoline-3-carboxylic acid (20 g, 39.4 mmol) in Tetrahydrofuran (THF) (100 mL) was added TEA (6.04 mL, 43.3 mmol) and isobutyl chloroformate (5.69 mL, 43.3 mmol). The resulting mixture was stirred at r.t. for 1 h. Then the mixture was cooled down to −78° C. and a solution of DIBAL-H (52.5 mL, 79 mmol) in toluene (1.5 M) was added. The mixture was stirred at the same temperature for 2 h, LCMS indicated completion of the reaction. The reaction was quenched with sat. NH$_4$Cl (aq.), and was warmed up to r.t., concentrated, diluted with sat. NH$_4$Cl and extracted with dichloromethane. The organic mixture was filtered through Celite to remove gummy precipitate. The combined organic solution was then washed with brine, dried over sodium sulfate, filtered and the filtrate was concentrated in vacuo to afford 1-ethyl-5-fluoro-3-(hydroxymethyl)-6,7-bis((4-methoxybenzyl)oxy)quinolin-4(1H)-one (11.5 g, 23.30 mmol, 59.1% yield) as a yellow solid, which was used in the next oxidation step without further purification. LCMS: (M+H)+: 494.2

Example 36j

1-Ethyl-5-fluoro-6,7-bis((4-methoxybenzyl)oxy)-4-oxo-1,4-dihydroquinoline-3-carbaldehyde

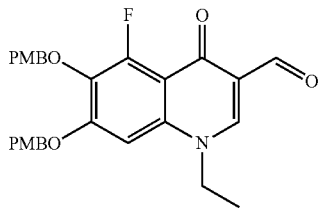

To a yellow solution of 1-ethyl-5-fluoro-3-(hydroxymethyl)-6,7-bis((4-methoxybenzyl)oxy) quinolin-4(1H)-one (11 g, 22.29 mmol) in Dichloromethane (DCM) (100 mL) was added manganese dioxide (19.38 g, 223 mmol). The mixture was stirred at rt for 6.5 h. The mixture was then filtered through Celite and washed with DCM, the filtrate was concentrated to afford 1-ethyl-5-fluoro-6,7-bis((4-methoxybenzyl)oxy)-4-oxo-1,4-dihydroquinoline-3-carbaldehyde (9.8 g, 19.94 mmol, 89% yield) as a yellow solid, which was used in the next step without further purification. LCMS: (M+H)+: 492.2.

Example 36k

1-Ethyl-5-fluoro-6,7-bis((4-methoxybenzyl)oxy)-3-(pyrrolidin-1-ylmethyl) quinolin-4(1H)-one

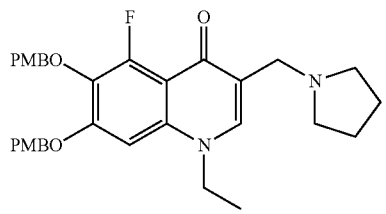

To a solution of 1-ethyl-5-fluoro-6,7-bis((4-methoxybenzyl)oxy)-4-oxo-1,4-dihydroquinoline-3-carbaldehyde (18 g, 36.6 mmol) in 1,2-Dichloroethane (DCE) (100 mL) was added pyrrolidine (4.53 mL, 54.9 mmol), sodium triacetoxyborohydride (15.52 g, 73.2 mmol) and AcOH (0.105 mL, 1.831 mmol). The reaction mixture was stirred at 25° C. for 3 h. LCMS indicated completion of the reaction. The mixture was extracted with DCM and washed with brine. The organic layer was dried over sodium sulfate and concentrated in vacuo. The crude material was purified by normal phase automatic silica column chromatography (Combinflash RF), using a 40 g gold column and eluting with MeOH/DCM (0-20%). The product was further purified by reverse phase automatic chromatography (Combinflash RF), using a 150 g gold C18 column and eluting with acetonitrile/Water (0%-60%) to afford 1-ethyl-5-fluoro-6,7-bis((4-methoxybenzyl)oxy)-3-(pyrrolidin-1-ylmethyl)quinolin-4(1H)-one (9.4 g, 17.20 mmol, 47.0% yield) as a pale yellow solid. LCMS: (M+H)+: 547.3.

Example 36l (6R,7R)-7-(((Z)-2-(2-amino-5-chlorothiazol-4-yl)-2-(((S)-1,2-dicarboxyethoxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

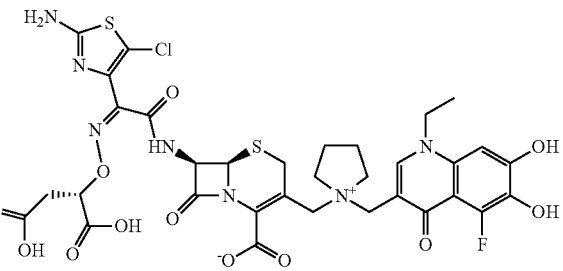

The compound was prepared according to the procedure described in Examples 21l-21m, utilizing 1-ethyl-5-fluoro-6,7-bis((4-methoxybenzyl)oxy)-3-(pyrrolidin-1-ylmethyl) quinolin-4(1H)-one (Example 36k) in place of 5-chloro-1- ethyl-6,7-bis((4-methoxybenzyl)oxy)-3-(pyrrolidin-1-ylmethyl)quinolin-4(1H-one in step 21l. LCMS: (M+H)+: 855.0. ¹H NMR (400 MHz, DEUTERIUM OXIDE) δ ppm 1.31 (t, J=7.07 Hz, 3 H) 2.02 (br. s., 4 H) 2.76 (br. s., 2 H) 3.24-3.47 (m, 6 H) 3.82-3.93 (m, 1 H) 3.94-4.04 (m, 1 H) 4.07-4.19 (m, 2 H) 4.20-4.38 (m, 2 H) 4.83-4.91 (m, 1 H) 5.22-5.31 (m, 1 H) 5.66-5.76 (m, 1 H) 6.75-6.83 (m, 1 H) 8.06 (s, 1 H)

Example 37

(6R,7R)-7-((Z)-2-(2-aminothiazol-4-yl)-2-(((2-carboxypropan-2-yl)oxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

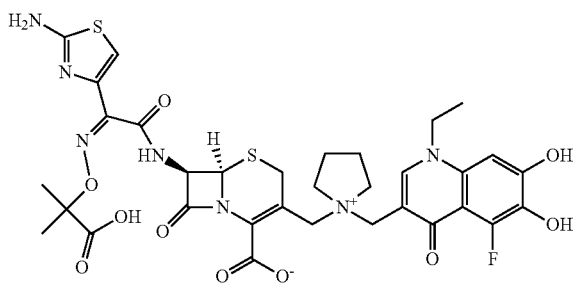 [SMILES: CCn1cc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2c(F)c(O)c(O)cc21]

The compound was prepared according to the procedure described in Examples 19b-19c, utilizing 1-ethyl-5-fluoro-6,7-bis((4-methoxybenzyl)oxy)-3-(pyrrolidin-1-ylmethyl)quinolin-4(1H)-one (Example 36k) in place of 5-chloro-1-ethyl-6,7-bis((4-methoxybenzyl)oxy)-3-(pyrrolidin-1-ylmethyl)quinolin-4(1H)-one in step 19b. LCMS: (M+H)+: 774.0. ¹H NMR (400 MHz, METHANOL-d₄) δ ppm 1.50 (t, J=7.07 Hz, 3 H) 1.61 (d, J=6.32 Hz, 6 H) 2.11-2.30 (m, 4 H) 3.42-3.65 (m, 6 H) 3.92-4.02 (m, 1 H) 4.07-4.17 (m, 1 H) 4.26-4.39 (m, 3 H) 4.46-4.55 (m, 1 H) 5.27-5.34 (m, 1 H) 5.92 (d, J=5.05 Hz, 1 H) 6.89 (s, 1 H) 6.91-6.96 (m, 1 H) 8.18-8.25 (m, 1 H).

Example 38

(6R,7R)-7-((Z)-2-(2-aminothiazol-4-yl)-2-(((S)-1,2-dicarboxyethoxy)imino)acetamido)-3-((1-((5-fluouro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

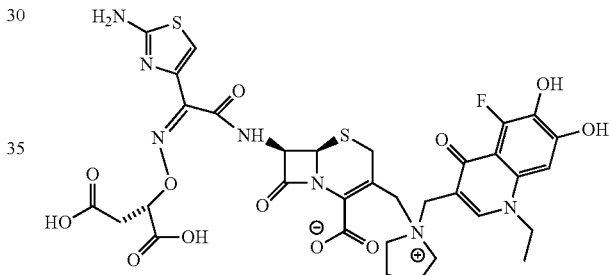

The compound was prepared according to the procedure described in Examples 16k-16l and 17, utilizing 1-ethyl-5-fluoro-6,7-bis((4-methoxybenzyl)oxy)-3-(pyrrolidin-1-ylmethyl)quinolin-4(1H)-one (Example 36k) in place of 5-chloro-1-ethyl-6,7-bis((4-methoxybenzyl)oxy)-3-(pyrrolidin-1-ylmethyl)quinolin-4(1H)-one in step 16k. LCMS: (M+H)+: 804.3; ¹H NMR (400 MHz, DEUTERIUM OXIDE) δ ppm 1.31-1.45 (m, 9 H) 2.13 (br. s., 4 H) 2.7 (br. s 2 H), 3.48 (br. s., 6 H) 3.75-4.16 (m, 4 H) 4.49 (d, J=7.58 Hz, 4 H) 5.31 (d, J=5.05 Hz, 1 H) 5.75 (s, 1 H) 6.80 (s, 1 H) 7.90 (s, 1 H), 8.05 (s, 1 H).

Example 39

(6R,7R)-7-(((Z)-2-(2-aminothiazol-4-yl)-2-(((S)-1,2-dicarboxyethoxy)imino)acetamido)-3-((1-(2-(1-ethyl-5-fluoro-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, sodium salt

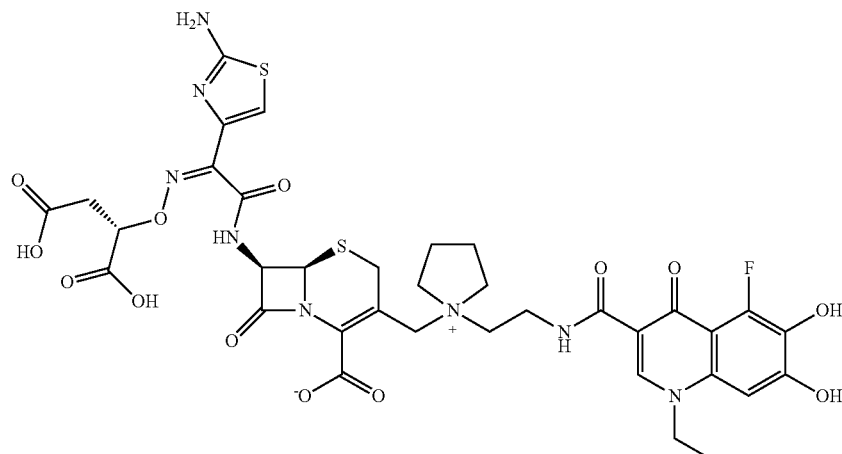

Example 39a

1-Ethyl-5-fluoro-6,7-bis((4-methoxybenzyl)oxy)-4-oxo-N-(2-(pyrrolidin-1-yl)ethyl)-1,4-dihydroquinoline-3-carboxamide

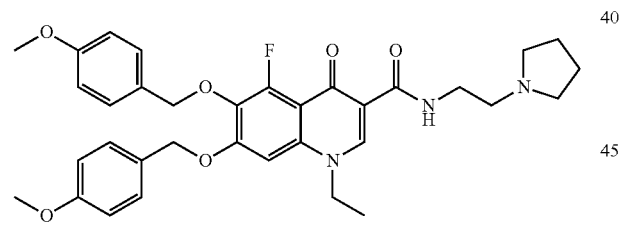

To a solution of 1-ethyl-5-fluoro-6,7-bis((4-methoxybenzyl)oxy)-4-oxo-1,4-dihydro quinoline-3-carboxylic acid (Example 36h) (5 g, 9.85 mmol) in N,N-Dimethylformamide (DMF) (5 mL) was added HATU (5.62 g, 14.78 mmol) and DIPEA (5.16 mL, 29.6 mmol), the resulting mixture was stirred at r.t. for 30 min. Then 2-(pyrrolidin-1-yl)ethanamine (1.861 mL, 14.78 mmol) was added and the resulting mixture was stirred at r.t. overnight. The mixture was concentrated and the residue was purified by normal phase automatic silica column chromatography (Combiflash RF) eluting with MeOH/DCM (0-20%). The product was further purified by reverse phase automatic chromatography (Combinflash RF), using a 150 g golden C18 column and eluting with acetonitrile/Water (0%-100%) to afford 1-ethyl-5-fluoro-6,7-bis((4-methoxybenzyl)oxy)-4-oxo-N-(2-(pyrrolidin-1-yl)ethyl)-1,4-dihydroquinoline-3-carboxamide (3.8 g, 6.29 mmol, 63.9% yield) as pale yellow solid. LCMS: (M+H)$^+$: 604.4.

Example 39b (6R,7R)-7-((Z)-2-(2-aminothiazol-4-yl)-2-(((S)-1,2-dicarboxyethoxy)imino)acetamido)-3-((1-(2-(1-ethyl-5-fluoro-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, sodium salt

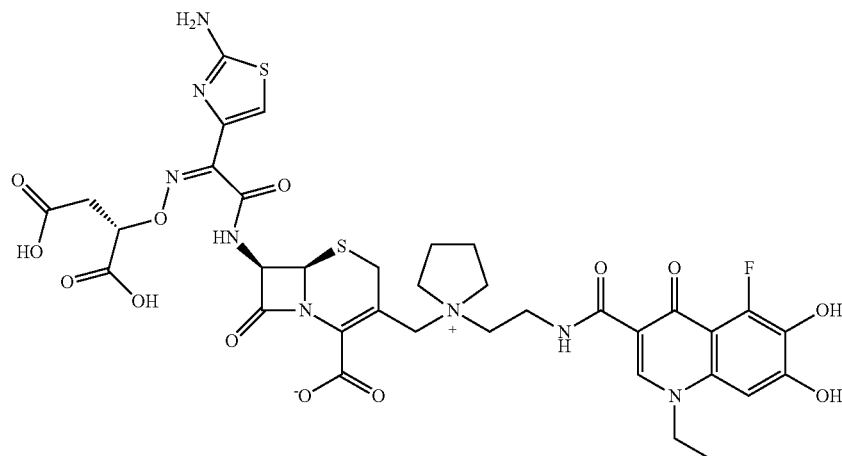

The compound was prepared according to the procedure described in Examples 16k-16l and 17, utilizing 1-ethyl-5-fluoro-6,7-bis((4-methoxybenzyl)oxy)-4-oxo-N-(2-(pyrrolidin-1-yl)ethyl)-1,4-dihydroquinoline-3-carboxamide (Example 39a) in place of 5-chloro-1-ethyl-6,7-bis((4-methoxybenzyl)oxy)-3-(pyrrolidin-1-ylmethyl)quinolin-4(1H)-one in step 16k. LCMS: (M+H)$^+$: 861.2; $^1$H NMR (400 MHz, DEUTERIUM OXIDE) δ ppm 1.30 (t, J=6.82 Hz, 3 H) 2.11 (br. s., 4 H) 2.61 (br. s., 2 H) 3.36-3.75 (m, 8 H) 3.83 (d, J=16.93 Hz, 2 H) 4.00-4.16 (m, 4 H) 4.83 (s, 1 H) 5.19-5.28 (m, 1 H) 5.72 (d, J=4.80 Hz, 1 H) 6.64-6.73 (m, 1 H) 6.83 (s, 1 H) 8.35 (s, 1 H)

Example 40

(6R,7R)-7-((Z)-2-(2-amino-5-chlorothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

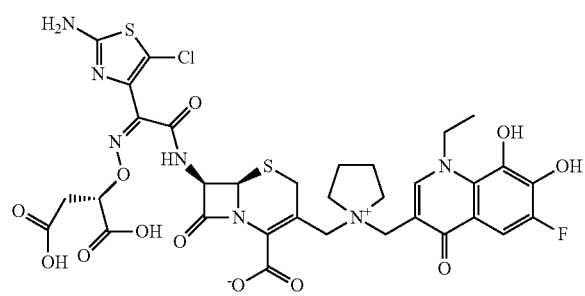

Example 40a

1-Ethyl-6-fluoro-7,8-bis((4-methoxybenzyl)oxy)-4-oxo-1,4-dihydroquinoline-3-carboxylic acid

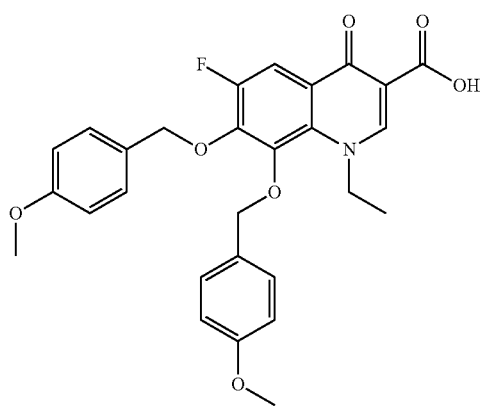 [SMILES: CCn1cc(C(=O)O)c(=O)c2cc(F)c(OCc3ccc(OC)cc3)c(OCc3ccc(OC)cc3)c21]

A mixture of ethyl 1-ethyl-6,7,8-trifluoro-4-oxo-1,4-dihydroquinoline-3-carboxylate (50 g, 167 mmol), KOH (94 g, 1671 mmol) and 4-methoxybenzyl alcohol (208 ml, 1671 mmol) was heated at 75° C. for 4 hours. LCMS showed completion of reaction. The solution was adjusted to pH 2 and was extracted with ethyl acetate. The organic layer was washed with water, dried with Na$_2$SO$_4$, filtered, and concentrated in vacuo. The residue was triturated with ethyl acetate, whereupon the crude product precipitated out as a solid substance. The precipitate was collected by filtration and washed with EA to afford 1-ethyl-6-fluoro-7,8-bis((4-methoxybenzyl)oxy)-4-oxo-1,4-dihydroquinoline-3-carboxylic acid (44 g, 87 mmol, 51.9% yield) as a yellow solid. LCMS: (M+H)⁺: 508.3.

Example 40b

1-Ethyl-6-fluoro-3-(hydroxymethyl)-7,8-bis((4-methoxybenzyl)oxy)quinolin-4(1H)-one

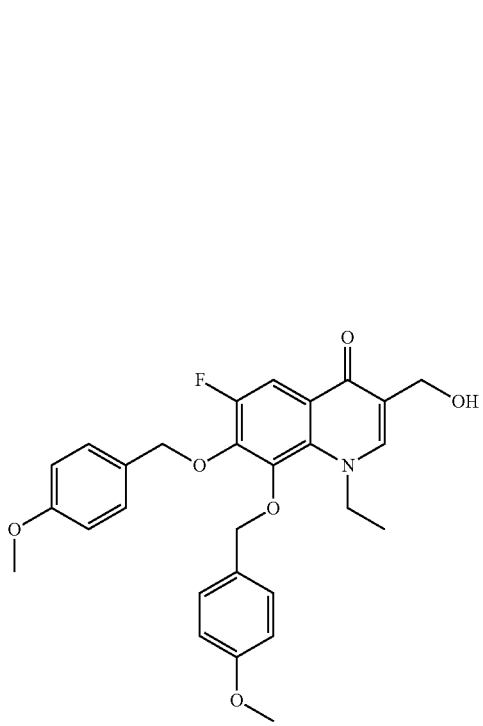 [SMILES: CCn1cc(CO)c(=O)c2cc(F)c(OCc3ccc(OC)cc3)c(OCc3ccc(OC)cc3)c21]

To a suspension of 1-ethyl-6-fluoro-7,8-bis((4-methoxybenzyl)oxy)-4-oxo-1,4-dihydroquinoline-3-carboxylic acid (40 g, 79 mmol) in Tetrahydrofuran (THF) (300 mL) was added TEA (12.08 mL, 87 mmol) and isobutyl chloroformate (11.39 mL, 87 mmol). The resulting mixture was stirred at r.t. for 1 h. LCMS showed completion of the reaction. Then the mixture was cooled down to −78° C. and a solution of DIBAL-H (158 mL, 236 mmol) in toluene (1.5 M) was added. The mixture was stirred at the same temperature for 1.5 h, LCMS indicated completion of the reaction. The reaction was quenched with sat. NH₄Cl (aq.), warmed up to r.t., concentrated, diluted with sat. NH₄Cl and extracted with dichloromethane twice. The organic mixture was filtered through Celite to remove any solids. The combined organic solution was then washed with brine and dried over sodium sulfate, filtered and the resulting filtrate was concentrated in vacuo to afford 1-ethyl-6-fluoro-3-(hydroxymethyl)-7,8-bis((4-methoxybenzyl)oxy)quinolin-4(1H)-one (33 g, 51.5 mmol, 65.3% yield) as yellow solid, which was used in the next oxidation step without further purification. LCMS: (M+H)⁺: 494.3.

Example 40c

1-Ethyl-6-fluoro-7,8-bis((4-methoxybenzyl)oxy)-4-oxo-1,4-dihydroquinoline-3-carbaldehyde

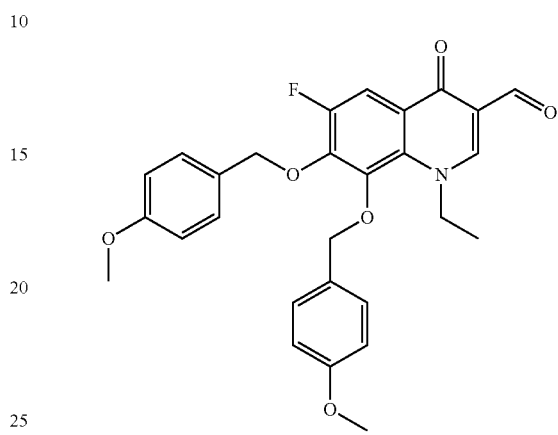

To a yellow solution of 1-ethyl-6-fluoro-3-(hydroxymethyl)-7,8-bis((4-methoxybenzyl)oxy) quinolin-4(1H)-one (33 g, 66.9 mmol) in Dichloromethane (DCM) (200 mL) was added manganese dioxide (58.1 g, 669 mmol), and the mixture was stirred at rt for 6.5 h. The mixture was then filtered through Celite and the solid was washed with DCM. The filtrate was concentrated in vacuo to afford 1-ethyl-6-fluoro-7,8-bis((4-methoxybenzyl)oxy)-4-oxo-1,4-dihydroquinoline-3-carbaldehyde (25 g, 50.9 mmol, 76% yield) as a yellow solid, which was used in the next step without further purification. LCMS: (M+H)⁺: 492.3.

Example 40d

1-Ethyl-6-fluoro-7,8-bis((4-methoxybenzyl)oxy)-3-(pyrrolidin-1-ylmethyl) quinolin-4(1H)-one

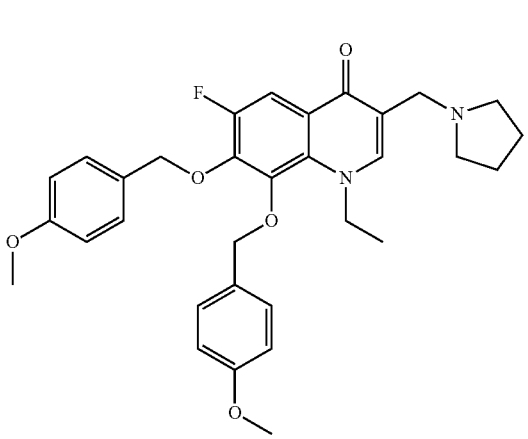 [SMILES: CCn1cc(CN2CCCC2)c(=O)c2cc(F)c(OCc3ccc(OC)cc3)c(OCc3ccc(OC)cc3)c21]

To a solution of 1-ethyl-6-fluoro-7,8-bis((4-methoxybenzyl)oxy)-4-oxo-1,4-dihydroquinoline-3-carbaldehyde (15 g, 30.5 mmol) in 1,2-Dichloroethane (DCE) (100 mL) was added pyrrolidine (3.78 mL, 45.8 mmol), sodium triacetoxyborohydride (12.94 g, 61.0 mmol) and AcOH (0.087 mL, 1.526 mmol). The reaction mixture was stirred at 25° C. for 3 h. LCMS showed completion of the reaction. The mixture was extracted with DCM and washed with brine. The organic solution was dried over sodium sulfate and evaporated in vacuo. The crude material was purified by normal phase automatic silica column chromatography (Combiflash RF), using a 40 g golden column and eluting with MeOH/DCM (0-20%). The product was further purified with reverse phase automatic silica column chromatography (Combiflash RF), using a 150 g golden column and eluting with acetonitrile/water (0-60%) to afford 1-ethyl-6-fluoro-7,8-bis((4-methoxybenzyl)oxy)-3-(pyrrolidin-1-ylmethyl)quinolin-4(1H)-one (9.8 g, 17.93 mmol, 58.7% yield) as a yellow solid. LCMS: (M+H)⁺: 547.4.

Example 40e (6R,7R)-7-((Z)-2-(2-amino-5-chlorothiazol-4-yl)-2-(((S)-1,2-dicarboxy ethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt The compound was prepared according to the procedure described in Examples 21l-21m, utilizing 1-ethyl-6-fluoro-7,8-bis((4-methoxybenzyl)oxy)-3-(pyrrolidin-1-ylmethyl)quinolin-4(1H)-one (Example 40d) in place of 5-chloro-1-ethyl-6,7-bis((4-methoxybenzyl)oxy)-3-(pyrrolidin-1-ylmethyl)quinolin-4(1H)-one in step 21l. LCMS: (M+H)⁺: 838.8. ¹H NMR (400 MHz, DEUTERIUM OXIDE) δ ppm 1.32 (t, J=6.95 Hz, 3 H) 2.01 (br. s., 4 H) 2.69-2.82 (m, 2 H) 3.40 (d, J=16.93 Hz, 6 H) 3.80-3.92 (m, 1 H) 3.94-4.06 (m, 1 H) 4.23-4.44 (m, 2 H) 4.53-4.64 (m, 2 H) 4.86 (s, 1 H) 5.22-5.29 (m, 1 H) 5.71 (d, J=5.05 Hz, 1 H) 7.43-7.50 (m, 1 H) 8.10 (s, 1 H)

Example 41

(6R,7R)-7-((Z)-2-(2-aminothiazol-4-yl)-2-(((2-carboxypropan-2-yl)oxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate

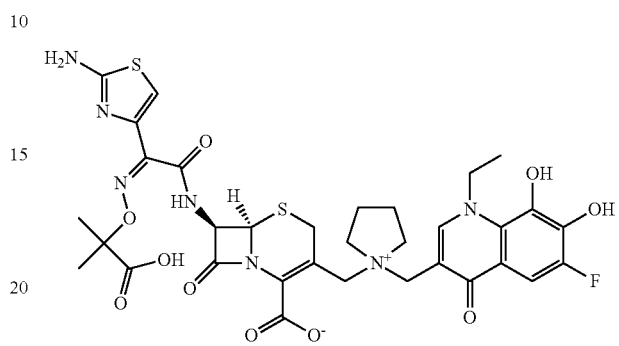

The compound was prepared according to the procedure described in Examples 19b-19c, utilizing 1-ethyl-6-fluoro-7,8-bis((4-methoxybenzyl)oxy)-3-(pyrrolidin-1-ylmethyl)quinolin-4(1H)-one (Example 40d) in place of 5-chloro-1-ethyl-6,7-bis((4-methoxybenzyl)oxy)-3-(pyrrolidin-1-ylmethyl)quinolin-4(1H)-one in step 19b. LCMS: (M+H)⁺: 773.9. ¹H NMR (400 MHz, METHANOL-d4) δ ppm 1.51 (br. s., 9 H) 2.20 (br. s., 4 H) 3.50 (d, J=1.52 Hz, 6 H) 3.91-4.04 (m, 1 H) 4.07-4.20 (m, 1 H) 4.31-4.44 (m, 1 H) 4.48-4.61 (m, 1 H) 4.69-4.83 (m, 2 H) 5.27-5.35 (m, 1 H) 5.86-6.01 (m, 1 H) 6.82-6.96 (m, 1 H) 7.55-7.69 (m, 1 H) 8.17-8.34 (m, 1 H)

Example 42

(6R,7R)-7-((Z)-2-(2-aminothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, sodium salt

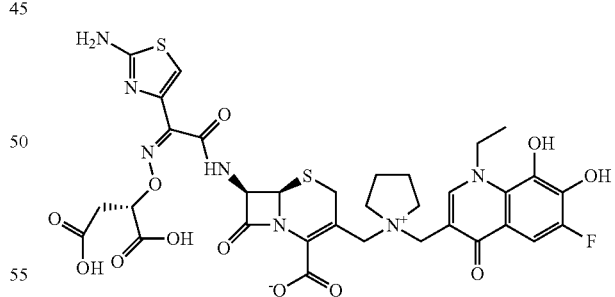

The compound was prepared according to the procedure described in Examples 16k-16l and 17, utilizing 1-ethyl-6-fluoro-7,8-bis((4-methoxybenzyl)oxy)-3-(pyrrolidin-1-ylmethyl)quinolin-4(1H)-one (Example 40d) in place of 5-chloro-1-ethyl-6,7-bis((4-methoxybenzyl)oxy)-3-(pyrrolidin-1-ylmethyl)quinolin-4(1H)-one in step 16k. LCMS: (M+H)⁺: 804.1. ¹H NMR (400 MHz, DEUTERIUM OXIDE) δ ppm 1.31 (t, J=6.95 Hz, 3 H) 2.02 (br. s., 4 H) 2.62-2.75 (m, 2 H) 3.18-3.48 (m, 6 H) 3.80-3.91 (m, 1 H) 3.95-4.07 (m, 1 H) 4.22-4.44 (m, 2 H) 4.52-4.63 (m, 2 H) 4.83-4.90 (m, 1 H)

5.21-5.31 (m, 1 H) 5.68-5.75 (m, 1 H) 6.90 (s, 1 H) 7.47 (d, J=10.61 Hz, 1 H) 8.07-8.18 (m, 1 H)

Example 43

(6R,7R)-7-(((Z)-2-(2-aminothiazol-4-yl)-2-(((2-carboxypropan-2-yl)oxy)imino)acetamido)-3-((1-(2-(1-ethyl-6-fluoro-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate

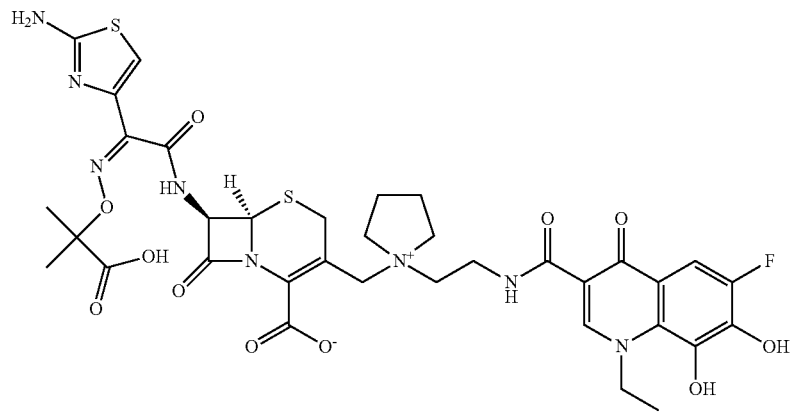 [SMILES: CCn1cc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(F)c(O)c(O)c21]

Example 43a

1-Ethyl-6-fluoro-7,8-bis((4-methoxybenzyl)oxy)-4-oxo-N-(2-(pyrrolidin-1-yl)ethyl)-1,4-dihydroquinoline-3-carboxamide

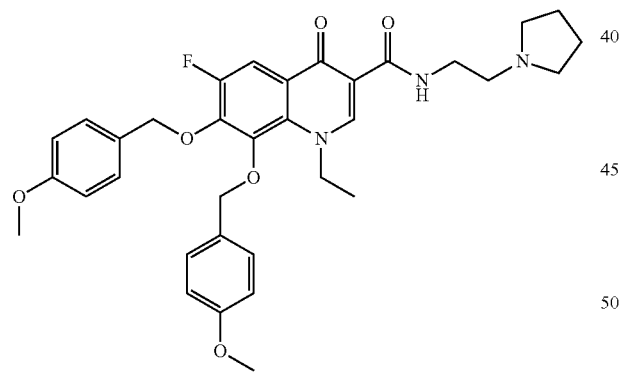

To a solution of 1-ethyl-6-fluoro-7,8-bis((4-methoxybenzyl)oxy)-4-oxo-1,4-dihydroquinoline-3-carboxylic acid (Example 40a) (8 g, 15.76 mmol) in N,N-Dimethylformamide (DMF) (15 mL) was added HATU (8.99 g, 23.64 mmol) and DIPEA (8.26 mL, 47.3 mmol), the resulting mixture was stirred at r.t. for 30 min. 2-(Pyrrolidin-1-yl)ethanamine (2.98 mL, 23.64 mmol) was added and the resulting mixture was stirred at r.t. for 3 h. The mixture was concentrated and the residue was purified by normal phase automatic silica column chromatography (Combiflash RF) eluting with MeOH/DCM (0-20%) to afford 1-ethyl-6-fluoro-7,8-bis((4-methoxybenzyl)oxy)-4-oxo-N-(2-(pyrrolidin-1-yl)ethyl)-1,4-dihydroquinoline-3-carboxamide (6.6 g, 10.93 mmol, 69.4% yield) as a pale yellow solid. LCMS: (M+H)$^+$: 604.5.

Example 43b (6R,7R)-7-((Z)-2-(2-aminothiazol-4-yl)-2-(((2-carboxypropan-2-yl)oxy)imino)acetamido)-3-((1-(2-(1-ethyl-6-fluoro-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate

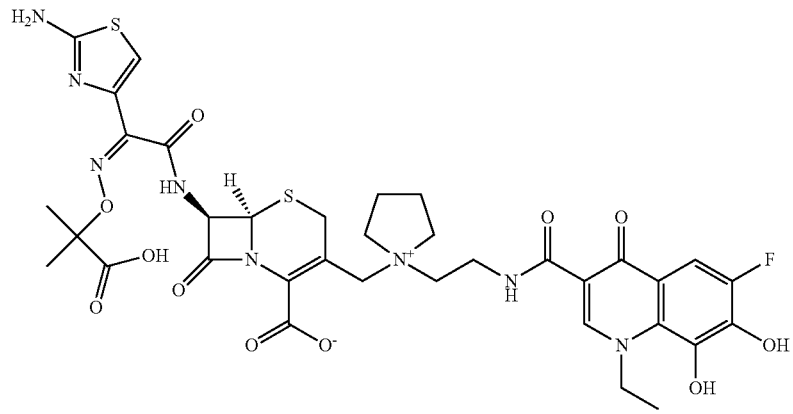 [SMILES: CCn1cc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(F)c(O)c(O)c21]

The compound was prepared according to the procedure described in Examples 19b-19c, utilizing 1-ethyl-6-fluoro-7,8-bis((4-methoxybenzyl)oxy)-4-oxo-N-(2-(pyrrolidin-1-yl)ethyl)-1,4-dihydroquinoline-3-carboxamide (Example 43a) in place of 5-chloro-1-ethyl-6,7-bis((4-methoxybenzyl)oxy)-3-(pyrrolidin-1-ylmethyl)quinolin-4(H)-one in step 19b. LCMS: (M+H)$^+$: 832.2. $^1$H NMR (400 MHz, METHANOL-$d_4$) δ ppm 1.61 (d, J=3.54 Hz, 9 H) 2.15-2.32 (m, 4 H) 3.46-3.73 (m, 6 H) 3.87-4.07 (m, 3 H) 4.11-4.22 (m, 1 H) 4.76-4.85 (m, 2 H) 5.27-5.33 (m, 1 H) 5.88-5.96 (m, 1 H) 6.85-6.92 (m, 1 H) 7.65-7.73 (m, 1 H) 8.64-8.71 (m, 1 H)

Example 44

(6R,7R)-7-((Z)-2-(2-aminothiazol-4-yl)-2-(((S)-1,2-dicarboxyethoxy)imino)acetamido)-3-((1-((1-ethyl-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, sodium salt

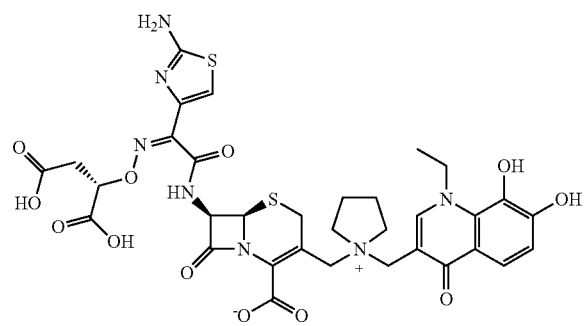

Example 44a

Diethyl 2-(((2,3-dimethoxyphenyl)amino)methylene)malonate

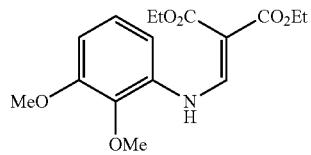 [SMILES: CCOC(=O)C(=CNc1cccc(OC)c1OC)C(=O)OCC]

To a mixture of 2,3-dimethoxyaniline (20 g, 131 mmol) in Ethanol (50 mL) was added diethyl 2-(ethoxymethylene)malonate (26.2 mL, 131 mmol). The mixture was heated at 80° C. for 1 h. LCMS indicated completion of the reaction. The mixture was concentrated in vacuo to remove ethanol, and washed with hexane to afford diethyl 2-(((2,3-dimethoxyphenyl)amino)methylene)malonate (38 g, 118 mmol, 90% yield) as a white solid. This crude mixture was directly used in next step. LCMS: (M+H)$^+$: 324.2.

Example 44b

Ethyl 7,8-dimethoxy-4-oxo-1,4-dihydroquinoline-3-carboxylate

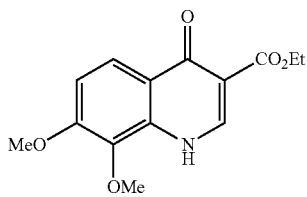 [SMILES: CCOC(=O)c1c[nH]c2c(OC)c(OC)ccc2c1=O]

To Dowtherm A (100 mL) heated at 250° C. was added diethyl 2-(((2,3-dimethoxyphenyl)amino)methylene)malonate (48 g, 148 mmol). The mixture was stirred at 250° C. for 1 h. LCMS indicated completion of the reaction. The reaction mixture was allowed to cool a bit and was then added to cold hexane, the precipitates were collected by filtration, washed with hexane and then allowed to dry in the air to afford ethyl 7,8-dimethoxy-4-oxo-1,4-dihydroquinoline-3-carboxylate (35 g, 126 mmol, 85% yield) as brown solid. LCMS: (M+H)$^+$: 278.2.

Example 44c

Ethyl 1-ethyl-7,8-dimethoxy-4-oxo-1,4-dihydroquinoline-3-carboxylate

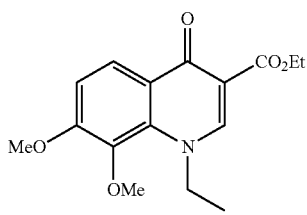 [SMILES: CCOC(=O)c1cn(CC)c2c(OC)c(OC)ccc2c1=O]

A mixture of ethyl 7,8-dimethoxy-4-oxo-1,4-dihydroquinoline-3-carboxylate (40 g, 144 mmol) and potassium carbonate (29.9 g, 216 mmol) in triethyl phosphate (123 ml, 721 mmol) was stirred at 120° C. for 24 h. LCMS indicated completion of the reaction. The reaction mixture was cooled down to rt and diluted with water, extracted with DCM, dried over sodium sulfate and evaporated in vacuo. The crude material was recrystallized in EtOH, the precipitate was collected by filtration, washed by cold EtOH and dried in air to afford ethyl 1-ethyl-7,8-dimethoxy-4-oxo-1,4-dihydroquinoline-3-carboxylate (26 g, 85 mmol, 59.0% yield) as a yellow solid. LCMS: (M+H)$^+$: 306.2.

Example 44d

Ethyl 1-ethyl-7,8-dihydroxy-4-oxo-1,4-dihydroquinoline-3-carboxylate and methyl 1-ethyl-7,8-dihydroxy-4-oxo-1,4-dihydroquinoline-3-carboxylate

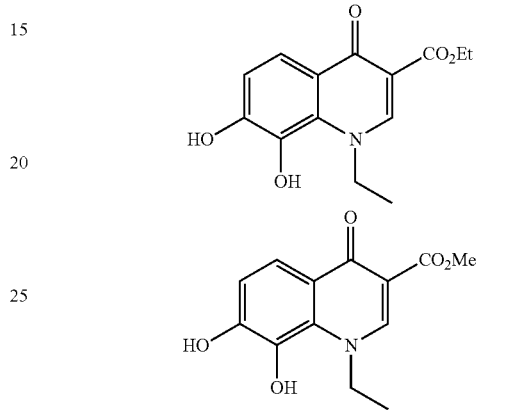

To a solution of ethyl 1-ethyl-7,8-dimethoxy-4-oxo-1,4-dihydroquinoline-3-carboxylate (12 g, 39.3 mmol) in Dichloromethane (DCM) (200 mL) was added BBr$_3$ (18.58 mL, 197 mmol) at −78° C. The mixture was allowed to warm up to rt, and stirred at rt for 5 h. LCMS indicated completion of the reaction and products were a mixture of ethyl and methyl esters. The mixture was diluted with MeOH and concentrated. This procedure was repeated for several times to afford a mixture of ethyl 1-ethyl-7,8-dihydroxy-4-oxo-1,4-dihydroquinoline-3-carboxylate and methyl 1-ethyl-7,8-dihydroxy-4-oxo-1,4-dihydroquinoline-3-carboxylate as yellow solid (ratio 1:1.5, 10 g, 36.1 mmol, 92% yield). The crude mixture was used in next step without further purification. LCMS: (M+H)$^+$: 278.1 (ethyl ester); 264.1 (methyl ester).

Example 44e

Methyl 1-ethyl-7,8-bis((4-methoxybenzyl)oxy)-4-oxo-1,4-dihydroquinoline-3-carboxylate, ethyl 1-ethyl-7,8-bis((4-methoxybenzyl)oxy)-4-oxo-1,4-dihydroquinoline-3-carboxylate and 4-methoxybenzyl 1-ethyl-7,8-bis((4-methoxybenzyl)oxy)-4-oxo-1,4-dihydroquinoline-3-carboxylate

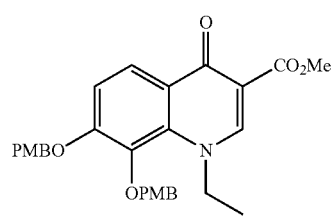

-continued

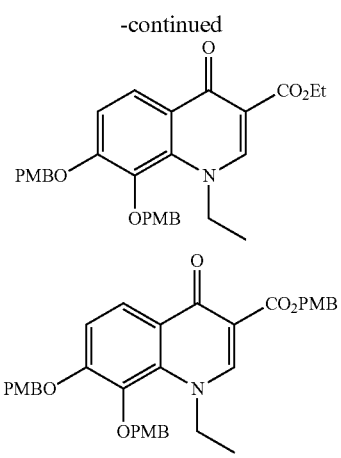

To a solution of the mixture from Example 44d (28 g, 106 mmol) in N,N-Dimethylformamide (DMF) (200 mL) was added $K_2CO_3$ (73.5 g, 532 mmol), followed by 1-(chloromethyl)-4-methoxybenzene (43.3 mL, 319 mmol). The reaction mixture was stirred at 50° C. for 4 h. LCMS indicated completion of the reaction and that the product was a mixture of Methyl, Ethyl and PMB esters. Water was added and the mixture was stirred at r.t for 15 min. The precipitates were collected by filtration and washed with water to afford a mixture of methyl 1-ethyl-7,8-bis((4-methoxybenzyl)oxy)-4-oxo-1,4-dihydroquinoline-3-carboxylate, ethyl 1-ethyl-7,8-bis((4-methoxybenzyl)oxy)-4-oxo-1,4-dihydroquinoline-3-carboxylate and 4-methoxybenzyl 1-ethyl-7,8-bis((4-methoxy benzyl)oxy)-4-oxo-1,4-dihydroquinoline-3-carboxylate (ratio 1:2:1.5, 45 g, 73.8 mmol, 69.4% yield) as a brown solid. The crude mixture was used in next step without further purification. LCMS: $(M+H)^+$: 504.3 (methyl ester); 518.3 (ethyl ester); 610.4 (PMB ester).

Example 44f

1-Ethyl-7,8-bis((4-methoxybenzyl)oxy)-4-oxo-1,4-dihydroquinoline-3-carboxylic acid

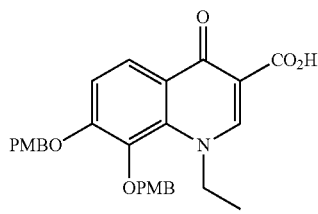

To a suspension of the mixture from Example 44e (45 g, 73.8 mmol) in a mixed solvent of Methanol (250 mL) and Water (125 mL) was added KOH (12.42 g, 221 mmol) portionwise. The resulting mixture was stirred at 90° C. for 3 h. LCMS indicated completion of the reaction. The reaction mixture was cooled down to r.t. and concentrated, and was then diluted with water and adjusted pH to 1 using 6 N HCl (aq.). The precipitates were collected by filtration and dried to afford 1-ethyl-7,8-bis((4-methoxybenzyl)oxy)-4-oxo-1,4-dihydroquinoline-3-carboxylic acid (35 g, 71.5 mmol, 97% yield) as pale yellow solid. LCMS: $(M+H)^+$: 490.3.

Example 44g

1-Ethyl-3-(hydroxymethyl)-7,8-bis((4-methoxybenzyl)oxy)quinolin-4(1H)-one

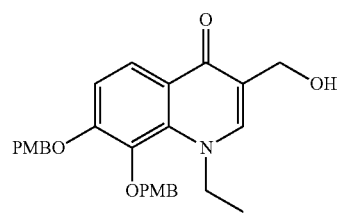

To a suspension of 1-ethyl-7,8-bis((4-methoxybenzyl)oxy)-4-oxo-1,4-dihydroquinoline-3-carboxylic acid (22 g, 44.9 mmol) in Tetrahydrofuran (THF) (300 mL) was added TEA (6.89 mL, 49.4 mmol) and isobutyl chloroformate (6.49 mL, 49.4 mmol). The resulting mixture was stirred at r.t. for 1 h. Then the mixture was cooled down to −78° C. and a solution of DIBAL-H (90 mL, 135 mmol) in toluene (1.5 M) was added. The mixture was stirred at the same temperature for 1.5 h, LCMS indicated completion of the reaction. The reaction was quenched with sat. $NH_4Cl$ (aq.), and subsequently warmed up to r.t. concentrated, diluted with sat. $NH_4Cl$ and extracted with dichloromethane twice. The organic phase was filtered through Celite to remove gummy precipitate, and was then washed with brine, dried over sodium sulfate, filtered and concentrated in vacuo to afford 1-ethyl-3-(hydroxymethyl)-7,8-bis((4-methoxybenzyl)oxy)quinolin-4(1H)-one (20 g, 23.55 mmol, 52.4% yield) as yellow solid, which was used in the next oxidation step without further purification. LCMS: $(M+H)^+$: 476.3.

Example 44h

1-Ethyl-7,8-bis((4-methoxybenzyl)oxy)-4-oxo-1,4-dihydroquinoline-3-carbaldehyde

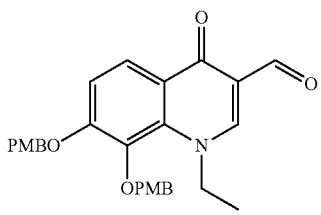

To a yellow solution of 1-ethyl-3-(hydroxymethyl)-7,8-bis((4-methoxybenzyl)oxy)quinolin-4(1H)-one (16 g, 33.6 mmol) in Dichloromethane (DCM) (200 mL) was added manganese dioxide (29.3 g, 336 mmol), and the mixture was stirred at rt for 6.5 h. The mixture was filtered through Celite and washed with DCM, the filtrate was concentrated to afford 1-ethyl-7,8-bis((4-methoxybenzyl)oxy)-4-oxo-1,4-dihydroquinoline-3-carbaldehyde (10 g, 21.12 mmol, 62.8% yield) as a brown solid, which was used in the next step without further purification. LCMS: (M+H)⁺: 474.3.

Example 44i

1-Ethyl-7,8-bis((4-methoxybenzyl)oxy)-3-(pyrrolidin-1-ylmethyl)quinolin-4(1H)-one

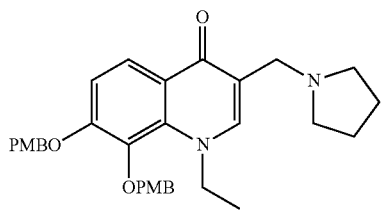

To a solution of 1-ethyl-7,8-bis((4-methoxybenzyl)oxy)-4-oxo-1,4-dihydroquinoline-3-carbaldehyde (10 g, 21.12 mmol) in Dichloromethane (DCM) (150 mL) was added pyrrolidine (2.61 mL, 31.7 mmol), sodium triacetoxyborohydride (8.95 g, 42.2 mmol) and AcOH (0.060 mL, 1.056 mmol). The reaction mixture was stirred at 25° C. for 3 h. LCMS showed completion of the reaction. The mixture was extracted with DCM and washed with brine. The organic layer was dried over sodium sulfate and evaporated in vacuo. The crude material was purified by normal phase automatic silica column chromatography (Combiflash RF), using a 120 g column and eluting with MeOH/DCM (0-20%). The product was further purified with reverse phase automatic silica column chromatography (Combiflash RF), using a 150 g golden column and eluting with acetonitrile/water (0-60%) to afford 1-ethyl-7,8-bis((4-methoxybenzyl)oxy)-3-(pyrrolidin-1-ylmethyl)quinolin-4(1H)-one (4.6 g, 8.70 mmol, 41.2% yield) as a pale yellow solid. LCMS: (M+H)⁺: 529.4.

Example 44j (6R,7R)-7-((Z)-2-(2-aminothiazol-4-yl)-2-(((S)-1,2-dicarboxyethoxy)imino)acetamido)-3-((1-((1-ethyl-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, sodium salt

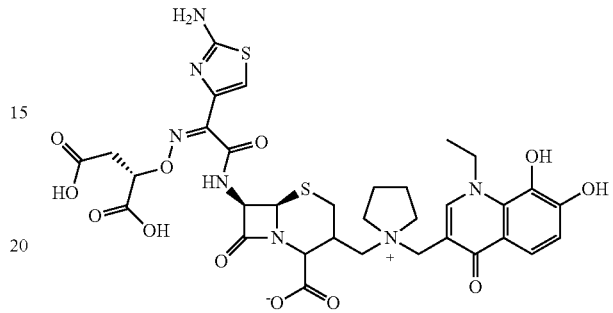

The compound was prepared according to the procedure described in Examples 16k-16l and 17, utilizing 1-ethyl-7,8-bis((4-methoxybenzyl)oxy)-3-(pyrrolidin-1-ylmethyl)quinolin-4(1H)-one (Example 44i) in place of 5-chloro-1-ethyl-6,7-bis((4-methoxybenzyl)oxy)-3-(pyrrolidin-1-ylmethyl)quinolin-4(1H)-one in step 16k. LCMS: (M+H)⁺: 786.4. ¹H NMR (400 MHz, DEUTERIUM OXIDE) δ ppm 1.32 (s, 3 H) 1.91-2.10 (m, 4 H) 2.59 (s, 2 H) 3.22-3.50 (m, 6 H) 3.80-3.89 (m, 1 H) 3.97-4.06 (m, 1 H) 4.23-4.34 (m, 1 H) 4.35-4.44 (m, 1 H) 4.56-4.65 (m, 2 H) 4.84 (dd, J=8.21, 4.93 Hz, 1 H) 5.22-5.32 (m, 1 H) 5.69-5.77 (m, 1 H) 6.89 (s, 1 H) 7.09 (d, J=9.09 Hz, 1H) 7.66-7.75 (m, 1 H) 8.08-8.16 (m, 1 H)

Example 45

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate

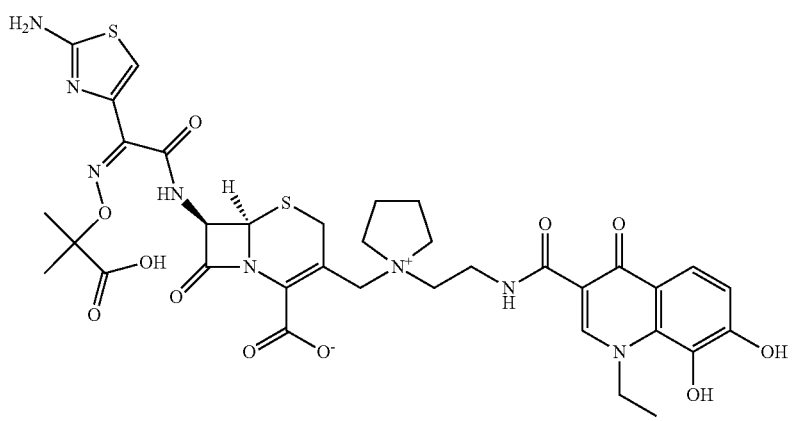 [SMILES: CCn1cc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2ccc(O)c(O)c21]

Example 45a

1-Ethyl-7,8-bis((4-methoxybenzyl)oxy)-4-oxo-N-(2-(pyrrolidin-1-yl)ethyl)-1,4-dihydroquinoline-3-carboxamide

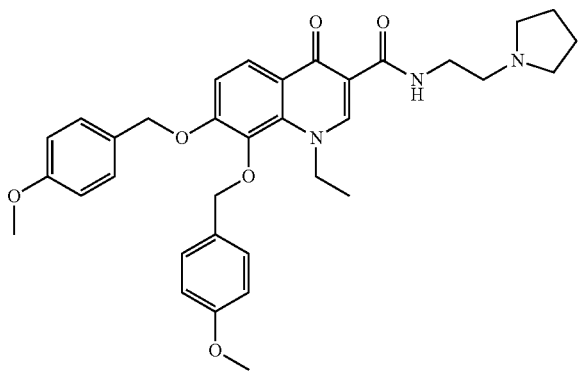 [SMILES: CCn1cc(C(=O)NCCN2CCCC2)c(=O)c2ccc(OCc3ccc(OC)cc3)c(OCc3ccc(OC)cc3)c21]

To a solution of 1-ethyl-7,8-bis((4-methoxybenzyl)oxy)-4-oxo-1,4-dihydroquinoline-3-carboxylic acid (Example 44f) (7 g, 14.30 mmol) in N,N-Dimethylformamide (DMF) (50 mL) was added HATU (8.16 g, 21.45 mmol) and DIPEA (7.49 mL, 42.9 mmol), the resulting mixture was stirred at r.t. for 30 min. 2-(Pyrrolidin-1-yl)ethanamine (2.70 mL, 21.45 mmol) was added and the resulting mixture was stirred at r.t. for 3 h. The mixture was concentrated and the residue was purified by normal phase automatic silica column chromatography (Combiflash RF), eluting with MeOH/DCM (0-30%) to afford 1-ethyl-7,8-bis((4-methoxybenzyl)oxy)-4-oxo-N-(2-(pyrrolidin-1-yl)ethyl)-1,4-dihydroquinoline-3-carboxamide (6.6 g, 11.27 mmol, 79% yield) as a pale yellow solid. LCMS: (M+H)$^+$: 586.5.

Example 45b (6R,7R)-7-(((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate

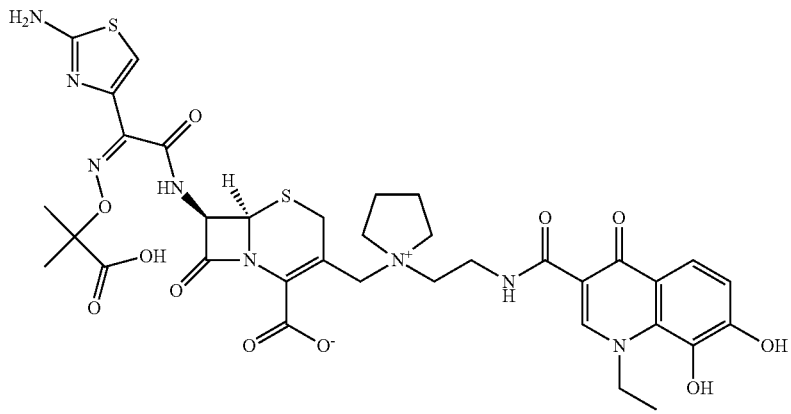 [SMILES: CCn1cc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2ccc(O)c(O)c21]

The compound was prepared according to the procedure described in Examples 19b-19c, utilizing 1-Ethyl-7,8-bis((4-methoxybenzyl)oxy)-4-oxo-N-(2-(pyrrolidin-1-yl)ethyl)-1,4-dihydroquinoline-3-carboxamide (Example 45a) in place of 5-chloro-1-ethyl-6,7-bis((4-methoxybenzyl)oxy)-3-(pyrrolidin-1-ylmethyl)quinolin-4(1H)-one in step 19b. LCMS: (M+H)$^+$: 813.4. $^1$H NMR (400 MHz, METHANOL-d4) δ ppm 1.52 (t, J=6.95 Hz, 3 H) 1.57-1.66 (m, 6 H) 2.13-2.32 (m, 4 H) 3.47-3.74 (m, 8 H) 3.84-4.21 (m, 4 H) 4.78-4.87 (m, 2 H) 5.27-5.33 (m, 1 H) 5.88-5.96 (m, 1 H) 6.86-6.93 (m, 1 H) 7.05-7.13 (m, 1 H) 7.86-7.93 (m, 1 H) 8.63-8.70 (m, 1 H)

Example 46

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt

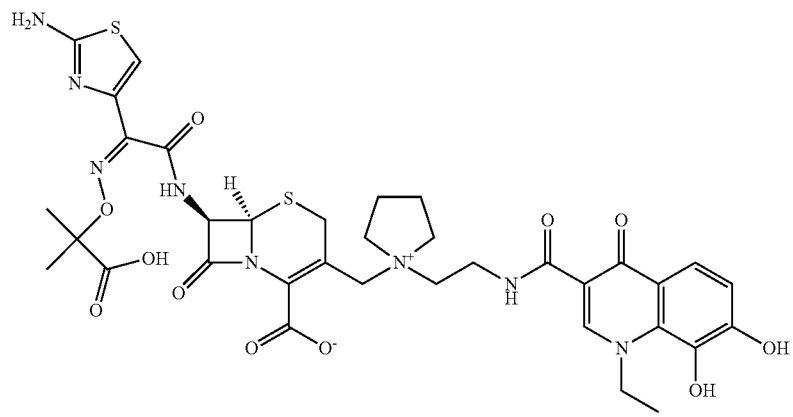 [SMILES: CCn1cc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2ccc(O)c(O)c21]

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate (Example 45b) (0.163 g, 91% pure, 0.182 mmol) was suspended in pure water (HPLC grade, 15 mL) with the help of sonication, and cooled to 0° C. With vigorous stirring, aq NaOH (1 N, 0.182 mL) was added slowly into the suspension from an Eppendorf Pipette. After the addition a small piece of dry ice was added to quench any extra NaOH. The pale yellow solution was then frozen and lyophilized to afford (6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt (0.164 g, 0.175 mmol, 96.15% yield) as a light brown solid. LCMS: (M+H)$^+$: 813.4. $^1$H NMR (400 MHz, DEUTERIUM OXIDE) δ ppm 1.21-1.42 (m, 9 H) 2.00-2.17 (m, 4 H) 3.32-3.60 (m, 8 H) 3.64-3.89 (m, 3 H) 3.98-4.09 (m, 1 H) 4.52 (d, J=7.07 Hz, 2 H) 5.22-5.29 (m, 1 H) 5.71-5.80 (m, 1 H) 6.78-6.83 (m, 1 H) 6.89-6.97 (m, 1 H) 7.47-7.54 (m, 1 H) 8.25-8.31 (m, 1 H)

Example 47

(6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, 2 Sodium salt

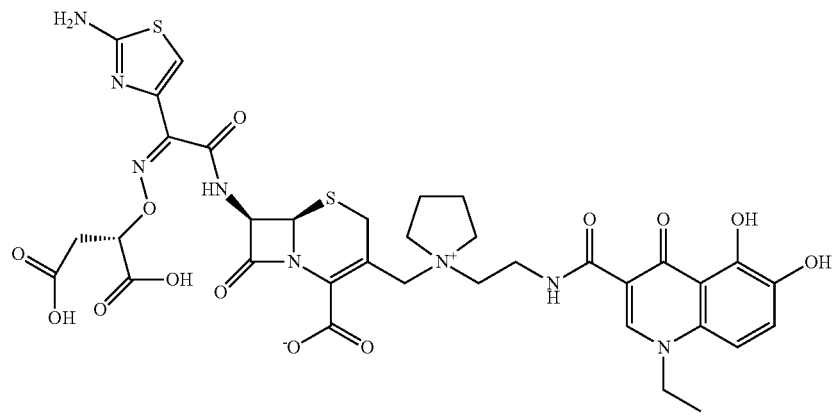

Example 47a tert-Butyl (3,4-dimethoxyphenyl)carbamate

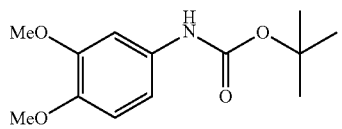 [SMILES: COc1ccc(NC(=O)OC(C)(C)C)cc1OC]

To a solution of 3,4-dimethoxyaniline (14 g, 91 mmol) in dry Tetrahydrofuran (THF) (385 mL) was added Boc$_2$O (101 mmol) in one portion. The resulting solution was refluxed for 2 h. After cooling, the solvent was evaporated and the solid residue was suspended in hexane (500 mL), and the mixture was heated to reflux. After cooling down to rt, the white solid was collected by filtration to afford tert-butyl (3,4-dimethoxyphenyl)carbamate (21 g, 81 mmol, 89% yield). LCMS: (M+H)$^+$: 254.0.

Example 47b 6-((tert-Butoxycarbonyl)amino)-2,3-dimethoxybenzoic acid

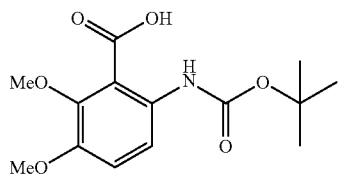 [SMILES: COc1ccc(NC(=O)OC(C)(C)C)c(C(=O)O)c1OC]

N-butyllithium (232 mL, 464 mmol) was added slowly to a solution of tert-butyl (3,4-dimethoxyphenyl)carbamate (50 g, 193 mmol) in Tetrahydrofuran (THF) (500 mL) under N$_2$ at −20° C. After being stirred for 2 h at −10° C. to −20° C., the mixture was cooled to −78° C. and diluted with Tetrahydrofuran (THF) (500 mL), followed by addition of solid carbon dioxide. The mixture was allowed to warm up to r.t. and was then partitioned between water and Et$_2$O. The aqueous layer was acidified with 6N HCl to pH 1-2 and extracted with Et$_2$O. The organic layer was separated, dried over Na$_2$SO$_4$ and evaporated. The crude product was purified by recrystallization from i-Pr$_2$O to afford 6-((tert-butoxycarbonyl)amino)-2,3-dimethoxybenzoic acid (27.9 g, 94 mmol, 48.5% yield) as a white solid. LCMS: (M+H)$^+$: 319.9.

Example 47c

6-Amino-2,3-dimethoxybenzoic acid, Hydrochloride

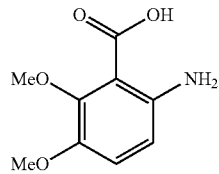 [SMILES: COc1ccc(N)c(C(=O)O)c1OC]

6-((tert-Butoxycarbonyl)amino)-2,3-dimethoxybenzoic acid (39 g, 131 mmol) was treated with HCl in dioxane (4N, 300 mL, 1200 mmol) at r.t. and the mixture was stirred at r.t. for 3 h. LCMS indicated completion of the reaction. The solid was collected by filtration, washed with ethyl ether and dried to afford 6-amino-2,3-dimethoxybenzoic acid, Hydrochloride (28.5 g, 120 mmol, 91% yield) as a white solid. LCMS: (M+H)$^+$: 198.2.

Example 47d 5,6-Dimethoxy-1H-benzo[d][1,3]oxazine-2,4-dione

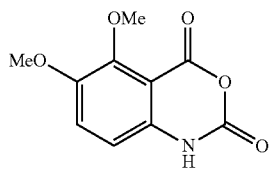

Bis(trichloromethyl) carbonate (24.89 g, 84 mmol) was added into a solution of 6-amino-2,3-dimethoxybenzoic acid, Hydrochloride (28 g, 120 mmol) in Water (1.1 L). The mixture was stirred at r.t. over the weekend. The reaction mixture was filtered, the solid was collected and dried to afford 5,6-dimethoxy-1H-benzo[d][1,3]oxazine-2,4-dione (24 g, 105 mmol, 88% yield) as a light yellow solid. LCMS: (M+H)$^+$: 223.9.

Example 47e

1-Ethyl-5,6-dimethoxy-1H-benzo[d][1,3]oxazine-2,4-dione

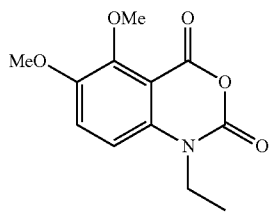

To a stirred suspension of sodium Hydride (4.64 g, 116 mmol) in N,N-Dimethyl formamide (DMF) (50 mL) in an ice bath under N$_2$ was added 5,6-dimethoxy-1H-benzo[d][1,3]oxazine-2,4-dione (22 g, 97 mmol) in N,N-Dimethylformamide (DMF) (350 mL). After stirring for 15 min at r.t., iodoethane (15.61 mL, 193 mmol) in N,N-Dimethylformamide (DMF) (50 mL) was added dropwise, and the resulting mixture was allowed to stir at r.t. overnight. The mixture was concentrated in vacuo to one-third of the original volume and then poured into ice-water (600 mL). The precipitate was collected by filtration and recrystallized from THF to afford 1-ethyl-5,6-dimethoxy-1H-benzo[d][1,3]oxazine-2,4-dione (15 g, 54.3 mmol, 56.2% yield) as a light brown pellet. LCMS: (M+H)$^+$: 252.0.

Example 47f

Ethyl 1-ethyl-5,6-dimethoxy-4-oxo-1,4-dihydro-quinoline-3-carboxylate

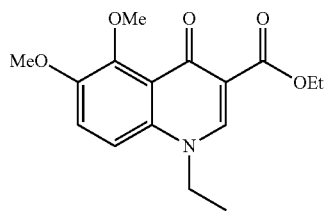 [SMILES: CCOC(=O)c1cn(CC)c2ccc(OC)c(OC)c2c1=O]

Under $N_2$, 1-ethyl-5,6-dimethoxy-1H-benzo[d][1,3]oxazine-2,4-dione (12 g, 43.5 mmol) in N,N-Dimethylformamide (DMF) (250 mL) was added to a solution of (Z)-3-ethoxy-3-oxoprop-1-en-1-olate, Sodium salt (18.01 g, 130 mmol) in N,N-Dimethylformamide (DMF) (150 mL) with stirring. The resulting solution was stirred at 110° C. for 3 h. After cooling down, the mixture was concentrated in vacuo and the orange residue was taken up in water. The aqueous solution was washed with ethyl ether (3×), acidified to pH~2 with 6 N HCl, and extracted with DCM (4×). The organic extracts were dried over $Na_2SO_4$, filtered and concentrated. The residue was purified by normal phase silica gel chromatography (CombiFlash), eluting with MeOH/DCM (0-15%) to afford ethyl 1-ethyl-5,6-dimethoxy-4-oxo-1,4-dihydroquinoline-3-carboxylate (4.5 g, 14.74 mmol, 33.9% yield) as a brown oil that turned into a brown solid after overnight. LCMS: $(M+H)^+$: 306.4.

Example 47g

Ethyl 1-ethyl-5,6-dihydroxy-4-oxo-1,4-dihydro-quinoline-3-carboxylate

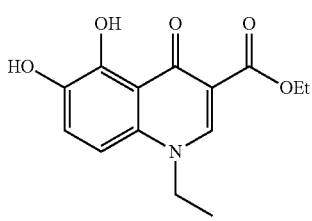 [SMILES: CCOC(=O)c1cn(CC)c2ccc(O)c(O)c2c1=O]

To a brown solution of ethyl 1-ethyl-5,6-dimethoxy-4-oxo-1,4-dihydroquinoline-3-carboxylate (6 g, 19.65 mmol) in Dichloromethane (DCM) (100 mL) was added $BBr_3$ (6.13 mL, 64.8 mmol) dropwise and the mixture was stirred at r.t. overnight. The resulting mixture was carefully poured into EtOH (50 mL) at −40° C. and the mixture was stirred at r.t. over the weekend. The precipitates were collected by filtration and washed with DCM and MeOH. The filtrate was concentrated a bit, the precipitates were collected and washed by DCM. The solids were combined to afford ethyl 1-ethyl-5,6-dihydroxy-4-oxo-1,4-dihydroquinoline-3-carboxylate (5 g, 9.02 mmol, 45.9% yield) as a yellow solid that contained also some 1-ethyl-5,6-dihydroxy-4-oxo-1,4-dihydroquinoline-3-carboxylic acid. This mixture was directly used in the next step without further purification. LCMS: $(M+H)^+$: 278.4 (ester); 250.3 (acid).

Example 47h

Ethyl 1-ethyl-5-hydroxy-6-((4-methoxybenzyl)oxy)-4-oxo-1,4-dihydro quinoline-3-carboxylate

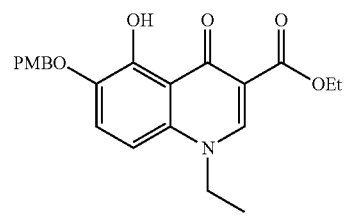

To a suspension of ethyl 1-ethyl-5,6-dihydroxy-4-oxo-1,4-dihydroquinoline-3-carboxylate (5 g, 18.03 mmol) and potassium carbonate (8.72 g, 63.1 mmol) in Acetone (120 mL) at r.t. was added 4-methoxybenzyl chloride (7.37 mL, 54.1 mmol) and KI (0.599 g, 3.61 mmol). The mixture was heated under reflux for 2 days. After cooling, the reaction mixture was filtered and the filtrate was concentrated. The residue was partitioned between DCM and water, and the organic layer was washed with sat. $NaHCO_3$ and brine, dried over $Na_2SO_4$ and concentrated. The crude product was purified by normal phase automatic silica column chromatography (Combiflash RF), eluting with EtOAc/hexanes (0-100%) to afford ethyl 1-ethyl-5-hydroxy-6-((4-methoxybenzyl)oxy)-4-oxo-1,4-dihydroquinoline-3-carboxylate (1.5 g, 3.77 mmol, 20.9% yield) as a light yellow solid that contained some PMB-ester. LCMS: $(M+H)^+$: 398.3.

Example 47i

1-Ethyl-5-hydroxy-6-((4-methoxybenzyl)oxy)-4-oxo-1,4-dihydroquinoline-3-carboxylic acid

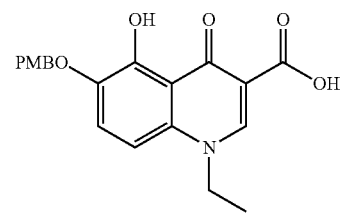

To a suspension of ethyl 1-ethyl-5-hydroxy-6-((4-methoxybenzyl)oxy)-4-oxo-1,4-dihydroquinoline-3-carboxylate (1.5 g, 3.77 mmol) in a mixture of Methanol (60.0 mL) and Water (20 mL) was added KOH (0.424 g, 7.55 mmol) portionwise. The resulting mixture was stirred under reflux for 1 h. The mixture was cooled down to r.t. and concentrated. Water was added and the mixture was adjusted to pH~2 using 6 N HCl (aq.). The precipitates were collected by filtration and dried in air to afford 1-ethyl-5-hydroxy-6-((4-methoxybenzyl)oxy)-4-oxo-1,4-dihydroquinoline-3-carboxylic acid (1.35 g, 3.65 mmol, 97% yield) as a light yellow solid. LCMS: (M+H)$^+$: 370.2.

Example 47j

1-Ethyl-5-hydroxy-6-((4-methoxybenzyl)oxy)-4-oxo-N-(2-(pyrrolidin-1-yl)ethyl)-1,4-dihydroquinoline-3-carboxamide

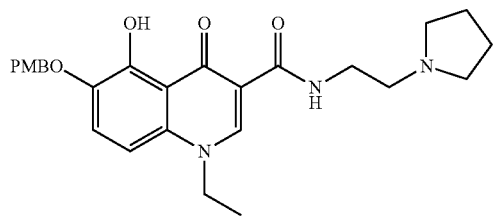

To a solution of 1-ethyl-5-hydroxy-6-((4-methoxybenzyl)oxy)-4-oxo-1,4-dihydroquinoline-3-carboxylic acid (1.4 g, 3.79 mmol) in N,N-Dimethylformamide (DMF) (30 mL) was added HATU (1.729 g, 4.55 mmol) and DIPEA (1.655 mL, 9.48 mmol), the resulting mixture was stirred at r.t. for 30 min. Then 2-(pyrrolidin-1-yl)ethanamine (0.656 mL, 4.17 mmol) was added and the resulting mixture was stirred at r.t. for 3 h. The reaction mixture was concentrated and the residue was dissolved in DCM and washed with water, sat. NaHCO$_3$ (aq.) and brine. The organic layer was separated and concentrated, the residue was purified by normal phase silica gel chromatography (CombiFlash), eluting with MeOH/DCM (0-20%) to afford 1-ethyl-5-hydroxy-6-((4-methoxybenzyl)oxy)-4-oxo-N-(2-(pyrrolidin-1-yl)ethyl)-1,4-dihydroquinoline-3-carboxamide (1 g, 2.148 mmol, 56.7% yield) as a yellow solid. LCMS: (M+H)$^+$: 466.3.

Example 47k (6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, 2 Sodium salt (6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate was prepared as a slightly brown solid according to the procedure described in Examples 16k-16l, utilizing 1-Ethyl-5-hydroxy-6-((4-methoxybenzyl)oxy)-4-oxo-N-(2-(pyrrolidin-1-yl)ethyl)-1,4-dihydroquinoline-3-carboxamide (Example 44j) in place of 5-chloro-1-ethyl-6,7-bis((4-methoxybenzyl)oxy)-3-(pyrrolidin-1-ylmethyl)quinolin-4(1H)-one in step 16k. This product (0.19 g, 0.225 mmol) was suspended in pure water (HPLC grade, 20 mL) with the help of sonication, and cooled to 0° C. With vigorous stirring, aq NaOH (0.2 N, 2.15 mL, 0.43 mmol) was added slowly into the suspension from an Eppendorf Pipette. After the addition a small piece of dry ice was added to quench any extra NaOH. The mixture was then frozen and lyophilized to afford (6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, 2 Sodium salt (0.19 g, 0.192 mmol) as a slightly brown solid. LCMS: (M+H)$^+$: 843.4. $^1$H NMR (400 MHz, DEUTERIUM OXIDE) δ ppm 1.29 (t, J=7.20 Hz, 3 H) 2.05-2.22 (m, 4 H) 2.56-2.64 (m, 2 H) 3.41-3.61 (m, 6 H) 3.63-4.09 (m, 6 H) 4.83-4.90 (m, 1 H) 5.23-5.29 (m, 1 H) 5.71-5.78 (m, 1 H) 6.77-6.83 (m, 1 H) 6.86 (s, 1 H) 7.03-7.12 (m, 1 H) 8.24-8.32 (m, 1 H)

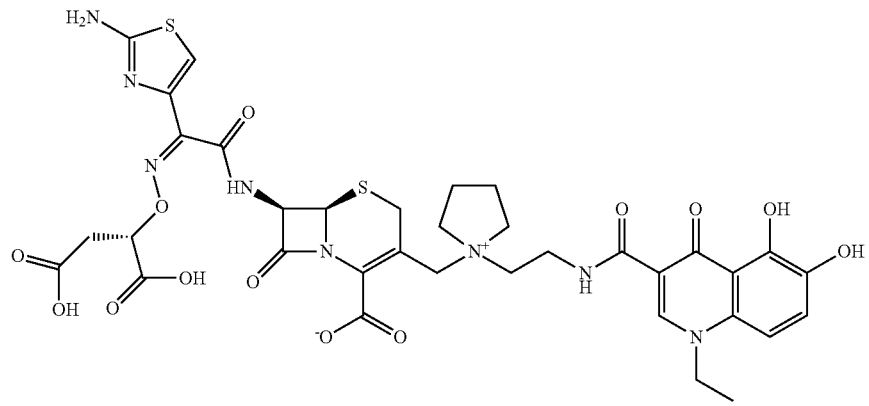

Example 48

(6R,7R)-7-((Z)-2-(2-aminothiazol-4-yl)-2-(((S)-1,2-dicarboxyethoxy)imino)acetamido)-3-((1-((1-(tert-butyl)-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

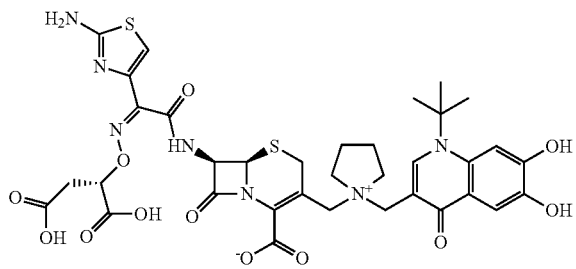

Example 48a

Ethyl 3-(dimethylamino)-2-(2,4,5-trifluorobenzoyl)acrylate

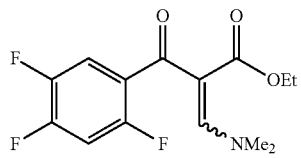

To a solution of triethylamine (107 mL, 771 mmol) and ethyl 3-(dimethylamino)acrylate (55.2 mL, 386 mmol) in toluene (250 mL) was added dropwise a toluene solution of 2,4,5-trifluorobenzoyl chloride (50 g, 257 mmol). The mixture was stirred at 90° C. for 3 h. LCMS showed completion of reaction. After cooling down, the reaction mixture was washed with water and extracted with EA. The organic layer was dried over $Na_2SO_4$, filtered and concentrated to afford ethyl 3-(dimethylamino)-2-(2,4,5-trifluorobenzoyl)acrylate (65 g, 216 mmol, 84% yield) as a brown oil. LCMS: $(M+H)^+$: 302.1.

Example 48b

Ethyl 1-(tert-butyl)-6,7-difluoro-4-oxo-1,4-dihydroquinoline-3-carboxylate

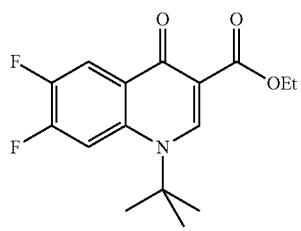 [SMILES: CCOC(=O)c1cn(C(C)(C)C)c2cc(F)c(F)cc2c1=O]

To a solution of ethyl 3-(dimethylamino)-2-(2,4,5-trifluorobenzoyl)acrylate (64 g, 212 mmol) in a mixed solvent of Ethanol (150 mL)/Diethyl ether (300 mL) was added tert-Butylamine (44.6 mL, 425 mmol), and the reaction mixture was stirred at rt for 2 h. The mixture was concentrated under reduced pressure, the resulting oily residue was dissolved in N,N-Dimethylformamide (DMF) (250 mL) and potassium carbonate (88 g, 637 mmol) was added. LCMS showed completion of the reaction after being stirred at 100° C. for 2 h. Cold water was added to the mixture, and the precipitates were collected by filtration and dried to afford ethyl 1-(tert-butyl)-6,7-difluoro-4-oxo-1,4-dihydroquinoline-3-carboxylate (60 g, 194 mmol, 91% yield) as pale yellow solid. LCMS: $(M+H)^+$: 310.1

Example 48c 1-(tert-Butyl)-6,7-bis((4-methoxybenzyl)oxy)-4-oxo-1,4-dihydroquinoline-3-carboxylic acid

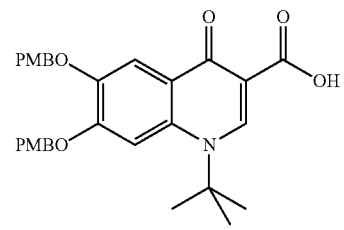

A mixture of ethyl 1-(tert-butyl)-6,7-difluoro-4-oxo-1,4-dihydroquinoline-3-carboxylate (50 g, 162 mmol), KOH (136 g, 2425 mmol) and 4-methoxybenzyl alcohol (201 ml, 1617 mmol) was heated at 80° C. under $N_2$ for 8 h. LCMS showed completion of reaction. The solution was adjusted to pH 2, extracted with EA and washed with water. The organic phase was concentrated in vacuo and the crude product was triturated in $Et_2O$ to afford 1-(tert-butyl)-6,7-bis((4-methoxybenzyl)oxy)-4-oxo-1,4-dihydroquinoline-3-carboxylic acid (61 g, 118 mmol, 72.9% yield) as pale yellow solid. LCMS: $(M+H)^+$: 518.3.

Example 48d 1-(tert-Butyl)-6,7-bis((4-methoxybenzyl)oxy)-3-(pyrrolidin-1-ylmethyl) quinolin-4(1H)-one

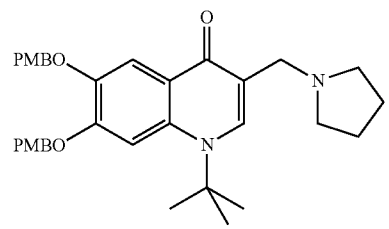

This compound was prepared according to the procedure described in Examples 44g-44i, utilizing 1-(tert-butyl)-6,7-bis((4-methoxybenzyl)oxy)-4-oxo-1,4-dihydroquinoline-3-carboxylic acid (Example 48c) in place of 1-ethyl-7,8-bis((4- methoxybenzyl)oxy)-4-oxo-1,4-dihydroquinoline-3-carboxylic acid in step 44g. LCMS: (M+H)+: 557.4.

Example 48e (6R,7R)-7-((Z)-2-(2-aminothiazol-4-yl)-2-(((S)-1,2-dicarboxyethoxy)imino)acetamido)-3-((1-((1-(tert-butyl)-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

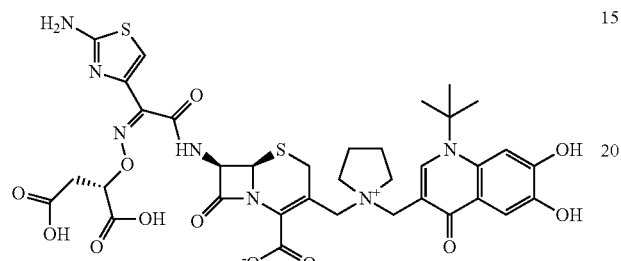

The compound was prepared according to the procedure described in Examples 16k-16l and 17, utilizing 1-(tert-butyl)-6,7-bis((4-methoxybenzyl)oxy)-3-(pyrrolidin-1-ylmethyl)quinolin-4(1H)-one (Example 48d) in place of 5-chloro-1-ethyl-6,7-bis((4-methoxybenzyl)oxy)-3-(pyrrolidin-1-ylmethyl)quinolin-4(1H)-one in step 16k. LCMS: (M+H)+: 814.3. $^1$H NMR (400 MHz, DEUTERIUM OXIDE) δ ppm 1.69-1.78 (m, 9 H) 1.95-2.11 (m, 4 H) 2.75 (s, 2 H) 3.22-3.47 (m, 6 H) 3.84-3.93 (m, 1 H) 3.95-4.05 (m, 1 H) 4.30-4.45 (m, 2 H) 4.84-4.91 (m, 1 H) 5.24-5.31 (m, 1 H) 5.71 (d, J=4.80 Hz, 1 H) 6.90 (s, 1 H) 7.51 (s, 1 H) 7.54 (s, 1 H) 8.22

Example 49

(6R,7R)-7-((Z)-2-(2-aminothiazol-4-yl)-2-(((S)-1,2-dicarboxyethoxy)imino)acetamido)-3-((1-(2-(1-(tert-butyl)-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt

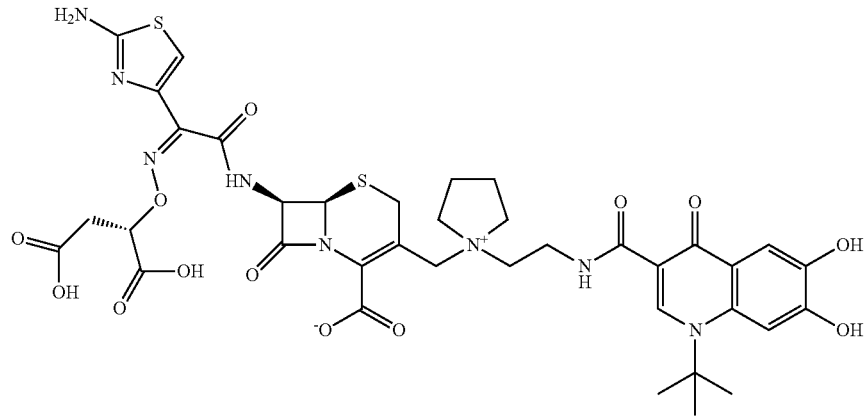

Example 49a 1-(tert-Butyl)-6,7-bis((4-methoxybenzyl)oxy)-4-oxo-N-(2-(pyrrolidin-1-yl)ethyl)-1,4-dihydroquinoline-3-carboxamide

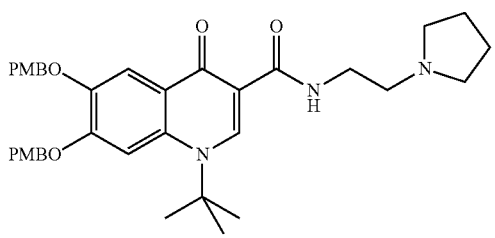

This compound was prepared according to the procedures described in Example 45a, utilizing 1-(tert-butyl)-6,7-bis((4-methoxybenzyl)oxy)-4-oxo-1,4-dihydroquinoline-3-carboxylic acid (Example 48c) in place of 1-ethyl-7,8-bis((4-methoxybenzyl)oxy)-4-oxo-1,4-dihydroquinoline-3-carboxylic acid. LCMS: (M+H)+: 614.5.

Example 49b (6R,7R)-7-(((Z)-2-(2-aminothiazol-4-yl)-2-(((S)-1,2-dicarboxyethoxy)imino)acetamido)-3-((1-(2-(1-(tert-butyl)-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt

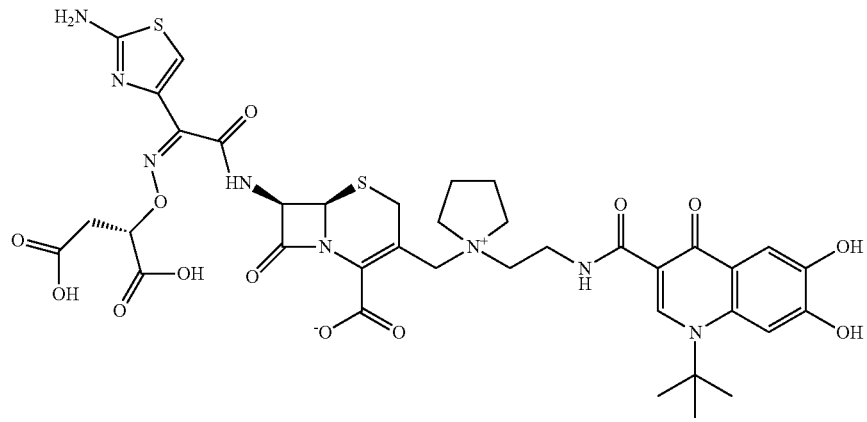

The compound was prepared according to the procedure described in Examples 16k-16l and 17, utilizing 1-(tert-butyl)-6,7-bis((4-methoxybenzyl)oxy)-4-oxo-N-(2-(pyrrolidin-1-yl)ethyl)-1,4-dihydroquinoline-3-carboxamide (Example 49a) in place of 5-chloro-1-ethyl-6,7-bis((4-methoxybenzyl)oxy)-3-(pyrrolidin-1-ylmethyl)quinolin-4(1H)-one in step 16k. LCMS: (M+H)$^+$: 871.4. $^1$H NMR (400 MHz, DEUTERIUM OXIDE) δ ppm 1.8 (s, 9 H) 2.03-2.21 (m, 4 H) 2.58-2.67 (m, 2 H) 3.34-3.60 (m, 7 H) 3.64-3.76 (m, 2 H) 3.78-3.90 (m, 2 H) 4.06 (d, J=14.15 Hz, 1 H) 4.78-4.87 (m, 1 H) 5.23 (d, J=5.05 Hz, 1 H) 5.71 (d, J=4.80 Hz, 1 H) 6.83 (s, 1 H) 7.39 (s, 1 H) 7.42-7.46 (m, 1 H) 8.67-8.74 (m, 1 H)

Example 50

(6R,7R)-7-(((Z)-2-(2-aminothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

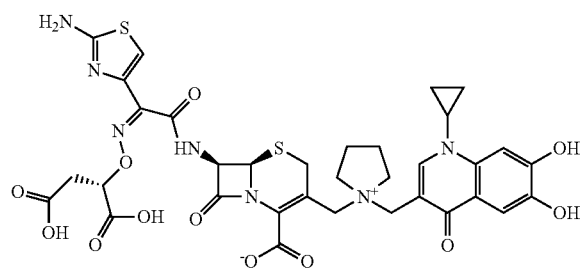

Example 50a

Ethyl 1-cyclopropyl-6,7-difluoro-4-oxo-1,4-dihydroquinoline-3-carboxylate

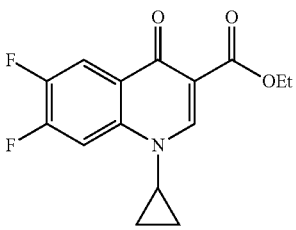 [SMILES: CCOC(=O)c1cn(C2CC2)c2cc(F)c(F)cc2c1=O]

A solution of ethyl 3-(dimethylamino)-2-(2,4,5-trifluorobenzoyl)acrylate (Example 48a) (75 g, 249 mmol) in a mixture of Ethanol (100 mL)/Diethyl ether (200 mL) was added to cyclopropanamine (34.5 mL, 498 mmol). After 2 h of stirring at rt, LCMS showed complete disappearance of starting material. The reaction mixture was evaporated under reduced pressure, the oily residue was dissolved in N,N-Dimethylformamide (DMF) (250 mL) and potassium carbonate (103 g, 747 mmol) was then added. The reaction mixture was stirred at 100° C. for 2 h, and LCMS showed completion of reaction. Cold water was added to the mixture. The precipitates were collected by filtration and dried to afford ethyl

235

1-cyclopropyl-6,7-difluoro-4-oxo-1,4-dihydroquinoline-3-carboxylate (71 g, 242 mmol, 97% yield) as a pale yellow solid. LCMS: [M+H]⁺: 294.1.

Example 50b

1-Cyclopropyl-6,7-dimethoxy-4-oxo-1,4-dihydroquinoline-3-carboxylic acid

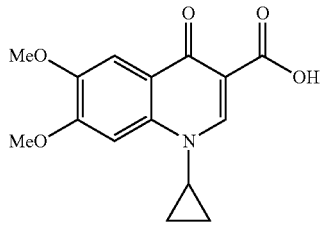 [SMILES: COc1cc2c(=O)c(C(=O)O)cn(C3CC3)c2cc1OC]

A mixture of ethyl 1-cyclopropyl-6,7-difluoro-4-oxo-1,4-dihydroquinoline-3-carboxylate (29 g, 99 mmol), KOH (83 g, 1483 mmol) and MeOH (400 ml, 9887 mmol) was heated at 130° C. under N$_2$ for 48 h. LCMS showed completion of reaction. The solution was adjusted to pH 2, concentrated in vacuo and washed with water to afford 1-cyclopropyl-6,7-dimethoxy-4-oxo-1,4-dihydroquinoline-3-carboxylic acid (20 g, 69.1 mmol, 69.9% yield) as pale yellow solid. The crude product was used in next step without further purification. LCMS: [M+H]⁺: 290.1.

Example 50c 1-cyclopropyl-6,7-dihydroxy-4-oxo-1,4-dihydroquinoline-3-carboxylic acid

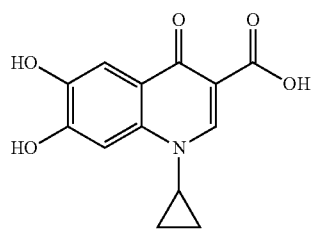 [SMILES: O=C(O)c1cn(C2CC2)c2cc(O)c(O)cc2c1=O]

To a solution of 1-cyclopropyl-6,7-dimethoxy-4-oxo-1,4-dihydroquinoline-3-carboxylic acid (10 g, 34.6 mmol) in Dichloromethane (DCM) (150 mL) was added BBr$_3$ (16.34 mL, 173 mmol) at −78° C. The mixture was allowed to warm up to rt, and stirred at rt overnight. LCMS indicated completion of the reaction. The mixture was diluted with MeOH and concentrated. This procedure was repeated several times to afford 1-cyclopropyl-6,7-dihydroxy-4-oxo-1,4-dihydroquinoline-3-carboxylic acid (8.2 g, 31.4 mmol, 91% yield) as yellow solid. The crude product was used in next step reaction without further purification.

LCMS: [M+H]⁺: 262.1.

236

Example 50d

4-Methoxybenzyl 1-cyclopropyl-6,7-bis((4-methoxybenzyl)oxy)-4-oxo-1,4-dihydroquinoline-3-carboxylate

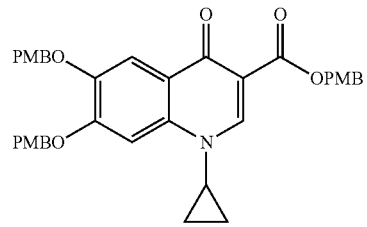

To a solution of 1-cyclopropyl-6,7-dihydroxy-4-oxo-1,4-dihydroquinoline-3-carboxylic acid (8.2 g, 31.4 mmol) in N,N-Dimethylformamide (DMF) (150 mL) was added potassium carbonate (21.69 g, 157 mmol), followed by 1-(chloromethyl)-4-methoxybenzene (17.04 mL, 126 mmol). The reaction mixture was stirred at 50° C. overnight. LCMS indicated completion of the reaction. Water was added and the mixture was stirred at r.t for 15 mins. The yellow precipitates were collected by filtration and washed with water to afford 4-methoxybenzyl 1-cyclopropyl-6,7-bis((4-methoxybenzyl)oxy)-4-oxo-1,4-dihydroquinoline-3-carboxylate (14 g, 22.52 mmol, 71.7% yield) as a yellow solid that contained 1-cyclopropyl-6,7-bis((4-methoxybenzyl)oxy)-4-oxo-1,4-dihydroquinoline-3-carboxylic acid (Example 50e). The crude mixture was used in next step without purification.

Example 50e

1-Cyclopropyl-6,7-bis((4-methoxybenzyl)oxy)-4-oxo-1,4-dihydroquinoline-3-carboxylic acid

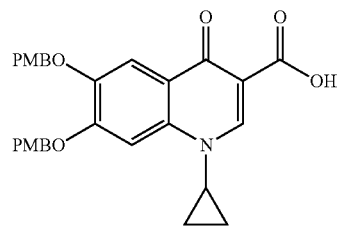

To a suspension of 4-methoxybenzyl 1-cyclopropyl-6,7-bis((4-methoxybenzyl)oxy)-4-oxo-1,4-dihydroquinoline-3-carboxylate (14 g, 22.52 mmol) in a mixture of Methanol (100 mL) and Water (50.0 mL) was added KOH (2.53 g, 45.0 mmol) portionwise. The resulting mixture was stirred at 90° C. for 2 h. LCMS indicated completion of the reaction. The reaction mixture was cooled down to r.t. and concentrated, and was then diluted with water and adjusted pH to 1 using 2 N HCl (aq.). The precipitates were collected by filtration and dried to afford 1-cyclopropyl-6,7-bis((4-methoxybenzyl)

oxy)-4-oxo-1,4-dihydroquinoline-3-carboxylic acid (11 g, 21.93 mmol, 97% yield) as pale yellow solid. LCMS: [M+H]⁺: 502.3.

Example 50f

1-Cyclopropyl-6,7-bis((4-methoxybenzyl)oxy)-3-(pyrrolidin-1-ylmethyl) quinolin-4(1H)-one

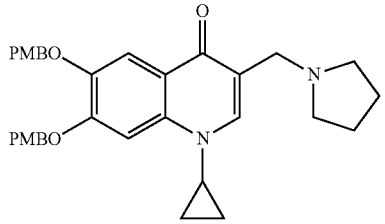

This compound was prepared according to the procedures described in Examples 44g-44i, utilizing 1-Cyclopropyl-6,7-bis((4-methoxybenzyl)oxy)-4-oxo-1,4-dihydroquinoline-3-carboxylic acid (Example 50e) in place of 1-ethyl-7,8-bis((4-methoxybenzyl)oxy)-4-oxo-1,4-dihydroquinoline-3-carboxylic acid in step 44g. LCMS: (M+H)⁺: 541.4.

Example 50g (6R,7R)-7-((Z)-2-(2-aminothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

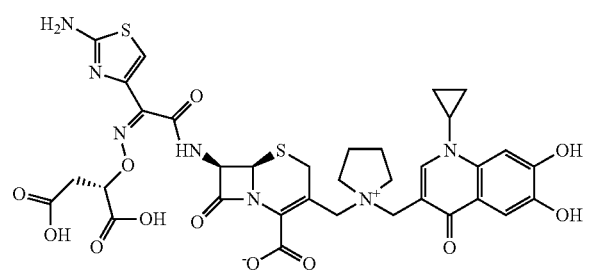

The compound was prepared according to the procedure described in Examples 16k-16l and 17, utilizing 1-cyclopropyl-6,7-bis((4-methoxybenzyl)oxy)-3-(pyrrolidin-1-ylmethyl)quinolin-4(1H)-one (Example 50f) in place of 5-chloro-1-ethyl-6,7-bis((4-methoxybenzyl)oxy)-3-(pyrrolidin-1-ylmethyl)quinolin-4(1H)-one in step 16k. LCMS: (M+H)⁺: 798.3. ¹H NMR (400 MHz, DEUTERIUM OXIDE) δ ppm 0.93-1.06 (m, 2 H) 1.15-1.29 (m, 2 H) 1.93-2.10 (m, 4 H) 2.65-2.76 (m, 2 H) 3.23-3.57 (m, 6 H) 3.83-3.95 (m, 1 H) 3.96-4.08 (m, 1 H) 4.24-4.43 (m, 2 H) 4.62-4.67 (m, 1 H) 4.83-4.91 (m, 1 H) 5.23-5.33 (m, 1 H) 5.69-5.77 (m, 1 H) 6.92 (s, 1 H) 7.43-7.47 (m, 1 H) 7.48-7.53 (m, 1 H) 8.17-8.24 (m, 1 H)

Example 51

(6R,7R)-7-((Z)-2-(2-amino-5-chlorothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl) methyl)pyrrolidin-1-ium-1-yl)methyl)-8-oxo-5-thia-1-azabicyclo[4.2.0]oct-2-ene-2-carboxylate, Sodium salt

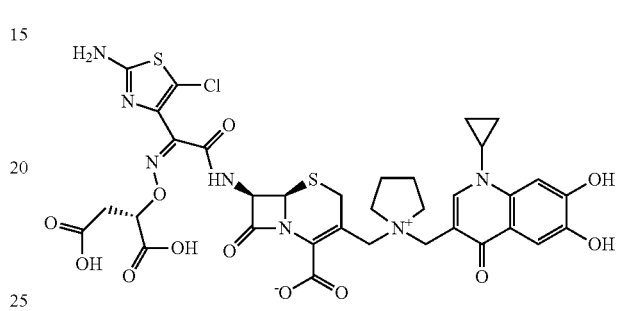

The compound was prepared according to the procedure described in Examples 21l-21m, utilizing 1-cyclopropyl-6,7-bis((4-methoxybenzyl)oxy)-3-(pyrrolidin-1-ylmethyl) quinolin-4(1H)-one (Example 50f) in place of 5-chloro-1-ethyl-6,7-bis((4-methoxybenzyl)oxy)-3-(pyrrolidin-1-ylmethyl)quinolin-4(1H)-one in step 21l. LCMS: (M+H)⁺: 832.0. ¹H NMR (400 MHz, DEUTERIUM OXIDE) δ ppm 0.89-1.04 (m, 2 H) 1.11-1.25 (m, 2 H) 1.88-2.09 (m, 4 H) 2.75 (s, 2 H) 3.25-3.50 (m, 6 H) 3.82-3.92 (m, 1 H) 3.94-4.04 (m, 1 H) 4.20-4.39 (m, 2 H) 4.61-4.67 (m, 1 H) 4.82-4.92 (m, 1 H) 5.21-5.30 (m, 1 H) 5.66-5.75 (m, 1 H) 7.33 (s, 1 H) 7.35-7.42 (m, 1 H) 8.07-8.16 (m, 1 H).

Example 52

(6R,7R)-7-((Z)-2-(2-amino-5-chlorothiazol-4-yl)-2-(((2-carboxypropan-2-yl)oxy)imino)acetamido)-3-((1-((1-cyclopropyl-6,7-dihydroxy-4-oxo-1,4-dihydroquinolin-3-yl)methyl)pyrrolidin-1-ium-1-yl) methyl)-8-oxo-5-thia-1-azabicyclo[4.2.0]oct-2-ene-2-carboxylate, Sodium salt

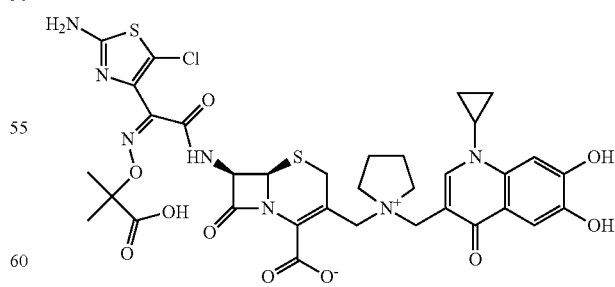

The compound was prepared according to the two-step sequence of Examples 22f-22g, utilizing 1-cyclopropyl-6,7-bis((4-methoxybenzyl)oxy)-3-(pyrrolidin-1-ylmethyl) quinolin-4(1H)-one (Example 50f) in place of 5-chloro-1-ethyl-6,7-bis((4-methoxybenzyl)oxy)-3-(pyrrolidin-1- ylmethyl)quinolin-4(1H)-one in step 22f. LCMS: (M+H)+: 801.9.1H NMR (400 MHz, DEUTERIUM OXIDE) δ ppm 0.90-1.03 (m, 2 H) 1.13-1.26 (m, 2 H) 1.39 (d, J=6.57 Hz, 6 H) 1.88-2.09 (m, 4 H) 3.21-3.52 (m, 6 H) 3.85-4.04 (m, 2 H) 4.20-4.40 (m, 2 H) 4.62-4.68 (m, 1 H) 5.24-5.34 (m, 1 H) 5.77 (d, J=5.05 Hz, 1 H) 7.35 (s, 2 H) 8.12 (s, 1 H).

Example 53

(6R,7R)-7-((Z)-2-(2-aminothiazol-4-yl)-2-(((S)-1,2-dicarboxyethoxy)imino)acetamido)-3-((1-(2-(1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, 2 Sodium salt

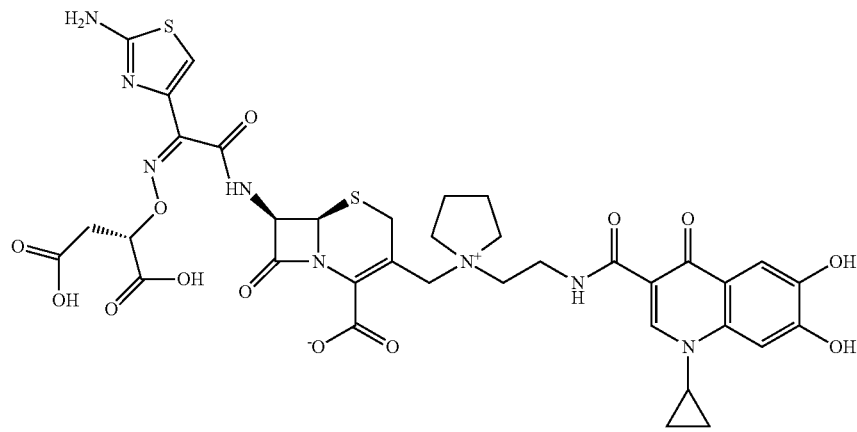

Example 53a

1-Cyclopropyl-6,7-bis((4-methoxybenzyl)oxy)-4-oxo-N-(2-(pyrrolidin-1-yl)ethyl)-1,4-dihydroquinoline-3-carboxamide

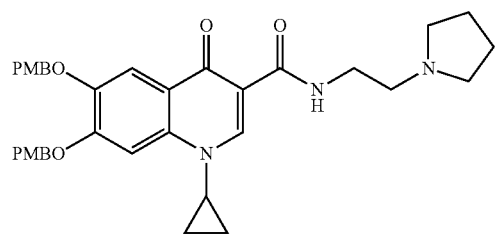

This compound was prepared according to the procedures described in Example 45a, utilizing 1-Cyclopropyl-6,7-bis((4-methoxybenzyl)oxy)-4-oxo-1,4-dihydroquinoline-3-carboxylic acid (Example 50e) in place of 1-ethyl-7,8-bis((4-methoxybenzyl)oxy)-4-oxo-1,4-dihydroquinoline-3-carboxylic acid. LCMS: (M+H)+: 598.4.

Example 53b (6R,7R)-7-(((Z)-2-(2-aminothiazol-4-yl)-2-(((S)-1,2-dicarboxyethoxy)imino)acetamido)-3-((1-(2-(1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate 2 Sodium salt

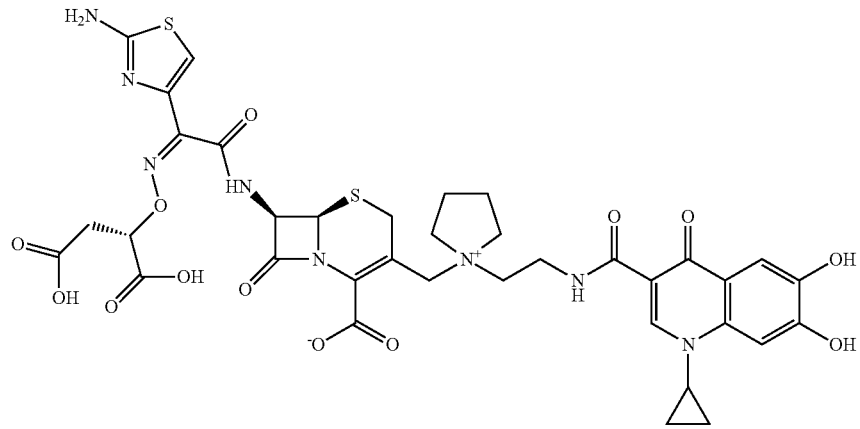

This compound was prepared according to the procedures described in Example 47k, utilizing 1-cyclopropyl-6,7-bis((4-methoxybenzyl)oxy)-4-oxo-N-(2-(pyrrolidin-1-yl)ethyl)-1,4-dihydro quinoline-3-carboxamide (Example 53a) in place of 1-Ethyl-5-hydroxy-6-((4-methoxy benzyl)oxy)-4-oxo-N-(2-(pyrrolidin-1-yl)ethyl)-1,4-dihydroquinoline-3 amide. LCMS: (M+H)⁺: 855.4. ¹H NMR (400 MHz, DEUTERIUM OXIDE) δ ppm 0.95 (d, J=3.03 Hz, 2 H) 1.14-1.26 (m, 2 H) 2.13 (d, J=3.03 Hz, 4 H) 2.55-2.66 (m, 2 H) 3.30-3.61 (m, 8 H) 3.63-3.76 (m, 2 H) 3.77-3.90 (m, 2 H) 4.03-4.14 (m, 1 H) 4.82-4.89 (m, 1 H) 5.23-5.29 (m, 1 H) 5.75 (d, J=4.80 Hz, 1 H) 6.83 (s, 1 H) 7.14-7.23 (m, 2 H) 8.27-8.33 (m, 1 H)

Example 54

(6R,7R)-7-((Z)-2-(2-aminothiazol-4-yl)-2-(((S)-1,2-dicarboxyethoxy)imino) acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

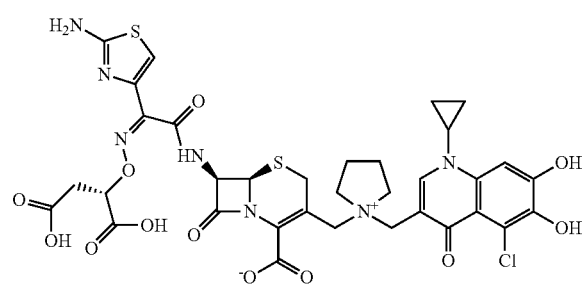

Example 54a

1-Cyclopropyl-6,7-dimethoxy-5-nitro-4-oxo-1,4-dihydroquinoline-3-carboxylic acid

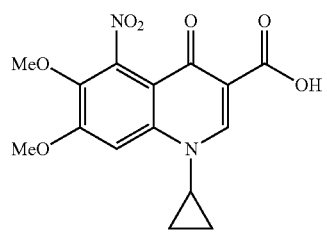

1-Cyclopropyl-6,7-dimethoxy-4-oxo-1,4-dihydroquinoline-3-carboxylic acid (Example 50b) (20 g, 69.1 mmol) was dissolved in sulfuric acid (44.2 ml, 830 mmol) with stirring. The thick dark solution was cooled to 0° C. and potassium nitrate (10.48 g, 104 mmol) was added in small portions, while the temperature was maintained below 10° C. by use of an ice-water bath. After the addition, the mixture was kept under 10° C. for 1 h, and then was allowed to warm up to r.t. and stirred overnight. LCMS showed completion of reaction. The mixture was poured into ice-water (300 mL). A yellow solid precipitated out and was collected by filtration, washed with water and ethanol, and dried in vacuo to afford 1-cyclopropyl-6,7-dimethoxy-5-nitro-4-oxo-1,4-dihydroquinoline- 3-carboxylic acid (14 g, 41.9 mmol, 60.6% yield) as a pale yellow solid. LCMS: [M+H]+: 335.1.

Example 54b

1-Cyclopropyl-6,7-dimethoxy-5-nitro-4-oxo-1,4-dihydroquinoline-3-carboxylic acid

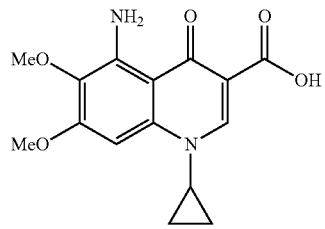 [SMILES: COc1cc2c(c([N+](=O)[O-])c1OC)c(=O)c(C(=O)O)cn2C1CC1]

Under N2, 1-cyclopropyl-6,7-dimethoxy-5-nitro-4-oxo-1,4-dihydroquinoline-3-carboxylic acid (10 g, 29.9 mmol) was treated with sodium sulfide nonahydrate (71.9 g, 299 mmol) in a mixture of Ethanol (100 mL) and Water (100 mL) for 2 h at 100° C. LCMS showed completion of reaction. After cooling down, the mixture was poured into cold water and the solution was adjusted to pH 2. The yellow precipitate was collected by filtration, washed with water and dried to afford 5-amino-1-cyclopropyl-6,7-dimethoxy-4-oxo-1,4-dihydroquinoline-3-carboxylic acid (8.9 g, 29.2 mmol, 98% yield) as a yellow solid.

LCMS: [M+H]+: 305.1.

Example 54c

5-Chloro-1-cyclopropyl-6-hydroxy-7-methoxy-4-oxo-1,4-dihydroquinoline-3-carboxylic acid

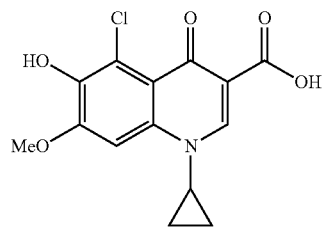 [SMILES: COc1cc2c(c(Cl)c1O)c(=O)c(C(=O)O)cn2C1CC1]

To a pale brown suspension of 5-amino-1-cyclopropyl-6,7-dimethoxy-4-oxo-1,4-dihydroquinoline-3-carboxylic acid (9 g, 29.6 mmol) in con. HCl (60 mL) stirred at 0° C. was added dropwise a cold solution of sodium nitrite (2.143 g, 31.1 mmol) in Water (20.00 mL). Stirring continued at 0° C. for 1 h. LCMS indicated completion of reaction. HCl (80 mL, 2633 mmol) was added and the mixture was heated at 95° C. for 6 h. LCMS indicated completion of reaction. The reaction mixture was cooled down to rt and then poured into water. The precipitates were collected by filtration and dried to afford 5-chloro-1-cyclopropyl-6-hydroxy-7-methoxy-4-oxo-1,4-dihydroquinoline-3-carboxylic acid (7.4 g, 23.89 mmol, 81% yield) as a pale yellow solid. LCMS: [M+H]+: 310.1.

Example 54d

5-Chloro-1-cyclopropyl-6,7-dihydroxy-4-oxo-1,4-dihydroquinoline-3-carboxylic acid

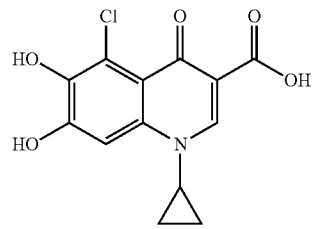 [SMILES: O=C(O)c1cn(C2CC2)c2cc(O)c(O)c(Cl)c2c1=O]

To a solution of 5-chloro-1-cyclopropyl-6-hydroxy-7-methoxy-4-oxo-1,4-dihydroquinoline-3-carboxylic acid (8.5 g, 27.4 mmol) in Dichloromethane (DCM) (100 mL) was added BBr3 (6.49 mL, 68.6 mmol) at −78° C. The mixture was allowed to warm up to rt. and stirred at rt overnight. LCMS indicated completion of the reaction. The mixture was diluted with MeOH and concentrated to dryness. This procedure was repeated several times to afford 5-chloro-1-cyclopropyl-6,7-dihydroxy-4-oxo-1,4-dihydroquinoline-3-carboxylic acid (7.8 g, 26.4 mmol, 96% yield) as yellow solid. LCMS: [M+H]+: 296.1.

Example 54e

4-Methoxybenzyl 5-chloro-1-cyclopropyl-6,7-bis((4-methoxybenzyl)oxy)-4-oxo-1,4-dihydroquinoline-3-carboxylate

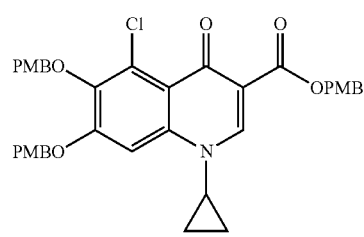

To a solution of 5-chloro-1-cyclopropyl-6,7-dihydroxy-4-oxo-1,4-dihydroquinoline-3-carboxylic acid (11 g, 37.2 mmol) in N,N-Dimethylformamide (DMF) (120 mL) was added potassium carbonate (25.7 g, 186 mmol), followed by 1-(chloromethyl)-4-methoxybenzene (20.20 mL, 149 mmol). The reaction mixture was stirred at 50° C. for 5 h. LCMS indicated completion of the reaction. Water was added and the mixture was stirred at r.t for 15 mins. The yellow precipitates were collected by filtration and washed with water to afford 4-methoxybenzyl 5-chloro-1-cyclopropyl-6, 7-bis((4-methoxy benzyl)oxy)-4-oxo-1,4-dihydroquinoline-3-carboxylate (20 g, 30.5 mmol, 82% yield) as a yellow solid. LCMS: [M+H]+: 656.5.

Example 54f

5-Chloro-1-cyclopropyl-6,7-bis((4-methoxybenzyl)oxy)-4-oxo-1,4-dihydroquinoline-3-carboxylic acid

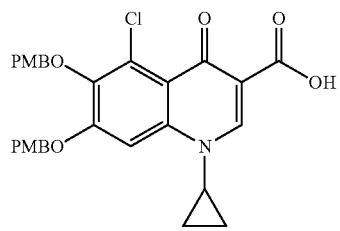

To a suspension of 4-methoxybenzyl 5-chloro-1-cyclopropyl-6,7-bis((4-methoxy benzyl)oxy)-4-oxo-1,4-dihydroquinoline-3-carboxylate (18 g, 27.4 mmol) in a mixture of Methanol (120 mL) and Water (60.0 mL) was added potassium hydroxide (3.08 g, 54.9 mmol) portionwise. The resulting mixture was stirred at 90° C. for 3 h. LCMS indicated completion of the reaction. The reaction mixture was cooled down to r.t. and concentrated, and was then diluted with water and adjusted pH to 1 using 2 N HCl (aq.). The precipitates were collected by filtration and dried to afford 5-chloro-1-cyclopropyl-6,7-bis((4-methoxybenzyl)oxy)-4-oxo-1,4-dihydroquinoline-3-carboxylic acid (12.6 g, 23.51 mmol, 86% yield) as pale yellow solid. LCMS: [M+H]+: 536.3.

Example 54g

5-Chloro-1-cyclopropyl-6,7-bis((4-methoxybenzyl)oxy)-3-(pyrrolidin-1-ylmethyl)quinolin-4(1H)-one

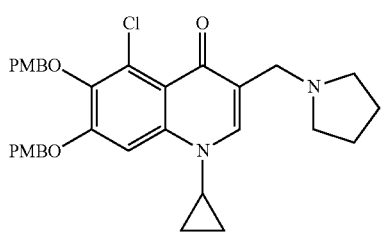

This compound was prepared according to the procedures described in Examples 44g-44i, utilizing 5-chloro-1-cyclopropyl-6,7-bis((4-methoxybenzyl)oxy)-4-oxo-1,4-dihydroquinoline-3-carboxylic acid (Example 54f) in place of 1-ethyl-7,8-bis((4-methoxybenzyl)oxy)-4-oxo-1,4-dihydroquinoline-3-carboxylic acid in step 44g. LCMS: (M+H)+: 575.2.

Example 54h (6R,7R)-7-(((Z)-2-(2-aminothiazol-4-yl)-2-(((S)-1,2-dicarboxyethoxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

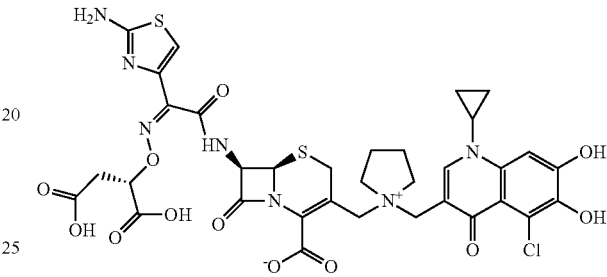

This compound was prepared according to the procedures described in Example 47k, utilizing 5-chloro-1-cyclopropyl-6,7-bis((4-methoxybenzyl)oxy)-3-(pyrrolidin-1-ylmethyl)quinolin-4(1H)-one (Example 54g) in place of 1-Ethyl-5-hydroxy-6-((4-methoxybenzyl)oxy)-4-oxo-N-(2-(pyrrolidin-1-yl)ethyl)-1,4-dihydroquinoline-3-carboxamide LCMS: (M+H)+: 832.1. 1H NMR (400 MHz, DEUTERIUM OXIDE) δ ppm 0.87-1.03 (m, 2 H) 1.13-1.26 (m, 2 H) 1.98-2.11 (m, 4 H) 2.57-2.69 (m, 2 H) 3.27-3.53 (m, 6 H) 3.83-3.94 (m, 1 H) 3.96-4.09 (m, 1 H) 4.16-4.34 (m, 2 H) 4.73-4.77 (m, 1 H) 4.85-4.92 (m, 1 H) 5.26-5.35 (m, 1 H) 5.74 (s, 1 H) 6.90 (s, 1 H) 7.29-7.38 (m, 1 H) 8.05-8.14 (m, 1 H).

Example 55

(6R,7R)-7-(((Z)-2-(2-aminothiazol-4-yl)-2-(((2-carboxypropan-2-yl)oxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, Sodium salt

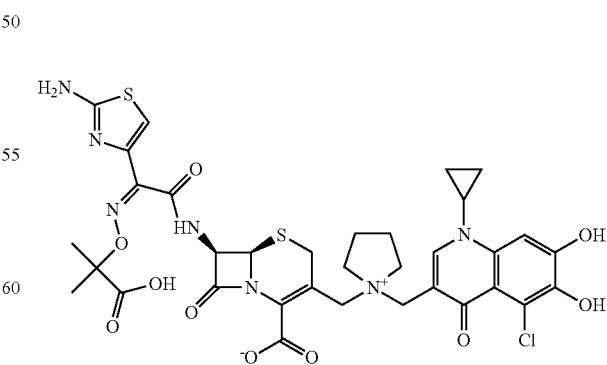

The compound was prepared according to the procedure described in Examples 19b-19c and 20, utilizing 5-chloro-1-cyclopropyl-6,7-bis((4-methoxybenzyl)oxy)-3-(pyrrolidin- 1-ylmethyl)quinolin-4(1H)-one (Example 54g) in place of 5-chloro-1-ethyl-6,7-bis((4-methoxybenzyl)oxy)-3-(pyrrolidin-1-ylmethyl)quinolin-4(1H)-one in step 19b. LCMS: (M+H)+: 802.0. ¹H NMR (400 MHz, DEUTERIUM OXIDE) δ ppm 0.87-1.03 (m, 2 H) 1.09-1.24 (m, 2 H) 1.39 (d, J=6.82 Hz, 6 H) 1.93-2.12 (m, 4 H) 3.37 (br. s., 6 H) 3.90 (br. s., 2 H) 4.14-4.36 (m, 2 H) 5.27-5.39 (m, 1 H) 5.73-5.81 (m, 1 H) 6.86 (s, 1 H) 7.24-7.34 (m, 1 H) 8.02-8.13 (m, 1 H).

Example 56

(6R,7R)-7-(((Z)-2-(2-aminothiazol-4-yl)-2-(((2-carboxypropan-2-yl)oxy)imino)acetamido)-3-((1-(2-(5-chloro-1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate, Sodium salt

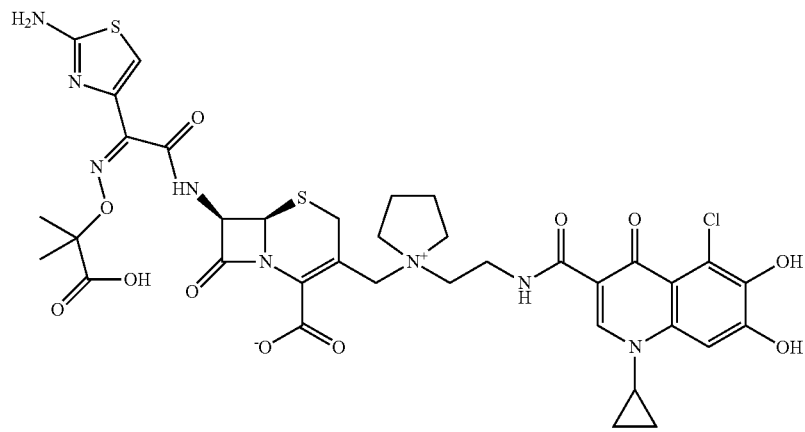

Example 56a

5-Chloro-1-cyclopropyl-6,7-bis((4-methoxybenzyl)oxy)-4-oxo-N-(2-(pyrrolidin-1-yl)ethyl)-1,4-dihydroquinoline-3-carboxamide

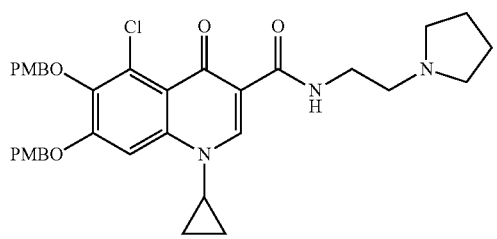

This compound was prepared according to the procedures described in Example 45a, utilizing 5-chloro-1-cyclopropyl-6,7-bis((4-methoxybenzyl)oxy)-4-oxo-1,4-dihydro quinoline-3-carboxylic acid (Example 54f) in place of 1-ethyl-7,8-bis((4-methoxybenzyl)oxy)-4-oxo-1,4-dihydroquinoline-3-carboxylic acid. LCMS: (M+H)+: 632.5.

Example 56b (6R,7R)-7-(((Z)-2-(2-aminothiazol-4-yl)-2-(((2-carboxypropan-2-yl)oxy)imino)acetamido)-3-(((1-(2-(5-chloro-1-cyclopropyl-6,7-dihydroxy-4-oxo-1,4-dihydro quinoline-3-carboxamido)ethyl)pyrrolidin-1-ium-1-yl)methyl)-8-oxo-5-thia-1-azabicyclo[4.2.0]oct-2-ene-2-carboxylate. Sodium salt

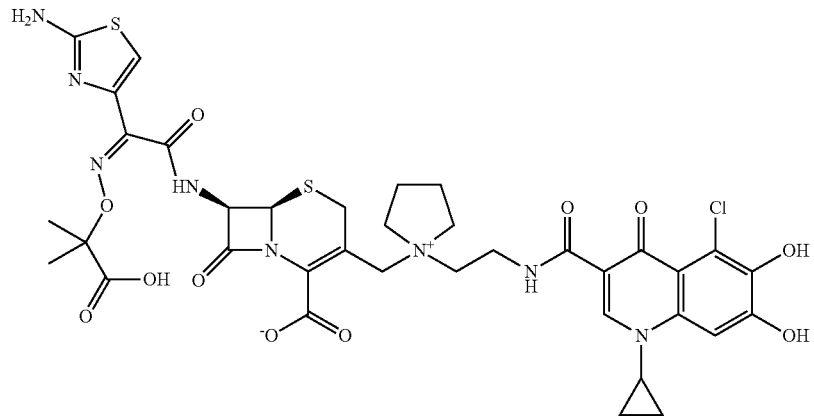

The compound was prepared according to the procedure described in Examples 19b-19c and 20, utilizing 5-chloro-1-cyclopropyl-6,7-bis((4-methoxybenzyl)oxy)-4-oxo-N-(2-(pyrrolidin-1-yl)ethyl)-1,4-dihydroquinoline-3-carboxamide (Example 56a) in place of 5-chloro-1-ethyl-6,7-bis((4-methoxybenzyl)oxy)-3-(pyrrolidin-1-ylmethyl)quinolin-4 (1H)-one in step 19b. LCMS: (M+H)$^+$: 859.0. $^1$H NMR (400 MHz, DEUTERIUM OXIDE) δ ppm 0.92-1.07 (m, 2 H) 1.16-1.28 (m, 2 H) 1.34 (s, 6 H) 2.04-2.20 (m, 4 H) 3.37-3.62 (m, 8 H) 3.68-3.81 (m, 1 H) 3.82-3.95 (m, 2 H) 4.00-4.12 (m, 1 H) 4.66 (m, 1 H) 5.24-5.31 (m, 1 H) 5.73-5.80 (m, 1 H) 6.83-6.89 (m, 1 H) 7.17-7.26 (m, 1 H) 8.43-8.52 (m, 1 H).

Example 57

(6R,7R)-7-(((Z)-2-(2-aminothiazol-4-yl)-2-(((S)-1,2-dicarboxyethoxy)imino)acetamido)-3-(((1-((6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

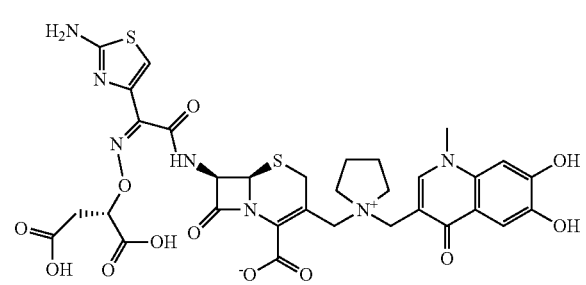

Example 57a 6,7-Bis((4-methoxybenzyl)oxy)-1-methyl-3-(pyrrolidin-1-ylmethyl)quinolin-4(1H)-one

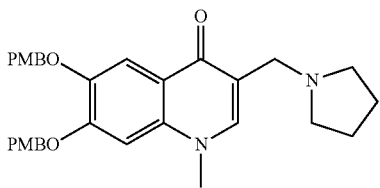

This compound was prepared according to the procedures described in Examples 50a-50f, utilizing methanamine in place of cyclopropanamine in Example 50a. LCMS: (M+H)$^+$: 515.3.

Example 57b (6R,7R)-7-((Z)-2-(2-aminothiazol-4-yl)-2-(((S)-1,2-dicarboxyethoxy)imino)acetamido)-3-((1-((6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

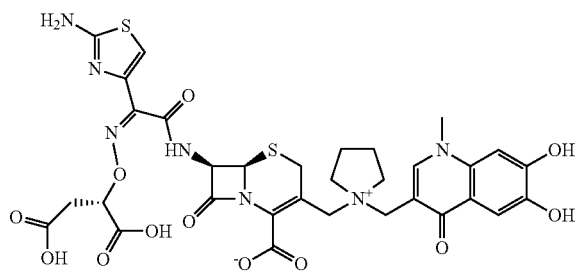

This compound was prepared according to the procedures described in Example 47k, utilizing 6,7-bis((4-methoxybenzyl)oxy)-1-methyl-3-(pyrrolidin-1-methyl)quinolin-4(1H)-one (Example 57a) in place of 1-Ethyl-5-hydroxy-6-((4-methoxybenzyl)oxy)-4-oxo-N-(2-(pyrrolidin-1-yl)ethyl)-1,4-dihydroquinoline-3-carboxamide. LCMS: (M+H)$^+$: 772.3. $^1$H NMR (400 MHz, DEUTERIUM OXIDE) δ ppm 1.85-2.08 (m, 4 H) 2.52-2.61 (m, 2 H) 3.23-3.45 (m, 6 H) 3.75 (s, 3 H) 3.80-3.91 (m, 1 H) 3.96-4.05 (m, 1 H) 4.21-4.31 (m, 1 H) 4.32-4.42 (m, 1 H) 4.83 (s, 1 H) 5.22-5.28 (m, 1 H) 5.68-5.75 (m, 1 H) 6.87 (s, 2 H) 7.41 (s, 1 H) 7.99-8.06 (m, 1 H).

Example 58

(6R,7R)-7-((Z)-2-(2-aminothiazol-4-yl)-2-(((S)-1,2-dicarboxyethoxy)imino)acetamido)-3-((1-((6,7-dihydroxy-1-isopropyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

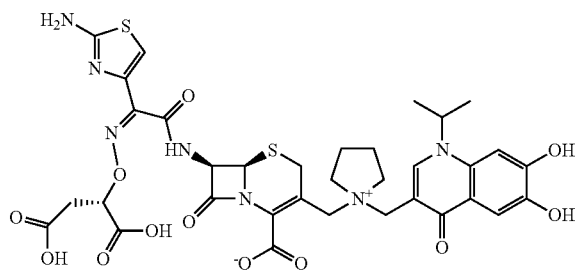

Example 58a

1-Isopropyl-6,7-bis((4-methoxybenzyl)oxy)-3-(pyrrolidin-1-ylmethyl)quinolin-4(1H)-one

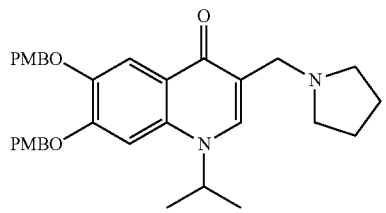

This compound was prepared according to the procedures described in Examples 50a-50f, utilizing propan-2-amine in place of cyclopropanamine in Example 50a. LCMS: (M+H)$^+$: 543.2.

Example 58b (6R,7R)-7-((Z)-2-(2-aminothiazol-4-yl)-2-(((S)-1,2-dicarboxyethoxy)imino)acetamido)-3-((1-((6,7-dihydroxy-1-isopropyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

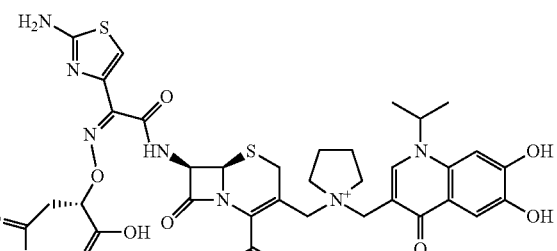

This compound was prepared according to the procedures described in Example 47k, utilizing 1-Isopropyl-6,7-bis((4-methoxybenzyl)oxy)-3-(pyrrolidin-1-ylmethyl)quinolin-4 (1H)-one (Example 58a) in place of 1-Ethyl-5-hydroxy-6-((4-methoxybenzyl)oxy)-4-oxo-N-(2-(pyrrolidin-1-yl)ethyl)-1,4-dihydroquinoline-3-carboxamide. LCMS: (M+H)$^+$: 800.1. $^1$H NMR (400 MHz, DEUTERIUM OXIDE) δ ppm 1.39-1.49 (m, 6 H) 1.92-2.10 (m, 4 H) 2.54-2.62 (m, 2 H) 3.20-3.48 (m, 6 H) 3.84-3.93 (m, 1 H) 3.95-4.06 (m, 1 H) 4.29-4.42 (m, 2 H) 4.84 (none, 2 H) 5.23-5.30 (m, 1 H) 5.69-5.76 (m, 1 H) 6.85-6.91 (m, 1 H) 7.10-7.17 (m, 1 H) 7.41-7.48 (m, 1 H) 8.09-8.15 (m, 1 H)

Example 59

1-((((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydroquinoline-3-carboxamido)ethyl)pyrrolidin-1-ium, Trifluoroacetic acid salt

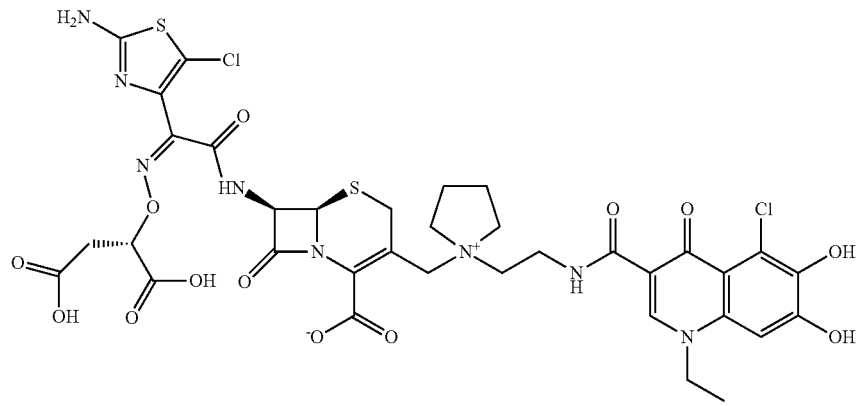

Example 59a 1-((((6R,7R)-2-((benzhydryloxy)carbonyl)-7-((Z)-2-(((((S)-4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-(2-(5-chloro-1-ethyl-6,7-bis((4-methoxybenzyl)oxy)-4-oxo-1,4-dihydroquinoline-3-carboxamido)ethyl)pyrrolidin-1-ium

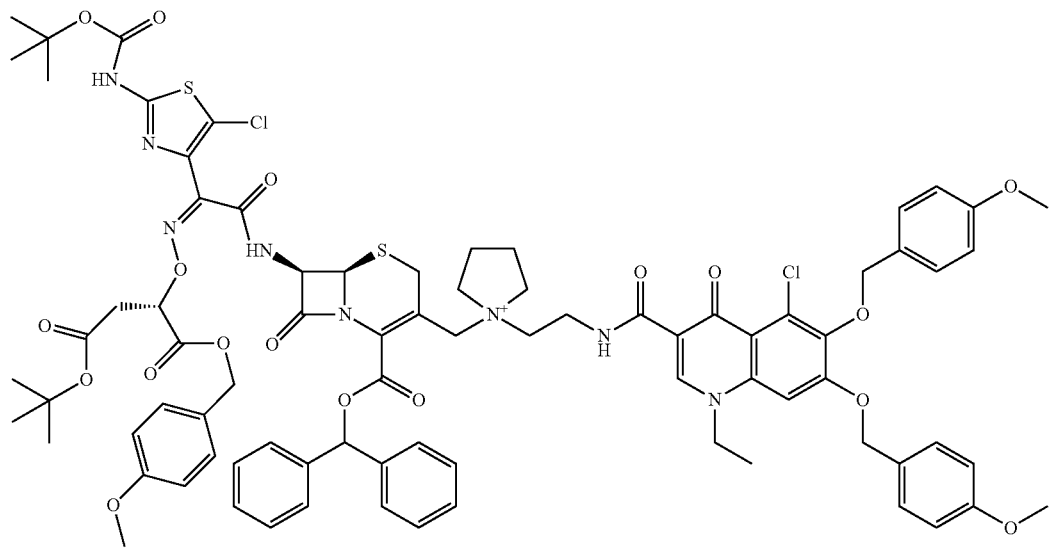 [SMILES: CCn1cc(C(=O)NCC[N+]2(CC3=C(C(=O)OC(c4ccccc4)c4ccccc4)N4C(=O)[C@@H](NC(=O)/C(=N\O[C@@H](CC(=O)OC(C)(C)C)C(=O)OCc5ccc(OC)cc5)c5nc(NC(=O)OC(C)(C)C)sc5Cl)[C@H]4SC3)CCCC2)c(=O)c2c(Cl)c(OCc3ccc(OC)cc3)c(OCc3ccc(OC)cc3)cc21]

The compound was prepared according to the procedure described in Examples 21l, utilizing 5-chloro-1-ethyl-6,7-bis((4-methoxybenzyl)oxy)-4-oxo-N-(2-(pyrrolidin-1-yl)ethyl)-1,4-dihydroquinoline-3-carboxamide (Example 27a) in place of 5-chloro-1-ethyl-6,7-bis((4-methoxybenzyl)oxy)-3-(pyrrolidin-1-ylmethyl)quinolin-4(1H)-one. LCMS: (M+H)$^+$: 1595.5.

Example 59b 1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydroquinoline-3-carboxamido)ethyl)pyrrolidin-1-ium, Trifluoroacetic acid salt

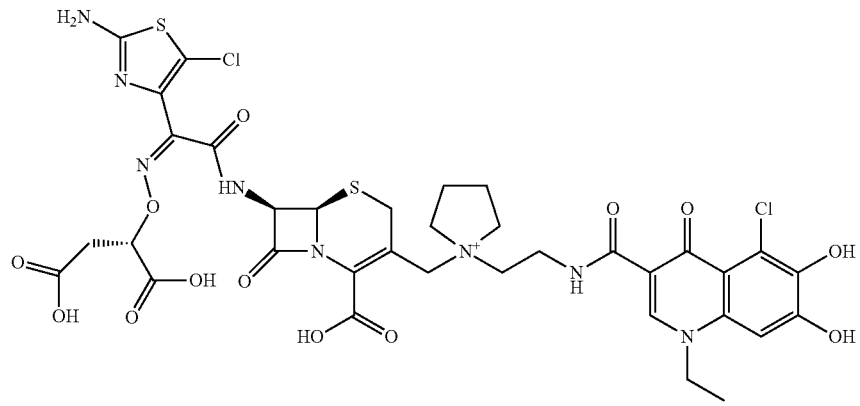 [SMILES: CCn1cc(C(=O)NCC[N+]2(CC3=C(C(=O)O)N4C(=O)[C@@H](NC(=O)/C(=N\O[C@@H](CC(=O)O)C(=O)O)c5nc(N)sc5Cl)[C@H]4SC3)CCCC2)c(=O)c2c(Cl)c(O)c(O)cc21]

To a solution of 1-(((6R,7R)-2-((benzhydryloxy)carbonyl)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)-5-chlorothiazol-4-yl)acetamido)-8-oxo-5-thia-1-azabicyclo[4.2.0]oct-2-en-3-yl)methyl)-1-(2-(5-chloro-1-ethyl-6,7-bis((4-methoxybenzyl)oxy)-4-oxo-1,4-dihydroquinoline-3-carboxamido)ethyl)pyrrolidin-1-ium (0.172 g, 0.108 mmol) in Dichloromethane (DCM) (3 mL) under N₂ at 0° C. was added anisole (0.118 mL, 1.078 mmol), followed by TFA (0.5 mL, 6.49 mmol). The mixture was warmed up to rt and stirred at rt over 24 h. LCMS indicated completion of the deprotection. Diisopropyl ether (6 mL) and water (1 mL) were then added. The mixture was stirred for 10 min and the solvents were decanted away from the solid. The solid was triturated twice with diisopropyl ether (5 mL) and dried under high vacuum to afford 1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydroquinoline-3-carboxamido)ethyl)pyrrolidin-1-ium, Trifluoroacetic acid salt (91 mg, 0.044 mmol, 41.1% yield) as a slightly brown solid. LCMS: (M+H)⁺: 913.0. ¹H NMR (400 MHz, METHANOL-d4) δ ppm 1.46-1.55 (m, 3 H) 2.19-2.34 (m, 4 H) 2.95-3.04 (m, 2 H) 3.41-4.47 (m, 14 H) 4.98-5.02 (m, 1 H) 5.28-5.33 (m, 1 H) 5.85-5.93 (m, 1 H) 7.11-7.14 (m, 1 H) 8.68-8.75 (m, 1 H)

Example 60

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(1-ethyl-8-fluoro-6,7-dihydroxy-4-oxo-1,4-dihydroquinoline-3-carboxamido)ethyl)pyrrolidin-1-ium, Trifluoroacetic acid salt

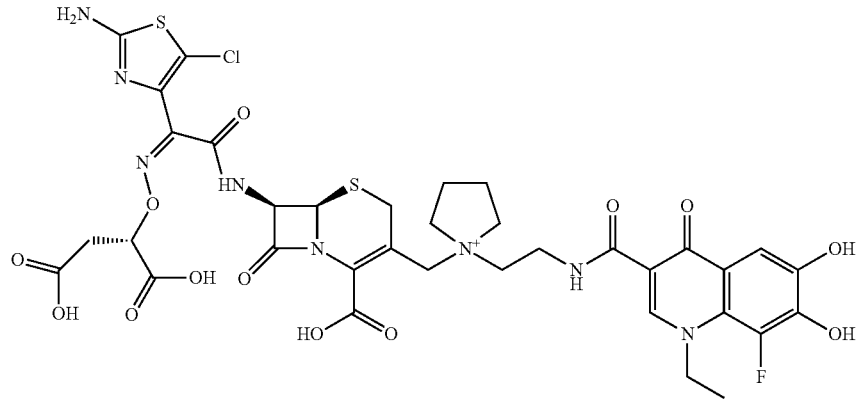 [SMILES: CCn1cc(C(=O)NCC[N+]2(CC3=C(C(=O)O)N4C(=O)[C@@H](NC(=O)/C(=N\O[C@@H](CC(=O)O)C(=O)O)c5nc(N)sc5Cl)[C@H]4SC3)CCCC2)c(=O)c2cc(O)c(O)c(F)c21]

Example 60a

1-Ethyl-8-fluoro-6,7-bis((4-methoxybenzyl)oxy)-4-oxo-N-(2-(pyrrolidin-1-yl)ethyl)-1,4-dihydroquinoline-3-carboxamide

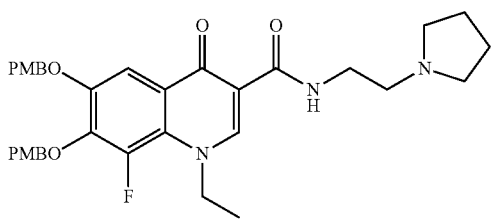

This compound was prepared according to the procedures described in Example 45a, utilizing 1-ethyl-8-fluoro-6,7-bis((4-methoxybenzyl)oxy)-4-oxo-1,4-dihydroquinoline-3-carboxylic acid (Example 15i) in place of 1-ethyl-7,8-bis((4-methoxybenzyl)oxy)-4-oxo-1,4-dihydroquinoline-3-carboxylic acid. LCMS: (M+H)$^+$: 604.5.

Example 60b 1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(1-ethyl-8-fluoro-6,7-dihydroxy-4-oxo-1,4-dihydroquinoline-3-carboxamido)ethyl)pyrrolidin-1-ium, Trifluoroacetic acid salt

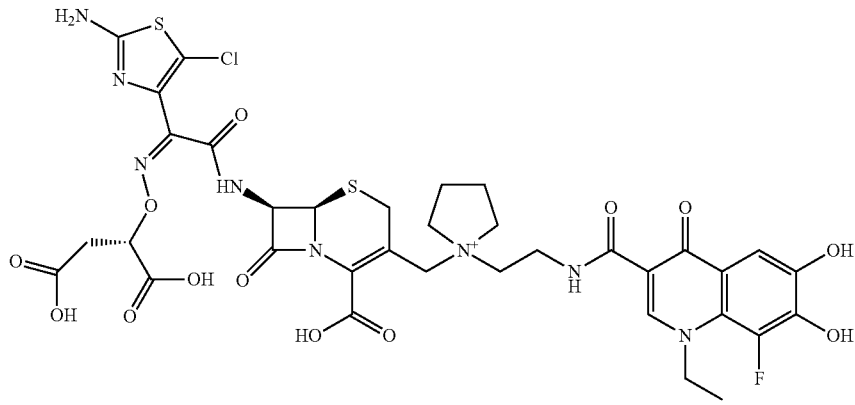 [SMILES: CCn1cc(C(=O)NCC[N+]2(CC3=C(C(=O)O)N4C(=O)[C@@H](NC(=O)/C(=N\O[C@@H](CC(=O)O)C(=O)O)c5nc(N)sc5Cl)[C@H]4SC3)CCCC2)c(=O)c2cc(O)c(O)c(F)c21]

The compound was prepared according to the procedure described in Examples 59a-59b, utilizing 1-ethyl-8-fluoro-6,7-bis((4-methoxybenzyl)oxy)-4-oxo-N-(2-(pyrrolidin-1-yl)ethyl)-1,4-dihydroquinoline-3-carboxamide (Example 60a) in place of 5-chloro-1-ethyl-6,7-bis((4-methoxybenzyl)oxy)-4-oxo-N-(2-(pyrrolidin-1-yl)ethyl)-1,4-dihydroquinoline-3-carboxamide. LCMS: (M+H)$^+$: 895.4. $^1$H NMR (400 MHz, DEUTERIUM OXIDE) $\delta$ ppm 1.32-1.43 (m, 3 H) 2.04-2.30 (m, 4 H) 2.70-2.89 (m, 2 H) 3.31-3.77 (m, 8 H) 4.13-4.20 (m, 1 H) 4.28-4.36 (m, 2 H) 4.41-4.49 (m, 1 H) 4.81-4.90 (m, 2 H) 5.00 (s, 1 H) 5.35-5.42 (m, 1 H) 5.51-5.58 (m, 1 H) 6.81-6.89 (m, 1 H) 7.25-7.34 (m, 1 H) 8.33-8.40 (m, 1 H)

Example 61

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-((1-ethyl-8-fluoro-6,7-dihydroxy-4-oxo-1,4-dihydroquinolin-3-yl)methyl)pyrrolidin-1-ium, Trifluoroacetic acid salt

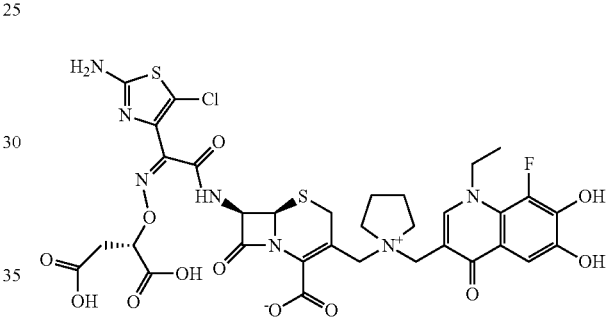

The compound was prepared according to the procedure described in Examples 59a-59b, utilizing 1-ethyl-8-fluoro-6,7-bis((4-methoxybenzyl)oxy)-3-(pyrrolidin-1-ylmethyl)quinolin-4(1H)-one (Example 151) in place of 5-chloro-1-ethyl-6,7-bis((4-methoxybenzyl)oxy)-4-oxo-N-(2-(pyrrolidin-1-yl)ethyl)-1,4-dihydroquinoline-3-carboxamide. LCMS: (M+H)$^+$: 838.2. $^1$H NMR (400 MHz, METHANOL-d4) $\delta$ ppm 1.43 (t, J=6.82 Hz, 3 H) 2.10-2.31 (m, 4 H) 2.95-3.04 (m, 2 H) 3.47-3.73 (m, 6 H) 4.26-4.67 (m, 6 H) 5.12-5.20 (m, 1 H) 5.35-5.39 (m, 1 H) 5.86-5.94 (m, 1 H) 6.98-7.05 (m, 1 H) 8.17-8.20 (m, 1 H).

Example 62

(6R,7R)-7-((Z)-2-(2-aminothiazol-4-yl)-2-(((S)-1,2-dicarboxyethoxy)imino)acetamido)-3-((1-((5-chloro-6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium salt

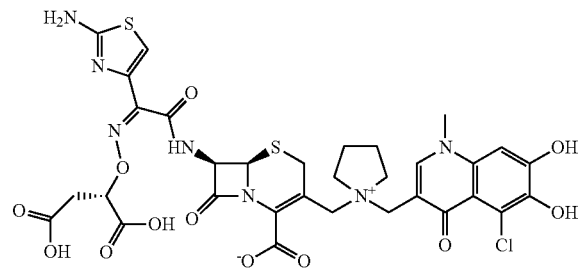

Example 62a

5-Chloro-6,7-bis((4-methoxybenzyl)oxy)-1-methyl-3-(pyrrolidin-1-ylmethyl)quinolin-4(1H)-one

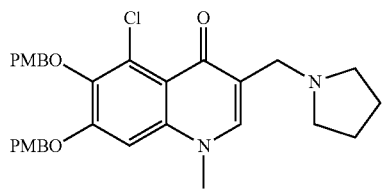

This compound was prepared according to the procedures for the preparation of 5-chloro-1-cyclopropyl-6,7-bis((4-methoxybenzyl)oxy)-3-(pyrrolidin-1-ylmethyl)quinolin-4(1H)-one as described in Examples 50a-50b and 54a-54g, utilizing methanamine in place of cyclopropanamine in Example 50a. LCMS: (M+H)$^+$: 549.3.

Example 62b (6R,7R)-7-((Z)-2-(2-aminothiazol-4-yl)-2-(((S)-1,2-dicarboxyethoxy)imino)acetamido)-3-((1-((5-chloro-6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate, 2 Sodium alt

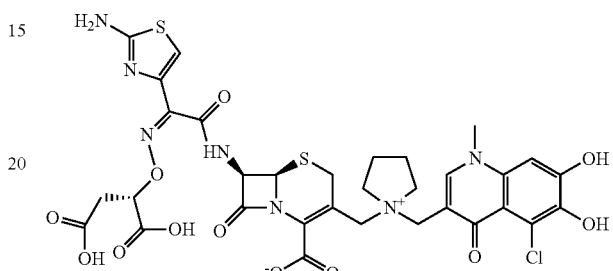

This compound was prepared according to the procedures described in Example 47k, utilizing 5-chloro-6,7-bis((4-methoxybenzyl)oxy)-1-methyl-3-(pyrrolidin-1-ylmethyl)quinolin-4(1H)-one (Example 62a) in place of 1-Ethyl-5-hydroxy-6-((4-methoxybenzyl)oxy)-4-oxo-N-(2-(pyrrolidin-1-yl)ethyl)-1,4-dihydroquinoline-3-carboxamide. LCMS: (M+H)$^+$: 895.4. $^1$H NMR (400 MHz, DEUTERIUM OXIDE) δ ppm 1.88-2.07 (m, 4 H) 2.50-2.66 (m, 2 H) 3.18-3.49 (m, 6 H) 3.65 (s, 3 H) 3.83-3.93 (m, 1 H) 3.94-4.06 (m, 1 H) 4.11-4.21 (m, 1 H) 4.22-4.32 (m, 1 H) 4.82-4.88 (m, 1 H) 5.24-5.32 (m, 1 H) 5.72 (d, J=4.80 Hz, 1 H) 6.63-6.74 (m, 1 H) 6.85-6.92 (m, 1 H) 7.88-7.98 (m, 1 H)

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:
1. A compound of Formula (II):

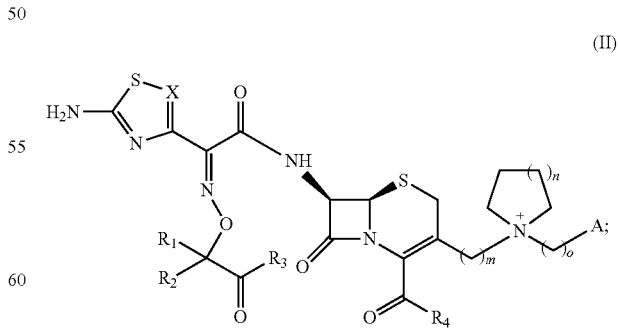

wherein:
X is N, or C—R$^a$;
R$^1$ and R$^2$ each are hydrogen, (C$_{1-6}$)alkyl, or (CH$_2$)p—C(O)OR$^b$;

$R^3$ and $R^4$ each are hydrogen, OH or $OR^c$;
  wherein:
    $R^a$ is hydrogen or halogen;
    $R^b$ or $R^c$ each is H, $(C_{1-6})$-alkyl, an alkali metal or negative charge;
A is $R^5$ or $-NR^dC(O)R^5$
  wherein $R^d$ is H or $(C_{1-6})$-alkyl
$R^5$ is an optionally saturated or unsaturated monocyclic heterocyclic ring or an optionally saturated or unsaturated bi-cyclic or fused heterocyclic ring;
  wherein:
    each monocyclic heterocyclic ring has from 3 to 7 ring atoms and contains up to four heteroatoms;
    each fused heterocyclic ring optionally includes carbocyclic rings or heterocyclic rings of up to four heteroatoms;
    $R^5$ optionally is substituted by one or more of the following substituents selected from $-H$, $-OH$, Oxo ($=O$), $-CN$, $-NO_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, $-OC(O)OH$, $-OC(O)R^e$, $-C(O)OR^f$, $-O(CH_2)_yOR^g$, $-NR^hR^i$, $-SO_2R^j$, $-S(CH_2)_qR^k$, $-NR^lC(O)R^m$, aryl or heteroaryl;
    wherein:
      hetero atoms are selected from oxygen, nitrogen or sulphur,
      carbocyclic rings or heterocyclic rings for each fused heterocyclic ring systems include non-aromatic rings or aromatic rings;
      monocyclic heterocyclic rings or fused heterocyclic rings include substituted aromatic and non-aromatics;
      each $R^e$, $R^f$, $R^g$, $R^h$, $R^i$, $R^j$, $R^k$, $R^l$, or $R^m$ each is selected from H, $C_{1-6}$ alkyl, $C_{1-6}$ haloalkyl, $C_{1-6}$ alkoxy;
      each aryl or heteroaryl as defined above is optionally substituted with one or more of the following substituents selected from H, $-OH$, $-CN$, $-NO_2$, -halogen, $C_{1-6}$-alkyl, $C_{1-6}$-haloalkyl, $C_{1-6}$-alkoxy, $-OC(O)OH$, $-OC(O)R^n$, $-C(O)OR^o$, $-O(CH_2)_yOR^p$, $-NR^qR^r$, $-SO_2R^s$, $-S(CH_2)_yR^t$, $-NR^uC(O)R^v$;
      wherein:
        $R^n$, $R^o$, $R^p$, $R^q$, $R^r$, $R^s$, $R^t$, $R^u$, or $R^v$ each are selected from $C_{1-6}$ alkyl, $C_{1-6}$-haloalkyl, or $C_{1-6}$-alkoxy;
n, m, o, p, q or y each are 0 or an integer from 1 to 5; or a pharmaceutically acceptable salt thereof.

2. The compound of Formula (III) according to claim 1:

(III)

wherein:
  X is N, or $C-R^a$;
  $R^1$ and $R^2$ each are hydrogen, $(C_{1-6})$alkyl, or $(CH_2)p-C(O)OR^b$;
  $R^3$ and $R^4$ each are hydrogen, OH or $OR^c$;
    wherein:
      $R^a$ is hydrogen or halogen;
      $R^b$ or $R^c$ each is H, $(C_{1-6})$-alkyl, an alkali metal or negative charge;
  A is $R^5$ or $-NR^dC(O)R^5$
    wherein:
      $R^d$ is H or $(C_{1-6})$-alkyl
  $R^5$ is a monocyclic 3 to 7 membered heterocyclic ring or a bicyclic 10 membered heterocyclic ring;
    wherein:
      each 3 to 7 membered heterocyclic ring contains up to four heteroatoms or
      each bicyclic 10 membered heterocyclic ring contains up to four heteroatoms;
      wherein:
        hetero atoms are selected from oxygen, nitrogen or sulphur;
        carbocyclic rings or heterocyclic rings for each 10 membered heterocyclic ring systems contain non-aromatic rings or aromatic rings;
      $R^5$ optionally is substituted by one or more of the following substituents selected from $-H$, $-OH$, Oxo ($=O$), $-CN$, $-NO_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, $-OC(O)OH$, $-OC(O)R^e$, $-C(O)OR^f$, $-O(CH_2)_yOR^g$, $-NR^hR^i$, $-SO_2R^j$, $-S(CH_2)_qR^k$, $-NR^lC(O)R^m$, aryl or heteroaryl;
      wherein:
        each $R^e$, $R^f$, $R^g$, $R^h$, $R^i$, $R^j$, $R^k$, $R^l$, or $R^m$ as defined above is selected from H, $C_{1-6}$ alkyl, $C_{1-6}$ haloalkyl, $C_{1-6}$ alkoxy;
        each aryl or heteroaryl as defined above is optionally substituted with one or more of the following substituents selected from H, $-OH$, $-CN$, $-NO_2$, -halogen, $C_{1-6}$-alkyl, $C_{1-6}$-haloalkyl, $C_{1-6}$-alkoxy, $-OC(O)OH$, $-OC(O)R^n$, $-C(O)OR^o$, $-O(CH_2)_yOR^p$, $-NR^qR^r$, $-SO_2R^s$, $-S(CH_2)_yR^t$, $-NR^uC(O)R^v$;
        wherein:
          $R^n$, $R^o$, $R^p$, $R^q$, $R^r$, $R^s$, $R^t$, $R^u$, or $R^v$ each as defined above are selected from $C_{1-6}$ alkyl, $C_{1-6}$-haloalkyl, or $C_{1-6}$-alkoxy;
n, m, o, p, q or y each are 0 or an integer from 1 to 5; or a pharmaceutically acceptable salt thereof.

3. The compound of Formula (IV):

(IV)

263 wherein:

X is C—$R^a$;

$R^1$ and $R^2$ each are hydrogen, $(C_{1-6})$alkyl, or $(CH_2)$p-C(O)$OR^b$;

$R^3$ and $R^4$ each are hydrogen, OH or $OR^c$;

wherein:

$R^a$ is hydrogen or halogen;

$R^b$ or $R^c$ each is H, $(C_{1-6})$-alkyl, an alkali metal or negative charge;

A is $R^5$ or —$NR^dC(O)R^5$ wherein $R^d$ is H or $(C_{1-6})$-alkyl;

$R^5$ is an optionally saturated or unsaturated monocyclic heterocyclic ring or an optionally saturated or unsaturated bi-cyclic or fused heterocyclic ring;

wherein:

each monocyclic heterocyclic ring has from 3 to 7 ring atoms and contains up to four heteroatoms;

each fused heterocyclic ring optionally includes carbocyclic rings or heterocyclic rings of up 4 heteroatoms;

R5 optionally is substituted by one or more of the following substituents selected from —H, —OH, Oxo (═O), —CN, —$NO_2$, -halogen, -straight or branched $C_{1-6}$ alkyl, -straight or branched $C_{1-6}$ haloalkyl, $C_{3-6}$cycloalkyl, -straight or branched $C_{1-6}$ straight or branched alkoxy, —OC(O)OH, —OC(O)$R^e$, —C(O)$OR^f$, —O$(CH_2)_y$$OR^g$, —$NR^hR^i$, —$SO_2R^j$, —$S(CH_2)_qR^k$, —$NR^lC(O)R^m$, aryl or heteroaryl;

wherein:

hetero atoms are selected from oxygen, nitrogen or sulphur, carbocyclic rings or heterocyclic rings for each fused heterocyclic ring systems include non-aromatic rings or aromatic rings;

monocyclic heterocyclic rings or fused heterocyclic rings include substituted aromatic and non-aromatics;

each $R^e$, $R^f$, $R^g$, $R^h$, $R^i$, $R^j$, $R^k$, $R^l$, or $R^m$ each is selected from H, $C_{1-6}$ alkyl, $C_{1-6}$ haloalkyl, $C_{1-6}$ alkoxy;

each aryl or heteroaryl as defined above is optionally substituted with one or more of the following substituents selected from H, —OH, —CN, —$NO_2$, -halogen, $C_{1-6}$-alkyl, $C_{1-6}$-haloalkyl, $C_{1-6}$-alkoxy, —OC(O)OH, —OC(O)$R^n$, —C(O)$OR^o$, —O$(CH_2)_v$$OR^p$, —$NR^qR^r$, —$SO_2R^s$, —$S(CH_2)_y$$R^t$, —$NR^uC(O)R^v$;

wherein:

$R^n$, $R^o$, $R^p$, $R^q$, $R^r$, $R^s$, $R^t$, $R^u$, or $R^v$ each are selected from $C_{1-6}$ alkyl, $C_{1-6}$-haloalkyl, or $C_{1-6}$-alkoxy;

n, m, o, p, q or y each are 0 or an integer from 1 to 5; or a pharmaceutically acceptable salt thereof.

4. The compound of Formula (IV) according to claim 3, wherein X is C—$R^a$ and $R^a$ is hydrogen.

264

5. The compound of Formula (V) according to claim 2:

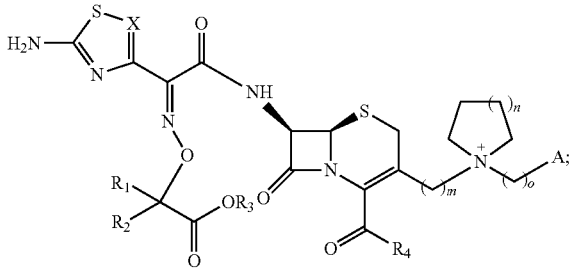

(V)

wherein:

X is C—$R^a$;

$R^1$ and $R^2$ each are hydrogen, $(C_{1-6})$alkyl, or $(CH_2)$p—C(O)$OR^b$;

$R^3$ and $R^4$ each are hydrogen, OH or $OR^c$;

wherein:

$R^a$ is hydrogen or halogen;

$R^b$ or $R^c$ each is H, $(C_{1-6})$-alkyl, an alkali metal or negative charge;

A is $R^5$ or —$NR^dC(O)R^5$ wherein:

$R^d$ is H or $(C_{1-6})$-alkyl $R^5$ is a monocyclic 3 to 7 membered heterocyclic ring or a bicyclic 10 membered heterocyclic ring;

wherein:

each 3 to 7 membered heterocyclic ring contains up to four heteroatoms;

each bicyclic 10 membered heterocyclic ring contains up to four heteroatoms;

wherein:

each heteroatom is selected from nitrogen, oxygen or sulfur;

each 10 membered heterocyclic ring optionally contains carbocyclic rings or heterocyclic rings;

wherein:

carbocyclic rings or heterocyclic rings for each 10 membered heterocyclic ring systems contain non-aromatic rings or aromatic rings;

$R^5$ optionally is substituted by one or more of the following substituents selected from —H, —OH, Oxo (═O), —CN, —$NO_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)$R^e$, —C(O)$OR^f$, —O$(CH_2)_y$$OR^g$, —$NR^hR^i$, —$SO_2R^j$, —$S(CH_2)_qR^k$, —$NR^lC(O)R^m$, aryl or heteroaryl;

wherein:

each $R^e$, $R^f$, $R^g$, $R^h$, $R^i$, $R^j$, $R^k$, $R^l$, or $R^m$ as defined above is selected from H, $C_{1-6}$ alkyl, $C_{1-6}$ haloalkyl, $C_{1-6}$ alkoxy;

each aryl or heteroaryl as defined above is optionally substituted with one or more of the following substituents selected from H, —OH, —CN, —$NO_2$, -halogen, $C_{1-6}$-alkyl, $C_{1-6}$-haloalkyl, $C_{1-6}$-alkoxy, —OC(O)OH, —OC(O)$R^n$, —C(O)$OR^o$, —O$(CH_2)_v$$OR^p$, —$NR^qR^r$, —$SO_2R^s$, —$S(CH_2)_y$$R^t$, —$NR^uC(O)R^v$;

wherein:
    $R^n$, $R^o$, $R^p$, $R^q$, $R^r$, $R^s$, $R^t$, $R^u$, or $R^v$ each as defined above are selected from $C_{1-6}$ alkyl, $C_{1-6}$-haloalkyl, or $C_{1-6}$-alkoxy;

n, m, o, p, q or y each are 0 or an integer from 1 to 5; or a pharmaceutically acceptable salt thereof.

6. The compound of Formula (VI) according to claim 2:

(VI)

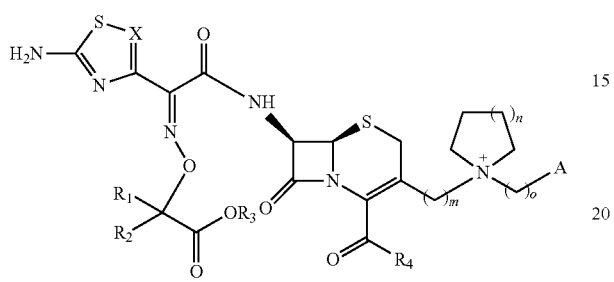

wherein:
X is C—$R^a$;
$R^1$ and $R^2$ each are hydrogen, $(C_{1-6})$alkyl, or $(CH_2)p$-C(O)O$R^b$;
$R^3$ and $R^4$ each are hydrogen, OH or O$R^c$;
    wherein:
        $R^a$ is hydrogen or halogen;
        $R^b$ or $R^c$ each is H, $(C_{1-6})$-alkyl, an alkali metal or negative charge;
A is

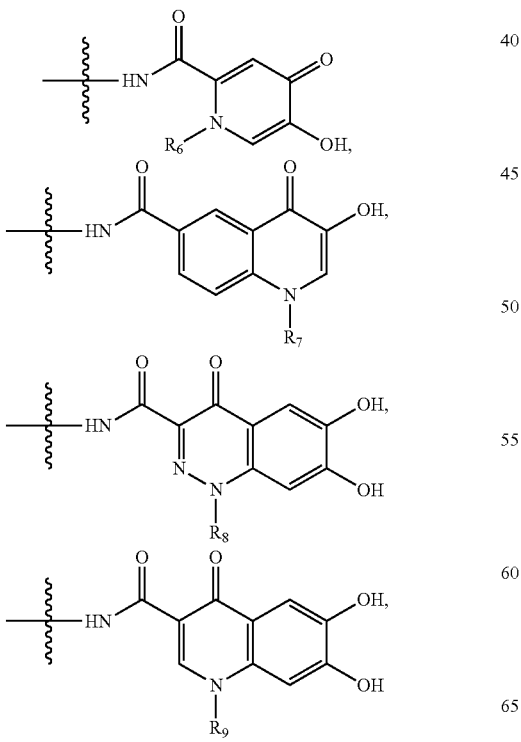

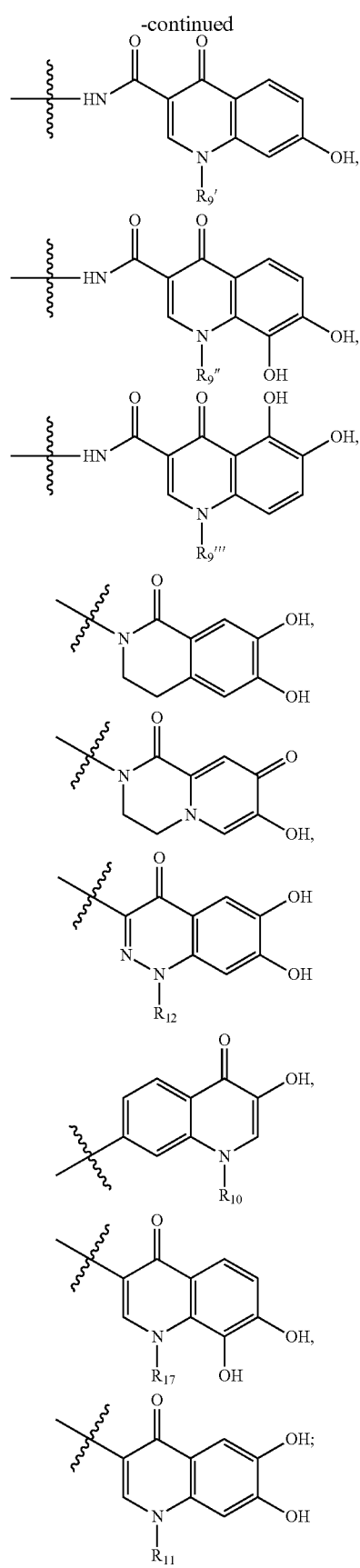

wherein:

R$_6$, R$_7$, R$_8$, R$_9$, R$_{9'}$, R$_{9''}$, R$_{9'''}$, R$_{10}$, R$_{11}$, R$_{12}$ or R$_{17}$ is H, straight or branched(C$_{1-6}$)-alkyl or C$_{3-6}$-cycloalkyl;

each A optionally further is substituted by one or more of the following substituents selected from —H, —OH, Oxo (=O), —CN, —NO$_2$, -halogen, -straight or branched C$_{1-6}$ alkyl, -straight or branched C$_{1-6}$ haloalkyl, C$_{3-6}$-cycloalkyl, -straight or branched C$_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;

where:

each R$^e$, R$^f$, R$^g$, R$^h$, R$^i$, R$^j$, R$^k$, R$^l$, or R$^m$ as defined above is selected from H, C$_{1-6}$ alkyl, C$_{1-6}$ haloalkyl, C$_{1-6}$ alkoxy;

each aryl or heteroaryl as defined above is optionally substituted with one or more of the following substituents selected from H, —OH, —CN, —NO$_2$, -halogen, C$_{1-6}$-alkyl, C$_{1-6}$-haloalkyl, C$_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;

where:

R$^n$, R$^o$, R$^p$, R$^q$, R$^r$, R$^s$, R$^t$, R$^u$, or R$^v$ each as defined above are selected from C$_{1-6}$ alkyl, C$_{1-6}$-haloalkyl, or C$_{1-6}$-alkoxy; and n, m, o, p, q or y each are 0 or an integer from 1 to 5; or a pharmaceutically acceptable salt thereof.

7. The compound of Formula according to claim 6, wherein A is

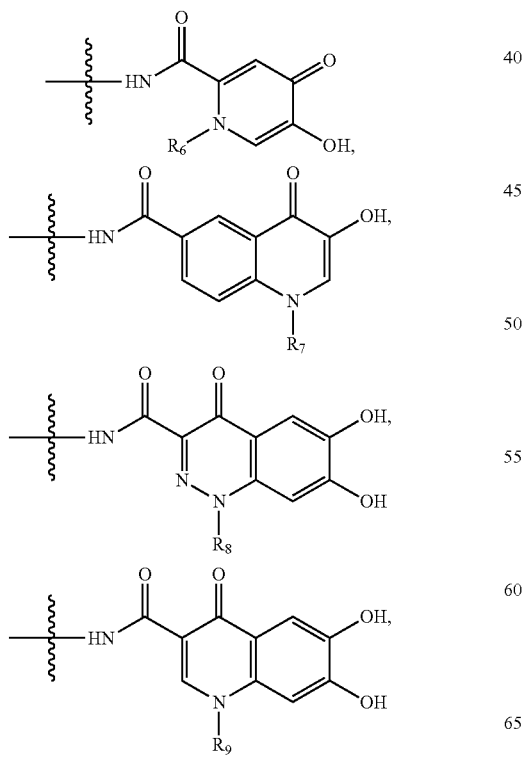

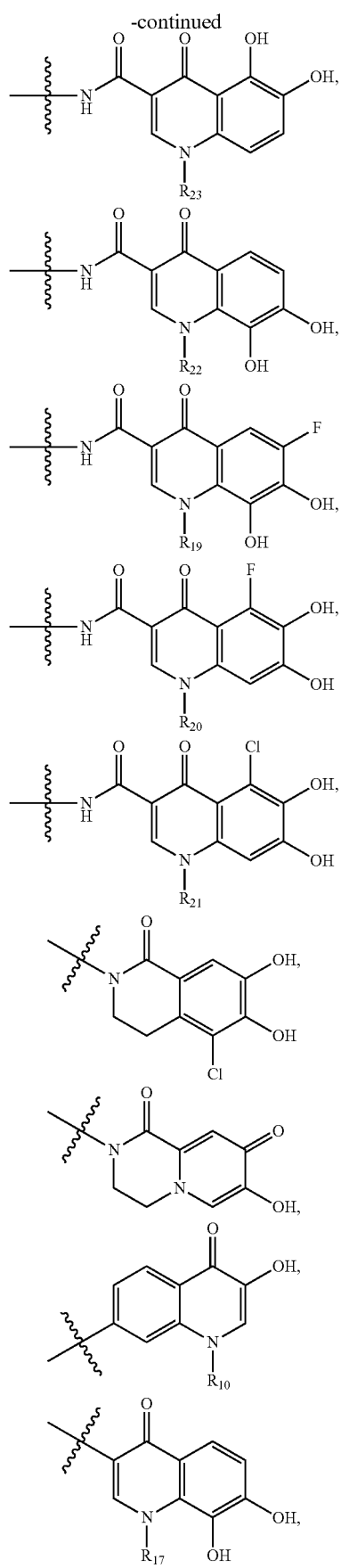

-continued

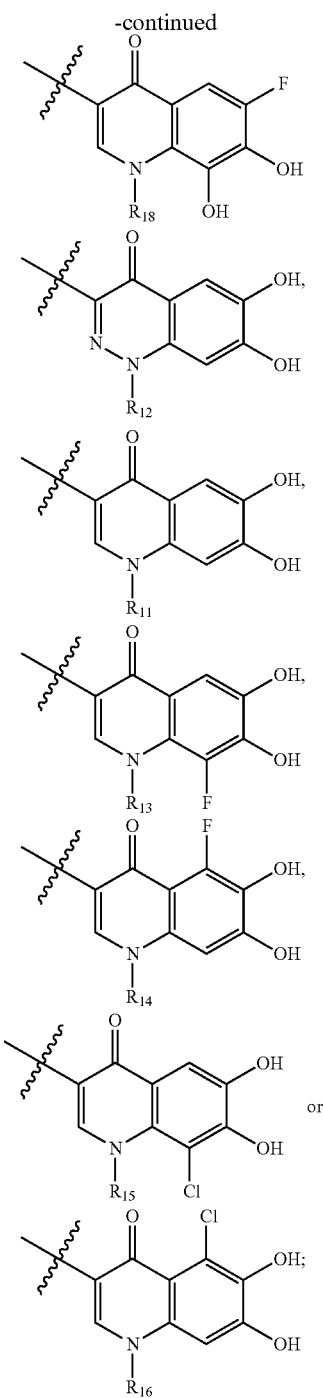

wherein:
R$_6$, R$_7$, R$_8$, R$_9$, R$_{10}$, R$_{11}$ or R$_{12}$, R$_{13}$, R$_{14}$, R$_{15}$, R$_{16}$, R$_{17}$, R$_{18}$, R$_{19}$, R$_{20}$, R$_{21}$, R$_{22}$, or R$_{23}$ is H, straight or branched (C$_{1-6}$)-alkyl or C$_{3-6}$-cycloalkyl.

each A optionally further is substituted by one or more of the following substituents selected from —H, —OH, Oxo (═O), —CN, —NO$_2$, -halogen, -straight or branched C$_{1-6}$ alkyl, -straight or branched C$_{1-6}$ haloalkyl, C$_{3-6}$-cycloalkyl, -straight or branched C$_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;

where:
each R$^e$, R$^f$, R$^g$, R$^h$, R$^i$, R$^j$, R$^k$, R$^l$, or R$^m$ as defined above is selected from H, C$_{1-6}$ alkyl, C$_{1-6}$ haloalkyl, C$_{1-6}$ alkoxy;

each aryl or heteroaryl as defined above is optionally substituted with one or more of the following substituents selected from H, —OH, —CN, —NO$_2$, -halogen, C$_{1-6}$-alkyl, C$_{1-6}$-haloalkyl, C$_{1-6}$-alkoxy, —OC(O)OH, —OC(O)R$^n$, —C(O)OR$^o$, —O(CH$_2$)$_y$—OR$^p$, —NR$^q$R$^r$, —SO$_2$R$^s$, —S(CH$_2$)$_y$—R$^t$, —NR$^u$C(O)R$^v$;

where:
R$^n$, R$^o$, R$^p$, R$^q$, R$^r$, R$^s$, R$^t$, R$^u$, or R$^v$ each as defined above are selected from C$_{1-6}$ alkyl, C$_{1-6}$-haloalkyl, or C$_{1-6}$-alkoxy; and n, m, o, p, q or y each are 0 or an integer from 1 to 5; or a pharmaceutically acceptable salt thereof.

8. The compound of Formula (VI) according to claim 6, wherein:
Ra is hydrogen;
R$^1$ and R$^2$ each are (C$_{1-6}$)alkyl;
R$^3$ and R$^4$ each are OH or OR$^c$;
wherein:
R$^c$ is H, (C$_{1-6}$)-alkyl, an alkali metal or negative charge;
A is

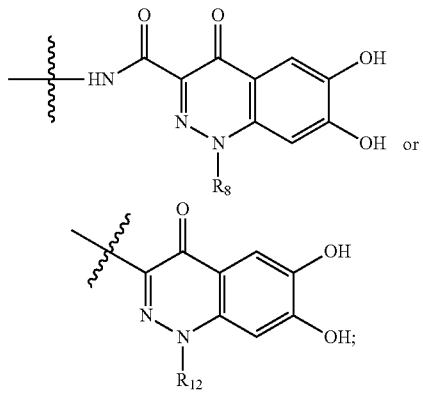

R$^8$ or R$^{12}$ is H, (C$_{1-6}$)-alkyl or (C$_{3-6}$)-cycloalkyl;
n is 1; or
a pharmaceutically acceptable salt thereof.

9. The compound of Formula (VIII) according to claim 2:

(VII)

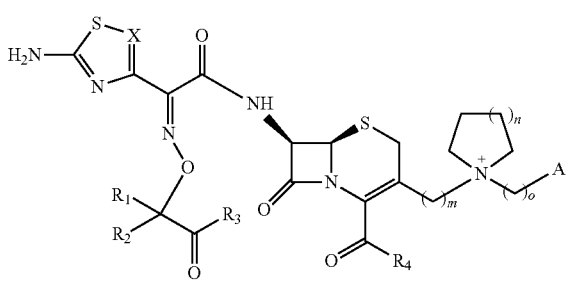

wherein:
X is C—R$^a$;
R$^1$ and R$^2$ each are hydrogen, (C$_{1-6}$)alkyl, or (CH$_2$)p-C(O)OR$^b$;

$R^3$ and $R^4$ each are hydrogen, OH or $OR^c$;
 wherein:
  $R^a$ is hydrogen or halogen;
  $R^b$ or $R^c$ each is H, $(C_{1-6})$-alkyl, an alkali metal or negative charge;
A is
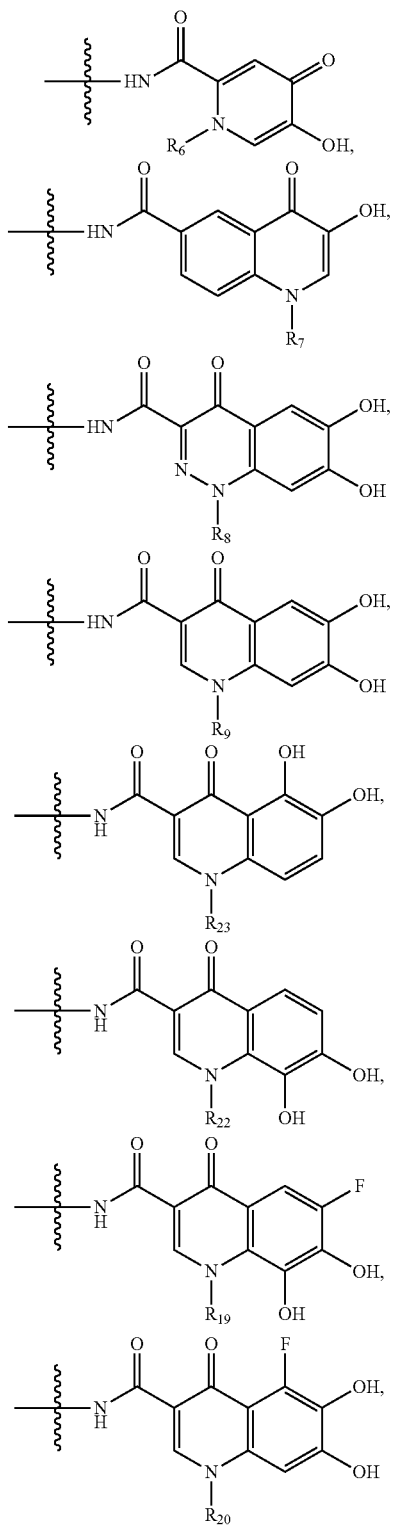
-continued
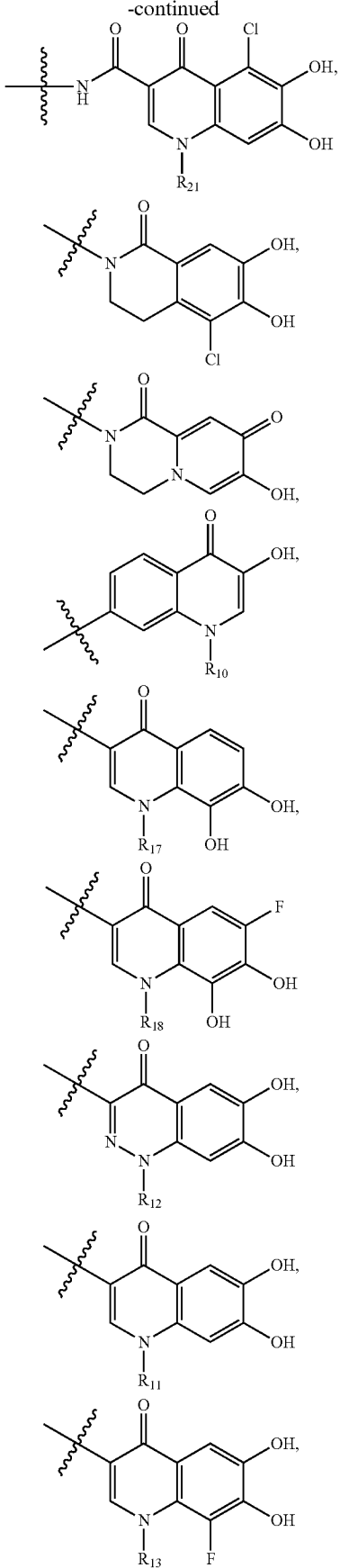

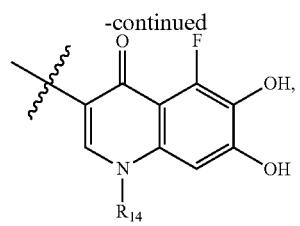

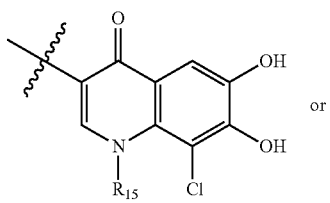

or

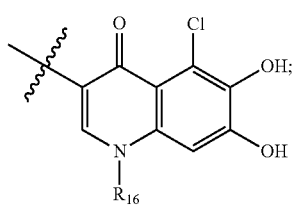

wherein:

$R_6, R_7, R_8, R_9, R_{10}, R_{11}$ or $R_{12}, R_{13}, R_{14}, R_{15}, R_{16}, R_{17}, R_{18}, R_{19}, R_{20}, R_{21}, R_{22}$, or $R_{23}$ is H, straight or branched $(C_{1-6})$-alkyl or $C_{3-6}$-cycloalkyl.

each A optionally further is substituted by one or more of the following substituents selected from —H, —OH, Oxo (=O), —CN, —NO$_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$(O)R$^m$, aryl or heteroaryl;

where:

each R$^e$, R$^f$, R$^g$, R$^h$, R$^i$, R$^j$, R$^k$, R$^l$, or R$^m$ as defined above is selected from H, $C_{1-6}$ alkyl, $C_{1-6}$ haloalkyl, $C_{1-6}$ alkoxy;

each aryl or heteroaryl as defined above is optionally substituted with one or more of the following substituents selected from H, —OH, —CN, —NO$_2$, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH$_2$)$_y$OR$^p$, —NR$^q$R$^r$, —SO$_2$R$^s$, —S(CH$_2$)$_y$R$^t$, —NR$^u$C(O)R$^v$;

where:

R$^n$, R$^o$, R$^p$, R$^q$, R$^r$, R$^s$, R$^t$, R$^u$, or R$^v$ each as defined above are selected from $C_{1-6}$ alkyl, $C_{1-6}$-haloalkyl, or $C_{1-6}$-alkoxy; and n, m, o, p, q or y each are 0 or an integer from 1 to 5; or a pharmaceutically acceptable salt thereof.

10. The compound of Formula (VII) according to claim 9, wherein X is C—R$^a$ and R$^a$ is hydrogen.

11. The compound of Formula (VIII) according to claim 1:

(VIII)

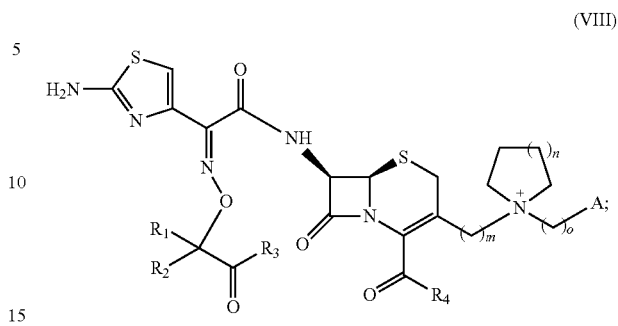

wherein:

$R^1$ and $R^2$ each are hydrogen, $(C_{1-6})$alkyl, or $(CH_2)$p-C(O)OR$^b$;

$R^3$ and $R^4$ each are hydrogen, OH or OR$^c$;

wherein:

R$^b$ or R$^c$ each is H, $(C_{1-6})$-alkyl, an alkali metal or negative charge;

A is R$^5$ or —NR$^d$C(O)R$^5$

Wherein:

R$^d$ is H or $(C_{1-6})$-alkyl

R$^5$ is an optionally saturated or unsaturated monocyclic heterocyclic ring or an optionally saturated or unsaturated bi-cyclic or fused heterocyclic ring;

wherein:

each monocyclic heterocyclic ring has from 3 to 7 ring atoms and contains up to four heteroatoms;

each fused heterocyclic ring optionally includes carbocyclic rings or heterocyclic rings of up to four heteroatoms;

R5 optionally is substituted by one or more of the following substituents selected from —H, —OH, Oxo (=O), —CN, —NO$_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;

wherein:

hetero atoms are selected from oxygen, nitrogen or sulphur, carbocyclic rings or heterocyclic rings for each fused heterocyclic ring systems include non-aromatic rings or aromatic rings;

monocyclic heterocyclic rings or fused heterocyclic rings include substituted aromatic and non-aromatics;

each R$^e$, R$^f$, R$^g$, R$^h$, R$^i$, R$^j$, R$^k$, R$^l$, or R$^m$ each is selected from H, $C_{1-6}$ alkyl, $C_{1-6}$ haloalkyl, $C_{1-6}$ alkoxy;

each aryl or heteroaryl as defined above is optionally substituted with one or more of the following substituents selected from H, —OH, —CN, —NO$_2$, -halogen, $C_{1-6}$-alkyl, $C_{1-6}$-haloalkyl, $C_{1-6}$-alkoxy, —OC(O)OH, —OC(O)R$^n$, —C(O)OR$^o$, —O(CH$_2$)$_y$OR$^p$, —NR$^q$R$^r$, —SO$_2$R$^s$, —S(CH$_2$)$_y$R$^t$, —NR$^u$C(O)R$^v$;

wherein:
R$^n$, R$^o$, R$^p$, R$^q$, R$^r$, R$^s$, R$^t$, R$^u$, or R$^v$ each are selected from C$_{1-6}$ alkyl, C$_{1-6}$-haloalkyl, or C$_{1-6}$-alkoxy;
n, m, o, p, q or y each are 0 or an integer from 1 to 5; or a pharmaceutically acceptable salt thereof.

12. The compound of Formula (IX) according to claim 11:

(IX)

wherein:
R$^1$ and R$^2$ each are hydrogen, (C$_{1-6}$)alkyl, or (CH$_2$)p-C(O)OR$^b$;
R$^3$ and R$^4$ each are hydrogen, OH or OR$^c$;
wherein:
R$^b$ or R$^c$ each is H, (C$_{1-6}$)-alkyl, an alkali metal or negative charge;
A is R$^5$ or —NR$^d$C(O)R$^5$
where R$^d$ is H or (C$_{1-6}$)-alkyl
R$^5$ is a monocyclic 3 to 7 membered heterocyclic ring or a bicyclic 10 membered heterocyclic ring;
wherein:
each 3 to 7 membered heterocyclic ring contains up to four heteroatoms;
each bicyclic 10 membered heterocyclic ring contains up to four heteroatoms;
where:
heteroatoms are selected from oxygen, nitrogen or sulphur,
each 10 membered heterocyclic ring optionally contains carbocyclic rings or heterocyclic rings;
wherein:
carbocyclic rings or heterocyclic rings for each 10 membered heterocyclic ring systems contain non-aromatic rings or aromatic rings;
R5 optionally is substituted by one or more of the following substituents selected from —H, —OH, Oxo (═O), —CN, —NO$_2$, -halogen, -straight or branched C$_{1-6}$ alkyl, -straight or branched C$_{1-6}$ haloalkyl, C$_{3-6}$-cycloalkyl, -straight or branched C$_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;
wherein:
each R$^e$, R$^f$, R$^g$, R$^h$, R$^i$, R$^j$, R$^k$, R$^l$, or R$^m$ as defined above is selected from H, C$_{1-6}$ alkyl, C$_{1-6}$ haloalkyl, C$_{1-6}$ alkoxy;
each aryl or heteroaryl as defined above is optionally substituted with one or more of the following substituents selected from H, —OH, —CN, —NO$_2$, -halogen, C$_{1-6}$-alkyl, C$_{1-6}$-haloalkyl, C$_{1-6}$-alkoxy, —OC(O)OH, —OC(O)R$^n$, —C(O)OR$^o$, —O(CH$_2$)$_y$OR$^p$, —NR$^q$R$^r$, —SO$_2$R$^s$, —S(CH$_2$)$_y$R$^t$, —NR$^u$C(O)R$^v$;

wherein:
R$^n$, R$^o$, R$^p$, R$^q$, R$^r$, R$^s$, R$^t$, R$^u$, or R$^v$ each as defined above are selected from C$_{1-6}$ alkyl, C$_{1-6}$-haloalkyl, or C$_{1-6}$-alkoxy;
n, m, o, p, q or y each are 0 or an integer from 1 to 5; or a pharmaceutically acceptable salt thereof.

13. The compound according to claim 12, wherein A is:

-continued

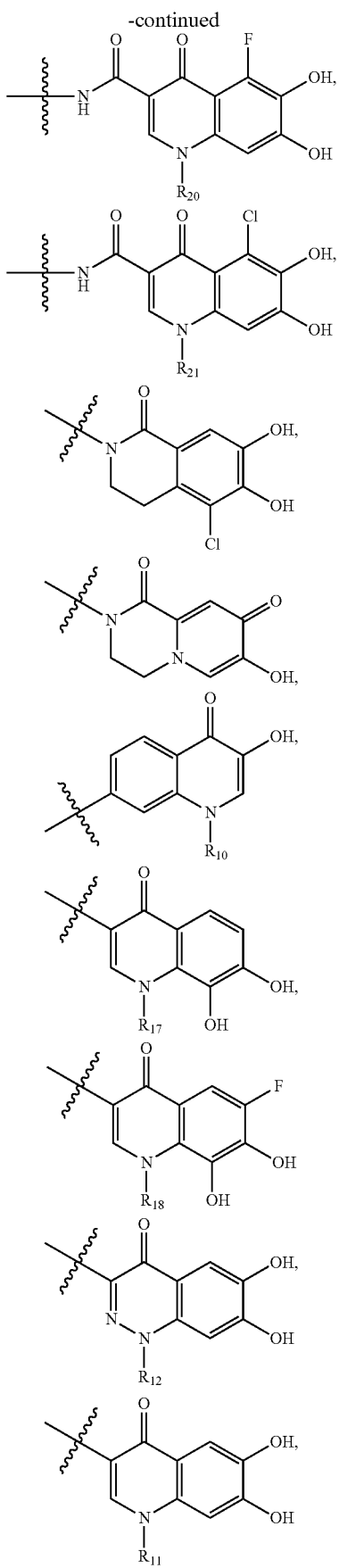

-continued

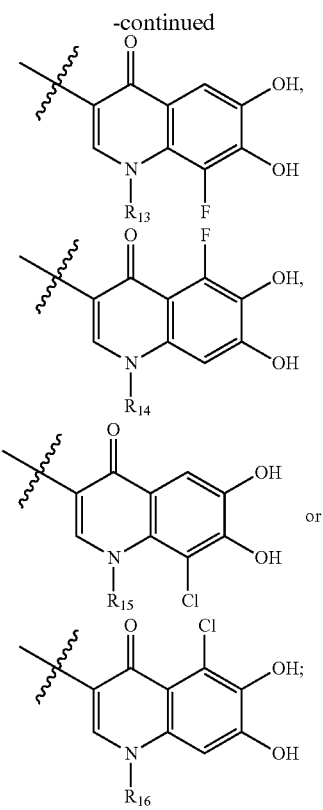

wherein:

$R_6, R_7, R_8, R_9, R_{10}, R_{11}$ or $R_{12}, R_{13}, R_{14}, R_{15}, R_{16}, R_{17}, R_{18}, R_{19}, R_{20}, R_{21}, R_{22}$, or $R_{23}$ is H, straight or branched $(C_{1-6})$-alkyl or $C_{3-6}$-cycloalkyl.

each A optionally further is substituted by one or more of the following substituents selected from —H, —OH, Oxo (=O), —CN, —NO$_2$, -halogen, -straight or branched $C_{1-6}$ alkyl, -straight or branched $C_{1-6}$ haloalkyl, $C_{3-6}$-cycloalkyl, -straight or branched $C_{1-6}$ straight or branched alkoxy, —OC(O)OH, —OC(O)R$^e$, —C(O)OR$^f$, —O(CH$_2$)$_y$OR$^g$, —NR$^h$R$^i$, —SO$_2$R$^j$, —S(CH$_2$)$_q$R$^k$, —NR$^l$C(O)R$^m$, aryl or heteroaryl;

where:

each R$^e$, R$^f$, R$^g$, R$^h$, R$^i$, R$^j$, R$^k$, R$^l$, or R$^m$ as defined above is selected from H, C$_{1-6}$ alkyl, C$_{1-6}$ haloalkyl, C$_{1-6}$ alkoxy;

each aryl or heteroaryl as defined above is optionally substituted with one or more of the following substituents selected from H, —OH, —CN, —NO$_2$, -halogen, C$_{1-6}$-alkyl, C$_{1-6}$-haloalkyl, C$_{1-6}$-alkoxy, —OC(O)OH, —OC(O)R$^n$, —C(O)OR$^o$, —O—(CH$_2$)$_y$OR$^p$, —NR$^q$R$^r$, —SO$_2$R$^s$, —S(CH$_2$)$_y$R$^t$, —NR$^u$C(O)R$^v$;

where:

R$^n$, R$^o$, R$^p$, R$^q$, R$^r$, R$^s$, R$^t$, R$^u$, or R$^v$ each as defined above are selected from C$_{1-6}$ alkyl, C$_{1-6}$-haloalkyl, or C$_{1-6}$-alkoxy; and n, m, o, p, q or y each are 0 or an integer from 1 to 5.

14. The compound according to claim 12, wherein:

R$^1$ and R$^2$ each are (C$_{1-6}$)alkyl;

R$^3$ and R$^4$ each are OH or OR$^c$;

wherein:
R$^c$ is H, (C$_{1-6}$)-alkyl, an alkali metal or negative charge;
A is

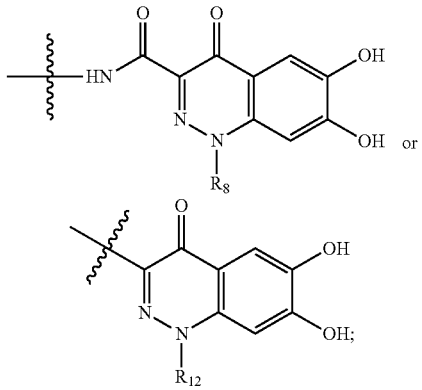

R$^8$ or R$^{12}$ is H, (C$_{1-6}$)-alkyl or (C$_{3-6}$)-cycloalkyl;
n is 1; or
a pharmaceutically acceptable salt thereof.

15. A compound which is:
1-(((6R,7R)-7-((Z)-2-((((S)-4-(tert-butoxy)-1-((4-methoxybenzyl)oxy)-1,4-dioxobutan-2-yl)oxy)imino)-2-(2-((tert-butoxycarbonyl)amino)thiazol-4-yl)acetamido)-2-(((4-methoxybenzyl)oxy)carbonyl)-8-oxo-5-thia-1-azabicyclo[4.2.0]oct-2-en-3-yl)methyl)-1-(2-(5-chloro-6,7-bis((4-methoxybenzyl)oxy)-1-oxo-3,4-dihydroisoquinolin-2(1H)-yl)ethyl)pyrrolidin-1-ium;

(6R,7R)-7-((Z)-2-(2-aminothiazol-4-yl)-2-(((S)-1,2-dicarboxyethoxy)imino)acetamido)-3-((1-(2-(5-hydroxy-1-methyl-4-oxo-1,4-dihydropyridine-2-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(7-hydroxy-1,8-dioxo-3,4-dihydro-1H-pyrido[1,2-a]pyrazin-2(8H)-yl)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((3-hydroxy-1-methyl-4-oxo-1,4-dihydroquinolin-6-yl)methyl)pyrrolidin-1-ium-1-yl)methyl)-8-oxo-5-thia-1-azabicyclo[4.2.0]oct-2-ene-2-carboxylate;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-6-carboxamido)ethyl)pyrrolidin-1-ium;

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium;

1-(((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydroquinoline-3-carboxamido)ethyl)pyrrolidin-1-ium;

1-(((6R,7R)-7-((E)-3-(2-aminothiazol-5-yl)-3-(((R)-1,2-dicarboxyethoxy)imino)-2-oxopropyl)-2-carboxy-8-oxo-5-thia-1-azabicyclo[4.2.0]oct-2-en-3-yl)methyl)-1-((1-ethyl-6,7-dihydroxy-4-oxo-1,4-dihydrocinnolin-3-yl)methyl)piperidin-1-ium;

1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(3-hydroxy-1-methyl-4-oxo-1,4-dihydroquinoline-8-carboxamido)ethyl)pyrrolidin-1-ium;

(6R,7R)-7-((Z)-2-(2-aminothiazol-4-yl)-2-(((2-carboxypropan-2-yl)oxy)imino)acetamido)-3-((1-((1-ethyl-8-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino) acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxylatopropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((5-chloro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(5-chloro-1-ethyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-ethyl-6,7-dihydroxy-4-oxo-1,4-dihydrocinnoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate;

1-(((6R,7R)-7-((Z)-2-(2-amino-5-chlorothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydrocinnoline-3-carboxamido)ethan-1-ylium-1-yl)pyrrolidin-1-ium;

(6R,7R)-7-((Z)-2-(2-amino-5-chlorothiazol-4-yl)-2-(((S)-1,2-dicarboxyethoxy)imino)acetamido)-3-((1-(2-(5-chloro-1-ethyl-6,7-dihydroxy-4-oxo-1,4-dihydrocinnoline-3-carboxamido)ethyl)pyrrolidin-1-ium-2-ylium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((5-chloro-1-ethyl-6,7-dihydroxy-4-oxo-1,4-dihydrocinnolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-fluouro-1-ethyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-ethyl-5-fluoro-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-ethyl-6-fluoro-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-6-fluoro-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-ethyl-7,8-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(1-ethyl-7,8-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-ethyl-5,6-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-(tert-butyl)-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-(tert-butyl)-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((S)-1,2-dicarboxyethoxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-amino-5-chlorothiazol-4-yl)-2-(((2-carboxypropan-2-yl)oxy)imino)acetamido)-3-((1-((1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-(2-(1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-((5-chloro-1-cyclopropyl-6,7-dihydroxy-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((2-carboxypropan-2-yl)oxy)imino)acetamido)-3-((1-(2-(5-chloro-1-cyclopropyl-6,7-dihydroxy-4-oxo-1,4-dihydroquinoline-3-carboxamido)ethyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

(6R,7R)-7-((Z)-2-(2-aminothiazol-4-yl)-2-(((S)-1,2-dicarboxyethoxy)imino)acetamido)-3-((1-((6,7-dihydroxy-1-isopropyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate;

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(5-chloro-1-ethyl-6,7-dihydroxy-4-oxo-1,4-dihydroquinoline-3-carboxamido)ethyl)pyrrolidin-1-ium;

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-(2-(1-ethyl-8-fluoro-6,7-dihydroxy-4-oxo-1,4-dihydroquinoline-3-carboxamido)ethyl)pyrrolidin-1-ium;

1-(((6R,7R)-7-((Z)-2-(2-amino-5-chlorothiazol-4-yl)-2-(((S)-1,2-dicarboxyethoxy)imino)acetamido)-2-carboxy-8-oxo-5-thia-1-azabicyclo[4.2.0]oct-2-en-3-yl)methyl)-1-((1-ethyl-8-fluoro-6,7-dihydroxy-4-oxo-1,4-dihydroquinolin-3-yl)methyl)pyrrolidin-1-ium;

(6R,7R)-7-((Z)-2-(2-aminothiazol-4-yl)-2-(((S)-1,2-dicarboxyethoxy)imino)acetamido)-3-((1-((5-chloro-6,7-dihydroxy-1-methyl-4-oxo-1,4-dihydroquinolin-3-yl)methyl)pyrrolidin-1-ium-1-yl)methyl)-8-oxo-5-thia-1-azabicyclo[4.2.0]oct-2-ene-2-carboxylate; or a pharmaceutically acceptable salt thereof.

16. The compound according to claim 15, wherein the pharmaceutically acceptable salt is a sodium salt, di-sodium salt or a trifluoroacetic acid salt.

17. A compound which is 1-(((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium:

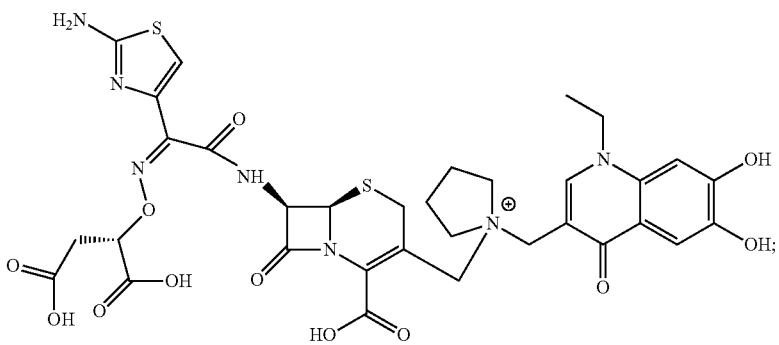 [SMILES: CCn1cc(C[N+]2(CC3=C(C(=O)O)N4C(=O)[C@@H](NC(=O)/C(=N\O[C@@H](CC(=O)O)C(=O)O)c5csc(N)n5)[C@H]4SC3)CCCC2)c(=O)c2cc(O)c(O)cc21]

or a pharmaceutically acceptable salt thereof.

18. A compound which is 1-(((6R,7R)-7-((Z)-2-(2-aminothiazol-4-yl)-2-(((R)-1,2-dicarboxyethoxy)imino)acetamido)-2-carboxy-8-oxo-5-thia-1-azabicyclo[4.2.0]oct-2-en-3-yl)methyl)-1-((1-ethyl-6,7-dihydroxy-4-oxo-1,4-dihydroquinolin-3-yl)methyl)pyrrolidin-1-ium disodium salt.

19. A compound which is 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2- en-yl)methyl)-1-((1-ethyl-6,7-dihydroxy-4-oxo-1,4-dihydrocinnolin-3-yl)methyl)pyrrolidin-1-ium;

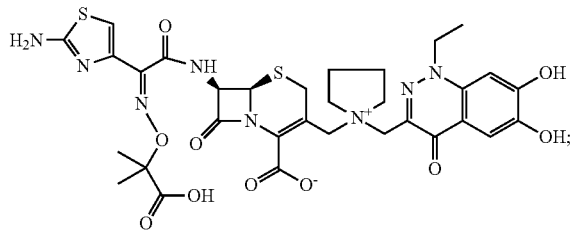 [SMILES: CCn1nc(C[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)cc21]

or
  a pharmaceutically acceptable salt thereof.
20. A compound which is 1-(((6R,7R)-7-((Z)-2-(2-aminothiazol-4-yl)-2-(((2-carboxypropan-2-yl)oxy)imino)acetamido)-2-carboxy-8-oxo-5-thia-1-azabicyclo[4.2.0]oct-2-en-3-yl)methyl)-1-(2-(1-ethyl-6,7-dihydroxy-4-oxo-1,4-dihydrocinnoline-3-carboxamido)ethyl)pyrrolidin-1-ium;

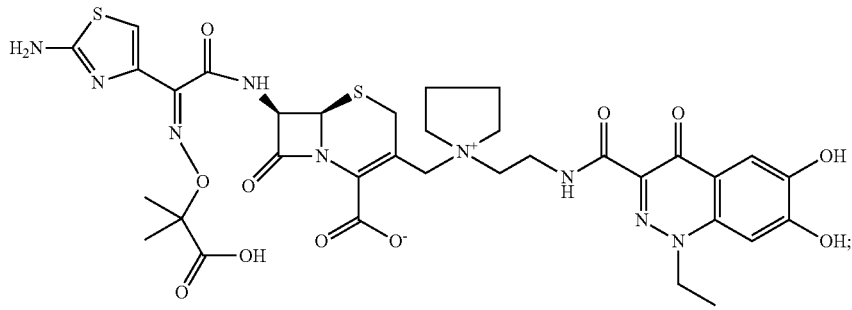 [SMILES: CCn1nc(C(=O)NCC[N+]2(CC3=C(C(=O)[O-])N4C(=O)[C@@H](NC(=O)/C(=N\OC(C)(C)C(=O)O)c5csc(N)n5)[C@H]4SC3)CCCC2)c(=O)c2cc(O)c(O)cc21]

or
  a pharmaceutically acceptable salt thereof.
21. A pharmaceutical composition comprising a compound according to claim 1 and at least one or more pharmaceutically acceptable excipients.
22. A method of treating a bacterial infection comprising administering a therapeutically effective amount of a compound according to claim 1 or a pharmaceutically acceptable salt thereof.
23. The method of treating a bacterial infection according to claim 22, wherein the bacterial infection is caused by Gram negative bacteria.
24. The method of treating a bacterial infection according to claim 23, wherein the Gram negative bacteria selected from Gram negative bacteria of enterobacteria, Gram negative bacteria colonized in respiratory, Gram negative bacteria of glucose non fermentation or β-lactam drug resistant Gram negative bacteria.
25. The method of treating a bacterial infection according to claim 24, wherein:
  the Gram negative bacteria of enterobacteria selected from
    E. coli, Klebsiella, Serratia, Enterobacter, Citrobacter,
    Morganella, Providencia or Proteus;
  the Gram negative bacteria colonized in respiratory system
    selected from Haemophilus or Moraxella;
  the Gram negative bacteria of glucose non fermentation
    selected from Pseudomonas aeruginosa, Pseudomonas
    other than P. aeruginosa, Stenotrophomonas or
    Burkholderia, Acinetobacter, and
  the beta-lactam drug resistant Gram negative bacteria is
    selected from ESBL producing bacteria.

26. The method according to claim 22, wherein the bacterial infection is an airway infection, urinary system infection, resipiratory system infection, sepsis infection, nephritis, cholecystitis, oral cavity infection, endocarditis, pneumonia, bone marrow membrane myelitis, otitis media, enteritis, empyema, wound infection or an opportunistic infection.
27. A method for treating a gram-negative bacterial infection comprising administering a therapeutically effective amount of a compound according to claim 1 or a pharmaceutically acceptable salt thereof to a human in need thereof.
28. The method of treating a gram-negative bacterial infection according to claim 27, wherein the bacterial infection is caused by Gram negative bacteria.
29. The method of treating a gram-negative bacterial infection according to claim 28, wherein the Gram negative bacteria selected from Gram negative bacteria of enterobacteria, Gram negative bacteria colonized in respiratory, Gram negative bacteria of glucose non fermentation or β-lactam drug resistant Gram negative bacteria.
30. The method of treating a gram-negative bacterial infection according to claim 29, wherein:
  the Gram negative bacteria of enterobacteria selected from
    E. coli, Klebsiella, Serratia, Enterobacter, Citrobacter,
    Morganella, Providencia or Proteus;
  the Gram negative bacteria colonized in respiratory system
    selected from Haemophilus or Moraxella;
  the Gram negative bacteria of glucose non fermentation
    selected from Pseudomonas aeruginosa, Pseudomonas
    other than P. aeruginosa, Stenotrophomonas or
    Burkholderia, Acinetobacter, and
  the beta-lactam drug resistant Gram negative bacteria is
    selected from ESBL producing bacteria.
31. A method for inhibiting activity of UDP-3-O—(R-3-hydroxydecanoyl)-N-acetylglucosamine deacetylase (LpxC) comprising administering a therapeutically effective amount of a compound of Formula (II) according to claim 1 or a pharmaceutically acceptable salt thereof to a human in need thereof.
32. A method for treating antimicrobial activity against Gram positive bacteria comprising administering a therapeutically effective amount of a compound according to claim 1 or a pharmaceutically acceptable salt thereof to a human in need thereof.
33. The method for treating antimicrobial activity against Gram positive bacteria according to claim 32, wherein the Gram positive bacteria is selected from methicillin-resistant Staphylococcus aureus (MRSA) or penicillin-resistant Streptococcus pneumoniae (PRSP).
34. A method for treating methicillin-resistant Staphylococcus aureus (MRSA), comprising administering a therapeutically effective amount of a compound according to claim 1 or a pharmaceutically acceptable salt thereof to a human in need thereof.

35. A method for treating penicillin-resistant *Streptococcus pneumoniae* (PRSP), comprising administering a therapeutically effective amount of a compound according to claim 1 or a pharmaceutically acceptable salt thereof to a human in need thereof.

36. A method of treating a bacterial infection comprising administering a therapeutically effective amount of a pharmaceutical composition according to claim 21.

37. The method of treating a bacterial infection according to claim 36, wherein the bacterial infection is caused by Gram negative bacteria.

* * * * *